(12) United States Patent
Butlin et al.

(10) Patent No.: US 6,960,688 B2
(45) Date of Patent: Nov. 1, 2005

(54) USE OF COMPOUNDS FOR THE ELEVATION OF PYRUVATE DEHYDROGENASE ACTIVITY

(75) Inventors: Roger J Butlin, Macclesfield (GB); Thorsten Nowak, Macclesfield (GB); Jeremy N Burrows, Macclesfield (GB); Michael H Block, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/277,957

(22) Filed: Oct. 23, 2002

(65) Prior Publication Data

US 2004/0009979 A1 Jan. 15, 2004

Related U.S. Application Data

(62) Division of application No. 09/700,370, filed on Nov. 15, 2000, now Pat. No. 6,498,275.

(30) Foreign Application Priority Data

May 29, 1998 (GB) .............................................. 9811427

(51) Int. Cl.$^7$ ........................ C07C 233/05; A61K 31/16
(52) U.S. Cl. ........................ 564/202; 564/138; 564/203; 544/301; 546/294; 548/186; 548/187; 548/323.5; 549/65; 549/479; 558/413; 558/414; 558/415; 558/418; 514/628; 514/522; 514/473; 514/445; 514/398; 514/369; 514/347; 514/274; 514/269
(58) Field of Search .................................. 564/202, 138, 564/203; 544/301; 546/294; 548/186, 187, 323.5; 549/65, 479; 558/413, 414, 415, 418; 574/269, 274, 347, 369, 398, 445, 473, 522, 628; 514/269, 274, 347, 369, 398, 445, 473, 522, 628

(56) References Cited

U.S. PATENT DOCUMENTS

| 4,537,618 A | 8/1985 | Schurter et al. ............. 544/321 |
| 5,248,693 A | 9/1993 | Gerspacher et al. ........ 548/511 |
| 5,482,969 A | * 1/1996 | Empfield et al. ............ 514/522 |
| 5,486,515 A | 1/1996 | Brown et al. |
| 5,510,386 A | 4/1996 | Empfield et al. ............. 546/89 |

FOREIGN PATENT DOCUMENTS

| CA | 1 228 355 | 10/1987 |
| EP | 0 002 309 | 6/1979 |
| EP | 0 002 892 | 7/1979 |
| EP | 0 040 932 | 12/1981 |
| EP | 0 079 191 | 5/1983 |
| EP | 0 096 002 | 12/1983 |
| EP | 0 100 172 | 2/1984 |
| EP | 0 253 500 | 1/1988 |
| EP | 0 253 503 | 1/1988 |
| EP | 0 524 781 | 1/1993 |
| EP | 0 617 010 | 9/1994 |
| EP | 0 625 511 | 11/1994 |
| EP | 0 625 516 | 11/1994 |
| GB | 2 278 054 | 11/1994 |
| WO | WO 93/10094 | 5/1993 |
| WO | WO 93/23358 | 5/1993 |
| WO | WO 94/26739 | 11/1994 |
| WO | WO 96/28151 | 9/1996 |
| WO | WO 97/38124 | 10/1997 |
| WO | WO 99/44618 | 9/1999 |
| WO | WO 99/47508 | 9/1999 |
| WO | WO 99/62506 | 12/1999 |
| WO | WO 99/62873 | 12/1999 |

OTHER PUBLICATIONS

Bayles et al., "A Smiles Rearrangement Involving Non–Activated Aromatic Systems; the Facile Conversion of Phenols to Anilines", Synthesis, 1977, vol. 1. pp. 33–34.

Bayles et al.,, "The Smiles Rearrangement of 2–Aryloxy–2–methylpropanamides. Synthesis of N–Aryl–2–hydroxy–2–methyl–propanamides", Synthesis, 1977, vol. 1, pp., 31–33.

Empfield et al., "4–sulfonamidoanilide Tertiary Carbinols: A Novel Series Of Potassium Channel Openers", Bioorg Med. Chem. Letters, 1997, vol. 7, No. 7, pp. 775–778, XP004136128 see table 1, compounds e, f.

Furr et al., "A Novel Non–Steroidal, Peripherally Selective Antiandrogen", J. Endrocrinol., 1987, vol. 113 (3), R7–R9.

Glen et al., Structure–Activity Relationships among Non–steriodal Antiandrogens, Third SCI–RSC Medicinal Chemistry Symposium, 1986, vol. 55, pp. 345–361.

Grant et al., "Anilide Tertiary Carbinols: A New Structural Class Of Potent Potassium Channel Openers", Bioorg. Med. Chem. Lett., 1993, vol. 3 (12), pp. 2723–2724.

(Continued)

*Primary Examiner*—Shailendra Kumar
(74) *Attorney, Agent, or Firm*—Morgan, Lewis & Bockius LLP

(57) ABSTRACT

The use of compounds of formula (I), and salts thereof; and pharmaceutically acceptable in vivo cleavable prodrugs of said compound of formula (I); and pharmaceutically acceptable salts of said compound or said prodrugs; in formula (I), Ring C is phenyl or a carbon linked heteroaryl ring substituted as defined within; $R^1$ is an ortho substituent as defined within; n is 1 or 2; A-B is a linking group as defined within; $R^2$ and $R^3$ are as defined within; $R^4$ is hydroxy, hydrogen, halo, amino or methyl; in the manufacture of a medicament for use in the elevation of PDH activity in warm-blooded animals such as humans is described. Pharmaceutical compositions, methods and processes for preparation of compounds of formula (I) are also described

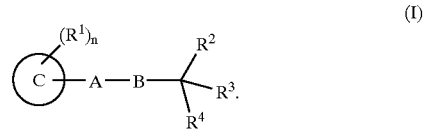

11 Claims, No Drawings

OTHER PUBLICATIONS

Howe et al., "Zeneca ZD6169: A Novel $K_{ATP}$ Channel Opener with in Vivo Selectivity for Urinary Bladder", J. Pharmacol. Exp. Ther. 1995, vol. 274 (2), pp., 884–890.

Jackman et al., "Studies in the Field of Diuretics", J. Pharm. and Pharmacol., vol. 12, 1960, pp. 648–655; Chemical Abstracts, vol. 55, No. 9, May 1, 1961, Columbus, Ohio, US; abstract No. 8336a, XP002107578 see abstract, column 8336, lines 8–9 &.

Li et al., "Zeneca ZD6169 and Its Analogs from a Novel Series of Anilide Tertiary Carbinols: in vitro $K_{ATP}$ Channel Opening Activity in Bladder Detrusor ", Pharmacology, 1995, vol. 51, pp. 33–42.

Morris et al., "Hydrogen Bonding Parameters In The S.A.R. of Non–Steroidal Anti–Androgens", Pharmacol. Libr., 1987, vol. 10, pp. 204–206.

Morris et al., "Non–Steroidal Antiandrogens. Design of Novel Compounds Based on an Infrared Study of the Dominant Conformationand Hydrogen–Bonding Properties of a Series of Anilide Antiandrogens", J. Med. Chem. 1991, vol. 34, pp., 447–455.

Ohnmacht et al., N–Aryl–3,3, 3–trifluoro–2–hydroxy–2–methylpropanamides: $K_{ATP}$ Potassium Channel Openers. Modifications on the Western Region', J. Med. Chem., 1996, vol. 39 (23), pp. 4592–4601.

Ohnmacht et al., N–Aryl–3,3, 3–trifluoro–2–hydroxy–2–methylpropanamides: $K_{ATP}$ Potassium Channel Openers. Modifications on the Western Region', J. Med. Chem., 1996, Additions and Corrections, vol. 39 (6), p. 1048.

Russell, "Crystal Receptor Models In Medicinal Chemistry: Application To The Generation of Highly Potent Potassium Channel Openers", Bioorg. Med. Chem. Lett. 1996, vol. 6 (7), pp. 913–918.

Tenthorey et al.; "New Antiarrhythmic Agents. 3. Primary β–Amino Anilides", J. Med. Chem. 1979, vol. 22 (10), pp. 1182–1186.

Trivedi et al., "K–Channel Opening Activity of ZD6169 and Its Analogs: Effect on $^{86}$Rb Efflux and $^3$H–1075 Binding in Bladder Smooth Muscle", Pharmacology, 1995, vol. 50 (6), pp. 388–397.

Tucker et al., "Nonsteroidal Antiandrogens. Synthesis and Structure–Activity Relationships of 3–Substituted Derivatives of 2–Hydroxypropionanilides", J. Med. Chem., 1988, vol. 31, pp. 954–959.

Tucker et al., "Resolution of the Nonsteriodal Antiandrogen 4'–Cyano–3–[(4–fluorophenyl)sulfonyl]– 2–hydroxy–2–methyl–3'–(trifluoromethyl)– propionanilide and the Determination of the Absolute Configuration of the Active Enantiomer", J. Med. Chem. 1988. vol. 31 (4), pp. 885–887.

Wakeling et al., "Receptor Binding And Biological Activity Of Steriodal and Nonsteriodal Antiandrogens", J. Steriod Biochem., 1981, vol. 15, pp. 355–359.

\* cited by examiner

USE OF COMPOUNDS FOR THE ELEVATION OF PYRUVATE DEHYDROGENASE ACTIVITY

This application is a DIV of Ser. No. 09/700,370, filed Nov. 1, 2000, U.S. Pat. No. 6,498,275.

The present invention relates to compounds which elevate pyruvate dehydrogenase (PDH) activity, processes for their preparation, pharmaceutical compositions containing them as active ingredient, methods for the treatment of disease states associated with reduced PDH activity, to their use as medicaments and to their use in the manufacture of medicaments for use in the elevation of PDH activity in warm-blooded animals such as humans.

Within tissues adenosine triphosphate (ATP) provides the energy for synthesis of complex molecules and, in muscle, for contraction. ATP is generated from the breakdown of energy-rich substrates such as glucose or long chain free fatty acids. In oxidative tissues such as muscle the majority of the ATP is generated from acetyl CoA which enters the citric acid cycle, thus the supply of acetyl CoA is a critical determinant of ATP production in oxidative tissues. Acetyl CoA is produced either by β-oxidation of fatty acids or as a result of glucose metabolism by the glycolytic pathway. The key regulatory enzyme in controlling the rate of acetyl CoA formation from glucose is PDH which catalyses the oxidation of pyruvate to acetyl CoA and carbon dioxide with concomitant reduction of nicotinamide adenine dinucleotide (NAD) to NADH.

In disease states such as both non-insulin dependent (NIDDM) and insulin-dependent diabetes mellitus (IDDM), oxidation of lipids is increased with a concomitant reduction in utilisation of glucose, which contributes to the hyperglycaemia. Reduced glucose utilisation in both IDDM and NIDDM is associated with a reduction in PDH activity. In addition, a further consequence of reduced PDH activity may be that an increase in pyruvate concentration results in increased availability of lactate as a substrate for hepatic gluconeogenesis. It is reasonable to expect that increasing the activity of PDH could increase the rate of glucose oxidation and hence overall glucose utilisation, in addition to reducing hepatic glucose output. Another factor contributing to diabetes mellitus is impaired insulin secretion, which has been shown to be associated with reduced PDH activity in pancreatic β-cells (in a rodent genetic model of diabetes mellitus Zhou et al. (1996) Diabetes 45: 580–586).

Oxidation of glucose is capable of yielding more molecules of ATP per mole of oxygen than is oxidation of fatty acids. In conditions where energy demand may exceed energy supply, such as myocardial ischaemia, intermittent claudication, cerebral ischaemia and reperfusion, (Zaidan et al., 1998; J. Neurochem. 70: 233–241), shifting the balance of substrate utilisation in favour of glucose metabolism by elevating PDH activity may be expected to improve the ability to maintain ATP levels and hence function.

An agent which is capable of elevating PDH activity may also be expected to be of benefit in treating conditions where an excess of circulating lactic acid is manifest such as in certain cases of sepsis.

The agent dichloroacetic acid (DCA) which increases the activity of PDH after acute administration in animals, (Vary et al., 1988; Circ. Shock. 24: 3–18), has been shown to have the predicted effects in reducing glycaemia, (Stacpoole et al. 1978; N. Engl. J. Med. 298: 526–530), and as a therapy for myocardial ischaemia (Bersin and Stacpoole 1997; American Heart Journal, 134: 841–855) and lactic acidaemia, (Stacpoole et al., 1983; N. Engl. J. Med. 309: 390–396).

PDH is an intramitochondrial multienzyme complex consisting of multiple copies of several subunits including three enzyme activities E1, E2 and E3, required for the completion of the conversion of pyruvate to acetyl CoA (Patel and Roche 1990; FASEB J., 4: 3224–3233). E1 catalyses the non-reversible removal of $CO_2$ from pyruvate; E2 forms acetyl CoA and E3 reduces NAD to NADH. Two additional enzyme activities are associated with the complex: a specific kinase which is capable of phosphorylating E1 at three serine residues and a loosely-associated specific phosphatase which reverses the phosphorylation. Phosphorylation of a single one of the three serine residues renders the E1 inactive. The proportion of the PDH in its active (dephosphorylated) state is determined by a balance between the activity of the kinase and phosphatase. The activity of the kinase may be regulated in vivo by the relative concentrations of metabolic substrates such as NAD/NADH, CoA/acetylCoA and adenine diphosphate (ADP)/ATP as well as by the availability of pyruvate itself.

European Patent Publication Nos. 617010 and 524781 describes compounds which are capable of relaxing bladder smooth muscle and which may be used in the treatment of urge incontinence. We have found that the compounds of the present invention are very good at elevating PDH activity, a property nowhere disclosed in EP 0617010 and EP 524781.

The present invention is based on the surprising discovery that certain compounds elevate PDH activity, a property of value in the treatment of disease states associated with disorders of glucose utilisation such as diabetes mellitus, obesity, (Curto et al., 1997; Int. J. Obes. 21: 1137–1142), and lactic acidaemia. Additionally the compounds may be expected to have utility in diseases where supply of energy-rich substrates to tissues is limiting such as peripheral vascular disease, (including intermittent claudication), cardiac failure and certain cardiac myopathies, muscle weakness, hyperlipidaemias and atherosclerosis (Stacpoole et al., 1978; N. Engl. J. Med. 298: 526–530). A compound that activates PDH may also be useful in treating Alzheimer's disease (AD) (J Neural Transm (1998) 105, 855–870).

According to one aspect of the present invention there is provided the use of compounds of the formula (I):

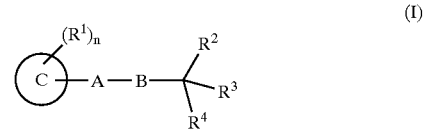

wherein:
ring C is as defined in (a) or (b);
$R^1$ is as defined in (c) or (d);
n is 1 or 2;
$R^2$ and $R^3$ are as defined in (e) or (f);
A-B is as defined in (g) or (h) and
$R^4$ is as defined in (i) or (j)
wherein (a) ring C is phenyl or carbon-linked heteroaryl selected from pyridyl, pyrazinyl, pyrimidinyl and pyridazinyl; wherein said phenyl or heteroaryl is substituted on carbon at one or both positions meta to the position of A-B attachment or on carbon at the position para to the position of A-B attachment by $P^1$ or $P^2$ (wherein $P^1$ and $P^2$ are as defined hereinafter), and further, wherein said phenyl or heteroaryl is optionally substituted on carbon at any remaining meta position(s) or para position by $P^1$ or $P^3$, (wherein $P^1$ and $P^3$ are as defined hereinafter);

(b) ring C is selected from the following five groups:

(i) phenyl or carbon-linked heteroaryl selected from pyridyl, pyrazinyl, pyrimidinyl and pyridazinyl, wherein said phenyl or heteroaryl is unsubstituted except by $(R^1)_n$ wherein $R^1$ and n are as defined hereinafter;

(ii) a carbon-linked triazine optionally substituted on a ring carbon at a position meta or para to A-B attachment by 1 substituent selected from $P^1$, $P^2$, $P^3$ and $P^4$, wherein $P^1$, $P^2$, $P^3$ and $P^4$ are as defined hereinafter;

(iii) a 6-membered carbon-linked heteroaryl group containing 1–3 nitrogen atoms wherein one or more ring nitrogen atoms are oxidised to form the N-oxide, which heteroaryl group is optionally substituted at any of the positions meta or para to A-B attachment by 1–3 substituents selected from $P^1$, $P^2$, $P^3$ and $P^4$, wherein $P^1$, $P^2$, $P^3$ and $P^4$ are as defined hereinafter;

(iv) phenyl or carbon-linked heteroaryl selected from pyridyl, pyrazinyl, pyrimidinyl and pyridazinyl, wherein said phenyl or heteroaryl is substituted at a position meta or para to A-B attachment by 1 substituent selected from $P^3$ and $P^4$, wherein $P^3$ and $P^4$ are as defined hereinafter; and (v) phenyl or carbon-linked heteroaryl selected from pyridyl, pyrazinyl, pyrimidinyl and pyridazinyl, wherein said phenyl or heteroaryl is substituted at any of the positions meta or para to A-B attachment by 2–3 substituents selected from $P^1$, $P^2$, $P^3$ and $P^4$, provided that if one or more of the substituents is $P^1$ or $P^2$ then at least one of the other substituents is $P^4$, wherein $P^1$, $P^2$, $P^3$ and $P^4$ are as defined hereinafter;

$P^1$ is cyano, trifluoromethyl, nitro, trifluoromethoxy or trifluoromethylsulphanyl;

$P^2$ is —$Y^1Ar^1$, wherein $Ar^1$ is selected from the group consisting of phenyl, a carbon-linked 6-membered heteroaryl ring containing 1–2 nitrogen atoms and a carbon-linked 5-membered heteroaryl ring containing 1–2 heteroatoms selected independently from O, N and S, wherein said phenyl or heteroaryl ring is optionally substituted at carbon, with 1–4 substituents selected from $Q^1$, wherein $Q^1$ is as defined hereinafter; and $Y^1$ is selected from —CO—, —SO— and —$SO_2$—;

$P^3$ is $C_{1-4}$alkyl, halo$C_{2-4}$alkyl, $C_{1-4}$alkoxy, halo$C_{2-4}$alkoxy, $C_{2-4}$alkenyloxy, halo or hydroxy;

$P^4$ is selected from the following eight groups:

1) halosulphonyl, cyanosulphanyl;

2) —$X^1$—$R^5$ wherein $X^1$ is a direct bond, —O—, —S—, —SO—, —$SO_2$—, —$OSO_2$—, —$SO_2O$—, —$NR^6$—, —$N^+O^-R^6$—, —CO—, —COO—, —OCO—, —$CONR^7$—, —$NR^8CO$—, —$OCONR^9$—, —$CONR^{10}SO_2$—, —$NR^{11}SO_2$—, —$CH_2$—, —$NR^{12}COO$—, —$CSNR^{13}$—, —$NR^{14}CS$—, —$NR^{15}CSNR^{16}$—, $NR^{17}CONR^{18}$— or —$NR^{19}CONR^{20}SO_2$—(wherein $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ each independently represents hydrogen or $C_{1-4}$alkyl which $C_{1-4}$alkyl may be optionally substituted by one or more groups selected from hydroxy, amino, halo, $C_{1-4}$alkoxycarbonyl, carboxy, $C_{1-6}$alkoxy or $C_{1-3}$alkylsulphanyl) and $R^5$ is selected from hydrogen, $C_{1-6}$alkyl, $C_{3-7}$cycloalkyl, $C_{2-6}$alkenyl and $C_{2-6}$alkynyl which $C_{1-6}$alkyl, $C_{3-7}$cycloalkyl, $C_{2-6}$alkenyl or $C_{2-6}$alkynyl is optionally substituted with one or more groups selected from hydroxy, amino, halo, $C_{1-4}$alkoxycarbonyl, carboxy, $C_{1-6}$alkoxy and hydroxy$C_{1-6}$ alkyl with the proviso that $P^4$ is not trifluoromethylsulphanyl, hydroxy, $C_{1-4}$alkyl, halo$C_{1-4}$alkyl, $C_{1-4}$alkoxy, halo$C_{1-4}$alkoxy or $C_{2-4}$alkenyloxy;

3) —$X^1$—$C_{1-6}$alkyl-$X^2$—$R^{21}$ wherein $X^1$ is as defined hereinbefore, $X^2$ is a direct bond, —O—, —S—, —SO—, —$SO_2$—, —$OSO_2$—, —$SO_2O$—, —$NR^{22}$—, —$N^+O^-R^{22}$—, —CO—, —COO—, —OCO—, —$CONR^{23}$—, —$NR^{24}CO$—, —$NR^{25}COO$—, —$SO_2NR^{26}$—, —$NR^{27}SO_2$—, —$CH_2$—, —$SO_2NR^{28}CO$—, —$OCONR^{29}$—, —$CSNR^{30}$—, —$NR^{31}CS$—, —$NR^{32}CSNR^{33}$—, —$NR^{34}CONR^{35}$—, —$CONR^{36}SO_2$—, —$NR^{37}CONR^{38}SO_2$—, —$SO_2NR^{39}CONR^{40}$— or —$SO_2NR^{39}CNNR^{40}$— (wherein $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$ and $R^{40}$, each independently represents hydrogen or $C_{1-4}$alkyl which $C_{1-4}$alkyl may be optionally substituted by one or more groups selected from hydroxy, amino, halo, $C_{1-4}$alkoxycarbonyl, carboxy, $C_{1-6}$alkoxy or $C_{1-3}$alkylsulphanyl) and $R^{21}$ is hydrogen or $C_{1-4}$alkyl which $C_{1-4}$alkyl is optionally substituted with one or more groups selected from hydroxy, amino, halo, $C_{1-4}$alkoxycarbonyl, carboxy, $C_{1-6}$alkoxy and hydroxy$C_{1-6}$alkyl or $R^{21}$ is $R^{41}$ wherein $R^{41}$ is phenyl or a 4–12 membered heterocyclic moiety containing 1–4 heteroatoms selected independently from O, N and S which heterocyclic moiety may be aromatic or non-aromatic and which phenyl or heterocyclic moiety is optionally substituted by 1–6 substituents selected from $Q^3$ wherein $Q^3$ is as defined hereinafter with the proviso that $P^4$ is not $C_{1-4}$alkyl, halo$C_{1-4}$alkyl, $C_{1-4}$alkoxy or halo$C_{1-4}$alkoxy;

4) —$X^1$—$C_{2-6}$alkenyl-$X^2$—$R^{21}$ wherein $X^1$, $X^2$ and $R^{21}$ are as defined hereinbefore with the proviso that $P^4$ is not $C_{2-4}$alkenyloxy;

5) —$X^1$—$C_{2-6}$alkynyl-$X^2$—$R^{21}$ wherein $X^1$, $X^2$ and $R^{21}$ are as defined hereinbefore;

6) —$X^1$—$C_{3-7}$cycloalkyl-$X^2$—$R^{21}$ wherein $X^1$, $X^2$ and $R^{21}$ are as defined hereinbefore;

7) —$X^1$—$C_{1-6}$alkyl$C_{3-7}$cycloalkyl-$X^2$—$R^{21}$ wherein $X^1$, $X^2$ and $R^{21}$ are as defined hereinbefore; and 8) —$Y^2Ar^2$ wherein $Y^2$ is $X^1$ wherein $X^1$ is as defined hereinbefore and $Ar^2$ is selected from the following six groups:

(i) phenyl, a carbon-linked 6-membered heteroaryl ring containing 1–2 nitrogen atoms and a carbon-linked 5-membered heteroaryl ring containing 1–2 heteroatoms selected independently from O, N and S, wherein said phenyl or heteroaryl ring is substituted at carbon, with 1–4 substituents selected from $Q^1$ and $Q^2$ including at least one substituent selected from $Q^2$ wherein $Q^1$ and $Q^2$ are as defined hereinafter;

(ii) a carbon-linked triazine or a carbon-linked 5-membered heteroaryl ring containing 3–4 heteroatoms selected independently from O, N and S; wherein said heteroaryl ring is optionally substituted with 1–4 substituents selected from $Q^1$ and $Q^2$ wherein $Q^1$ and $Q^2$ are as defined hereinafter;

(iii) a 4–12 membered non-aromatic heterocyclic moiety containing 1–4 heteroatoms selected independently from O, N and S wherein said heterocyclic moiety is optionally substituted with 1–6 substituents selected from $Q^3$ wherein $Q^3$ is as defined hereinafter, with the proviso that if $Ar^2$ is a nitrogen linked heterocyclic ring $Y^2$ is not —$SO_2$—;

(iv) a 5-membered heteroaryl ring containing 1–4 heteroatoms selected independently from O, N and S, which heteroaryl ring contains at least one nitrogen atom substituted by a group selected from $C_{1-6}$alkyl, $C_{1-6}$alkanoyl, $C_{1-6}$alkylsulphonyl, $C_{1-6}$alkoxycarbonyl, carbamoyl, N-($C_{1-6}$alkyl)carbamoyl, N,N-($C_{1-6}$alkyl)$_2$carbamoyl, benzoyl or phenylsulphonyl and which heteroaryl ring is optionally substituted by 1–3 substituents selected from $Q^3$ wherein $Q^3$ is as defined hereinafter;

(v) a carbon linked 7–12 membered aromatic heterocyclic moiety containing 1–4 heteroatoms selected independently from O, N and S wherein said heterocyclic moiety is optionally substituted with 1–6 substituents selected from $Q^3$ wherein $Q^3$ is as defined hereinafter; and (vi) $Ar^1$ with the proviso that if $Ar^2$ has a value $Ar^1$ then $Y^2$ is not —CO—, —SO— or —$SO_2$—;

$Q^1$ is $C_{1-4}$alkyl, halo$C_{1-4}$alkyl, $C_{1-4}$alkoxy, halo$C_{1-4}$alkoxy, $C_{2-4}$alkenyloxy, cyano, nitro, halo or trifluoromethylsulphanyl;

$Q^2$ is selected from the following ten groups:

1) oxygen (forming an oxo group when linked to a ring carbon and forming an N-oxide when a ring nitrogen is oxidised);
2) halosulphonyl, cyanosulphanyl;
3) —$X^3$—$R^5$ wherein $X^3$ is a direct bond, —O—, —S—, —SO—, —$SO_2$—, —$OSO_2$—, —$SO_2O$—, —$NR^{42}$—, —$N^+O^-R^{42}$—, —CO—, —COO—, —OCO—, —$CONR^{43}$—, —$NR^{44}CO$—, —$NR^{45}COO$—, —$SO_2NR^{46}$—, —$NR^{47}SO_2$—, —$CH_2$—, —$SO_2NR^{48}CO$—, —$OCONR^{49}$—, —$CSNR^{50}$—, —$NR^{51}CS$—, —$NR^{52}CSNR^{53}$—, —$NR^{54}CONR^{55}$—, —$CONR^{56}SO_2$—, —$NR^{57}CONR^{58}SO_2$—, —$SO_2NR^{57}CNNR^{58}$— or —$SO_2NR^{59}CONR^{60}$— (wherein $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, and $R^{60}$ each independently represents hydrogen or $C_{1-4}$alkyl which $C_{1-4}$alkyl may be optionally substituted by one or more groups selected from hydroxy, amino, halo, $C_{1-4}$alkoxycarbonyl, carboxy, $C_{1-6}$alkoxy or $C_{1-3}$alkylsulphanyl) and $R^5$ is as defined hereinbefore but with the proviso that $Q^2$ is not trifluoromethylsulphanyl, $C_{1-4}$alkyl, halo$C_{1-4}$alkyl, $C_{1-4}$alkoxy, halo$C_{1-4}$alkoxy or $C_{2-4}$alkenyloxy;
4) $R^{41}$ wherein $R^{41}$ is as defined hereinbefore;
5) —$X^3$—$C_{1-6}$alkyl-$X^2$—$R^{21}$ wherein $X^3$, $X^2$ and $R^{21}$ are as defined hereinbefore but with the proviso that $Q^2$ is not $C_{1-4}$alkyl, halo$C_{1-4}$alkyl, $C_{1-4}$alkoxy or halo$C_{1-4}$alkoxy;
6) —$X^3$—$C_{2-6}$alkenyl-$X^2$—$R^{21}$ wherein $X^3$, $X^2$ and $R^{21}$ are as defined hereinbefore but with the proviso that $Q^2$ is $C_{2-4}$alkenyloxy;
7) —$X^3$—$C_{2-6}$alkynyl-$X^2$—$R^{21}$ wherein $X^3$, $X^2$ and $R^{21}$ are as defined hereinbefore;
8) —$X^3$—$C_{3-7}$cycloalkyl-$X^2$—$R^{21}$ wherein $X^3$, $X^2$ and $R^{21}$ are as defined hereinbefore;
9) —$X^3$—$C_{1-6}$alkyl$C_{3-7}$cycloalkyl-$X^2$—$R^{21}$ wherein $X^3$, $X^2$ and $R^{21}$ are as defined hereinbefore; and
10) —$X^3$—$R^{41}$ wherein $R^{41}$ and $X^3$ are as defined hereinbefore;

$Q^3$ is selected from the following four groups:

1) oxygen (forming an oxo group when linked to a ring carbon and forming an N-oxide when a ring nitrogen is oxidised);
2) cyano, nitro or halo:
3) halosulphonyl, cyanosulphanyl; and
4) —$X^4$—$R^{61}$ wherein $X^4$ is a direct bond, —O—, —S—, —SO—, —$SO_2$—, —$OSO_2$—, —$SO_2O$—, —$NR^{62}$—, —$N^+O^-R^{62}$—, —CO—, —COO—, —OCO—, —$CONR^{63}$—, —$NR^{64}CO$—, —$NR^{65}COO$—, —$SO_2NR^{66}$—, —$NR^{67}SO_2$—, —$CH_2$—, —$SO_2NR^{68}CO$—, —$OCONR^{69}$—, —$CSNR^{70}$—, —$NR^{71}CS$—, —$NR^{72}CSNR^{73}$—, —$NR^{74}CONR^{75}$—, —$CONR^{76}SO_2$—, —$NR^{77}CONR^{78}SO_2$—, —$SO_2NR^{79}CNNR^{80}$— or —$SO_2NR^{79}CONR^{80}$— (wherein $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{75}$, $R^{76}$, $R^{77}$, $R^{78}$, $R^{79}$ and $R^{80}$ each independently represents hydrogen or $C_{1-4}$alkyl which $C_{1-4}$alkyl may be optionally substituted by one or more groups selected from hydroxy, amino, halo, $C_{1-4}$alkoxycarbonyl, carboxy, $C_{1-6}$alkoxy or $C_{1-3}$alkylsulphanyl) and $R^{61}$ is selected from hydrogen, $C_{1-6}$alkyl, $C_{3-7}$cycloalkyl, $C_{2-6}$alkenyl and $C_{2-6}$alkynyl which $C_{1-6}$alkyl, $C_{3-7}$cycloalkyl, $C_{2-6}$alkenyl or $C_{2-6}$alkynyl is optionally substituted with one or more groups selected from hydroxy, amino, halo, $C_{1-4}$alkoxycarbonyl, carboxy, $C_{1-6}$alkoxy and hydroxy$C_{1-6}$alkyl;

(c) $R^1$ is linked to ring C at a carbon ortho to the position of A-B attachment and is selected from the group consisting of $C_{1-4}$alkyl, halo$C_{1-4}$alkyl, $C_{1-4}$alkoxy, halo$C_{1-4}$alkoxy, $C_{2-4}$alkenyloxy, cyano, nitro, halo, trifluoromethylsulphanyl and hydroxy;

(d) $R^1$ is linked to ring C at a ring carbon atom ortho to the position of A-B attachment and is selected from the following two groups:

1) —$X^5$—$R^{81}$ wherein $X^5$ is a direct bond, —O—, —S—, —SO—, —$SO_2$—, —$OSO_2$—, —$SO_2O$—, —$NR^{82}$—, —CO—, —COO—, —OCO—, —$CONR^{83}$—, —$NR^{84}CO$—, —$NR^{85}COO$—, —$SO_2NR^{86}$—, —$NR^{87}SO_2$—, —$CH_2$—, —$SO_2NR^{88}CO$—, —$OCONR^{89}$—, —$CSNR^{90}$—, —$NR^{91}CS$—, —$NR^{92}CSNR^{93}$—, —$NR^{94}CONR^{95}$—, —$CONR^{96}SO_2$—, —$NR^{97}CONR^{98}SO_2$—, —$SO_2NR^{99}CNNR^{100}$— or —$SO_2NR^{99}CONR^{100}$— (wherein $R^{82}$, $R^{83}$, $R^{84}$, $R^{85}$, $R^{86}$, $R^{87}$, $R^{88}$, $R^{89}$, $R^{90}$, $R^{91}$, $R^{92}$, $R^{93}$, $R^{94}$, $R^{95}$, $R^{96}$, $R^{97}$, $R^{98}$, $R^{99}$ and $R^{100}$ each independently represents hydrogen or $C_{1-4}$alkyl which $C_{1-4}$alkyl may be optionally substituted by one or more groups selected from hydroxy, amino, halo, $C_{1-4}$alkoxycarbonyl, carboxy, $C_{1-6}$alkoxy or $C_{1-3}$alkylsulphanyl) and $R^{81}$ is selected from hydrogen, $C_{1-6}$alkyl, $C_{3-7}$cycloalkyl, $C_{2-6}$alkenyl and $C_{2-6}$alkynyl which $C_{1-6}$alkyl, $C_{3-7}$cycloalkyl, $C_{2-6}$alkenyl or $C_{2-6}$alkynyl is optionally substituted with one or more groups selected from hydroxy, amino, halo, $C_{1-4}$alkoxycarbonyl, carboxy, $C_{1-6}$alkoxy and hydroxy$C_{1-6}$ alkyl with the proviso that $R^1$ is not trifluoromethylsulphanyl, hydroxy, $C_{1-4}$alkyl, halo$C_{1-4}$alkyl, $C_{1-4}$alkoxy, halo$C_{1-4}$alkoxy or $C_{2-4}$alkenyloxy; and 2) —$X^6$—$R^{101}$ wherein $X^6$ is selected from a direct bond, —CO—, —O—, —$OCH_2$—, —S—, —SO—, —$SO_2$— and —$NR^{102}$— (wherein $R^{102}$ is hydrogen or $C_{1-4}$alkyl which $C_{1-4}$alkyl may be optionally substituted by one or more groups selected from hydroxy, amino, halo, $C_{1-4}$alkoxycarbonyl, carboxy, $C_{1-6}$alkoxy or $C_{1-3}$alkylsulphanyl) and $R^{101}$ is phenyl which is optionally substituted by 1–4 substituents selected from cyano, nitro, trifluoromethylsulphanyl, $C_{1-6}$alkyl, halo$C_{1-6}$alkyl, $C_{1-6}$alkoxy, halo$C_{1-6}$alkoxy, $C_{2-6}$alkenyloxy, halo, hydroxy and amino;

n is 1 or 2;

(e) either $R^2$ and $R^3$ are independently $C_{1-3}$alkyl optionally substituted by from 1 to 2k+1 atoms selected from fluoro and chloro wherein k is the number of carbon atoms in the said $C_{1-3}$alkyl, provided that $R^2$ and $R^3$ are not both methyl;

or $R^2$ and $R^3$, together with the carbon atom to which they are attached, form a 3–5 membered cycloalkyl ring optionally substituted by from 1 to 2m−2 fluorine atoms wherein m is the number of carbon atoms in said ring;

(f) $R^2$ and $R^3$ are both methyl or one of $R^2$ and $R^3$ is hydrogen or halo and the other is halo or $C_{1-3}$alkyl optionally substituted by from 1 to 2k+1 atoms selected from fluoro and chloro wherein k is the number of carbon atoms in the said $C_{1-3}$alkyl, with the proviso that when either $R^2$ or $R^3$ is halo $R^4$ is not hydroxy and with the proviso that when either $R^2$ or $R^3$ is hydrogen, $R^4$ is not hydrogen;

(g) A-B is selected from —NHCO—, —OCH$_2$—, —SCH$_2$—, —NHCH$_2$—, trans-vinylene, and ethynylene;

(h) A-B is —NHCS— or —COCH$_2$—;

(i) $R^4$ is hydroxy;

(j) $R^4$ is hydrogen, halo, amino or methyl;

but excluding compounds wherein ring C is selected from (a) and $R^1$ is selected only from (c) and $R^2$ and $R^3$ are selected from (e) and A-B is selected from (g) and $R^4$ is selected from (i);

and salts thereof;

and pharmaceutically acceptable in vivo cleavable prodrugs of said compound of formula (I);

and pharmaceutically acceptable salts of said compound or said prodrugs;

in the manufacture of a medicament for use in the elevation of PDH activity in warm-blooded animals such as humans.

Advantageously $Q^1$ is $C_{1-2}$alkyl, halo$C_{1-2}$alkyl, $C_{1-2}$alkoxy, cyano or halo.

In one embodiment of the present invention $Ar^1$ is phenyl or 4-pyridyl and is optionally substituted as defined hereinbefore.

In another embodiment of the present invention $Ar^1$ is phenyl and is optionally substituted as defined hereinbefore.

Preferably $Y^1$ is —SO$_2$— or —SO—, more preferably —SO$_2$—.

Advantageous values for $X^1$ are a direct bond, —O—, —S—, —SO—, —SO$_2$—, —NR$^6$—, —CO—, —COO—, —OCO—, —CONR$^7$—, —NR$^8$CO—, —OCONR$^9$—, —CONR$^{10}$SO$_2$—, —NR$^{11}$SO$_2$—, —CH$_2$—, —NR$^{12}$COO—, —CSNR$^{13}$—, —NR$^{14}$CS—, —NR$^{15}$CSNR$^{16}$—, NR$^{17}$CONR$^{18}$— and —NR$^{19}$CONR$^{20}$SO$_2$— (wherein $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ each independently represents hydrogen, $C_{1-2}$alkyl or $C_{1-2}$alkoxyethyl).

Preferred values for $X^1$ are —O—, —SO—, —SO$_2$—, —NR$^6$—, —COO—, —CONR$^7$—, —NR$^8$CO—, —NR$^{11}$SO$_2$—, —CH$_2$— and —NR$^{12}$COO— (wherein $R^6$, $R^7$, $R^8$, $R^{11}$ and $R^{12}$ each independently represents hydrogen, $C_{1-2}$alkyl or $C_{1-2}$alkoxyethyl).

More preferred values of $X^1$ are —SO— and —SO$_2$—.

Advantageously $R^5$ is selected from hydrogen, $C_{1-4}$alkyl, $C_{3-7}$cycloalkyl, $C_{2-4}$alkenyl and $C_{2-4}$alkynyl which $C_{1-4}$alkyl, $C_{3-7}$cycloalkyl, $C_{2-4}$alkenyl or $C_{2-4}$alkynyl is optionally substituted as defined hereinbefore.

Preferably $R^5$ is selected from hydrogen, $C_{1-4}$alkyl and $C_{3-7}$cycloalkyl, which $C_{1-4}$alkyl or $C_{3-7}$cycloalkyl, is optionally substituted as defined hereinbefore.

Advantageous values for $X^2$ are —O—, —NR$^{22}$—, —S—, —SO— and —SO$_2$—, (wherein $R^{22}$ is hydrogen or $C_{1-4}$alkyl).

Preferred values for $X^2$ are —O—, —NR$^{22}$—, —S—, —SO— and —SO$_2$— (wherein $R^{22}$ is hydrogen or $C_{1-2}$alkyl).

More preferred values for $X^2$ are —O— and —NR$^{22}$— (wherein $R^{22}$ is hydrogen or $C_{1-2}$alkyl).

Advantageous values for $X^4$ are a direct bond, —O—, —S—, —SO—, —SO$_2$—, —NR$^{62}$—, —CO—, —COO—, —OCO—, —CONR$^{63}$—, —NR$^{64}$CO—, —NR$^{65}$COO—, —SO$_2$NR$^{66}$—, —NR$^{67}$SO$_2$—, —CH$_2$—, —SO$_2$NR$^{68}$CO—, —OCONR$^{69}$—, —CSNR$^{70}$—, —NR$^{71}$CS—, —NR$^{72}$CSNR$^{73}$—, —NR$^{74}$CONR$^{75}$—, —CONR$^{76}$SO$_2$—, —NR$^{77}$CONR$^{78}$SO$_2$— and —SO$_2$NR$^{79}$CONR$^{80}$— (wherein $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{75}$, $R^{76}$, $R^{77}$, $R^{78}$, $R^{79}$ and $R^{80}$ each independently represents hydrogen, $C_{1-2}$alkyl or $C_{1-2}$alkoxyethyl).

Preferred values for $X^4$ are —O—, —S—, —SO—, —SO$_2$—, —NR$^{62}$—, —COO—, —CONR$^{63}$—, —NR$^{64}$CO— and —NR$^{67}$SO$_2$— (wherein $R^{62}$, $R^{63}$, $R^{64}$ and $R^{67}$ each independently represents hydrogen, $C_{1-2}$alkyl or $C_{1-2}$alkoxyethyl).

More preferred values for $X^4$ are —O—, —S—, —SO— and —SO$_2$—.

In another aspect of the invention more preferred values for $X^4$ are —O—, —S—, —SO—, —CONR$^{63}$— and —SO$_2$—.

Advantageously $R^{61}$ is selected from hydrogen, $C_{1-4}$alkyl, $C_{3-7}$cycloalkyl, $C_{2-4}$alkenyl and $C_{2-4}$alkynyl which $C_{1-4}$alkyl, $C_{3-7}$cycloalkyl, $C_{2-4}$alkenyl or $C_{2-4}$alkynyl is optionally substituted as hereinbefore defined.

Preferably $R^{61}$ is selected from hydrogen, $C_{1-4}$alkyl and $C_{3-7}$cycloalkyl, which $C_{1-4}$alkyl or $C_{3-7}$cycloalkyl is optionally substituted as hereinbefore defined.

Advantageously $Q^3$ is selected from the following three groups:

(i) oxygen (forming an oxo group when linked to a ring carbon and forming an N-oxide when a ring nitrogen is oxidised);

(ii) cyano, nitro or halo; and (iii) —X$^4$—R$^{61}$ wherein $X^4$ and $R^{61}$ are as defined hereinbefore.

Advantageously $R^{41}$ is phenyl, a 5–6 membered heterocyclic aromatic ring containing 1–4 heteroatoms selected independently from O, N and S or a 5–7 membered heterocyclic non-aromatic moiety containing 1–2 heteroatoms selected independently from O, N and S which phenyl, heterocyclic aromatic ring or heterocyclic non-aromatic moiety is optionally substituted as defined hereinbefore.

Advantageously $R^{21}$ is hydrogen or $C_{1-4}$alkyl.

Advantageously $X^3$ is a direct bond, —O—, —S—, —SO—, —SO$_2$—, —NR$^{42}$—, —CO—, —COO—, —OCO—, —CONR$^{43}$—, —NR$^{44}$CO—, —NR$^{45}$COO—, —SO$_2$NR$^{46}$—, —NR$^{47}$SO$_2$—, —CH$_2$—, —SO$_2$NR$^{48}$CO—, —OCONR$^{49}$—, —CSNR$^{50}$—, —NR$^{51}$CS—, —NR$^{52}$CSNR$^{53}$—, —NR$^{54}$CONR$^{55}$—, —CONR$^{56}$SO$_2$—, —NR$^{57}$CONR$^{58}$SO$_2$— or —SO$_2$NR$^{59}$CONR$^{60}$— (wherein $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$ and $R^{60}$ each independently represents hydrogen, $C_{1-2}$alkyl or $C_{1-2}$alkoxyethyl).

Preferably $X^3$ is —O—, —S—, —SO—, —SO$_2$—, —NR$^{42}$—, —COO—, —CONR$^{43}$—, —NR$^{44}$CO—, —SO$_2$NR$^{46}$—, —NR$^{47}$SO$_2$—, —SO$_2$NR$^{48}$CO— or —CONR$^{56}$SO$_2$— (wherein $R^{42}$, $R^{43}$, $R^{44}$, $R^{46}$, $R^{47}$, $R^{48}$ and $R^{56}$ each independently represents hydrogen, $C_{1-2}$alkyl or $C_{1-2}$alkoxyethyl).

Advantageously $Q^2$ is selected from the following seven groups:

1) oxygen (forming an oxo group when linked to a ring carbon and forming an N-oxide when a ring nitrogen is oxidised);

2) halosulphonyl, cyanosulphanyl;

3) —X$^3$—R$^5$ wherein $X^3$ and $R^5$ are as defined hereinbefore but with the proviso that $Q^2$ is not trifluoromethylsulphanyl, $C_{1-4}$alkyl, halo$C_{1-4}$alkyl, $C_{1-4}$alkoxy, halo$C_{1-4}$alkoxy or $C_{2-4}$alkenyloxy;
4) $R^{41}$ wherein $R^{41}$ is as defined hereinbefore;
5) —$X^3$—$C_{1-4}$alkyl-$X^2$—$R^{21}$ wherein $X^3$, $X^2$ and $R^{21}$ are as defined hereinbefore;
6) —$X^3$—$C_{3-7}$cycloalkyl-$X^2$—$R^{21}$ wherein $X^3$, $X^2$ and $R^{21}$ are as defined hereinbefore; and
7) —$X^3$—$R^{41}$ wherein $R^{41}$ and $X^3$ are as defined hereinbefore.

Preferably $Q^2$ is —$X^3$—$R^5$ wherein $X^3$ and $R^5$ are as defined hereinbefore but with the proviso that $Q^2$ is not trifluoromethylsulphanyl, $C_{1-4}$alkyl, halo$C_{1-4}$alkyl, $C_{1-4}$alkoxy, halo$C_{1-4}$alkoxy or $C_{2-4}$alkenyloxy.

Advantageously $Ar^2$ is selected from the following two groups:
1) phenyl, a carbon-linked 6-membered heteroaryl ring containing 1–2 nitrogen atoms and a carbon-linked 5-membered heteroaryl ring containing 1–2 heteroatoms selected independently from O, N and S, wherein said phenyl or heteroaryl ring is substituted at carbon, with 1–4 substituents selected from $Q^1$ and $Q^2$ including at least one substituent selected from $Q^2$ wherein $Q^1$ and $Q^2$ are as defined hereinafter; and
2) $Ar^1$ with the proviso that if $Ar^2$ has a value $Ar^1$ then $Y^2$ is not —CO—, —SO— or —$SO_2$—.

Preferably $Ar^2$ is phenyl substituted with one substituent selected from $Q^2$.

Advantageously $P^4$ is selected from the following five groups:
1) halosulphonyl, cyanosulphanyl;
2) —$X^1$—$R^5$ wherein $X^1$ and $R^5$ are as defined hereinbefore with the proviso that $P^4$ is not trifluoromethyl, trifluoromethoxy, trifluoromethylsulphanyl, hydroxy, $C_{1-4}$alkyl, halo$C_{1-4}$alkyl, $C_{1-4}$alkoxy, halo$C_{1-4}$alkoxy or $C_{2-4}$alkenyloxy;
3) —$X^1$—$C_{1-4}$alkyl-$X^2$—$R^{21}$ wherein $X^1$, $X^2$ and $R^{21}$ are as defined hereinbefore;
4) —$X^1$—$C_{3-7}$cycloalkyl-$X^2$—$R^{21}$ wherein $X^1$, $X^2$ and $R^{21}$ are as defined hereinbefore; and
5) —$Y^2Ar^2$ wherein $Y^2$ and $Ar^2$ are as defined hereinbefore.

Preferably $P^4$ is selected from the following three groups:
1) halosulphonyl, cyanosulphanyl;
2) —$X^1$—$R^5$ wherein $X^1$ and $R^5$ are as defined hereinbefore with the proviso that $P^4$ is not trifluoromethyl, trifluoromethoxy, trifluoromethylsulphanyl, hydroxy, $C_{1-4}$alkyl, halo$C_{1-4}$alkyl, $C_{1-4}$alkoxy, halo$C_{1-4}$alkoxy or $C_{2-4}$alkenyloxy; and
3) —$Y^2A^2$ wherein $Y^2$ and $Ar^2$ are as defined hereinbefore.

Advantageously $R^{101}$ is phenyl which is optionally substituted by 1–4 substituents selected from cyano, nitro, trifluoromethylsulphanyl, $C_{1-4}$alkyl, halo$C_{1-4}$alkyl, $C_{1-4}$alkoxy, halo$C_{1-4}$alkoxy, $C_{2-4}$alkenyloxy, halo, hydroxy and amino.

Advantageously $X^6$ is selected from a direct bond, —CO—, —O—, —$OCH_2$—, —S—, —SO—, —$SO_2$— and —$NR^{102}$— (wherein $R^{102}$ is hydrogen or $C_{1-2}$alkyl).

Advantageously $R^{81}$ is selected from hydrogen, $C_{1-4}$alkyl, $C_{3-7}$cycloalkyl, $C_{2-4}$alkenyl and $C_{2-4}$alkynyl which $C_{1-4}$alkyl, $C_{3-7}$cycloalkyl, $C_{2-4}$alkenyl or $C_{2-4}$alkynyl is optionally substituted as defined hereinbefore.

Preferably $R^{81}$ is selected from hydrogen, $C_{1-4}$alkyl and $C_{3-7}$cycloalkyl, which $C_{1-4}$alkyl and $C_{3-7}$cycloalkyl is optionally substituted as defined hereinbefore.

Advantageously $X^5$ is a direct bond, —O—, —S—, —SO—, —$SO_2$—, —$NR^{82}$—, —CO—, —COO—, —OCO—, —$CONR^{83}$—, —$NR^{84}CO$—, —$NR^{85}COO$—, —$SO_2NR^{86}$—, —$NR^{87}SO_2$—, —$CH_2$—, —$SO_2NR^{88}CO$—, —$OCONR^{89}$—, —$CSNR^{90}$—, —$NR^{91}CS$—, —$NR^{92}CSNR^{93}$—, —$NR^{94}CONR^{95}$—, —$CONR^{96}SO_2$— —$NR^{97}CONR^{98}SO_2$— or —$SO_2NR^{99}CONR^{100}$ (wherein $R^{82}$, $R^{83}$, $R^{84}$, $R^{85}$, $R^{86}$, $R^{87}$, $R^{88}$, $R^{89}$, $R^{90}$, $R^{91}$, $R^{92}$, $R^{93}$, $R^{94}$, $R^{95}$, $R^{96}$, $R^{97}$, $R^{98}$, $R^{99}$ and $R^{100}$ each independently represents hydrogen, $C_{1-2}$alkyl or $C_{1-2}$alkoxyethyl).

Preferably $X^5$ is a direct bond, —O—, —$NR^{82}$—, —CO—, —COO—, —$CONR^{83}$—, $NR^{84}CO$—, —$NR^{87}SO_2$— (wherein $R^{82}$, $R^{83}$, $R^{84}$, and $R^{87}$ each independently represents hydrogen, $C_{1-2}$alkyl or $C_{1-2}$alkoxyethyl).

Advantageous values for $R^1$ in group (c) are $C_{1-4}$alkyl, $C_{1-4}$haloalkyl, $C_{1-4}$alkoxy, cyano, nitro, halo and hydroxy.

Preferred values for $R^1$ in group (c) are $C_{1-2}$alkyl, $C_{1-2}$alkoxy, cyano, nitro, halo and hydroxy.

More preferred values for $R^1$ in group (c) are methyl, methoxy, nitro, fluoro, chloro, bromo and hydroxy.

Particular values for $R^1$ in group (c) are methoxy, nitro, fluoro, chloro, bromo and hydroxy.

In one aspect of the invention preferably $R^1$ is selected from halo, nitro, $C_{1-4}$alkyl, $C_{1-4}$alkoxy, $C_{2-4}$alkenyl, $C_{2-4}$alkynyl and hydrogen.

In another aspect of the invention preferably $R^1$ is selected from $C_{1-4}$alkoxy, halo, nitro or $R^1$ is $X^5$—$R^{81}$ wherein $X^5$ is a direct bond, —NH—, —NHCO—, —SO—, —$SO_2$—, —$NHSO_2$— and $R^{81}$ is H, $C_{1-6}$alkyl, $C_{2-6}$alkenyl, $C_{2-6}$alkynyl or $R^1$ is —$X^6$—$R^{101}$ wherein —$X^6$ is —CO— and $R^{101}$ is phenyl substituted by halo.

In a further aspect of the invention preferably $R^1$ is selected from fluoro and chloro.

In an additional aspect of the invention, preferably $R^1$ is not hydrogen.

Preferably n is 1.

A preferred value for A-B in group (g) is NHCO.

Advantageous values for ring C in group (a) are:
phenyl or carbon-linked pyridyl wherein said phenyl or pyridyl is substituted as defined hereinbefore.

More advantageous values for ring C in group (a) are:
phenyl or carbon-linked pyridyl wherein said phenyl or pyridyl is substituted on carbon at the position para to the position of A-B attachment by a group selected from cyano, trifluoromethyl, nitro, trifluoromethoxy, trifluoromethylsulphanyl and a group $P^2$ (wherein A-B and $P^2$ are as defined hereinbefore).

Preferred values for ring C in group (a) are:
phenyl or carbon-linked pyridyl wherein said phenyl or pyridyl is substituted on carbon at the position para to the position of A-B attachment by a group selected from cyano, trifluoromethyl, nitro and a group $P^2$ (wherein A-B and $P^2$ are as defined hereinbefore).

More preferred values for ring C in group (a) are:
phenyl or carbon-linked pyridyl wherein said phenyl or pyridyl is substituted on carbon at the position para to the position of A-B attachment by a group $P^2$ (wherein A-B and $P^2$ are as defined hereinbefore).

A particular value for ring C in group (a) is phenyl which is substituted as defined hereinbefore.

A more particular value for ring C in group (a) is phenyl which is substituted on carbon at the position para to the position of A-B attachment by a group $P^2$ (wherein A-B and $P^2$ are as defined hereinbefore).

Advantageous values for ring C in group (b) are:
(i) phenyl or pyridyl wherein said phenyl or pyridyl is unsubstituted except by $(R^1)_n$ wherein $R^1$ and n are as defined hereinbefore;
(ii) a carbon-linked triazine optionally substituted on a ring carbon at a position para to A-B attachment by 1 substituent selected from $P^1$, $P^2$, $P^3$ and $P^4$, wherein A-B, $P^1$, $P^2$, $P^3$ and $P^4$ are as defined hereinbefore;
(iii) a 6-membered carbon-linked heteroaryl group containing 1–3 nitrogen atoms wherein one or more ring nitrogen atoms are oxidised to form the N-oxide, which heteroaryl group is optionally substituted at a position para to A-B attachment by 1 substituent selected from $P^1$, $P^2$, $P^3$ and $P^4$, wherein A-B, $P^1$, $P^2$, $P^3$ and $P^4$ are as defined hereinbefore;
(iv) phenyl or carbon-linked pyridyl wherein said phenyl or pyridyl is substituted at a position para to A-B attachment by 1 substituent selected from $P^3$ and $P^4$, wherein A-B, $P^3$ and $P^4$ are as defined hereinbefore; and
(v) phenyl or carbon-linked pyridyl wherein said phenyl or pyridyl is substituted at any of the positions meta or para to A-B attachment by 2–3 substituents selected from $P^1$, $P^2$, $P^3$ and $P^4$, provided that if one or more of the substituents is $P^1$ or $P^2$ then at least one of the other substituents is $P^4$, wherein A-B, $P^1$, $P^2$, $P^3$ and $P^4$ are as defined hereinbefore.

More advantageous values for ring C in group (b) are:
(i) phenyl or pyridyl wherein said phenyl or pyridyl is unsubstituted except by $(R^1)_n$ wherein $R^1$ and n are as defined hereinbefore;
(ii) a 6-membered carbon-linked heteroaryl group containing 1–3 nitrogen atoms wherein one or more ring nitrogen atoms are oxidised to form the N-oxide, which heteroaryl group is optionally substituted at a position para to A-B attachment by 1 substituent selected from $P^1$, $P^2$, $P^3$ and $P^4$, wherein A-B, $P^1$, $P^2$, $P^3$ and $P^4$ are as defined hereinbefore; and
(iii) phenyl or carbon-linked pyridyl wherein said phenyl or pyridyl is substituted at a position para to A-B attachment by 1 substituent selected from $P^3$ and $P^4$, wherein A-B, $P^3$ and $P^4$ are as defined hereinbefore.

Preferred values for ring C in group (b) are:
(i) phenyl or pyridyl wherein said phenyl or pyridyl is unsubstituted except by $(R^1)_n$ wherein $R^1$ and n are as defined hereinbefore; and
(ii) phenyl or carbon-linked pyridyl wherein said phenyl or pyridyl is substituted at a position para to A-B attachment by 1 substituent selected from $P^3$ and $P^4$, wherein A-B, $P^3$ and $P^4$ are as defined hereinbefore.

More preferred values for ring C in group (b) are:
(i) phenyl or pyridyl wherein said phenyl or pyridyl is unsubstituted except by $(R^1)_n$ wherein $R^1$ and n are as defined hereinbefore;
(ii) phenyl or carbon-linked pyridyl wherein said phenyl or pyridyl is substituted at a position para to A-B attachment by —$Y^2Ar^2$ wherein A-B, $Y^2$ and $Ar^2$ are as defined hereinbefore.

A particular value for ring C in group (b) is phenyl wherein said phenyl is substituted at a position para to A-B attachment by —$Y^2Ar^2$ wherein A-B, $Y^2$ and $Ar^2$ are as defined hereinbefore.

In an further feature of the invention preferably ring C is phenyl substituted by one group selected from $P^4$ wherein $P^4$ is as defined above.

More preferably ring C is phenyl substituted at a position para to A-B by a group selected from:
1) —$X^1$—$R^5$ wherein $X^1$ is a direct bond, —O—, —S—, —SO—, —$SO_2$—, —$NR^6$— or —$CONR^7$— (wherein $R^6$ and $R^7$ each independently represents hydrogen or $C_{1-4}$alkyl which $C_{1-4}$alkyl may be optionally substituted by one or more groups selected from hydroxy or $C_{1-6}$alkoxy) and $R^5$ is selected from hydrogen and $C_{1-6}$alkyl, which $C_{1-6}$alkyl, is optionally substituted with one or more groups selected from hydroxy and $C_{1-6}$alkoxy and hydroxy$C_{1-6}$alkyl with the proviso that —$X^1$—$R^5$ is not hydroxy, $C_{1-4}$alkyl or $C_{1-4}$alkoxy;
2) —$X^1$—$C_{1-6}$alkyl-$X^2$—$R^{21}$ wherein $X^1$ is a direct bond, —O—, —S—, —SO—, —$SO_2$—, —$NR^6$— or —$CONR^7$— (wherein $R^6$ and $R^7$ each independently represents hydrogen or $C_{1-4}$alkyl which $C_{1-4}$alkyl may be optionally substituted by one or more groups selected from hydroxy or $C_{1-6}$alkoxy), $X^2$ is a direct bond, —O—, —S—, —SO—, —$SO_2$—, —$NR^{22}$— or —$CONR^{23}$— (wherein $R^{22}$ and $R^{23}$ each independently represents hydrogen or $C_{1-4}$alkyl which $C_{1-4}$alkyl may be optionally substituted by one or more groups selected from hydroxy or $C_{1-6}$alkoxy) and $R^{21}$ is hydrogen or $C_{1-4}$alkyl, which $C_{1-4}$alkyl is optionally substituted with one or more groups selected from hydroxy or $C_{1-6}$alkoxy or $R^{21}$ is $R^{41}$ wherein $R^{41}$ is as defined hereinbefore with the proviso that —$X^1$—$C_{1-6}$alkyl-$X^2$—$R^{21}$ is not $C_{1-4}$alkyl or $C_{1-4}$alkoxy;
3) —$Y^2Ar^2$ wherein $Y^2$ is $X^1$ wherein $X^1$ is a direct bond, —O—, —S—, —SO—, —$SO_2$—, —$NR^6$— or —$CONR^7$— (wherein $R^6$ and $R^7$ each independently represents hydrogen or $C_{1-4}$alkyl which $C_{1-4}$alkyl may be optionally substituted by one or more groups selected from hydroxy or $C_{1-6}$alkoxy) and $Ar^2$ is as defined hereinbefore.

Advantageously when selected from group (e) $R^2$ and $R^3$ are independently $C_{1-3}$alkyl optionally substituted by from 1 to 2k+1 atoms selected from fluoro and chloro, wherein k is the number of carbon atoms in the said $C_{1-3}$alkyl, provided that $R^2$ and $R^3$ are not both methyl; or $R^2$ and $R^3$, together with the carbon atom to which they are attached, form a cyclopropane ring optionally substituted by from 1 to 4 fluorine atoms.

Preferably when selected from group (e) $R^2$ and $R^3$ are independently $C_{1-3}$alkyl optionally substituted by from 1 to 2k+1 fluorine atoms, wherein k is the number of carbon atoms in the said $C_{1-3}$alkyl, provided that $R^2$ and $R^3$ are not both methyl; or $R^2$ and $R^3$, together with the carbon atom to which they are attached, form a cyclopropane ring optionally substituted by from 1 to 4 fluorine atoms.

More preferably when selected from group (e) $R^2$ and $R^3$ are independently methyl, fluoromethyl, difluoromethyl, trifluoromethyl, 2,2,2-trifluoroethyl and perfluoroethyl provided that $R^2$ and $R^3$ are not both methyl; or $R^2$ and $R^3$, together with the carbon atom to which they are attached, form a cyclopropane ring optionally substituted by from 1 to 4 fluorine atoms.

Particularly when selected from group (e) $R^2$ and $R^3$ are independently methyl, fluoromethyl, difluoromethyl and trifluoromethyl, provided that $R^2$ and $R^3$ are not both methyl; or $R^2$ and $R^3$, together with the carbon atom to which they are attached, form a cyclopropane ring optionally substituted by from 1 to 4 fluorine atoms.

Advantageously when selected from group (f) $R^2$ and $R^3$ are both methyl or one of $R^2$ and $R^3$ is hydrogen or halo and the other is halo or $C_{1-3}$alkyl optionally substituted by from 1 to 2k+1 atoms selected from fluoro and chloro wherein k is the number of carbon atoms in the said $C_{1-3}$alkyl, with the proviso that when either $R^2$ or $R^3$ is halo $R^4$ is not hydroxy and with the proviso that when either $R^2$ or $R^3$ is hydrogen, $R^4$ is not hydrogen.

More advantageously when selected from group (f) $R^2$ and $R^3$ are both methyl or one of $R^2$ and $R^3$ is hydrogen or chloro and the other is chloro or methyl with the proviso that when either $R^2$ or $R^3$ is chloro $R^4$ is not hydroxy and with the proviso that when either $R^2$ or $R^3$ is hydrogen, $R^4$ is not hydrogen.

Preferably when selected from group (f) $R^2$ and $R^3$ are both methyl or both chloro with the proviso that when $R^2$ and $R^3$ are both chloro $R^4$ is not hydroxy.

More preferably when selected from group (f) $R^2$ and $R^3$ are both methyl.

Preferably when selected from group (j) $R^4$ is hydrogen.

Where applicable, the R-configuration generally represents a preferred stereochemistry for compounds of formula (I).

Preferably $R^1$ is selected from group (c) as defined hereinbefore.

Preferably A-B is selected from group (g) as defined hereinbefore.

Preferably $R^4$ is selected from group (i) as defined hereinbefore.

In another aspect of the invention, preferably $R^4$ is hydroxy, hydrogen or methyl.

Advantageously ring C is selected from the following values from group (a):

phenyl substituted at the position para to the position of A-B attachment by —$Y^1Ar^1$ wherein $Y^1$ is —SO— or —$SO_2$— and $Ar^1$ is phenyl or 3-pyridyl which phenyl or 3-pyridyl is optionally substituted as defined hereinbefore;

or from the following values from group (b):

(i) phenyl unsubstituted except by $(R^1)_n$ wherein $R^1$ and n are as defined hereinbefore; and (ii) phenyl substituted at the position para to A-B attachment by 1 substituent selected from $P^3$ and $P^4$ wherein $P^3$ and $P^4$ are as defined hereinbefore.

More advantageously ring C is selected from the following values from group (a):

phenyl substituted at the position para to the position of A-B attachment by —$Y^1Ar^1$ wherein $Y^1$ is —SO— or —$SO_2$— and $Ar^1$ is phenyl or 3-pyridyl which phenyl or 3-pyridyl is optionally substituted as defined hereinbefore;

or from the following values from group (b):

(i) phenyl unsubstituted except by $(R^1)_n$ wherein $R^1$ and n are as defined hereinbefore; and (ii) phenyl substituted at the position para to A-B attachment by 1 substituent selected from halo and $P^4$ wherein $P^4$ is selected from the three following groups:

1) halosulphonyl, cyanosulphanyl;

2) —$X^1$—$R^5$ wherein $X^1$ and $R^5$ are as defined hereinbefore with the proviso that $P^4$ is not trifluoromethyl, trifluoromethoxy, trifluoromethylsulphanyl, hydroxy, $C_{1-4}$alkyl, halo$C_{1-4}$alkyl, $C_{1-4}$alkoxy, halo$C_{1-4}$alkoxy or $C_{2-4}$alkenyloxy; and 3) —$Y^2Ar^2$ wherein $Y^2$ and $Ar^2$ are as defined hereinbefore.

Preferably ring C is selected from the following values from group (a):

phenyl substituted at the position para to the position of A-B attachment by —$Y^1Ar^1$ wherein $Y^1$ is —SO— or —$SO_2$— and $Ar^1$ is phenyl or 3-pyridyl which phenyl or 3-pyridyl is optionally substituted as defined hereinbefore;

or from the following values from group (b):

(i) phenyl unsubstituted except by $(R^1)_n$ wherein $R^1$ and n are as defined hereinbefore; and (ii) phenyl substituted at the position para to A-B attachment by 1 substituent selected from halo and $P^4$ wherein $P^4$ is selected from the three following groups:

1) halosulphonyl;

2) —$X^1$—$R^5$ wherein $X^1$ and $R^5$ are as defined hereinbefore with the proviso that $P^4$ is not trifluoromethyl, trifluoromethoxy, trifluoromethylsulphanyl, hydroxy, $C_{1-4}$alkyl, halo$C_{1-4}$alkyl, $C_{1-4}$alkoxy, halo$C_{1-4}$alkoxy or $C_{2-4}$alkenyloxy; and 3) —$Y^2Ar^2$ wherein either (i) $Ar^2$ is phenyl or 3-pyridyl wherein said phenyl or pyridyl is substituted at carbon with 1–4 substituents selected from $Q^1$ and $Q^2$ including at least one substituent selected from $Q^2$ wherein $Q^1$ and $Q^2$ are as defined hereinbefore, and $Y^2$ is —S—, —SO—, —$SO_2$— or —$CONR^7$— wherein $R^7$ is hydrogen, $C_{1-4}$alkyl or $C_{1-3}$alkoxy$C_{2-3}$alkyl; or (ii) $Ar^2$ is phenyl or 3-pyridyl wherein said phenyl or pyridyl is substituted at carbon with 1–4 substituents selected from $Q^1$ wherein $Q^1$ is as defined hereinbefore and $Y^2$ is —S— or —$CONR^7$— wherein $R^7$ is hydrogen, $C_{1-4}$alkyl or $C_{1-3}$alkoxy$C_{2-3}$alkyl.

Preferably $R^2$ and $R^3$ are selected from the following values from group (e):

$R^2$ and $R^3$ are independently methyl, fluoromethyl, difluoromethyl and trifluoromethyl, provided that $R^2$ and $R^3$ are not both methyl; or $R^2$ and $R^3$ are selected from the following values from group (f):

$R^2$ and $R^3$ are both methyl.

More preferably one of $R^2$ and $R^3$ is trifluoromethyl and the other is methyl or both $R^2$ and $R^3$ are methyl.

In one aspect of the invention preferably $R^2$ and $R^3$ are independently $C_k$alkyl optionally substituted by from 1 to 2k+1 atoms selected from fluoro and chloro wherein k is 1–3, or $R^2$ and $R^3$ together with the carbon atom to which they are attached, form a 3-membered cycloalkyl ring.

In another aspect of the invention preferably $R^2$ and $R^3$ are independently $C_k$alkyl optionally substituted by from 1 to 2k+1 atoms selected from fluoro and chloro wherein k is 1–3.

According to a further aspect of the present invention there are provided compounds of the formula (I), as defined hereinbefore, and salts thereof; and pharmaceutically acceptable in vivo cleavable prodrugs of said compound of formula (I); and pharmaceutically acceptable salts of said compound or said prodrugs; but excluding the following compounds: 2-hydroxy-N-(2-methoxyphenyl)-2-methylpropanamide; 2-hydroxy-N-(2-methylphenyl)-2-methylpropanamide; 2-hydroxy-N-(2-methylphenyl)propanamide; N-(2,4-dimethylphenyl)-2-hydroxypropanamide; N-(2,5-dimethylphenyl)-2-hydroxypropanamide; N-(2,6-dimethylphenyl)-2-hydroxypropanamide; N-(2-chlorophenyl)-2-hydroxypropanamide; 2-hydroxy-N-(2-methoxyphenyl)propanamide; N-(2,5-dimethoxyphenyl)-2-hydroxypropanamide; N-(2-ethoxyphenyl)-2-hydroxypropanamide; N-(2,5-dimethoxyphenyl)-2-hydroxy-2-methylpropanamide; N-(2-ethoxyphenyl)-2-hydroxy-2-methylpropanamide; 3-chloro-N-(2,5-dichlorophenyl)-2-hydroxy-2-methylpropanamide; 3-chloro-N-(2,4-dichlorophenyl)-2-hydroxy-2-methylpropanamide; N-(2,3-dichloro-5-nitrophenyl)-2-hydroxy-2-methylpropanamide; 2-hydroxy-2-methyl-N-(2,3,4-trichlorophenyl)propanamide; 1-(2,5-dihydroxyphenyl)-3-hydroxy-3-methylbut-1-ene; 1-(2,4-dichlorophenyl)-3-hydroxy-4,4,4-trifluoro-3-trifluoromethylbut-1-ene; 2-hydroxy-N-(5-methoxycarbonyl-2-methylphenyl)-2-methylpropylamine; 1-(2,6-dimethoxyphenoxy)-2-isopropylpropan-2-ol; 1-(2,6-dimethoxyphenoxy)-2-methylpentan-2-ol; 1-(2,6-dimethoxyphenoxy)-2-methylbutan-2-ol; 1-(2,5-dimethoxyphenoxy)-2- methylpentan-2-ol; 1-(2,4-dimethoxyphenoxy)-2-methylpentan-2-ol; 1-(2,3-dimethoxyphenoxy)-2-methylpentan-2-ol; 1-(2,6-dimethoxyphenoxy)-2-ethylbutan-2-ol; 2-ethyl-1-(2-methylphenoxy)butan-2-ol; 1-(2-[2-ethyl-2-hydroxybutoxy]phenoxy)-2-ethylbutan-2-ol; 2-ethyl-1-(2-methoxyphenoxy)butan-2-ol; 1-(2-methoxyphenoxy)-2-methylbutan-2-ol and 2-ethyl-1-(2-methoxyphenoxy)pentan-2-ol; for use as medicaments.

According to a further aspect of the present invention there are provided compounds of the formula (I), as defined hereinbefore, with the provisos that:

(i) ring C bears a group other than hydrogen at the position para to A-B attachment;
(ii) when A-B is —COCH$_2$—, —SCH$_2$—, —OCH$_2$—, trans-vinylene or ethynylene, ring C does not have an oxygen atom linked at a position ortho to A-B attachment;
(iii) when A-B is ethynylene, ring C does not have fluorine atoms linked at both of the positions ortho to A-B attachment;
(iv) when A-B is trans-vinylene, ring C does not bear methyl groups at both of the positions ortho to A-B attachment, and does not bear a formyl group at a position ortho to A-B attachment;
(v) when A-B is —COCH$_2$—, ring C does not bear methyl groups at both of the positions ortho to A-B attachment;
(vi) when A-B is —OCH$_2$—, ring C does not have chlorine atoms linked at both of the positions ortho to A-B attachment and does not bear nitro groups at both of the positions ortho to A-B attachment;
(vii) when A-B is —NHCH$_2$—, ring C does not bear two nitro groups at positions ortho and para to A-B attachment and does not bear two methyl groups at positions meta and para to A-B attachment; and
(viii) when A-B is —SCH$_2$—, ring C does not simultaneously bear an amino group at a position ortho to A-B attachment and a nitro group at the position para to A-B attachment; and excluding the following compounds: N-(4-chloro-2-nitrophenyl)-2-hydroxy-2-methylpropanamide; N-(4,5-dichloro-2-(2-hydroxy-2-methylpropanamido)phenyl)-2-hydroxy-2-methylpropanamide; N-(4-chloro-2-benzoylphenyl)-2-hydroxy-2-methylpropanamide; N-(2,4-dimethylphenyl)-2-hydroxypropanamide; 3-chloro-N-(2,4-dichlorophenyl)-2-hydroxy-2-methylpropanamide; 2-hydroxy-2-methyl-N-(2,3,4-trichlorophenyl)propanamide; 1-(2,4-dichlorophenyl)-3-hydroxy-4,4,4-trifluoro-3-trifluoromethylbut-1-ene; 1-(4-bromo-2-fluorophenyl)-3-hydroxy-3-methylbut-1-yne; 1-(2-fluoro-4-pent-1-enylphenyl)-3-hydroxy-3-methylbut-1-yne; 1-(4-[3-hydroxy-3-methylbut-1-yn-1-yl]-2-phenylphenyl)-3-hydroxy-3-methylbut-1-yne; 1-(2-fluoro-4-pentoxyphenyl)-3-hydroxy-3-methylbut-1-yne; 1-(2-fluoro-4-trifluoromethylphenyl)-3-hydroxy-3-methylbut-1-yne; 1-(2,5-dimethyl-4-[3-hydroxy-3-methylbut-1-yn-1-yl]phenyl)-3-hydroxy-3-methylbut-1-yne; 1-(2,4-di[3-hydroxy-3-methylbut-1-yn-1-yl]phenyl)-3-hydroxy-3-methylbut-1-yne; 3-hydroxy-3-methyl-1-(2,4,5-tri[3-hydroxy-3-methylbut-1-yn-1-yl]phenyl)but-1-yne; 3-hydroxy-3-methyl-1-(2,3,4,5-tetra[3-hydroxy-3-methylbut-1-yn-1-yl]phenyl)but-1-yne and 3-hydroxy-3-methyl-1-(2,3,4,5,6-penta[3-hydroxy-3-methylbut-1-yn-1-yl]phenyl)but-1-yne; and salts thereof;

and pharmaceutically acceptable in vivo cleavable prodrugs of said compound of formula (I);
and pharmaceutically acceptable salts of said compound or said prodrugs.

According to a further aspect of the present invention there are provided compounds of the formula (I), as defined hereinbefore, wherein A-B is —NHCO— and with the proviso that ring C bears a group other than hydrogen at the position para to A-B attachment and excluding the following compounds: N-(4-chloro-2-nitrophenyl)-2-hydroxy-2-methylpropanamide; N-(4,5-dichloro-2-(2-hydroxy-2-methylpropanamido)phenyl)-2-hydroxy-2-methylpropanamide; N-(4-chloro-2-benzoylphenyl)-2-hydroxy-2-methylpropanamide; N-(2,4-dimethylphenyl)-2-hydroxypropanamide; 3-chloro-N-(2,4-dichlorophenyl)-2-hydroxy-2-methylpropanamide and 2-hydroxy-2-methyl-N-(2,3,4-trichlorophenyl)propanamide; and salts thereof;

and pharmaceutically acceptable in vivo cleavable prodrugs of said compound of formula (I);
and pharmaceutically acceptable salts of said compound or said prodrugs.

According to a further aspect of the present invention there is provided the use of compounds of the formula (I):

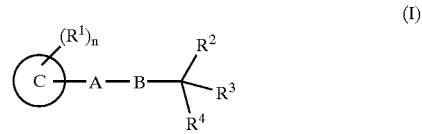

(I)

wherein:
ring C is as defined in (a) or (b);
$R^1$ is as defined in (c) or (d);
n is 1 or 2;
$R^2$ and $R^3$ are as defined in (e) or (f);
A-B is as defined in (g) or (h) and
$R^4$ is as defined in (i) or (j)
wherein (a) ring C is phenyl or carbon-linked heteroaryl selected from pyridyl, pyrazinyl, pyrimidinyl and pyridazinyl; wherein said phenyl or heteroaryl is substituted on carbon at one or both positions meta to the position of A-B attachment or on carbon at the position para to the position of A-B attachment by $P^1$ or $P^2$ (wherein $P^1$ and $P^2$ are as defined hereinafter), and further, wherein said phenyl or heteroaryl is optionally substituted on carbon at any remaining meta position(s) or para position by $P^1$ or $P^3$, (wherein $P^1$ and $P^3$ are as defined hereinafter);

(b) ring C is selected from the following five groups:

(i) phenyl or carbon-linked heteroaryl selected from pyridyl, pyrazinyl, pyrimidinyl and pyridazinyl wherein said phenyl or heteroaryl is unsubstituted except by $(R^1)_n$ wherein $R^1$ and n are as defined hereinafter;

(ii) a carbon-linked triazine optionally substituted on a ring carbon at a position meta or para to A-B attachment by 1 substituent selected from $P^1$, $P^2$, $P^3$ and $P^4$, wherein $P^1$, $P^2$, $P^3$ and $P^4$ are as defined hereinafter;

(iii) a 6-membered carbon-linked heteroaryl group containing 1–3 nitrogen atoms wherein one or more ring nitrogen atoms are oxidised to form the N-oxide, which heteroaryl group is optionally substituted at any of the positions meta or para to A-B attachment by 1–3 substituents selected from $P^1$, $P^2$, $P^3$ and $P^4$, wherein $P^1$, $P^2$, $P^3$ and $P^4$ are as defined hereinafter;

(iv) phenyl or carbon-linked heteroaryl selected from pyridyl, pyrazinyl, pyrimidinyl and pyridazinyl, wherein said phenyl or heteroaryl is substituted at a position meta or para to A-B attachment by 1 substituent selected from $P^3$ and $P^4$, wherein $P^3$ and $P^4$ are as defined hereinafter; and (v) phenyl or carbon-linked heteroaryl selected from pyridyl, pyrazinyl, pyrimidinyl and pyridazinyl, wherein said phenyl or heteroaryl is substituted at any of the positions meta or para to A-B attachment by 2–3 substituents selected from $P^1$, $P^2$, $P^3$ and $P^4$, provided that if one or more of the substituents is $P^1$ or $P^2$ then at least one of the other substituents is $P^4$, wherein $P^1$, $P^2$, $P^3$ and $P^4$ are as defined hereinafter;

$P^1$ is cyano, trifluoromethyl, nitro, trifluoromethoxy or trifluoromethylsulphanyl;

$P^2$ is —$Y^1Ar^1$, wherein $Ar^1$ is selected from the group consisting of phenyl, a carbon-linked 6-membered heteroaryl ring containing 1–2 nitrogen atoms and a carbon-linked 5-membered heteroaryl ring containing 1–2 heteroatoms selected independently from O, N and S, wherein said phenyl or heteroaryl ring is optionally substituted at carbon, with 1–4 substituents selected from $Q^1$, wherein $Q^1$ is as defined hereinafter; and $Y^1$ is selected from —CO—, —SO— and —$SO_2$—;

$P^3$ is $C_{1-4}$alkyl, halo$C_{2-4}$alkyl, $C_{1-4}$alkoxy, halo$C_{2-4}$alkoxy, $C_{2-4}$alkenyloxy, halo or hydroxy;

$P^4$ is selected from the following five groups:
1) halosulphonyl, cyanosulphanyl;
2) —$X^1$—$R^5$ wherein $X^1$ is a direct bond, —O—, —S—, —SO—, —$SO_2$—, —$NR^6$—, —CO—, —COO—, —OCO—, —$CONR^7$—, —$NR^8CO$—, —$OCONR^9$—, —$CONR^{10}SO_2$—, —$NR^{11}SO_2$—, —$CH_2$—, —$NR^{12}COO$—, —$CSNR^{13}$—, —$NR^{14}CS$—, —$NR^{15}CSNR^{16}$—, $NR^{17}CONR^{18}$— or —$NR^{19}CONR^{20}SO_2$— (wherein $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$ each independently represents hydrogen, $C_{1-4}$alkyl or $C_{1-3}$alkoxy$C_{2-3}$alkyl) and $R^5$ is selected from hydrogen, $C_{1-6}$alkyl, $C_{3-7}$cycloalkyl, $C_{2-6}$alkenyl and $C_{2-6}$alkynyl which $C_{1-6}$alkyl, $C_{3-7}$cycloalkyl, $C_{2-6}$alkenyl or $C_{2-6}$alkynyl is optionally substituted with one or more groups selected from hydroxy, amino, halo, $C_{1-4}$alkoxycarbonyl, carboxy, $C_{1-6}$alkoxy and hydroxy$C_{1-6}$ alkyl with the proviso that $P^4$ is not trifluoromethyl, trifluoromethoxy, trifluoromethylsulphanyl, hydroxy, $C_{1-4}$alkyl, halo$C_{1-4}$alkyl, $C_{1-4}$alkoxy, halo$C_{1-4}$alkoxy or $C_{2-4}$alkenyloxy;
3) —$X^1$—$C_{1-6}$alkyl-$X^2$—$R^{21}$ wherein $X^1$ is as defined hereinbefore, $X^2$ is a direct bond, —O—, —S—, —SO—, —$SO_2$—, —$NR^{22}$—, —CO—, —COO—, —OCO—, —$CONR^{23}$—, —$NR^{24}CO$—, —$NR^{25}COO$—, —$SO_2NR^{26}$—, —$NR^{27}SO_2$—, —$CH_2$—, —$SO_2NR^{28}CO$—, —$OCONR^{29}$—, —$CSNR^{30}$—, —$NR^{31}CS$—, —$NR^{32}CSNR^{33}$—, —$NR^{34}CONR^{35}$—, —$CONR^{36}SO_2$—, —$NR^{37}CONR^{38}SO_2$— or —$SO_2NR^{39}CONR^{40}$— (wherein $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$ and $R^{40}$, each independently represents hydrogen, $C_{1-4}$alkyl or $C_{1-3}$alkoxy$C_{2-3}$alkyl) and $R^{21}$ is hydrogen, $C_{1-4}$alkyl or $R^{41}$ wherein $R^{41}$ is phenyl or a 4–12 membered heterocyclic moiety containing 1–4 heteroatoms selected independently from O, N and S which heterocyclic moiety may be aromatic or non-aromatic and which phenyl or heterocyclic moiety is optionally substituted by 1–6 substituents selected from $Q^3$ wherein $Q^3$ is as defined hereinafter;
4) —$X^1$—$C_{3-7}$cycloalkyl-$X^2$—$R^{21}$ wherein $X^1$, $X^2$ and $R^{21}$ are as defined hereinbefore; and
5) —$Y^2Ar^2$ wherein $Y^2$ is $X^1$ wherein $X^1$ is as defined hereinbefore and $Ar^2$ is selected from the following four groups:
(i) phenyl, a carbon-linked 6-membered heteroaryl ring containing 1–2 nitrogen atoms and a carbon-linked 5-membered heteroaryl ring containing 1–2 heteroatoms selected independently from O, N and S, wherein said phenyl or heteroaryl ring is substituted at carbon, with 1–4 substituents selected from $Q^1$ and $Q^2$ including at least one substituent selected from $Q^2$ wherein $Q^1$ and $Q^2$ are as defined hereinafter;
(ii) a carbon-linked triazine or a carbon-linked 5-membered heteroaryl ring containing 3–4 heteroatoms selected independently from O, N and S; wherein said heteroaryl ring is optionally substituted with 1–4 substituents selected from $Q^1$ and $Q^2$ wherein $Q^1$ and $Q^2$ are as defined hereinafter;
(iii) a 4–12 membered non-aromatic heterocyclic moiety containing 1–4 heteroatoms selected independently from O, N and S wherein said heterocyclic moiety is optionally substituted with 1–6 substituents selected from $Q^3$ wherein $Q^3$ is as defined hereinafter, with the proviso that if $Ar^2$ is a nitrogen linked heterocyclic ring $Y^2$ is not —$SO_2$—; and
(iv) $Ar^1$ with the proviso that if $Ar^2$ has a value $Ar^1$ then $Y^2$ is not —CO—, —SO— or —$SO_2$—;

$Q^1$ is $C_{1-4}$alkyl, halo$C_{1-4}$alkyl, $C_{1-4}$alkoxy, halo$C_{1-4}$alkoxy, $C_{2-4}$alkenyloxy, cyano, nitro, halo or trifluoromethylsulphanyl;

$Q^2$ is selected from the following seven groups:
1) oxygen (forming an oxo group when linked to a ring carbon and forming an N-oxide when a ring nitrogen is oxidised);
2) halosulphonyl, cyanosulphanyl;
3) —$X^3$—$R^5$ wherein $X^3$ is a direct bond, —O—, —S—, —SO—, —$SO_2$—, —$NR^{42}$—, —CO—, —COO—, —OCO—, —$CONR^{43}$—, —$NR^{44}CO$—, —$NR^{45}COO$—, —$SO_2NR^{46}$—, —$NR^{47}SO_2$—, —$CH_2$—, —$SO_2NR^{48}CO$—, —$OCONR^{49}$—, —$CSNR^{50}$—, —$NR^{51}CS$—, —$NR^{52}CSNR^{53}$—, —$NR^{54}CONR^{55}$—, —$CONR^{56}SO_2$—, —$NR^{57}CONR^{58}SO_2$— or —$SO_2NR^{59}CONR^{60}$— (wherein $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$ and $R^{60}$ each independently represents hydrogen, $C_{1-4}$alkyl or $C_{1-3}$alkoxy$C_{2-3}$alkyl) and $R^5$ is as defined hereinbefore but with the proviso that $Q^2$ is not trifluoromethylsulphanyl, $C_{1-4}$alkyl, halo$C_{1-4}$alkyl, $C_{1-4}$alkoxy, halo$C_{1-4}$alkoxy or $C_{2-4}$alkenyloxy;
4) $R^{41}$ wherein $R^{41}$ is as defined hereinbefore;
5) —$X^3$—$C_{1-6}$alkyl-$X^2$—$R^{21}$ wherein $X^3$, $X^2$ and $R^{21}$ are as defined hereinbefore;
6) —$X^3$—$C_{3-7}$cycloalkyl-$X^2$—$R^{21}$ wherein $X^3$, $X^2$ and $R^{21}$ are as defined hereinbefore; and
7) —$X^3$—$R^{41}$ wherein $R^{41}$ and $X^3$ are as defined hereinbefore;

$Q^3$ is selected from the following four groups:
1) oxygen (forming an oxo group when linked to a ring carbon and forming an N-oxide when a ring nitrogen is oxidised);
2) cyano, nitro or halo;
3) halosulphonyl, cyanosulphanyl; and
4) —$X^4$—$R^{61}$ wherein $X^4$ is a direct bond, —O—, —S—, —SO—, —$SO_2$—, —$NR^{62}$—, —CO—, —COO—, —OCO—, —$CONR^{63}$—, —$NR^{64}CO$—, —$NR^{65}COO$—, —$SO_2NR^{66}$—, —$NR^{67}SO_2$—, —$CH_2$—, —$SO_2NR^{68}CO$—, —$OCONR^{69}$—, —$CSNR^{70}$—, —$NR^{71}CS$—, —$NR^{72}CSNR^{73}$—, —$NR^{74}CONR^{75}$—, —$CONR^{76}SO_2$—, —$NR^{77}CONR^{78}SO_2$— or —$SO_2NR^{79}CONR^{80}$— (wherein $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{75}$, $R^{76}$, $R^{77}$, $R^{78}$, $R^{79}$ and $R^{80}$ each independently represents hydrogen, $C_{1-4}$alkyl or $C_{1-3}$alkoxy$C_{2-3}$alkyl) and $R^{61}$ is selected from hydrogen, $C_{1-6}$alkyl, $C_{3-7}$cycloalkyl, $C_{2-6}$alkenyl and $C_{2-6}$alkynyl which $C_{1-6}$alkyl, $C_{3-7}$cycloalkyl, $C_{2-6}$alkenyl or $C_{2-6}$alkynyl is optionally substituted with one or more groups selected from hydroxy, amino, halo, $C_{1-4}$alkoxycarbonyl, carboxy, $C_{1-6}$alkoxy and hydroxy$C_{1-6}$ alkyl;

(c) $R^1$ is linked to ring C at a carbon ortho to the position of A-B attachment and is selected from the group consisting of $C_{1-4}$alkyl, halo$C_{1-4}$alkyl, $C_{1-4}$alkoxy, halo$C_{1-4}$alkoxy, $C_{2-4}$alkenyloxy, cyano, nitro, halo, trifluoromethylsulphanyl and hydroxy;

(d) $R^1$ is linked to ring C at a ring carbon atom ortho to the position of A-B attachment and is selected from the following two groups:

1) —$X^5$—$R^{81}$ wherein $X^5$ is a direct bond, —O—, —S—, —SO—, —$SO_2$—, —$NR^{82}$—, —CO—, —COO—, —OCO—, —$CONR^{83}$—, —$NR^{84}CO$—, —$NR^{85}COO$—, —$SO_2NR^{86}$—, —$NR^{87}SO_2$—, —$CH_2$—, —$SO_2NR^{88}CO$—, —$OCONR^{89}$—, —$CSNR^{90}$—, —$NR^{91}CS$—, —$NR^{92}CSNR^{93}$—, —$NR^{94}CONR^{95}$—, —$CONR^{96}SO_2$—, —$NR^{97}CONR^{98}SO_2$— or —$SO_2NR^{99}CONR^{100}$— (wherein $R^{82}$, $R^{83}$, $R^{84}$, $R^{85}$, $R^{86}$, $R^{87}$, $R^{88}$, $R^{89}$, $R^{90}$, $R^{91}$, $R^{92}$, $R^{93}$, $R^{94}$, $R^{95}$, $R^{96}$, $R^{97}$, $R^{98}$, $R^{99}$ and $R^{100}$ each independently represents hydrogen, $C_{1-4}$ alkyl or $C_{1-3}$alkoxy$C_{2-3}$alkyl) and $R^{81}$ is selected from hydrogen, $C_{1-6}$alkyl, $C_{3-7}$cycloalkyl, $C_{2-6}$alkenyl and $C_{2-6}$alkynyl which $C_{1-6}$alkyl, $C_{3-7}$cycloalkyl, $C_{2-6}$alkenyl or $C_{2-6}$alkynyl is optionally substituted with one or more groups selected from hydroxy, amino, halo, $C_{1-4}$alkoxycarbonyl, carboxy, $C_{1-6}$alkoxy and hydroxy$C_{1-6}$ alkyl with the proviso that $R^1$ is not trifluoromethylsulphanyl, hydroxy, $C_{1-4}$alkyl, halo$C_{1-4}$alkyl, $C_{1-4}$alkoxy, halo$C_{1-4}$alkoxy or $C_{2-4}$alkenyloxy; and 2) —$X^6$—$R^{101}$ wherein $X^6$ is selected from a direct bond, —CO—, —O—, —$OCH_2$—, —S—, —SO—, —$SO_2$— and —$NR^{102}$— (wherein $R^{102}$ is hydrogen or $C_{1-4}$alkyl) and $R^{101}$ is phenyl which is optionally substituted by 1–4 substituents selected from cyano, nitro, trifluoromethylsulphanyl, $C_{1-6}$alkyl, halo$C_{1-6}$alkyl, $C_{1-6}$alkoxy, halo$C_{1-6}$alkoxy, $C_{2-6}$alkenyloxy, halo, hydroxy and amino;

n is, 1 or 2;

(e) either $R^2$ and $R^3$ are independently $C_{1-3}$alkyl optionally substituted by from 1 to 2k+1 atoms selected from fluoro and chloro wherein k is the number of carbon atoms in the said $C_{1-3}$alkyl, provided that $R^2$ and $R^3$ are not both methyl;

or $R^2$ and $R^3$, together with the carbon atom to which they are attached, form a 3–5 membered cycloalkyl ring optionally substituted by from 1 to 2m–2 fluorine atoms wherein m is the number of carbon atoms in said ring;

(f) $R^2$ and $R^3$ are both methyl or one of $R^2$ and $R^3$ is hydrogen or halo and the other is halo or $C_{1-3}$alkyl optionally substituted by from 1 to 2k+1 atoms selected from fluoro and chloro wherein k is the number of carbon atoms in the said $C_{1-3}$alkyl, with the proviso that when either $R^2$ or $R^3$ is halo $R^4$ is not hydroxy and with the proviso that when either $R^2$ or $R^3$ is hydrogen, $R^4$ is not hydrogen;

(g) A-B is selected from —NHCO—, —$OCH_2$—, —$SCH_2$—, —$NHCH_2$—, trans-vinylene, and ethynylene;

(h) A-B is —NHCS— or —$COCH_2$—;

(i) $R^4$ is hydroxy;

(j) $R^4$ is hydrogen, halo or methyl;

but excluding compounds wherein ring C is selected from (a) and $R^1$ is selected only from (c) and $R^2$ and $R^3$ are selected from (e) and A-B is selected from (g) and $R^4$ is selected from (i);

and salts thereof;

and pharmaceutically acceptable in vivo cleavable prodrugs of said compound of formula (I);

and pharmaceutically acceptable salts of said compound or said prodrugs;

in the manufacture of a medicament for use in the elevation of PDH activity in warm-blooded animals such as humans.

In a further aspect of the invention there is provided a compound of formula (I'):

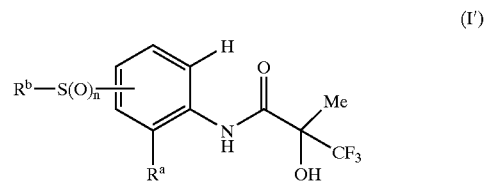

(I')

wherein:

n is 1 or 2;

$R^a$ is chloro, fluoro, bromo, nitro or methoxy;

$R^b$ is $C_{1-6}$alkyl optionally substituted by one or more groups selected from hydroxy, amino, halo, $C_{1-4}$alkoxycarbonyl, carboxy or $C_{1-6}$alkoxy or $R^b$ is phenyl, a carbon-linked 6-membered heteroaryl ring containing 1–2 nitrogen atoms or a carbon-linked 5-membered heteroaryl ring containing 1–3 heteroatoms selected independently from O, N and S, wherein said phenyl or heteroaryl ring is substituted by one or more groups selected from i)–iii) and is optionally further substituted with a group selected from iv):

i) —$X^a$—$R^c$ wherein $X^a$ is a direct bond, —O—, —S—, —SO—, —$SO_2$—, —$NR^d$— or —$CONR^e$— (wherein $R^d$ and $R^e$ each independently represents hydrogen or $C_{1-4}$alkyl which $C_{1-4}$alkyl is optionally substituted with one or more groups selected from hydroxy or $C_{1-4}$alkoxy) and $R^c$ is selected from hydrogen or $C_{1-6}$alkyl which $C_{1-6}$alkyl is optionally substituted with one or more hydroxy or $C_{1-4}$alkoxy with the proviso that —$X^a$—$R^c$ is not $C_{1-4}$alkyl or $C_{1-4}$alkoxy;

ii) a 4–12 membered heterocyclic moiety containing 1–4 heteroatoms selected independently from O, N and S which heterocyclic moiety may be aromatic or non-aromatic and is optionally substituted with one or more groups selected from hydroxy, halo, $C_{1-4}$alkoxy, $C_{1-4}$alkyl or cyano;

iii) —$X^a$—$C_{1-6}$alkyl-$X^b$—$R^c$ wherein $X^a$ and $R^c$ are as defined hereinbefore and $X^b$ is —S—, —SO— or —$SO_2$—;

iv) cyano, hydroxy, halo, $C_{1-4}$alkoxy, $C_{1-4}$alkyl; and and salts thereof;

and pharmaceutically acceptable in vivo cleavable prodrugs of said compound of formula (I);

and pharmaceutically acceptable salts of said compound or said prodrugs.

Preferable values for a compound of formula (I') are as follows:

Preferably $R^a$ is chloro or fluoro.

More preferably $R^a$ is chloro.

Preferably $R^b$ is $C_{1-4}$alkyl optionally substituted by one or more hydroxy or $R^b$ is phenyl, a carbon-linked 6-membered heteroaryl ring containing 1–2 nitrogen atoms or a carbon-linked 5-membered heteroaryl ring containing 1–2 heteroatoms wherein said phenyl or heteroaryl ring is substituted by one or more groups selected from i)–iii):

i) —$X^a$—$R^c$ wherein $X^a$ is —SO—, —$SO_2$—, —$NR^d$— or —$CONR^e$— (wherein $R^d$ and $R^e$ each independently represents hydrogen or $C_{1-4}$alkyl) and $R^c$ is selected from hydrogen or $C_{1-6}$alkyl which $C_{1-6}$alkyl is optionally substituted with one or more hydroxy;

ii) a 4–12 membered heterocyclic moiety containing 1–4 heteroatoms selected independently from O, N and S which heterocyclic moiety may be aromatic or non-aromatic;

iii) —$X^a$—$C_{1-6}$alkyl-$X^b$—$R^c$ wherein $X^a$ and $R^c$ are as defined hereinbefore and $X^b$ is —S—.

More preferably $R^b$ is $C_{1-4}$alkyl optionally substituted by hydroxy or $R^b$ is phenyl wherein said phenyl is substituted by one group selected from i)–iii):

i) —$X^a$—$R^c$ wherein $X^a$ is —SO—, —$SO^2$—, —$NR^d$— or —$CONR^e$— (wherein $R_d$ and $R^e$ each independently represents hydrogen or $C_{1-4}$alkyl) and $R^c$ is selected from hydrogen or $C_{1-6}$alkyl which $C_{1-6}$alkyl is optionally substituted with one or more hydroxy;

ii) a 4–12 membered heterocyclic moiety containing 1–4 heteroatoms selected independently from O, N and S which heterocyclic moiety may be aromatic or non-aromatic;

iii) —$X^a$—$C_{1-6}$alkyl-$X^1$—$R^1$ wherein $X^a$ and $R^c$ are as defined hereinbefore and $X^b$ is —S—.

Particularly $R^b$ is ethyl, 2-hydroxyethyl, 4-N,N-dimethylcarbamoylphenyl, 4-(2-hydroxyethlyamino) phenyl, 4-methylsulphinylphenyl, 4-mesylphenyl, 4-aminophenyl, 4-(2-oxopyrrolidi-1-yl)phenyl and 4-(2-methylthioethylamino)phenyl.

In one aspect of the invention preferably n is 1.

In another aspect of the invention preferably n is 2.

In one aspect of the invention preferably the group $R^b$—S(O)$_n$— is para to the —NH—C(O)— group.

In another aspect of the invention preferably the group $R^b$—S(O)$_n$— is meta to the —NH—C(O)— group.

Preferably the tertiary centre of formula (I') —C(OH)(CF$_3$)(Me) has the R stereochemistry.

Preferred compounds of formula (I) or (I') are those of Examples 14, 43, 63, 71, 74, 87, 128, 144, 215 and 355 and salts thereof; and pharmaceutically acceptable in vivo cleavable prodrugs of said compound of formula (I); and pharmaceutically acceptable salts of said compound or said prodrugs.

Compounds of the present invention include:

N-(2,6-dimethylphenyl)-2-hydroxy-2-methyl-3,3,3-trifluoropropanamide.

N-(2-cyanophenyl)-2-hydroxy-2-methyl-3,3,3-trifluoropropanamide;

N-2-chloro-4-[(2-hydroxy-2-methyl-3,3,3-trifluoropropanamide]phenyl-2-hydroxy-2-methyl-3,3,3-trifluoropropanamide;

N-2-nitro-4-[(2-hydroxy-2-methyl-3,3,3-trifluoropropanamide]phenyl-2-hydroxy-2-methyl-3,3,3-trifluoropropanamide;

N-[2-(4-chlorobenzoyl)phenyl]-2-hydroxy-2-methyl-3,3,3-trifluoropropanamide;

N-[2-carboxy-4-(phenylsulphonyl)phenyl]-2-hydroxy-2-methyl-3,3,3-trifluoropropanamide;

N-(4-bromo-2-chlorophenyl)-2-hydroxy-2-methyl-3,3,3-trifluoropropanamide;

N-(2,4-dichlorophenyl)-2-hydroxy-2-methyl-3,3,3-trifluoropropanamide;

N-(2-chlorophenyl)-2-hydroxy-2-methyl-3,3,3-trifluoropropanamide;

N-(2-fluorophenyl)-2-hydroxy-2-methyl-3,3,3-trifluoropropanamide;

N-(biphen-2-yl)-2-hydroxy-2-methyl-3,3,3-trifluoropropanamide;

N-(2-acetylphenyl)-2-hydroxy-2-methyl-3,3,3-trifluoropropanamide;

N-(2-iodophenyl)-2-hydroxy-2-methyl-3,3,3-trifluoropropanamide;

N-(2-bromophenyl)-2-hydroxy-2-methyl-3,3,3-trifluoropropanamide;

2-hydroxy-2-methyl-N-[2-(phenylsulphonyl)phenyl]-3,3,3-trifluoropropanamide;

N-(2-methoxyphenyl)-2-hydroxy-2-methyl-3,3,3-trifluoropropanamide;

N-(2-hydroxyphenyl)-2-hydroxy-2-methyl-3,3,3-trifluoropropanamide;

(R)-N-(4-bromo-2,6-dichlorophenyl)-2-hydroxy-2-methyl-3,3,3-trifluoropropanamide;

(R)-N-[2-chloro-4-(phenylsulphanyl)phenyl]-2-hydroxy-2-methyl-3,3,3-trifluoropropanamide;

(S)-N-[2-chloro-4-(phenylsulphanyl)phenyl]-2-hydroxy-2-methyl-3,3,3-trifluoropropanamide;

(R)-N-[2-fluoro-4-(phenylsulphanyl)phenyl]-2-hydroxy-2-methyl-3,3,3-trifluoropropanamide;

(R)-N-(4-bromo-2-methylphenyl)-2-hydroxy-2-methyl-3,3,3-trifluoropropanamide;

N-[2-chloro-4-(phenylsulphonyl)phenyl]-2-hydroxypropanamide;

N-(2-fluoro-4-iodophenyl)-2-hydroxypropanamide;

N-{4-[(benzyloxycarbonyl)amino]-2-fluorophenyl}-2-hydroxy-2-methyl-3,3,3-trifluoropropanamide;

N-[2-(hydroxymethyl)-4-iodophenyl]-2-hydroxy-2-methyl-3,3,3-trifluoropropanamide;

N-(4-benzyl-2-methylphenyl)-2-hydroxy-2-methyl-3,3,3-trifluoropropanamide;

N-(2-carbamoyl-4-iodophenyl)-2-hydroxy-2-methyl-3,3,3-trifluoropropanamide;

N-(4-iodo-2-methoxycarbonylphenyl)-2-hydroxy-2-methyl-3,3,3-trifluoropropanamide;

N-(4-iodo-2-nitrophenyl)-2-hydroxy-2-methyl-3,3,3-trifluoropropanamide;

N-(2-bromo-4-methoxycarbonylphenyl)-2-hydroxy-2-methyl-3,3,3-trifluoropropanamide;

N-(4-bromo-2-methylphenyl)-2-hydroxy-2-methyl-3,3,3-trifluoropropanamide;

N-[2-chloro-4-(benzoylamino)phenyl]-2-hydroxy-2-methylpropanamide;

N-2-chloro-4-[(phenylsulphonyl)amino]phenyl-2-hydroxy-2-methylpropanamide;

N-(4-chloro-2-methoxyphenyl)-2-hydroxy-2-methyl-3,3,3-trifluoropropanamide;

2-hydroxy-N-(4-methoxy-2-methylphenyl)-2-methyl-3,3,3-trifluoropropanamide;

N-(2,3-dimethylphenyl)-2-hydroxy-2-methyl-3,3,3-trifluoropropanamide;

N-(3-chloro-2-methylphenyl)-2-hydroxy-2-methyl-3,3,3-trifluoropropanamide;

N-(4-bromo-2-trifluoromethylphenyl)-2-hydroxy-2-methyl-3,3,3-trifluoropropanamide;

N-(4-chloro-2-benzoylphenyl)-2-hydroxy-2-methyl-3,3,3-trifluoropropanamide;

N-(4-chloro-2-trifluoromethylphenyl)-2-hydroxy-2-methyl-3,3,3-trifluoropropanamide;

N-(4-chloro-2-methylphenyl)-2-hydroxy-2-methyl-3,3,3-trifluoropropanamide;

N-[4-chloro-2-(2-chlorobenzoyl)phenyl]-2-hydroxy-2-methyl-3,3,3-trifluoropropanamide;

N-(2-chloro-4-mesylphenyl)-2-hydroxy-2-methyl-3,3,3-trifluoropropanamide;

N-(2-chloro-4-fluorosulphonylphenyl)-2-hydroxy-2-methyl-3,3,3-trifluoropropanamide;

N-(2,4-diiodophenyl)-2-hydroxy-2-methyl-3,3,3-trifluoropropanamide;
N-(2-bromo-4-methylphenyl)-2-hydroxy-2-methyl-3,3,3-trifluoropropanamide;
N-(2-bromo-4-butylphenyl)-2-hydroxy-2-methyl-3,3,3-trifluoropropanamide;
N-(2-chloro-4-thiocyanatophenyl)-2-hydroxy-2-methyl-3,3,3-trifluoropropanamide;
N-[2-fluoro-4-(allyloxycarbonyl)phenyl]-2-hydroxy-2-methyl-3,3,3-trifluoropropanamide;
N-[2-fluoro-4-{N-[(1,3-diethoxycarbonyl)propyl]carbamoyl}phenyl]-2-hydroxy-2-methyl-3,3,3-trifluoropropanamide;
N-(4-amino-2-chlorophenyl)-2-hydroxy-2-methylpropanamide:
N-[2-chloro-4-(4-aminophenylsulphanyl)phenyl]-2-hydroxy-2-methylpropanamide;
and Examples 106, 108, 110–113, 149, 151, 171, 173, 197 and 205;
and salts thereof and pharmaceutically acceptable in vivo cleavable esters or sulphides of said compounds; and pharmaceutically acceptable salts of said compounds or esters or sulphides.

Advantageous compounds of the present invention include Examples 184–186 and salts thereof and pharmaceutically acceptable in vivo cleavable esters or sulphides of said compounds; and pharmaceutically acceptable salts of said compounds or esters or sulphides.

Preferred compounds of the present invention include Examples 15, 114, 171, 172 and 182 and salts thereof and pharmaceutically acceptable in vivo cleavable esters or sulphides of said compounds; and pharmaceutically acceptable salts of said compounds or esters or sulphides.

More preferred compounds of the present invention include Examples 14 and 87 and salts thereof and pharmaceutically acceptable in vivo cleavable esters or sulphides of said compounds; and pharmaceutically acceptable salts of said compounds or esters or sulphides.

Particular compounds of the present invention include Examples 1, 2, 13, 16, 54, 86, 104, 212, 213 and 214 and salts thereof and pharmaceutically acceptable in vivo cleavable esters or sulphides of said compounds; and pharmaceutically acceptable salts of said compounds or esters or sulphides.

In another aspect of the invention, preferred compounds of the invention are any one of Examples 1–428 and salts thereof; and pharmaceutically acceptable in vivo cleavable prodrugs of said compound of formula (I); and pharmaceutically acceptable salts of said compound or said prodrugs.

Preferred aspects of the invention are those which relate to the compound or a pharmaceutically acceptable salt thereof.

In this specification the term "alkyl" includes both straight and branched chain alkyl groups but references to individual alkyl groups such as "propyl" are specific for the straight chain version only. An analogous convention applies to other generic terms. Unless otherwise stated the term "alkyl" advantageously refers to chains with 1–6 carbon atoms, preferably 1–4 carbon atoms.

In this specification the term "alkoxy" refers to an alkyl group as defined hereinbefore linked to an oxygen atom.

In this specification the term "cycloalkyl" refers to cyclic non-aromatic rings of carbon atoms.

In this specification the term "cycloalkoxy" refers to a cycloalkyl group as defined hereinbefore linked to an oxygen atom.

In this specification the term "halo" includes fluoro, chloro, bromo and iodo unless stated otherwise.

In this specification the term "haloalkyl" includes an alkyl group as defined hereinbefore substituted with one or more halo groups, including for example trifluoromethyl.

In this specification the term "hydroxyalkyl" includes an alkyl group as defined hereinbefore substituted with one or more hydroxy groups.

In this specification the term "aryl" includes $C_{5-12}$aromatic groups which may, if desired and unless otherwise defined, carry one or more substituents selected from halo, alkyl, alkoxy, cyano, nitro or trifluoromethyl (wherein alkyl and alkoxy are as hereinbefore defined). Suitable values for aryl include phenyl and naphthyl.

The term "aryloxy" means an aryl group as defined hereinbefore linked to an oxygen atom. Suitable values for aryloxy include phenoxy and naphth-1-yloxy.

The term "heteroaryl" includes aryl groups, as defined hereinbefore, containing one or more heteroatoms selected from O, N and S.

Suitable values for "a 6-membered carbon-linked heteroaryl group containing 1–3 nitrogen atoms wherein one or more ring nitrogen atoms are oxidised to form the N-oxide" include pyridyl-N-oxide, pyrimidyl-N-oxide and pyrazinyl-N-oxide.

Suitable values for "a carbon-linked 6-membered heteroaryl ring containing 1–2 nitrogen atoms" include pyridyl, pyrimidyl, pyrazinyl and pyridadzinyl.

Suitable values for "a carbon-linked 5-membered heteroaryl ring containing 1–2 heteroatoms selected independently from O, N and S" include furyl, thienyl, pyrrolyl, thiazolyl, isoxazolyl, oxazolyl, imidazolyl and pyrazolyl.

Suitable values for "a carbon-linked 5-membered heteroaryl ring containing 3–4 heteroatoms selected independently from O, N and S" include oxadiazolyl, furazanyl, triazolyl and thiadiazolyl.

Suitable values for a "5–6 membered heterocyclic aromatic ring containing 1–4 heteroatoms selected independently from O, N and S" include furyl, thienyl, pyrrolyl, thiazolyl, isoxazolyl, oxazolyl and pyrazolyl, tetrazolyl, imidazolyl, oxadiazolyl, furazanyl, triazolyl, thiadiazolyl pyridyl, pyrimidyl, pyrazinyl and pyridazinyl.

Suitable values for a "5–7 membered heterocyclic non-aromatic moiety containing 1–2 heteroatoms selected independently from O, N and S" include morpholino, piperazinyl, piperidinyl, homopiperazinyl, oxazolidinyl, thiazolinyl, oxaxolinyl, dihydropyranyl and tetrapyranyl.

Suitable values for "a 5-membered heteroaryl ring containing 1–4 heteroatoms selected independently from O, N and S" include pyrrolyl, furyl, thienyl, pyrazolyl, imidazolyl, triazolyl and tetrazolyl.

Suitable values for "a carbon-linked 5-membered heteroaryl ring containing 1–3 heteroatoms" include pyrrolyl, furyl, thienyl, pyrazolyl, imidazolyl and triazolyl.

Suitable values for "a 7–12 membered aromatic heterocyclic moiety containing 1–4 heteroatoms selected independently from O, N and S" include indolyl, benzofuryl, benzothienyl, benzimidazolyl, purinyl, quinolinyl and isoquinolinyl.

A "4–12 membered heterocyclic moiety containing 1–4 heteroatoms selected independently from O, N and S which heterocyclic moiety may be aromatic or non-aromatic" is a saturated, partially saturated or unsaturated (including aromatic) mono or bicyclic ring, which may, unless otherwise specified, be carbon or nitrogen linked, and, unless otherwise specified, any (optional) substituents may be substituents on a ring carbon or nitrogen (where said ring is a ring containing an —NH— moiety the substitution thus replacing the hydrogen), wherein a —CH$_2$— group can optionally be replaced by a —C(O)—, a ring nitrogen atom may optionally bear a $C_{1-6}$alkyl group and form a quaternary compound or a ring nitrogen and/or sulphur atom may be optionally oxidised to form the N-oxide and/or the S-oxides. Examples and suitable values of the term "heterocyclic group" are morpholino, piperidyl, pyridyl, pyranyl, pyrrolyl, isothiazolyl, oxazolinyl, oxazolidinyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, tetrahydropyranyl, imidazolyl, pyrimidyl, pyrazinyl, pyridazinyl, isoxazolyl, N-methylpyrrolyl, 4-pyridone, 1-isoquinolone, 2-pyrrolidone, 4-thiazolidone, pyridine-N-oxide and quinoline-N-oxide.

A "4–12 membered non-aromatic heterocyclic moiety containing 1–4 heteroatoms selected independently from O, N and S" is as defined in the above paragraph, but excludes those compounds which are fully aromatic.

In this specification "non-aromatic" includes fully saturated rings as well as partially saturated rings but does not include aromatic unsaturated rings.

The term "heterocyclic" includes aromatic and non-aromatic cyclic moieties containing one or more heteroatoms selected from O, N and S.

In this specification unless stated otherwise the term "alkenyl" includes both straight and branched chain alkenyl groups but references to individual alkenyl groups such as 2-butenyl are specific for the straight chain version only. In this specification unless stated otherwise the term "alkynyl" includes both straight and branched chain alkynyl groups but references to individual alkynyl groups such as 2-butynyl are specific for the straight chain version only.

For the avoidance of any doubt, it is to be understood that when $X^1$ is, for example, a group of formula —NR$^8$CO—, it is the nitrogen atom bearing the $R^8$ group which is attached to ring C and the carbonyl group is attached to $R^5$, whereas when $X^1$ is, for example, a group of formula —CONR$^7$—, it is the carbonyl group which is attached to ring C and the nitrogen atom bearing the $R^7$ group is attached to $R^5$. When $X^1$ is —NR$^{11}$SO$_2$— it is the nitrogen atom bearing the $R^{11}$ group which is attached to ring C and the sulphonyl group which is attached to $R^5$. Analogous conventions apply to similar groups. When $X^1$ is —NR$^6$— it is the nitrogen atom bearing the $R^6$ group which is linked to ring C and to $R^5$. When $X^1$ is —OCO— it is the first oxygen atom which is attached to ring C and the carbonyl group is attached to $R^5$. When $X^1$ is —COO— it is the carbonyl group which is linked to ring C and the other oxygen atom is attached to $R^5$. Analogous conventions apply to similar groups. It is further to be understood that when $X^1$ represents —NR$^6$— and $R^6$ is $C_{1-3}$alkoxy$C_{2-3}$alkyl it is the $C_{2-3}$alkyl moiety which is linked to the nitrogen atom of $X^1$ and an analogous convention applies to other groups.

When $X^3$ is —OCONR$^{49}$— it is the first oxygen which is linked to ring Ar$^2$ and the carbonyl group while the nitrogen atom is linked to the carbonyl group, $R^{49}$ and $R^5$.

When $X^3$ is —NR$^{47}$SO$_2$— it is the nitrogen atom which is linked to Ar$^2$, $R^{47}$ and the sulphonyl group, and it is the sulphonyl group which is linked to $R^5$ and analogous conventions apply to similar groups.

For the avoidance of any doubt, it is to be understood that when a group $C_{5-6}$alkyl carries a $C_{1-4}$alkoxycarbonyl substituent it is the carbonyl moiety which is attached to $C_{5-6}$alkyl and an analogous convention applies to other groups.

Within the present invention it is to be understood that a compound of the formula (I) or a salt thereof may exhibit the phenomenon of tautomerism and that the formulae drawings within this specification can represent only one of the possible tautomeric forms. It is to be understood that the invention encompasses any tautomeric form which elevates PDH activity and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It will be appreciated by those skilled in the art that certain compounds of formula (I) contain an asymmetrically substituted carbon and/or sulphur atom, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the elevation of PDH activity, it being well known in the art how to prepare optically-active forms (for example, by resolution of the racemic form by recrystallization techniques, by synthesis from optically-active starting materials, by chiral synthesis, by enzymatic resolution, (for example WO 9738124), by biotransformation, or by chromatographic separation using a chiral stationary phase) and how to determine efficacy for the elevation of PDH activity by the standard tests described hereinafter.

In vivo cleavable prodrugs of compounds of formula (I) include for example in vivo hydrolysable esters of compounds of the formula (I) containing a carboxy group, for example, a pharmaceutically acceptable ester which is hydrolysed in the human or animal body to produce the parent acid, for example, a pharmaceutically acceptable ester formed with a $C_{1-6}$alcohol such as methanol, ethanol, ethylene glycol, propanol or butanol, or with a phenol or benzyl alcohol such as phenol or benzyl alcohol or a substituted phenol or benzyl alcohol wherein the substituent is, for example, a halo (such as fluoro or chloro), $C_{1-4}$alkyl (such as methyl) or $C_{1-4}$alkoxy (such as methoxy) group.

In vivo cleavable prodrugs of compounds of formula (I) also include for example in vivo hydrolysable amides of compounds of the formula (I) containing a carboxy group, for example, a N—$C_{1-6}$alkyl or N,N-di-$C_{1-6}$alkyl amide such as N-methyl, N-ethyl, N-propyl, N,N-dimethyl, N-ethyl-N-methyl or N,N-diethyl amide.

It is also to be understood that certain compounds of the formula (I) and salts thereof can exist in solvated as well as unsolvated forms such as, for example, hydrated forms. It is to be understood that the invention encompasses all such solvated forms which elevate PDH activity.

A compound of the formula (I), or salt thereof, and other compounds of the invention (as hereinafter defined) may be prepared by any process known to be applicable to the preparation of chemically-related compounds. Such processes include, for example, those illustrated in European Patent Applications, Publication Nos. 0524781, 0617010, 0625516, and in GB 2278054, WO 9323358 and WO 9738124.

Another aspect of the present invention provides a process for preparing a compound of formula (I) or a pharmaceutically acceptable salt or an in vivo hydrolysable ester thereof, which process (in which variable groups are as defined for formula (I) unless otherwise stated) comprises of:

(a) for compounds of formula (I) where $R^4$ is hydroxy: deprotecting a protected compound of formula (II):

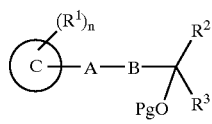
(II)

where Pg is an alcohol protecting group;

(b) for compounds of formula (I) where $Y^1$, $Y^2$ or $X^1$ is —C(O)—: oxidising a corresponding alcohol of formula (III):

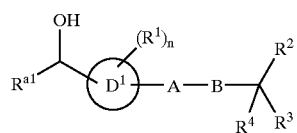
(III)

wherein ring $D^1$ has any of the values defined hereinbefore for ring C but in which the place of one of the possible substituents on ring C is taken by ArCH(OH) and $R^{a1}$ is a group attached to $Y^1$, $Y^2$ or $X^1$ (possible valued as defined above);

(c) for compounds of formula (I) where $Y^1$, $Y^2$ or $X^1$ is —C(O)—: deprotecting a corresponding compound of formula (IV):

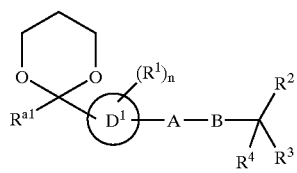
(IV)

wherein ring $D^2$ has any of the values defined hereinbefore for ring C but in which the place of one of the possible substituents on ring C is taken by Ar—C(—O—(CH$_2$)$_3$—O—)— and $R^{a1}$ is as defined above;

(d) for compounds of formula (I) where Ring C has an $R^{a2}$—CH$_2$— substituent attached to it wherein $R^{a2}$ is a group that is attached via —CH$_2$— moiety to ring C (possible values as defined above): reduction of a compound of formula (III) or (V):

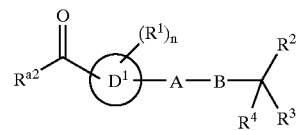
(V)

wherein ring $D^1$ has any of the values defined hereinbefore for ring C but in which the place of one of the possible substituents on ring C is taken by ArC(O)—;

(e) for compounds of formula (I) where ring C has a $R^{a3}$—C(O)— substituent wherein $R^{a3}$ is and aromatic moiety or alkenyl moiety (possible values as defined above): treating a compound of formula (VI):

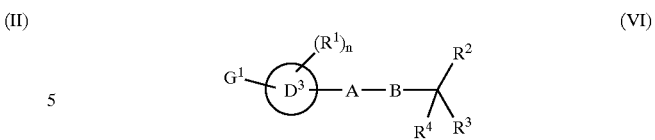
(VI)

wherein ring $D^3$ has any of the values defined hereinbefore for ring C but in which the place of one of the possible substituents on ring C is taken by $G^1$ and $G^1$ is a leaving group; with carbon monoxide and a tin compound having the formula $(R^6)_{p1}Sn(R^{a3})_{p2}$ (wherein $R^6$ is $C_{1-4}$alkyl and p1+p2=4) or an aluminium compound having the formula $(R^6)_{p3}Al(R^{a3})_{p4}$ (wherein $R^6$ is $C_{1-4}$alkyl and p3+p4=3);

(f) for compounds of formula (I) where Ring C has an $R^{a4}S(O)$— or $R^{a4}S(O)_2$— substituent, $R^{a4}$ is a group attached through a sulphoxide or sulphone moiety (possible values as defined above) and A-B is not SCH$_2$ or NHCH$_2$: oxidising a compound of formula (VI) wherein $G^1$ is $R^{a4}S$;

(g) for a compound of formula (I) in which A-B is —NHC(O)—: coupling compounds of formula (VII):

(VII)

wherein J is NH$_2$, with an acid of formula (VIII):

(VIII)

wherein X is OH;

(h) for a compound of formula (I) in which A-B is —NHC(O)—: coupling an aniline of formula (VII) wherein J is —NH$_2$ with an activated acid derivative of formula (VIII);

(i) for a compound of formula (I) in which A-B is —NHC(O)— or —NHC(S)— and $R^4$ is hydroxy: reacting a compound of formula (IX):

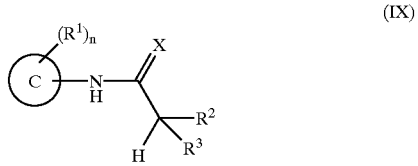
(IX)

wherein X is O or S: with a base to yield the dianion, followed by treatment of the dianion with oxygen in the presence of a reducing agent; or by treatment with a peroxyacid;

(j) for a compound of formula (I) in which A-B is —NHC(O)—: reacting a compound of formula (VII) wherein J is chloro or fluoro, with an alkali metal amide anion having formula (X):

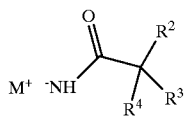

(X)

wherein M is an alkali metal;

(k) for a compound of formula (I) that contains no carbonyl moieties, $R^4$ is hydroxy and $R^2=R^3$: reacting a compound of formula (XI):

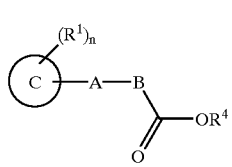

(XI)

wherein $R^4$ is $C_{1-4}$ alkyl, with a Grignard reagent of formula $R^2MgBr$ or $R^2MgCl$ or an organolithium reagent of formula $LiR^2$;

(l) for a compound of formula (I) that contains no carbonyl moieties and $R^4$ is hydroxy: reacting a compound of formula (XII):

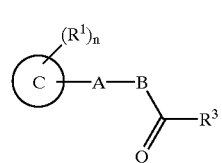

(XII)

with a compound of formula $R^2M$ wherein M is an alkali metal or a Grignard compound of formula $R^2MgBr$ or $R^2MgCl$;

(m) for a compound of formula (I) which has an N-linked sulphonamide, an N-linked N-alkyl sulphonamide or a sulphinate ester substituent attached to ring C: treating a corresponding compound of formula (XIII):

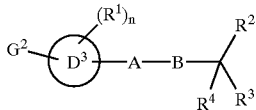

(XIII)

wherein ring $D^3$ has any of the values defined hereinbefore for ring C but in which the place of one of the possible substituents on ring C is taken by $G^2$ wherein $G^2$ is amino or hydroxy with a sulphonyl chloride;

(n) for a compound of formula (I) in which A-B is ethynylene and $R^4$ is not chloro and when $R^4$ is hydroxy it is protected: coupling a corresponding compound of formula (VII) wherein J is a leaving group, with a corresponding acetylene of formula (XIV):

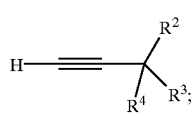

(XIV)

(o) for a compound of formula (I) in which A-B is ethynylene and $R^4$ is hydroxy: reacting a corresponding alkyne of formula (XV):

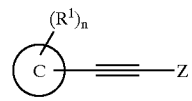

(XV)

wherein Z is hydrogen, with a base, followed by treatment with a ketone of formula (XVI):

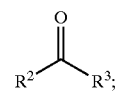

(XVI)

(p) for a compound of formula (I) in which A-B is trans-vinylene: reducing a corresponding compound of formula (I) in which A-B is ethynylene with a suitable reducing agent;

(q) for a compound of formula (I) in which A-B is trans-vinylene: dehydration of a compound of formula (XVII):

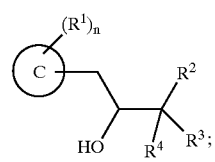

(XVII)

(r) for a compound of formula (I) in which A-B is trans-vinylene and $R^4$ is hydroxy: base catalysed opening of an epoxide of formula (XVIII):

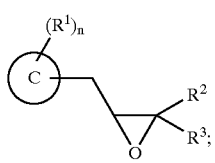

(XVIII)

(s) for a compound of formula (I) in which A-B is —NHCH$_2$—: reducing a corresponding compound of formula (I) in which A-B is —NHC(O)—;

(t) for a compound of formula (I) in which A-B is —OCH$_2$—, —SCH$_2$— or —NHCH$_2$: reacting an ethylene oxide of formula (XIX):

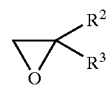

(XIX)

with a corresponding compound of formula (VII) where J is —OH, —SH or —NH$_2$;

(u) for a compound of formula (I) in which A-B is —NHC(S)—: reacting a compound of formula (I) in which A-B is —NHC(O)— with a sulphonating reagent;

(v) a compound of formula (I) in which ring C is substituted by ArC(O)— wherein Ar is an aromatic group (possible values as defined for formula (I) above) and A-B is —NHCO—: by acylation of a compound of formula (I);

w) for a compound of formula (I) in which A-B is —C(O)CH$_2$— and $R^4$ is hydroxy: reacting a ketone of formula (XX)

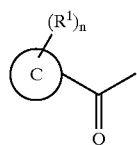
(XX)

with a strong base followed by reaction with a ketone of formula (XVI);

x) for a compound of formula (I) in which A-B is —C(O)CH$_2$— and R$^4$ is hydroxy: reaction of a compound of formula (XXI):

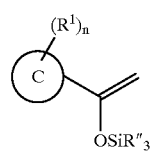
(XXI)

wherein R″ is a C$_{1-6}$alkyl group, with a ketone of formula (XVI);

y) for a compound of formula (I) in which A-B is —C(O)CH$_2$—: reaction of a compound of formula (VII) wherein J is Li with a compound of formula (XXII):

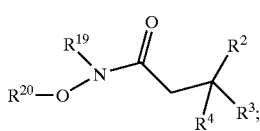
(XXII)

z) for a compound of formula (I) in which A-B is —C(O)CH$_2$—: reaction of a compound of formula (XXIII):

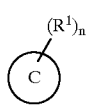
(XXIII)

with a compound of formula (XXIV):

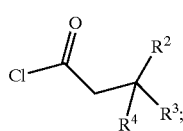
(XXIV)

a1) for compounds of formula (I) where Ring C has an PhS— substituent: treatment of a compound of formula (VI), wherein G$^1$ is a leaving group, with a thiophenol in the presence of a catalyst;

b1) for compounds of formula (I) where Ring C has an ArS— substituent wherein Ar as defined above: treating a compound of formula (VI), wherein G$^1$ is SH with an aromatic compound containing a displaceable group, in the presence of a catalyst;

c1) for compounds of formula (I) where Ring C has an ArS— substituent wherein Ar is as defined above and A-B is not NHCO: treating a compound of formula (VI), wherein G$^1$ is a leaving group with a compound of formula ArSH in the presence of a base;

d1) for compounds of formula (I) where ring C has a R$^{a2}$—NC(O)— substituent wherein R$^{a2}$ is a group that is attached through an amide linker (possible values as defined above): treating a compound of formula (VI) wherein ring D$^3$ has any of the values defined hereinbefore for ring C but in which the place of one of the possible substituents on ring C is taken by G$^1$ and G$^1$ is a leaving group; with carbon monoxide and an amine having the formula —NR$^{a2}$; and e1) for compounds of formula (I) where ring C has a R$^{a2}$—OSO$_2$— substituent wherein R$^{a2}$ is a group that is attached through a sulphinate ester linker (possible values as defined above): treating a compound of formula (VI) wherein ring D$^3$ has any of the values defined hereinbefore for ring C but in which the place of one of the possible substituents on ring C is taken by G$^1$ and G$^1$ is a sulphonyl chloride ClO$_2$S—; with an alcohol having the formula —OR$^{a2}$; and thereafter if necessary:

i) converting a compound of the formula (I) into another compound of the formula (I);
ii) removing any protecting groups; or
iii) forming a pharmaceutically acceptable salt or in vivo hydrolysable ester.

Examples of reactions to convert a compound of the formula (I) into another compound of the formula (I) are known in the art. By way of illustration these include:

(i) formation of a hydroxy as a substituent on an aryl or heteroaryl group by cleaving the corresponding alkyl ether or acyloxy ester. Convenient methods include, for example, the cleavage of a methoxy group using boron tribromide and the cleavage of a tert-butoxy group using trifluoroacetic acid; and the cleavage of an acetate group using for example lithium hydroxide in a lower alcohol (such as for example methanol or ethanol);

(ii) formation of R$^4$ as hydroxy. For example, a compound of formula (I) where R$^4$ is chloro can be prepared by reaction of a compound of formula (I) in which R$^4$ is hydroxy with a reagent such as thionyl chloride in a suitable solvent such as dichloromethane or tetrahydrofuran and at a temperature in the range of 0 to 70° C. The reaction can optionally be carried out in the presence of a catalyst such as N,N-dimethylformamide.

Pg is an alcohol protecting group suitable values for Pg are groups such as a benzyl groups, silyl groups or a acetyl protecting groups.

When G$^1$ is a leaving group suitable values are bromo, iodo or triflate.

Where formula (VIII) is an activated acid derivative, suitable values for X include halo (for example chloro or bromo), anhydrides and aryloxys (for example phenoxy or pentafluorophenoxy).

In formula (X) M is an alkali metal, suitable values for M include sodium or lithium. Suitable values for M in formula (XII) include lithium.

In formula (VII) wherein J is a leaving group suitable values are bromo, iodo or triflate.

Specific conditions of the above reactions are as follows:

(a) Examples of suitable reagents for deprotecting an alcohol of formula (II) are:
1) when Pg is benzyl:
  (i) hydrogen in the presence of palladium/carbon catalyst, i.e. hydrogenolysis: or
  (ii) hydrogen bromide or hydrogen iodide;
2) when Pg is a silyl protecting group:
  (i) tetrabutylammonium fluoride; or
  (ii) aqueous hydrofluoric acid;
3) when Pg is acetyl:
  i) mild aqueous base for example lithium hydroxide.

The reaction can be conducted in a suitable solvent such as ethanol, methanol, acetonitrile, or dimethylsulphoxide and may conveniently be performed at a temperature in the range of −40 to 100° C.

(b) These conditions are well known in the art for example suitable oxidising agents such as pyridinium dichromate and solvents such as methanol or dichloromethane, may be employed.

(c) A saturated aqueous acid such as oxalic or a mineral acid such as hydrochloric acid or sulphuric acid may conveniently be employed for this deprotection. The reaction may conveniently be performed at a temperature in the range of 0 to 100° C. in a solvent such as a lower alcohol (e.g. methanol or ethanol), or mixtures of solvent pairs such as water/dichloromethane, water/tetrahydrofuran or water/acetone.

(d) Reducing agents such as sodium borohydride (for compounds of formula (V) yielding compounds of formula (III)) and triethylsilane (for compounds of formula (III)) may be used. A reduction involving sodium borohydride is conveniently carried out in solvents such as for example a lower alcohol (e.g. methanol or ethanol) and a reduction using triethylsilane is conveniently carried out in a solvent such as trifluoromethylsulphonic acid.

(e) This reaction with the tin compound is conveniently performed in the presence of a suitable catalyst such as for example bis(triphenylphosphine)palladium dichloride, and at a temperature in the range of 0 to 100° C. and in a solvent such as for example tetrahydrofuran, 1,3-dimethyl-3,4,5,6-tetrahydro-2(1H)-pyrimidinone, or dimethyl sulphoxide. The reaction with the aluminium compound is conveniently performed in the presence of a similar catalyst and temperature and in a solvent such as for example diethyl ether, benzene, toluene, or tetrahydrofuran.

(f) Suitable oxidising agents include potassium permanganate, OXONE, sodium periodate, tert-butyl hydroperoxide (as solution in toluene), peracids (such as for example 3-chloroperoxybenzoic acid), hydrogen peroxide, TPAP (tetrapropylammonium perruthenate) or oxygen. The reaction may be conducted in a suitable solvent such as diethyl ether, dichloromethane, methanol, ethanol, water, acetic acid, or mixtures of two or more of these solvents. The reaction may conveniently be performed at a temperature in the range of −40 to 100° C.

(g) The reaction can be conducted in the presence of a suitable coupling reagent. Standard peptide coupling reagents known in the art can be employed as suitable coupling reagents, for example dicyclohexyl-carbodiimide, optionally in the presence of a catalyst such as dimethylaminopyridine or 4-pyrrolidinopyridine, optionally in the presence of a base for example triethylamine, pyridine, or 2,6-di-alkyl-pyridines (such as 2,6-lutidine or 2,6-di-tert-butylpyridine) or 2,6-diphenylpyridine. Suitable solvents include dimethylacetamide, dichloromethane, benzene, tetrahydrofuran, and dimethylformamide. The coupling reaction may conveniently be performed at a temperature in the range of −40 to 40° C.

(h) This coupling may be achieved optionally in the presence of a base for example triethylamine, pyridine, 2,6-di-alkyl-pyridines (such as 2,6-lutidine or 2,6-di-tert-butylpyridine) or 2,6-diphenylpyridine. Suitable solvents include dimethylacetamide, dichloromethane, benzene, tetrahydrofuran, and dimethylformamide. The coupling reaction may conveniently be performed at a temperature in the range of −40 to 40° C.

(i) Suitable bases to yield a dianion are strong bases such as a lithium dialkylamides (for example lithium diisopropyl amide). Suitable reducing agents include triphenylphosphine. Suitable peroxyacids include 3-chloroperoxybenzoic acid. The reactions may conveniently be performed at a temperature in the range of −100° C. to room temperature, in a suitable solvent such as tetrahydrofuran or diethyl ether.

(j) The reaction may conveniently be performed at a temperature in the range of −40 to 100° C. and in a suitable solvent such as dimethylformamide, DMSO, or tetrahydrofuran. Where $R^4$ is hydroxy the corresponding dianion is formed.

(k) The reaction may conveniently be performed at a temperature in the range of −100 to 20° C., preferably at a temperature in the range of −20 to 20° C., in a suitable solvent such as tetrahydrofuran or diethyl ether.

(l) The reaction may conveniently be performed at a temperature in the range of −100 to 25° C. and in a solvent such as tetrahydrofuran, diethyl ether, or 1,2-dimethoxyethane.

(m) The reaction may be conveniently carried out in the presence of a base such as for example pyridine, triethylamine or potassium carbonate, at a temperature in the range of 0 to 120° C. in a suitable solvent such as for example N,N-dimethylformamide, or acetonitrile. For N-linked N-alkylsulphonamides this is followed by alkylation with, for example, an alkyl iodide or bromide. The alkylation reaction may conveniently be performed at a temperature in the range of 0 to 120° C. in a suitable solvent such as for example N,N-dimethylformamide, or acetone in the presence of a base such as for example potassium carbonate.

(n) The reaction may be conveniently carried out in the presence of a catalyst such as a combination of cuprous iodide and bis(triphenyl-phosphine)palladium dichloride or palladium (II) acetate. The reaction can be conducted in an inert solvent such as tetrahydrofuran, benzene, or toluene, or in a basic solvent such as diethylamine (DEA) or triethylamine (TEA), and at a temperature in the range of −20 to 110° C.

(o) Suitable bases include lithium diisopropylamide (LDA), n-butyllithium or tert-butyllithium. The reaction may be performed at a temperature in the range of −100 to −40° C. preferably at a temperature in the range of −70 to −40° C. and in a solvent such as tetrahydrofuran, diethyl ether, or 1,2-dimethoxyethane.

(p) Suitable reducing agents are, for example, lithium aluminium hydride or sodium bis(methoxyethoxy) aluminium hydride. The reaction can be conducted in a suitable solvent such as tetrahydrofuran or diethyl ether, and at a temperature in the range of 0 to 50° C.

(q) This reaction may be conveniently performed in the presence of an acid catalyst (for example p-toluenesulphonic acid), in a solvent such as toluene or dichloromethane at a temperature in the range of 0 to 200° C. preferably a temperature in the range of 20 to 100° C.

(r) The opening may be carried out in a suitable organic solvent for example, ethers or toluene. Ethers such as tetrahydrofuran are preferred. Suitable bases include potassium tert-butoxide or sodium hydride. The opening may be carried out at a temperature in the range of −50 to 100° C., preferably at a temperature in the range of 0 to 50° C.

(s) Suitable reducing agent include lithium aluminium hydride or borane. The reaction can conveniently be carried out at a temperature in the range of 0° C. to reflux, in solvents such as for example diethyl ether, tetrahydrofuran, or 1,2-dimethoxyethane.

(t) Where J is —OH or —SH; the reaction may be conveniently carried out in the presence of a base for example sodium hydride or triethylamine. The reaction can be conducted at a temperature of 0° C. to reflux in a solvent such as dichloromethane, tetrahydrofuran, or diethyl ether. Where J is —NH$_2$; the reaction may be conveniently carried out by the procedure as described in JOC (1999), 64, p. 287–289 using copper (I) triflate as a catalyst.

(u) Suitable sulphonating reagents are for example phosphorus pentasulphide or Lawesson's reagent (2,4-bis(4-methoxyphenyl)-1,3-dithia-2,4-diphosphetane-2,4-disulphide). The reaction may optionally be carried out in the presence of a suitable base such as for example pyridine or triethylamine. Suitable solvents for the reaction include for example toluene, tetrahydrofuran, 1,3-dioxane or acetonitrile. The reaction is conveniently performed at a temperature in the range of from 0° C. to reflux.

(v) Acylating reagents such as carboxylic acids, or derivatives thereof, may be employed in the presence of the appropriate activating reagent such as for example polyphosphoric acid. The reaction may conveniently be performed at a temperature in the range of 0 to 200° C. employing a solvent such as N,N-dimethylformamide, 1,3-dimethyl-3,4,5,6-tetra-hydro-2(1H)-pyrimidinone, DMSO, or ethylene glycol if required, followed by (2) the formation of an amide as described in (g) or (h) hereinbefore (Staskum, B., J. Org. Chem. (1964), 29, 2856–2860; Ohnmacht C., J. Med. Chem. (1996), 39, 4592–4601).

(w) suitable strong bases are for example:
i) sodium hydride in a suitable solvent such as tetrahydrofuran or N,N-dimethylformamide. The reaction is conveniently performed at a temperature in the range of from −78° C. to 25° C.
ii) lithium diisopropylamide in a suitable solvent such as tetrahydrofuran. The reaction is conveniently performed at a temperature in the range of from −78 to 25° C.

(x) R" is preferably methyl. This reaction may be carried out in the presence of a Lewis acid such as titanium tetrachloride in a suitable solvent such as dichloromethane. This reaction is conveniently performed at a temperature in the range of −78 to 50° C.

(y) This reaction is preferably carried out in a suitable solvent, for example tetrahydrofuran at a temperature of −78 to 100° C.

(z) This reaction is conveniently performed under standard Friedel Crafts conditions, for example in the presence of aluminium trichloride in a solvent such as dichloromethane or nitrobenzene at a temperature of 0 to 150° C.

a1) Suitable catalysts include tetrakis(triphenylphosphine)palladium(0), cuprous chloride or a stoichiometric amount of cuprous oxide. The reaction may conveniently be conducted in a suitable inert solvent such as a lower alcohol, a mixture of pyridine and quinoline, dimethylformamide, N-methylpyrrolidinone or toluene and optionally in the presence of a base such as for example sodium methoxide or potassium carbonate.

b1) Suitable displaceable groups include halo or triflate. Suitable catalysts include tetrakis(triphenylphosphine)palladium(0), cuprous chloride or a stoichiometric amount of cuprous oxide. The reaction may conveniently be conducted in a suitable inert solvent such as a lower alcohol or a mixture of pyridine and quinoline or N-methylpyrrolidinone or dimethylformamide and in the presence of a base such as for example sodium methoxide if required at a temperature of 25–180° C.

c1) A suitable leaving group is fluoro. A suitable base is potassium carbonate. The reaction may conveniently be performed at a temperature in the range of 30 to 200° C. and in a solvent such as N,N-dimethylformamide, 1,3-dimethyl-3,4,5,6-tetra-hydro-2(1H)-pyrimidinone, DMSO, or ethylene glycol.

d1) This reaction with an amine is conveniently performed in the presence of a suitable catalyst such as for example bis(triphenylphosphine)palladium dichloride or dichlorobis-(triphenylphosphine) palladium(II), and at a temperature in the range of 0° C. to reflux and in a solvent such as for example tetrahydrofuran, 1,3-dimethyl-3,4,5,6-tetrahydro-2(1H)-pyrimidinone, dimethyl sulphoxide or using an amine as the required solvent such as for example tributylamine.

e2) The reaction may be conveniently carried out in the presence of a base such as for example pyridine, triethylamine or potassium carbonate, at a temperature in the range of 0 to 120° C. in a suitable solvent such as for example dichloromethane, diethyl ether, N,N-dimethylformamide, or acetonitrile.

If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples.

For example, it will be appreciated that certain of the optional aromatic substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acylhalide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by, for example, catalytic hydrogenation with a nickel catalyst or treatment with iron in the presence of hydrochloric acid with heating; oxidation of alkylthio to alkylsulphinyl or alkylsulphonyl using, for example, hydrogen peroxide in acetic acid with heating or 3-chloroperoxybenzoic acid.

Specific examples of the techniques used to make the starting materials described above are illustrated, but not limited by, the following examples in which variable groups are as defined for formula (I) unless otherwise stated.

1) Preparation of Compounds of Formula (II)
a) compounds of formula (II) in which A-B is —OCH$_2$—, —SCH$_2$— or —NHCH$_2$—may be made by treating the corresponding compound of formula (VII) wherein J is —OH, —SH or —NH$_2$ with a compound of formula (XXV):

where Z is a leaving group for example mesylate; in the presence of a base such as an alkali metal hydride (e.g. sodium hydride), in a solvent such as tetrahydrofuran, dimethyl sulphoxide, N,N-dimethylformamide or 1,3-Dimethyl-3,4,5,6-tetrahydro-2(1H)-pyrimidinone, and at a temperature of room temperature to reflux.

A compound of formula (XXV), wherein Z is mesylate may be prepared by reacting a compound of formula (XXV) wherein Z is OH with methanesulphonyl chloride in the presence of a base such as triethylamine, in a solvent such as dichloromethane, and at a temperature of about −78 to 25° C.

Compounds of formula (XXV) wherein Z is OH are prepared by reducing a compound of formula (VIII) wherein X is OH and R$^4$ is a protected hydroxy group or a compound of formula (XXVI):

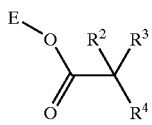

where E is a carboxy protecting group (e.g. Me) and R$^4$ is a protected hydroxy group with a suitable reducing agent such as lithium aluminium hydride in a solvent such as diethyl ether or tetrahydrofuran and at a temperature of about 0 to about 25° C.

b) A compound of formula (II), wherein A-B is —NHC(O)—, may be made by coupling a compound of formula (VII) wherein J is —NH$_2$ with a compound of formula (VIII) wherein X is OH and R$^4$ is a protected hydroxy group in a manner analogous to that described for procedure (g) or (h) of preparations of a compound of formula (I) hereinabove. Compounds of formula (VIII) wherein X is OH and R$^4$ is a protected hydroxy group may be made by conventional procedures. For example, cleavage of the ester group of a compound of formula (XXVI) where E is a carboxy protecting group (e.g. Me), under standard conditions such as mild alkaline conditions, for example, aqueous lithium hydroxide.

Compounds of formula (XXVI) where R$^4$ is protected hydroxy may be prepared by protecting a compound of formula (XXVI) where R$^4$ is hydroxy by reaction with a compound such as benzyl chloride or benzyl bromide (in the presence of a suitable base such as sodium hydride and optionally with a catalyst such as sodium or ammonium iodide, to provide a benzyl protecting group) or any of the conventional silylating agents known and used for such purpose (for example 2-trimethylsilylethoxymethyl chloride, in the presence of a suitable base such as triethylamine optionally in the presence of a catalyst such as N,N-dimethylaminopyridine).

Compounds of formula (XXVI) where R$^4$ is hydroxy are prepared by esterifying an acid of formula (VIII) wherein X is OH by a conventional esterification procedure such as reaction with a C$_{1-6}$alcohol (e.g. methanol) in the presence of an acid catalyst (for example sulphuric acid).

c) A compound of formula (II), wherein A-B is ethynylene, may be made by reacting a compound of formula (VII) wherein J is a leaving group such as bromo, iodo, or triflate, with an acetylene of formula (XXVII)

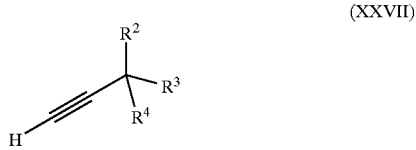

wherein if R$^4$ is protected hydroxy in the presence of a catalyst such as a combination of copper (I) iodide and bis(triphenylphosphine)palladium dichloride or palladium (II) acetate. The reaction can be conducted in an inert solvent such as tetrahydrofuran, benzene, or toluene, or in a basic solvent such as diethylamine or triethylamine, and at a temperature in the range of −20 to 110° C.

A compound of formula (XXVII) wherein R$^4$ is a protected hydroxy group may be made by reacting a compound of formula (XXVII) where R$^4$ is OH with a conventional hydroxy protecting group reagent such as those described herein before and herein after.

d) A compound of formula (II), wherein A-B is trans-vinylene, may be made by reacting a compound of formula (XXVIII):

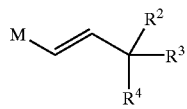

where M is an alkylmetal group such as a trialkyltin (for example tributyl- or trimethyl-tin) or a bisalkyloxyborane (for example catecholborane) and R$^4$ is protected hydroxy with a compound of formula (VII), wherein J is a leaving group for example iodide, bromide or triflate in the presence of a catalyst such as bis(triphenylphosphine)palladium dichloride or tetrakis(triphenylphosphine)palladium (0). The reaction may conveniently be conducted in a suitable inert solvent such as a tetrahydrofuran or dimethylformamide at a temperature of 0–150° C. under an inert atmosphere.

A compound of formula (XXVIII) may be made by a reaction of a compound of formula (XXVII)
i) with an agent such as catecholborane, to form the vinylborane compound of formula (XXVIII) where M is catecholborane; or
ii) a trialkyltinhydride in the presence of a catalytic amount of a radical chain initiator such as, for example, aza-bis-isobutyronitrile or by using trialkyltinhydride pre-treated with a strong base (such as an alkyllithium) and copper (I) cyanide, or by using a transition metal catalyst such as, for example, tetrakis(triphenylphosphine)palladium(0) to form a compound of formula (XXVIII) where M is trialkyltin.

These reactions may conveniently be conducted in a suitable inert solvent such as tetrahydrofuran, toluene or xylene at a temperature of from 0–150° C. under an inert atmosphere.

Compounds of formula (XXVII) may be made by reacting a compound of formula (XVI) with an alkali metal acetylide (for example lithium acetylide) or alkaline earth metal acetylide (for example magnesium acetylide). The reaction may be conducted in a solvent such as tetrahydrofuran, diethyl ether, or 1,2-dimethoxyethane and at a temperature of −100 to 25° C.

2) Preparation of a Compound of Formula (IV):

a) A compound of formula (IV), wherein A-B is ethynylene and $R^4$ is OH, may be made by reacting a corresponding compound of formula (XXIX):

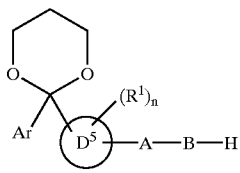

(XXIX)

wherein ring $D^5$ has any of the values defined hereinbefore for ring C but in which the place of one of the possible substituents on ring C is taken by Ar(—C—O—(CH$_2$)$_3$—O—)— with a base such as an alkyllithium (for example, butyllithium) followed by addition of a ketone having the formula (XVI). The reaction may be conducted at a temperature of from about −100 to about −40° C. and in a solvent such as tetrahydrofaran, dimethyl ether, or 1,2-dimethoxyethane.

b) A compound of formula (IV), wherein A-B is trans-vinylene, may be made by reducing a corresponding compound of formula (IV), wherein A-B is ethynylene, with a suitable reducing agent such as lithium aluminium hydride or sodium bis(2-methoxyethoxy)aluminium, in a solvent such as tetrahydrofuran. The reaction may be conducted at a temperature of from about −40 to about 40° C.

c) a compound of formula (XXIX) may be made by treating the corresponding ketone with 1,3-propanediol in the presence of an acid catalyst such as p-toluenesulphonic acid (TsOH) and in a refluxing solvent such as toluene using a Dean Stark apparatus or dried Molecular Sives.

3) Preparation of a Compound of Formula (VI):

a) A compound of formula (VI) wherein $G^1$ is halo, such as for example bromo or iodo may be made by (1) treating a corresponding compound of formula (VI), wherein $G^1$ is nitro, with a reducing agent such as tin(II)chloride, in the presence of an aqueous acid such as acetic acid to obtain the corresponding amine, followed by (2) treating the amine with a combination of nitric acid and sulphuric acid or tert-butyl nitrite to effect diazotization, and thereafter (3) treating the diazotized compound with a corresponding copper(I)halide such as for example cuprous bromide or potassium iodide.

b) A compound of formula (VI), wherein $G^1$ is SH can be made by:

(1) coupling of a compound of formula (VI) wherein $G^1$ is a leaving group such as halo or triflate with triisopropylsilanethiolate under palladium catalysis as described by Arnould et. al. in Tet. Let. (1996), 37 (26), p. 4523, followed by deprotection with tetrabutylammonium fluoride in a solvent such as tetrahydrofuran at a temperature of −78 to about 25° C.; or (2) by Pummerer rearrangement as described in Tet. Let. (1984), 25 (17), p. 1753 of a compound of formula (VI) wherein $G^1$ is CH$_3$S(O)—, which can be made from a compound of formula (VI) wherein $G^1$ is a leaving group such as halo of triflate, using a palladium catalysed coupling with methanethiol as described for example in Zheng et. al. in J. Org. Chem. (1998), 63, p. 9606 followed by an oxidation of the resulting sulphide to the corresponding sulphoxide using, for example, tert-butyl hydroperoxide as oxidant; or (3) reduction of a compound of formula (VI), wherein $G^1$ is SO$_2$Cl, by reducing the sulphonyl chloride using a small excess of for example triphenylphosphine in a solvent such as, for example, dichloromethane in the presence of a catalyst such as, for example, dimethylformamide, followed by an acidic workup.

c) a compound of formula (VI), wherein $G^1$ is SO$_2$Cl can be made by treatment with chlorosulphonic acid of a compound of formula (VI), wherein $G^1$ is H, under standard conditions.

4) Preparation of Compounds of Formula (XII).

A compound of formula (XII), wherein A-B is ethynylene, may be made by treating a corresponding compound of formula (XV) wherein Z is a protecting group such as, for example, trimethylsilyl with a fluoride base (for example, tetrabutylammonium fluoride (TBAF)) and an acid chloride of formula $R^3$—CO—Cl, thereby making the desired compound.

5) Preparation of Compounds of Formula (VII).

A compound of formula (VII), wherein J is halo, may be made by treating a corresponding compound of formula (VII), wherein J is nitro, with (1) as tin (II) chloride or (2) iron dust and concentrated hydrochloric acid in 95% ethanol to reduce the nitro group and thereby form the corresponding amine; (2) the amine may then be treated for example with a nitrite (such as tert-butyl nitrite or sodium nitrite in the presence of a mineral acid) to form the corresponding diazonium salt which may in turn be treated with a copper(I) salt (such as copper(I)bromide or copper(I)chloride) or potassium iodide. The diazotization and displacement reactions may be conducted in a solvent such as acetonitrile and at a temperature of from 0 to 25° C.

6) Preparation of Compounds of Formula (XIV).

A compound of formula (XIV) wherein $R^4$ is OH may be made by reacting a corresponding ketone having the formula (XVI) with an alkali metal acetylide (for example lithium acetylide) or alkaline earth metal acetylide (for example magnesium acetylide). The reaction may be conducted in a solvent such as tetrahydrofuran, diethyl ether, or 1,2-dimethoxyethane and at a temperature of about −100 to about 25° C.

7) Preparation of Compounds of Formula (XIII).

A compound of formula (XIII), wherein $G^2$ is amino and A-B is NHCO may be made by treating a compound of formula (XIII), wherein $G^2$ is nitro, under standard conditions for example by a reducing agent such as tin (II) chloride or iron dust in conjunction with concentrated acid, or using palladium metal supported on charcoal and hydrogen gas in a solvent such as a lower alcohol (methanol or ethanol) or ethyl acetate.

8) Preparation of Compounds of Formula (VII).

i) a compound of formula (VII) wherein $R^1$ is ortho-halo or ortho-hydroxy and J is —NH$_2$, may be made by treatment of a compound of formula (XXX):

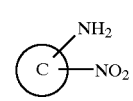

(XXX)

wherein the amino group is in a position ortho to the nitro group, with (1) a combination of nitric acid and sulphuric acid or tert-butyl nitrite to effect diazotization, and thereafter (2) treating the diazotized compound with a corresponding copper (I) halide such as for example cuprous bromide or chloride, or heating in dilute sulphuric acid to form the corresponding phenol, followed by (3) reduction of the nitro group (see 8) ii) or 7)). The diazotization and displacement reactions may be conducted in a solvent such as acetonitrile and at a temperature of from 0–25° C. A compound of formula (XXX) may be made for example according to procedures similar to those described in J. Med. Chem., (1975), 18, 1164.

ii) a compound of formula (VII) wherein J is $NH_2$ may be prepared by reducing a compound of formula (XXXI):

(XXXI)

under standard conditions for example by a reducing agent such as tin (II) chloride or iron dust in conjunction with concentrated acid, or using palladium metal supported on charcoal and hydrogen gas in a solvent such as a lower alcohol (methanol or ethanol) or ethyl acetate.

iii) a compound of formula (VII) wherein J is $NH_2$, $R^1$ is —$NO_2$ and ring C is substituted by $ArSO_2$: reacting a compound of formula (XXXII):

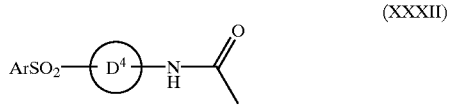

(XXXII)

wherein ring $D^4$ has any of the values defined hereinbefore for ring C but in which the place of one of the possible substituents on ring C is taken by $ArSO_2$, with nitric acid, followed by treating the nitrated compound under mild alkaline conditions (i.e. employing a base such as lithium hydroxide) to cleave the acetate group to yield the amine.

iv) a compound of formula (VII) wherein J is —OH, may be prepared by diazotizing a compound of formula (VII) wherein J is —$NH_2$ under standard conditions followed by heating the resulting compound in dilute sulphuric acid.

v) a compound of formula (VII), wherein J is —SH, may be prepared by reacting a compound of formula (VII) where J is a leaving group (for example fluoro or chloro) with an excess of methanethiol in the presence of sodium hydride.

vi) a compounds of formula (VII) wherein J is Li may be prepared by a) halogen metal exchange. For example by treatment of a compound of formula (VII) wherein J is Br or I; with an organolithium reagent such as n-butyl lithium or t-butyllithium in a solvent such as tetrahydrofuran at low temperature such as −100–−50° C.

b) for compounds where $R^1$ is an ortho directing metallating substituent by treatment of a compound of formula (XXIII) with an alkyl lithium base. Reactions of this type are reviewed in V. Snieckus, Chem Rev, 1990, 90, 879–933.

9) Resolution of Compounds of Formula (VIII) wherein X is OH.

If the resolved acid is required it may be prepared by any of the known methods for preparation of optically-active forms (for example, by recrystallization of the chiral salt {for example WO 9738124}, by enzymatic resolution, by biotransformation, or by chromatographic separation using a chiral stationary phase). For example if an (R)-(+) resolved acid is required it may be prepared by the method of Scheme 2 in World Patent Application Publication No. WO 9738124 for preparation of the (S)-(−) acid, i.e. using the classical resolution method described in European Patent Application Publication No. EP 0524781, also for preparation of the (S)-(−) acid, except that (1S,2R)-norephedrine may be used in place of (S)-(−)-1-phenylethylamine.

10) Preparation of Compounds of Formula (XV).

A compound of formula (XV) wherein Z is H, may be prepared by reacting a compound of formula (VII), wherein J is a leaving group such as bromo, iodo or triflate with trimethylsilylacetylene in the presence of a catalyst such as a combination of bis(triphenylphosphine)palladium dichloride and copper(I) iodide in diethylamine or triethylamine, followed by treatment with a base (for example potassium carbonate) in a $C_{1-6}$alcohol (such as methanol) as the solvent to remove the trimethylsilyl group.

11) Preparation of Compounds of Formula (XVII).

A compound of formula (XVII) may be prepared from a compound of formula (XXXIII):

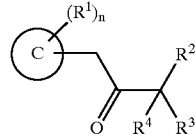

(XXXIII)

by reduction under standard conditions for example by using a hydride, such as sodium borohydride.

A compound of formula (XXXIII) may be prepared by deprotonation of a compound of formula (VII) where J is Me, with a strong base, for example lithium diisopropyl amide in an organic solvent, for example tetrahydrofuran at a temperature of −78 to 100° C. followed by addition of an amide of formula (XXXIV):

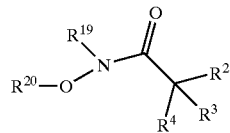

(XXXIV)

in which $R^{19}$ and $R^{20}$ are each independently $C_{1-6}$alkyl, preferably methyl, or together with the atoms to which they are attached form a 5–7 membered ring.

An amide of formula (XXXIV) may be prepared from an acid of formula (VIII), or a reactive derivative thereof, by reaction with a hydroxyamine of formula $R^{19}(R^{20}O)NH$ under standard conditions such as those described in process (g) or (h) for preparation of a compound of formula (I) hereinabove.

12) Preparation of Compounds of Formula (XVIII).

A compound of formula (XVIII) may be prepared from a diol of formula (XXXV):

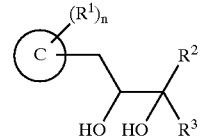

(XXXV)

using a suitable dehydrating agent, for example bis[α,α-bis (trifluoromethyl)benzene methanolato]diphenyl sulphur.

13) Preparation of Compounds of Formula (XIX).

A compound of formula (XIX) may be made by treating a compound of formula (XVI) with a trimethylsulphonium salt (such as trimethylsulphonium iodide) and a base (such as an alkali metal hydroxide) in a solvent such as dichloromethane.

14) Preparation of Compounds of Formula (XX).

Compounds of formula (XX) can be made by synthetic reactions well known in the art for example:
i) a Friedel Crafts acylation of a compound of formula (XXIII) with acetyl chloride under conditions such as those described in (z) above.
ii) reaction of a compound of formula (VII) wherein J is Li with an amide of formula (XXXVI):

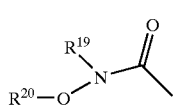

(XXXVI)

under conditions such as those described in 8)vi)b) hereinabove.

iii) oxidation of a compound of formula (XXXVII):

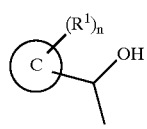

(XXXVII)

15) Preparation of Compounds of Formula (XXI).

Compounds of formula (XXI) can be prepared from compounds of formula (XX) by treatment with a base such as lithium diisopropylamide or triethylamine and a silylating agent such as trimethylsilyl chloride in a solvent such as tetrahydrofuran or trimethylsilyl triflate in a solvent such as dichloromethane. The reaction can conveniently be performed at a temperature in the range of −78 to 70° C.

16) Preparation of Compounds of Formula (XXII).

Compounds of formula (XXII) can be prepared from an acid of formula (XXXVIII):

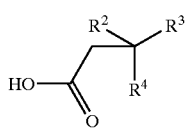

(XXXVIII)

or a reactive derivative thereof, by reaction with a hydroxyamine of formula $R^{19}(R^{20}O)NH$ under standard conditions such as those described in process (g) or (h) for preparation of a compound of formula (I) hereinabove.

According to a further feature of the invention, there is provided a process for preparing a compound of formula (I') using any one of processes a), f), g), h), i) or l); and thereafter if necessary:
i) converting a compound of the formula (I') into another compound of the formula (I');
ii) removing any protecting groups; or
iii) forming a pharmaceutically acceptable salt or in vivo cleavable ester.

It is noted that many of the starting materials for synthetic methods as described above are commercially available and/or widely reported in the scientific literature, or could be made from commercially available compounds using adaptations of processes reported in the scientific literature.

It will also be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a phenol is, for example, an alkylether, for example, methyl, a silyl ether, for example, trimethylsilyl ether or t-butyldimethylsilyl ether, an oxyalkylether, for example, methoxymethyl ether or methoxyethoxymethyl ether or an ester, for example acetate or benzoate. The deprotection conditions for the above protecting groups will necessarily vary with the choice of protecting group. Thus, for example, an alkylether may be removed by treatment with a suitable reagent such as iodotrimethylsilane or a suitable Lewis acid such as borontribromide. Alternatively a silyl ether may be removed by acid- or fluoride ion-catalysed hydrolysis. Alternatively oxyalkylethers may be removed by treatment with a suitable acid such as acetic acid or hydrochloric acid. Alternatively esters may be removed by hydrolysis by a suitable acid or a suitable base.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

In cases where compounds of formula (I) are sufficiently basic or acidic to form stable acid or basic salts, administration of the compound as a salt may be appropriate, and pharmaceutically acceptable salts may be made by conventional methods such as those described following. Examples of suitable pharmaceutically acceptable salts are organic acid addition salts formed with acids which form a physiologically acceptable anion, for example, tosylate, methanesulphonate, acetate, tartrate, citrate, succinate, benzoate, ascorbate, α-ketoglutarate, and α-glycerophosphate. Suitable inorganic salts may also be formed such as sulphate, nitrate, and hydrochloride.

Pharmaceutically acceptable salts may be obtained using standard procedures well known in the art, for example by reacting a sufficiently basic compound of formula (I) (or its ester) with a suitable acid affording a physiologically acceptable anion. It is also possible with most compounds of the invention to make a corresponding alkali metal (e.g., sodium, potassium, or lithium) or alkaline earth metal (e.g., calcium) salt by treating a compound of formula (I) (and in some cases the ester) with one equivalent of an alkali metal or alkaline earth metal hydroxide or alkoxide (e.g. the ethoxide or methoxide in aqueous medium followed by conventional purification techniques.

In vivo cleavable esters of compounds of the invention may be made by coupling with a pharmaceutically acceptable carboxylic acid or an activated derivative thereof. For example, the coupling may be carried out by treating a compound of formula (I) with an appropriate acid chloride (for example, acetyl chloride, propionyl chloride, or benzoyl chloride) or acid anhydride (for example, acetic anhydride, propionic anhydride, or benzoic anhydride) in the presence of a suitable base such as triethylamine. Those skilled in the art will appreciate that other suitable carboxylic acids (including their activated derivatives) for the formation of in vivo cleavable esters are known to the art and these are also intended to be included within the scope of the invention. Catalysts such as 4-dimethylaminopyridine may also be usefully employed.

Many of the intermediates defined herein are novel and these are provided as a further feature of the invention.

The identification of compounds which elevate PDH activity is the subject of the present invention. These properties may be assessed, for example, using one or more of the procedures set out below:

(a) In Vitro Elevation of PDH Activity

This assay determines the ability of a test compound to elevate PDH activity. cDNA encoding PDH kinase may be obtained by Polymerase Chain Reaction (PCR) and subsequent cloning. This may be expressed in a suitable expression system to obtain polypeptide with PDH kinase activity. For example rat PDHkinaseII (rPDHKII) obtained by expression of recombinant protein in Escherichia coli (E. Coli), was found to display PDH kinase activity.

In the case of the rPDHKII (Genbank accession number U10357) a 1.3 kb fragment encoding the protein was isolated by PCR from rat liver cDNA and cloned into a vector (for example pQE32—Quiagen Ltd.). The recombinant construct was transformed into E. coli (for example M15pRep4—Quiagen Ltd.). Recombinant clones were identified, plasmid DNA was isolated and subjected to DNA sequence analysis. One clone which had the expected nucleic acid sequence was selected for the expression work. Details of the methods for the assembly of recombinant DNA molecules and the expression of recombinant proteins in bacterial systems can be found in standard texts for example Sambrook et al, 1989, Molecular Cloning—A Laboratory Manual, $2^{nd}$ edition, Cold Spring Harbour Laboratory Press. Other known PDH kinases for use in assays, may be cloned and expressed in a similar manner.

For expression of rPDHKII activity, E. coli strain M15pRep4 cells were transformed with the pQE32 vector containing rPDHKII cDNA. This vector incorporates a 6-His tag onto the protein at its N-terminus. E. coli were grown to an optical density of 0.6 (600 nM) and protein expression was induced by the addition of 10 μM isopropylthio-β-galactosidase. Cells were grown for 18 hours at 18° C. and harvested by centrifugation. The resuspended cell paste was lysed by homogenisation and insoluble material removed by centrifugation at 24000×g for 1 hour. The 6-His tagged protein was removed from the supernatant using a nickel chelating nitrilotriacetic acid resin (Ni—NTA: Quiagen Ltd.) matrix (Quiagen) which was washed with 20 mM tris(hydroxymethyl)aminomethane-hydrogen chloride, 20 mM imidazole, 0.5 M sodium chloride pH 8.0, prior to elution of bound protein using a buffer containing 20 mM tris(hydroxymethyl)aminomethane-hydrogen chloride, 200 mM imidazole, 0.15 M sodium chloride pH 8.0. Eluted fractions containing 6-His protein were pooled and stored in aliquots at −80° C. in 10% glycerol.

Each new batch of stock enzyme was titrated in the assay to determine a concentration giving approximately 90% inhibition of PDH in the conditions of the assay. For a typical batch, stock enzyme was diluted to 7.5 μg/ml.

For assay of the activity of novel compounds, compounds were diluted with 10% dimethylsulphoxide (DMSO) and 10 μl transferred to individual wells of 96-well assay plates. Control wells contained 20 μl 10% DMSO instead of compound. 40 μl Buffer containing 50 mM potassium phosphate buffer pH 7.0, 10 mM ethylene glycol-bis(β-aminoethyl ether)-N,N,N,N-tetracetic acid (EGTA), 1 mM benzamidine, 1 mM phenylmethylsulphonyl fluoride (PMSF), 0.3 mM tosyl-L-lysine chloromethyl ketone (TLCK), 2 mM dithiothreitol (DTT), recombinant rPDHKII and compounds were incubated in the presence of PDH kinase at room temperature for 45 minutes. In order to determine the maximum rate of the PDH reaction a second series of control wells were included containing 10% DMSO instead of compound and omitting rPDHKII. PDH kinase activity was then initiated by the addition of 5 μM ATP, 2 mM magnesium chloride and 0.04 U/ml PDH (porcine heart PDH Sigma P7032) in a total volume of 50 μl and plates incubated at ambient temperature for a further 45 minutes. The residual activity of the PDH was then determined by the addition of substrates (2.5 mM coenzyme A. 2.5 mM thiamine pyrophosphate (cocarboxylase), 2.5 mM sodium pyruvate, 6 mM NAD in a total volume of 80 μl and the plates incubated for 90 minutes at ambient temperature. The production of reduced NAD (NADH) was established by measured optical density at 340 nm using a plate reading spectrophotometer. The $ED_{50}$ for a test compound was determined in the usual way using results from 12 concentrations of the compound.

(b) In Vitro Elevation of PDH Activity in Isolated Primary Cells

This assay determines the ability of compounds to stimulate pyruvate oxidation in primary rat hepatocytes.

Hepatocytes were isolated by the two-step collagenase digestion procedure described by Seglen (Methods Cell Biol. (1976) 13, 29–33) and plated out in 6-well culture plates (Falcon Primaria) at 600000 viable cells per well in Dulbecco's Modified Eagles Medium (DMEM, Gibco BRL) containing 10% foetal calf serum (FCS), 10% penicillin/streptomycin (Gibco BRL) and 10% non-essential amino acids (NEAA, Gibco BRL). After 4 hours incubation at 37° C. in 5% $CO_2$, the medium was replaced with Minimum Essential Medium (MEM, Gibco BRL) containing NEAA and penicillin/streptomycin as above in addition to 10 nM dexamethasone and 10 nM insulin.

The following day cells were washed with phosphate buffered saline (PBS) and medium replaced with 1 ml HEPES-buffered Krebs solution (25 mM HEPES, 0.15M sodium chloride, 25 mM sodium hydrogen carbonate, 5 mM potassium chloride, 2 mM calcium chloride, 1 mM magnesium sulphate, 1 mM potassium dihydrogen phosphate) containing the compound to be tested at the required concentration in 0.1% DMSO. Control wells contained 0.1% DMSO only and a maximum response was determined using a 10 $\mu$M treatment of a known active compound. After a preincubation period of 40 minutes at 37° C. in 5% $CO_2$, cells were pulsed with sodium pyruvate to a final concentration of 0.5 mM (containing 1-$^{14}$C sodium pyruvate (Amersham product CFA85) 0.18 Ci/mmole) for 12 minutes. The medium was then removed and transferred to a tube which was immediately sealed with a bung containing a suspended centre well. Absorbent within the centre well was saturated with 50% phenylethylamine, and $CO_2$ in the medium released by the addition of 0.2 $\mu$l 60% (w/v) perchloric acid (PCA). Released $^{14}CO_2$ trapped in the absorbent was determined by liquid scintillation counting. The $ED_{50}$ for a test compound was determined in the usual way using results from 7 concentrations of the compound.

(c) In vivo Elevation of PDH Activity

The capacity of compounds to increase the activity of PDH in relevant tissues of rats may be measured using the test described hereinafter. Typically an increase in the proportion of PDH in its active, nonphosphorylated form may be detected in muscle, heart, liver and adipose tissue after a single administration of an active compound. This may be expected to lead to a decrease in blood glucose after repeated administration of the compound. For example a single administration of DCA, a compound known to activate PDH by inhibition of PDH kinase (Whitehouse, Cooper and Randle (1974) Biochem. J. 141, 761–774) 150 mg/kg, intraperitoneally, increased the proportion of PDH in its active form (Vary et al. (1988) Circ. Shock 24, 3–18) and after repeated administration resulted in a significant decrease in plasma glucose (Evans and Stacpoole (1982) Biochem. Pharmacol. 31, 1295–1300).

Groups of rats (weight range 140–180 g) are treated with a single dose or multiple doses of the compound of interest by oral gavage in an appropriate vehicle. A control group of rats is treated with vehicle only. At a fixed time after the final administration of compound, animals are terminally anaesthetised, tissues are removed and frozen in liquid nitrogen. For determination of PDH activity, muscle samples are disrupted under liquid nitrogen prior to homogenisation by one thirty-second burst in a Polytron homogenizer in 4 volumes of a buffer containing 40 mM potassium phosphate pH 7.0, 5 mM EDTA, 2 mM DTT, 1% Triton X-100, 10 mM sodium pyruvate, 10 $\mu$M phenylmethylsulphonyl chloride (PMSF) and 2 $\mu$g/ml each of leupeptin, pepstain A and aprotinin. Extracts are centrifuged before assay. A portion of the extract is treated with PDH phosphatase prepared from pig hearts by the method of Siess and Wieland (Eur. J. Biochem (1972) 26, 96): 20 $\mu$l extract, 40 $\mu$l phosphatase (1:20 dilution), in a final volume of 125 $\mu$l containing 25 mM magnesium chloride, 1 mM calcium chloride. The activity of the untreated sample is compared with the activity of the dephosphorylated extract thus prepared. PDH activity is assayed by the method of Stansbie et al., (Biochem. J. (1976)154, 225). 50 $\mu$l Extract is incubated with 0.75 mM NAD, 0.2 mM CoA, 1.5 mM thiamine pyrophosphate (TPP) and 1.5 mM sodium pyruvate in the presence of 20 $\mu$g/ml p-(p-amino-phenylazo) benzene sulphonic acid (AABS) and 50 mU/ml arylamine transferase (AAT) in a buffer containing 100 mM tris(hydroxymethyl)aminomethane, 0.5 mM EDTA, 50 mM sodium fluoride, 5 mM 2-mercaptoethanol and 1 mM magnesium chloride pH 7.8. AAT is prepared from pigeon livers by the method of Tabor et al. (J. Biol. Chem. (1953) 204, 127). The rate of acetyl CoA formation is determined by the rate of reduction of AABS which is indicated by a decrease in optical density at 460 nm.

Liver samples are prepared by an essentially similar method, except that sodium pyruvate is excluded from the extraction buffer and added to the phosphatase incubation to a final concentration of 5 mM.

Treatment of an animal with an active compound results in an increase in the activity of PDH complex in tissues. This is indicated by an increase in the amount of active PDH (determined by the activity of untreated extract as a percentage of the total PDH activity in the same extract after treatment with phosphatase).

According to a further aspect of the invention there is provided a pharmaceutical composition which comprises a compound of the formula (I) as defined hereinbefore or a pharmaceutically acceptable salt thereof, in association with a pharmaceutically acceptable excipient or carrier.

According to an additional aspect of the invention there is provided a pharmaceutical composition which comprises a compound of the formula (I') as defined hereinbefore or a pharmaceutically acceptable salt thereof, in association with a pharmaceutically acceptable excipient or carrier.

The composition may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square metre body area of the animal, i.e. approximately 0.1–100 mg/kg. A unit dose in the range, for example, 1–100 mg/kg, preferably 1–50 mg/kg is envisaged and this normally provides a therapeutically-effective dose. A unit dose form such as a tablet or capsule will usually contain, for example 1–250 mg of active ingredient.

According to a further aspect of the present invention there is provided a compound of the formula (I) or a pharmaceutically acceptable salt thereof as defined hereinbefore for use in a method of treatment of the human or animal body by therapy.

According to an additional aspect of the present invention there is provided a compound of the formula (I') or a pharmaceutically acceptable salt thereof as defined hereinbefore for use in a method of treatment of the human or animal body by therapy.

We have found that compounds of the present invention elevate PDH activity and are therefore of interest for their blood glucose-lowering effects.

A further feature of the present invention is a compound of formula (I), or a pharmaceutically acceptable salt thereof, for use as a medicament, conveniently a compound of formula (I), or a pharmaceutically acceptable salt thereof, for use as a medicament for producing an elevation of PDH activity in a warm-blooded animal such as a human being.

A further feature of the present invention is a compound of formula (I'), or a pharmaceutically acceptable salt thereof, for use as a medicament, conveniently a compound of formula (I'), or a pharmaceutically acceptable salt thereof, for use as a medicament for producing an elevation of PDH activity in a warm-blooded animal such as a human being.

Thus according to a further aspect of the invention there is provided the use of a compound of the formula (I), or a pharmaceutically acceptable salt thereof in the manufacture of a medicament for use in the production of an elevation of PDH activity in a warm-blooded animal such as a human being.

Thus according to an additional aspect of the invention there is provided the use of a compound of the formula (I'), or a pharmaceutically acceptable salt thereof in the manufacture of a medicament for use in the production of an elevation of PDH activity in a warm-blooded animal such as a human being.

According to a further feature of the invention there is provided a method for producing an elevation of PDH activity in a warm-blooded animal, such as a human being, in need of such treatment which comprises administering to said animal an effective amount of a compound of formula (I) or a pharmaceutically acceptable salt thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The elevation of PDH activity described herein may be applied as a sole therapy or may involve, in addition to the subject of the present invention, one or more other substances and/or treatments. Such conjoint treatment may be achieved by way of the simultaneous, sequential or separate administration of the individual components of the treatment. For example in the treatment of diabetes mellitus chemotherapy may include the following main categories of treatment:

i) insulin;
ii) insulin secretagogue agents designed to stimulate insulin secretion (for example glibenclamide, tolbutamide, other sulphonylureas);
iii) oral hypoglycaemic agents such as metformin, thiazolidinediones;
iv) agents designed to reduce the absorption of glucose from the intestine (for example acarbose);
v) agents designed to treat complications of prolonged hyperglycaemia;
vi) other agents used to treat lactic acidaemia;
vii) inhibitors of fatty acid oxidation;
viii) lipid lowering agents;
ix) agents used to treat coronary heart disease and peripheral vascular disease such as aspirin, pentoxifylline, cilostazol; and/or
x) thiamine.

As stated above the compounds defined in the present invention are of interest for their ability to elevate the activity of PDH. Such compounds of the invention may therefore be useful in a range of disease states including diabetes mellitus, peripheral vascular disease, (including intermittent claudication), cardiac failure and certain cardiac myopathies, myocardial ischaemia, cerebral ischaemia and reperfusion, muscle weakness, hyperlipidaemias, Alzheimer's disease and atherosclerosis.

In addition to their use in therapeutic medicine, the compounds of formula (I) and their pharmaceutically acceptable salts are also useful as pharmacological tools in the development and standardisation of in vitro and in vivo test systems for the evaluation of the effects of elevators of PDH activity in laboratory animals such as cats, dogs, rabbits, monkeys, rats and mice, as part of the search for new therapeutic agents.

It is to be understood that where the term "ether" is used anywhere in this specification it refers to diethyl ether.

The invention will now be illustrated by the following non-limiting examples in which, unless stated otherwise:

(i) temperatures are given in degrees Celsius (° C.); operations were carried out at room or ambient temperature, that is, at a temperature in the range of 18–25° C. and under an atmosphere of an inert gas such as argon;

(ii) organic solutions were dried over anhydrous magnesium sulphate; evaporation of solvent was carried out using a rotary evaporator under reduced pressure (600–4000 Pascals; 4.5–30 mmHg) with a bath temperature of up to 60° C.;

(iii) chromatography means flash chromatography on silica gel; thin layer chromatography (TLC) was carried out on silica gel plates; where a silica Mega Bond Elut column is referred to, this means a column containing 10 g or 20 g of silica of 40 micron particle size, the silica being contained in a 60 ml disposable syringe and supported by a porous disc, obtained from Varian. Harbor City, Calif., USA under the name "Mega Bond Elut SI"; "Mega Bond Elut" is a trademark;

(iv) where a Chem Elut column is referred to, this means a "Hydromatrix" extraction cartridge for adsorption of aqueous material, i.e. a polypropylene tube containing a special grade of flux-calcined, high purity, inert diatomaceous earth, pre-buffered to pH 4.5 or 9.0, incorporating a phase-separation filtering material, used according to the manufacturers instructions, obtained from Varian, Harbor City, Calif., USA under the name of "Extube, Chem Elut"; "Extube" is a registered trademark of International Sorbent Technology Limited;

(v) where an ISOLUTE column is referred to, this means an "ion exchange" extraction cartridge for adsorption of basic or acid material, i.e. a polypropylene tube containing a special grade of ion exchange sorbent, high purity, surface to pH~7, incorporating a phase-separation filtering material, used according to the manufacturers instructions, obtained from Varian, Harbor City, Calif., USA under the name of "Extube, Chem Elut, ISOLUTE"; "Extube" is a registered trademark of International Sorbent Technology Limited;

(vi) in general, the course of reactions was followed by TLC and reaction times are given for illustration only;

(vii) melting points are uncorrected and (dec) indicates decomposition; the melting points given are those obtained for the materials prepared as described; polymorphism may result in isolation of materials with different melting points in some preparations;

(viii) final products had satisfactory proton nuclear magnetic resonance (NMR) spectra and/or mass spectral data;

(ix) yields are given for illustration only and are not necessarily those which can be obtained by diligent process development; preparations were repeated if more material was required;

(x) where given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$\delta_6$) as solvent unless otherwise indicated, other solvents (where indicated in the text) include deuterated chloroform —$CDCl_3$ and deuterated acetic acid AcOH-$\delta_4$; coupling constants (J) are given in Hz; Ar designates an aromatic proton when such an assignment is made;

(xi) chemical symbols have their usual meanings; SI units and symbols are used;

(xii) reduced pressures are given as absolute pressures in Pascals (Pa); elevated pressures are given as gauge pressures in bars;

(xiii) solvent ratios are given in volume : volume (v/v) terms;

(xiv) mass spectra (MS) were run with an electron energy of 70 electron volts in the chemical ionisation (CI) mode using a direct exposure probe; where indicated ionisation was effected by electron impact (EI), fast atom bombardment (FAB) or electrospray (ESP); values for m/z are given; generally, only ions which indicate the parent mass are reported and unless otherwise stated the value quoted is $(M-H)^-$;

(xv) Oxone is a Trademark of E.I. du Pont de Nemours & Co., Inc., and refers to potassium peroxymonosulphate;

(xvi) The following abbreviations are used:

| | |
|---|---|
| EA | elemental analysis; |
| DMF | N,N-dimethylformamide; |
| DMA | N,N-dimethylacetamide; |
| TFA | trifluoroacetic acid; |
| NMP | N-methylpyrrolidin-2-one |
| SM | starting material; |
| DCM | dichloromethane; and |
| THF | tetrahydrofuran; |

(xvii) HPLC Methods referred to in the text are as follows:

| Methods a and b LC/MS method: | |
|---|---|
| Machine Model | HP1100 |
| Column | 4.6 mm × 10 cm Hichrom RPB 100A |
| Wavelength | 254 nm |
| Injection | 10 μl |
| Flow rate | 1 ml/minute |
| Solvent A | 0.1% Formic Acid/Water |
| Solvent B | 0.1% Formic Acid/Acetonitrile. |

| Time/minutes | A% | B% |
|---|---|---|
| Solvent gradient for Method a: | | |
| 0.00 | 95 | 5 |
| 1.50 | 95 | 5 |
| 7.50 | 5 | 95 |
| 9.00 | 5 | 95 |
| Solvent gradient for Method b: | | |
| 0.00 | 95 | 5 |
| 1.50 | 95 | 5 |
| 11.50 | 5 | 95 |
| 13.50 | 5 | 95 |

| Method c: | |
|---|---|
| Column | 7.5 mm × 25 cm Dynamax –60A C18 83-201-C |
| Flow rate | 1 ml/minute |

| Time/minutes | % MeCN in water + 0.1% TFA |
|---|---|
| Solvent gradient for Method c: | |
| 0 | 10 |
| 2 | 10 |
| 32 | 90 |

| Method d: | |
|---|---|
| Column | 4.5 mm × 10 cm HIRPB |
| Flow rate | 1 ml/min |
| Solvent Gradient | 50–70% MeOH in water + 0.1% TFA over 10 minutes (xviii) where (R) or (S) stereochemistry is quoted at the beginning of a name, unless further clarified, it is to be understood that the indicated stereochemistry refers to the A-B-C*$(R^2)(R^3)(R^4)$ centre as depicted in formula (I). |

EXAMPLE 1

(R)-N-[2-Chloro-4-(2-methylsulphanylphenylsulphonyl)phenyl]-2-hydroxy-2-methyl-3,3,3-trifluoropropanamide Sodium methanethiolate (49.5 mg) was added to a solution of (R)-N-[2-chloro-4-(2-fluorophenylsulphonyl)phenyl]-2-hydroxy-2-methyl-3,3,3-trifluoropropanamide (Method 63) (0.15 g) in NMP (1.5 ml) and the mixture was heated at 120° C. for 18 hours then cooled. Saturated aqueous ammonium chloride solution (15 ml) was added and the mixture was extracted with ethyl acetate (2×50 ml). The organic extracts were combined, washed with brine and dried. Volatile material was removed by evaporation and the residue was purified by chromatography on a silica gel Mega Bond Elut column eluting with 0–20% ethyl acetate/hexane to give the title compound (0.10 g) as a solid. NMR: ($CDCl_3$): 1.75 (s, 3H), 2.4 (s, 3H), 3.6 (brs, 1H), 7.3 (t, 1H), 7.35 (t, 1H), 7.55 (m, 1H), 7.9 (dd, 1H), 8.05 (d, 1H) 8.25 (dd, 1H), 8.6 (d, 1H), 9.25 (brs, 1H); MS (ESP$^-$): 452.

EXAMPLES 2–12

Following the procedure of Example 1 and using the appropriate starting materials the following compounds were prepared.

| Ex | Compound | NMR (CDCl$_3$) | MS | SM |
|---|---|---|---|---|
| 2 | (R)-N-[2-Chloro-4-(4-methyl-sulphanylphenylsulphonyl)phenyl]-2-hydroxy-2-methyl-3,3,3-trifluoropropanamide | 1.75 (s, 3H), 2.5 (s, 3H), 3.7 (s, 1H), 7.28 (d, 2H), 7.8 (d, 2H), 7.83 (dd, 1H), 7.98 (d, 1H), 8.6 (d, 1H), 9.25 (brs, 1H) | 452 | Meth 69 |
| 3 | (R)-N-{2-Chloro-4-[2-(ethylsulphanyl)phenylsulphonyl]phenyl}-2-hydroxy-2-methyl-3,3,3-trifluoropropanamide | 1.25 (t, 3H), 1.75 (s, 3H), 2.90 (q, 2H), 3.75 (s, 1H), 7.30–7.35 (m, 2H), 7.45–7.50 (m, 1H), 7.90–7.95 (m, 1H), 8.10 (d, 1H), 8.25 (d, 1H), 8.60 (d, 1H), 9.30 (s, 1H) | 466 | Meth 63 |
| 4 | (R)-N-[2-Chloro-4-(3-methyl-sulphanylphenylsulphonyl)phenyl]-2-hydroxy-2-methyl-3,3,3-trifluoropropanamide | 1.75 (s, 3H), 2.52 (s, 3H), 3.5 (s, 1H), 7.37–7.41 (m, 2H), 7.6–7.65 (m, 1H), 7.75 (s, 1H), 7.85 (d, 1H), 8.0 (d, 1H), 8.60 (d, 1H), 9.2 (s, 1H) | 452 | Meth 70 |
| 5 | (R)-N-[2-Chloro-4-(4-methyl-sulphanylphenylsulphinyl)phenyl]-2-hydroxy-2-methyl-3,3,3-trifluoropropanamide | 1.72 (s, 3H), 2.5 (s, 3H), 4.45 (2xbrs, 1H), 7.3 (d, 2H), 7.49 (m, 1H), 7.5 (d, 2H), 7.7 (m, 1H), 8.5 (2xd, 1H), 9.2 (2xbrs, 1H) | 436 | Meth 75 |
| 6 | (R)-N-{2-Chloro-4-[4-(iso-propylsulphanyl)phenyl-sulphonylphenyl]-2-hydroxy-2-methyl-3,3,3-trifluoropropanamide | 1.35 (d, 6H), 1.7 (s, 3H), 3.5 (m, 1H), 5.35 (s, 1H), 7.35 (d, 2H), 7.75–7.85 (m, 3H), 8.0 (dd, 1H), 8.6 (d, 1H), 9.5 (brs, 1H) | 480 | Meth 69 |
| 7 | (R)-N-[2-Chloro-4-(4-ethyl-sulphanylphenylsulphonyl)phenyl]-2-hydroxy-2-methyl-3,3,3-trifluoropropanamide | 1.35 (t, 3H), 1.7 (s, 3H), 3.0 (q, 2H), 5.2 (s, 1H), 7.3 (m, 1H), 7.7–8.0 (m, 5H), 8.6 (d, 1H), 9.45 (brs, 1H) | 466 | Meth 69 |
| 8 | (R)-N-[2-Chloro-4-(3-chloro-4-methylsulphanylphenylsulphonyl)phenyl]-2-hydroxy-2-methyl-3,3,3-trifluoropropanamide | 1.75 (s, 3H), 2.5 (s, 3H), 3.80 (s, 1H), 7.2 (d, 1H), 7.75 (dd, 1H). 7.8–7.85 (m, 2H), 7.95 (d, 1H), 8.6 (d, 1H), 9.30 (brs, 1H) | 488 (M + H)$^+$ | Meth 72 |
| 9 | (R)-N-[2-Chloro-4-(3-fluoro-4-methylsulphanylphenylsulphonyl)phenyl]-2-hydroxy-2-methyl-3,3,3-trifluoropropanamide | 1.75 (s, 3H), 2.5 (s, 3H), 3.6 (s, 1H), 7.25 (m, 1H), 7.5 (dd, 1H), 7.65 (d, 1H), 7.85 (dd, 1H), 7.95 (d, 1H), 8.6 (d, 1H), 9.25 (brs, 1H) | 470 | Meth 66 |
| 10 | (R)-N-[2-Fluoro-4-(4-ethyl-sulphanylphenylsulphonyl)phenyl]-2-hydroxy-2-methyl-3,3,3-trifluoropropanamide | | 450 | Meth 71 |
| 11[1] | (R)-N-[2-Methylsulphanyl-4-(2-methylsulphanylphenylsulphonyl)phenyl]-2-hydroxy-2-methyl-3,3,3-trifluoropropanamide | R.f. = 0.37; 1:1 iso-hexane:Ethyl acetate | | Meth 64 |
| 12 | (R)-N-[2-Fluoro-4-(2-methyl-sulphanylphenylsulphonyl)phenyl]-2-hydroxy-2-methyl-3,3,3-trifluoropropanamide | | 436 | Meth 64 |

[1]Three equivalents of sodium methanethiolate were added.

EXAMPLE 13

(R)-N-{2-Chloro-4-[2-(methylsulphinyl)phenylsulphonyl]phenyl}-2-hydroxy-2-methyl-3,3,3-trifluoropropanamide m-Chloroperoxybenzoic acid (50%, 0.293 g) was added to a solution of (R)-N-[2-chloro-4-(2-methylsulphanylphenylsulphonyl)phenyl]-2-hydroxy-2-methyl-3,3,3-trifluoropropanamide (Example 1) (0.384 g) in DCM (40 ml). The mixture was stirred at ambient temperature for 6 hours then washed with saturated aqueous sodium hydrogen carbonate solution (3×100 ml), water (100 ml) and brine and then dried. Volatile material was removed by evaporation and the residue was purified by chromatography on a silica gel Mega Bond Elut column eluting with 50–70% ethyl acetate/hexane to give the title compound (0.26 g) as a solid. Mp 118–120° C.; NMR (CDCl$_3$): 1.70 (s, 3H), 3.0 (m, 3H), 4.85 (brs, 1H), 7.75 (t, 1H), 7.85 (m, 2H), 8.0 (m, 1H), 8.15 (d, 1H), 8.3 (d, 1H), 8.65 (dd, 1H), 9.40 (brs, 1H); MS (ESP$^-$): 468; EA: found: C, 44.3; H, 3.7; N, 2.6%; $C_{17}H_{15}ClF_3NO_5S_2$.0.125 $C_4H_8O_2$.0.3 $C_4H_{10}O$ requires: C, 44.64; H, 3.81; N, 2.78%.

EXAMPLES 14–15

Following the procedure of Example 13 and using the appropriate starting materials the following compound was prepared.

| Ex | Compound | NMR (CDCl₃) | MS | SM |
|---|---|---|---|---|
| 14[1] | (R)-N-[2-Chloro-4-(4-mesylphenylsulphinyl)-phenyl]-2-hydroxy-2-methyl-3,3,3-trifluoropropanamide | 1.72 (s, 3H), 3.02 (s, 3H), 3.9 (brs, 1H), 7.58 (m, 1H), 7.72 (m, 1H), 7.82 (d, 2H), 8.05 (d, 2H), 8.58 (m, 1H), 9.2 (brs, 1H) | 468 | Ex 87 |
| 15[2] | N-(2-Fluoro-4-phenyl-sulphinylphenyl)-2-hydroxy-2-methylpropanamide | 1.35 (s, 6H), 6.0 (brs, 1H), 7.5–7.56 (m, 4H), 7.64 (d, 1H), 7.7 (m, 2H), 8.18 (t, 1H), 9.4 (brs, 1H) | 320 | Ex 205 |

[1]A second molar equivalent of m-chloroperoxybenzoic acid was added after 4 hours and the reaction was allowed to proceed for a further 18 hours at ambient temperature.
[2]Chromatography was using 30–50% ethyl acetate/hexane and the resultant material was triturated with ether.

EXAMPLE 16

(R)-N-[2-Chloro-4-(2-mesylphenylsulphonyl)phenyl]-2-hydroxy-2-methyl-3,3,3-trifluoropropanamide m-Chloroperoxybenzoic acid (50%, 2.39 g) was added to a solution of (R)-N-[2-chloro-4-(2-methylsulphanylphenylsulphonyl)phenyl]-2-hydroxy-2-methyl-3,3,3-trifluoropropanamide (Example 1) (1.3 g) in DCM (100 ml) and the mixture was stirred at ambient temperature for 3 hours. A further portion of m-chloroperoxybenzoic acid (0.82 g) was added and the mixture was stirred for 24 hours and then washed with saturated aqueous sodium hydrogen carbonate solution (3×70 ml), water (50 ml) and brine and then dried. Volatile material was removed by evaporation and the residue was purified by flash chromatography eluting with 50% ethyl acetate/hexane to give the title compound (0.606 g) as a solid. Mp 114–116° C.; NMR (CDCl₃): 1.75 (s, 3H), 3.45 (s, 3H), 3.65 (brs, 1H), 7.8–7.95 (m, 3H), 8.10 (d, 1H), 8.35 (dd, 1H), 8.55 (dd, 1H), 8.60 (d, 1H) 9.30 (brs, 1H); MS (ESP⁻): 484; EA: found: C, 42.3; H, 3.3; N, 2.6%; $C_{17}H_{15}ClF_3NO_6S_2$ requires: C, 42.02; H, 3.11; N, 2.88%.

EXAMPLES 17–53

Following the procedure of Example 16 and using the appropriate starting materials the following compounds were prepared.

| Ex | Compound | NMR | MS | SM |
|---|---|---|---|---|
| 17 | (R)-N-{2-Chloro-4-[2-(ethyl-sulphonyl)phenylsulphonyl]phenyl}-2-hydroxy-2-methyl-3,3,3-trifluoropropanamide | (CDCl₃) 1.25 (t, 3H), 1.75 (s, 3H), 3.70 (q, 2H), 3.75 (brs, 1H). 7.80–7.95 (m, 3H), 8.10 (s, 1H), 8.30 (d, 1H), 8.60 (d, 2H), 9.25 (s, 1H) | 498 | Ex 3 |
| 18 | (R)-N-{2-Chloro-4-[4-(2-hydroxyethylsulphonyl)phenyl-sulphonyl]phenyl}-2-hydroxy-2-methyl-3,3,3-trifluoropropanamide | (CDCl₃ + trace of DMSO-δ₆) 1.59 (s, 3H), 3.29 (t, 2H), 3.85 (m, 2H), 4.0 (m, 1H), 7.3 (s, 1H), 7.78 (dd, 1H), 7.9 (d, 1H), 8.0 (s, 4H), 8.6 (d, 1H), 9.72 (brs, 1H) | 514 | Ex 284 |
| 19 | (R)-N-{2-Chloro-4-[2-(2-hydroxyethylsulphonyl)phenyl-sulphonyl]phenyl}-2-hydroxy-2-methyl-3,3,3-trifluoropropanamide | (CDCl₃ + AcOH-δ₄) 1.71 (s, 3H), 4.0 (t, 2H), 4.08 (t, 2H), 7.8–7.95 (m, 3H), 8.08 (d, 1H), 8.31 (d, 1H), 8.52 (d, 1H), 8.62 (d, 1H) | 514 | Ex 290 |
| 20 | (R)-N-[2-Chloro-4-(3-mesyl-phenylsulphonyl)phenyl]-2-hydroxy-2-methyl-3,3,3-trifluoropropanamide | (CDCl₃) 1.75 (s, 3H), 3.08 (s, 3H), 3.5 (s, 1H), 7.75 (t, 1H), 7.88 (dd, 1H), 8.01 (d, 1H), 8.17 (dd, 1H), 8.48 (s, 1H), 8.67 (d, 1H), 9.3 (brs, 1H) | 484 | Ex 4 |
| 21 | (R)-N-[2-Chloro-4-(4-benzoyl-aminophenylsulphonyl)phenyl]-2-hydroxy-2-methyl-3,3,3-trifluoropropanamide | 1.6 (s, 3H), 7.6 (m, 3H), 8.0 (m, 8H), 8.1 (s, 1H), 8.3 (d, 1H), 9.9 (s, 1H), 10.6 (s, 1H) | 525 | Ex 337 |
| 22 | (R)-N-{2-Chloro-4-[4-(t-butyl-carbonylamino)phenylsulphonyl]phenyl}-2-hydroxy-2-methyl-3,3,3-trifluoropropanamide | 1.2 (s, 9H), 1.6 (s, 3H), 7.9 (s, 5H), 8.1 (s, 1H), 8.3 (d, 1H), 9.6 (s, 1H) | 505 | Ex 338 |
| 23 | (R)-N-{2-Chloro-4-[4-(4-chloro-benzoylamino)phenylsulphonyl]phenyl}-2-hydroxy-2-methyl-3,3,3-trifluoropropanamide | 1.6 (s, 3H), 7.6 (d, 2H), 8.0 (m, 8H), 8.1 (s, 1H), 8.3 (d, 1H), 9.9 (s, 1H), 10.7 (s, 1H) | 559 | Ex 339 |
| 24 | (R)-N-{2-Chloro-4-[4-(2-methoxy-acetylamino)phenylsulphonyl]phenyl}-2-hydroxy-2-methyl-3,3,3-trifluoropropanamide | 1.6 (s, 3H), 3.3 (s, 3H), 4.0 (s, 2H), 7.9 (m, 6H), 8.1 (s, 1H), 8.3 (d, 1H), 10.2 (s, 1H) | 493 | Ex 340 |
| 25 | (R)-N-{2-Chloro-4-[4-(1-oxy-pyridin-3-ylcarbonylamino)phenyl- | 1.6 (s, 3H), 8.0 (m, 8H), 8.1 (s, 1H), 8.3 (d, 1H), 8.4 (d, 2H), | 542 | Ex 341 |

| Ex | Compound | NMR | MS | SM |
|---|---|---|---|---|
|  | sulphonyl]phenyl}-2-hydroxy-2-methyl-3,3,3-trifluoropropanamide | 9.9 (s, 1H), 10.75 (s, 1H) |  |  |
| 26 | (R)-N-[2-Chloro-4-(4-ureido-phenylsulphonyl)phenyl]-2-hydroxy-2-methyl-3,3,3-trifluoropropanamide | 1.6 (s, 3H), 4.0 (d, 1H), 6.1 (s, 2H), 7.6 (d, 2H), 7.8 (d, 2H), 7.9 (d, 1H), 8.0 (s, 1H), 8.3 (d, 1H), 9.0 (s, 1H), 9.8 (s, 1H) | 464 | Ex 174 |
| 27 | (R)-N-[2-Chloro-4-(2-ureido-phenylsulphonyl)phenyl]-2-hydroxy-2-methyl-3,3,3-trifluoropropanamide | 1.6 (s, 3H), 6.7 (s, 2H), 7.2 (t, 1H), 7.6 (m, 2H), 8.0 (m, 3H), 8.2 (d, 2H), 8.3 (s, 1H), 9.9 (s, 1H) | 464 | Ex 175 |
| 28 | (R)-N-[2-Chloro-4-(2-mesylamino-phenylsulphonyl)phenyl]-2-hydroxy-2-methyl-3,3,3-trifluoropropanamide | 1.6 (s, 3H), 3.3 (s, 3H), 7.4 (t, 1H), 7.5 (d, 1H), 7.7 (t, 1H), 8.0 (m, 4H), 8.3 (d, 1H), 9.1 (s, 1H), 9.9 (s, 1H) | 499 | Ex 342 |
| 29 | (R)-N-[2-Chloro-4-(2-acetylamino-phenylsulphonyl)phenyl]-2-hydroxy-2-methyl-3,3,3-trifluoropropanamide | 1.6 (s, 3H), 2.0 (s, 3H), 7.4 (m, 1H), 7.7 (d, 2H), 7.9 (d, 1H), 8.0 (d, 2H), 8.1 (d, 1H), 8.3 (d, 1H), 9.4 (s, 1H), 9.9 (s, 1H) | 463 | Ex 343 |
| 30 | (R)-N-[2-Chloro-4-(N-methyl-4-mesylaminophenylsulphonyl)phenyl]-2-hydroxy-2-methyl-3,3,3-trifluoropropanamide | 1.6 (s, 3H), 3.0 (s, 3H), 3.3 (s, 3H), 7.6 (d, 2H), 8.0 (m, 4H), 8.1 (s, 1H), 8.3 (d, 1H), 9.9 (s, 1H) | 513 | Ex 263 |
| 31 | (R)-N-[2-Chloro-4-(4-mesylamino-phenylsulphonyl)phenyl]-2-hydroxy-2-methyl-3,3,3-trifluoropropanamide | 1.6 (s, 3H), 3.1 (s, 3H), 7.4 (d, 2H), 7.9 (m, 3H), 8.0 (s, 1H), 8.1 (s, 1H), 8.3 (d, 1H), 9.9 (s, 1H), 10.48 (s, 1H) | 499 | Ex 344 |
| 32 | (R)-N-{2-Chloro-4-[4-(phenyl-sulphonylamino)phenylsulphonyl]phenyl}-2-hydroxy-2-methyl-3,3,3-trifluoropropanamide | 1.6 (s, 3H), 7.2 (d, 2H), 7.6 (m, 3H), 7.8 (m, 5H), 8.0 (d, 2H), 8.2 (d, 1H), 9.9 (s, 1H), 11.0 (s, 1H) | 561 | Ex 345 |
| 33 | (R)-N-[2-Chloro-4-(4-ethenyl-sulphonylaminophenylsulphonyl)phenyl]-2-hydroxy-2-methyl-3,3,3-trifluoropropanamide | 1.6 (s, 3H), 6.1 (d, 1H), 6.2 (d, 1H), 6.9 (m, 1H), 7.3 (d, 2H), 7.9 (d, 3H), 8.0 (s, 1H), 8.1 (s, 1H), 8.3 (d, 1H), 9.9 (s, 1H), 10.75 (s, 1H) | 511 | Ex 346 |
| 34 | (R)-N-[2-Chloro-4-(3-mesylamino-phenylsulphonyl)phenyl]-2-hydroxy-2-methyl-3,3,3-trifluoropropanamide | 1.6 (s, 3H), 3.0 (s, 3H), 7.5 (d, 1H), 7.6 (t, 1H), 7.7 (m, 2H), 8.0 (m, 3H), 8.3 (d, 1H), 9.9 (s, 1H), 10.2 (s, 1H) | 499 | Ex 347 |
| 35 | (R)-N-[2-Fluoro-4-(4-mesylamino-phenylsulphonyl)phenyl]-2-hydroxy-2-methyl-3,3,3-trifluoropropanamide | 1.6 (s, 3H), 3.2 (s, 3H), 7.3 (d, 2H), 7.7 (m, 2H), 7.9 (m, 3H), 8.0 (t, 1H), 9.9 (s, 1H), 10.5 (s, 1H) | 483 | Ex 348 |
| 36 | (R)-N-[2-Fluoro-4-(4-acetylamino-phenylsulphonyl)phenyl]-2-hydroxy-2-methyl-3,3,3-trifluoropropanamide | 1.6 (s, 3H), 2.1 (s, 3H), 7.7 (m, 4H), 7.8 (m, 3H), 8.0 (t, 1H), 9.9 (s, 1H), 10.35 (s, 1H) | 447 | Ex 349 |
| 37 | (R)-N-{2-Chloro-4-[4-(2-chloro-acetylamino)phenylsulphonyl]phenyl}-2-hydroxy-2-methyl-3,3,3-trifluoropropanamide | 1.6 (s, 3H), 4.3 (s, 2H), 7.8 (d, 2H), 8.0 (m, 4H), 8.1 (s, 1H), 8.3 (d, 1H), 9.9 (s, 1H), 10.72 (s, 1H) | 497 | Ex 177 |
| 38 | (R)-N-(2-Chloro-4-{4-[2-(N'-oxy-N',N'-dimethylamino)acetylamino]phenylsulphonyl}phenyl)-2-hydroxy-2-methyl-3,3,3-trifluoropropanamide | 1.6 (s, 3H), 3.2 (s, 6H), 4.0 (s, 2H), 7.7 (d, 2H), 7.9 (m, 4H), 8.0 (s, 1H), 8.3 (d, 1H) | 522 | Ex 353 |
| 39 | (R)-N-{2-Chloro-4-[4-(3-t-butylureido)phenylsulphonyl]phenyl}-2-hydroxy-2-methyl-3,3,3-trifluoropropanamide | 1.2 (s, 9H), 1.6 (s, 3H), 6.2 (s, 1H), 7.5 (d, 2H), 7.8 (d, 2H), 7.9 (d, 1H), 8.0 (d, 2H), 8.2 (d, 1H), 8.8 (s, 1H), 9.9 (s, 1H) | 520 | Ex 179 |
| 40 | (R)-N-{2-Chloro-4-[4-(3-phenyl-ureido)phenylsulphonyl]phenyl}-2-hydroxy-2-methyl-3,3,3-trifluoropropanamide | 1.6 (s, 3H), 7.0 (t, 1H), 7.3 (t, 2H), 7.4 (d, 2H), 7.7 (d, 2H), 7.9 (m, 4H), 8.0 (s, 1H), 8.3 (d, 1H), 8.8 (s, 1H), 9.2 (s, 1H), 9.8 (s, 1H) | 540 | Ex 180 |
| 41 | (R)-N-[2-Chloro-4-(2,3-H-2-oxo-3-methylbenzoxazol-6-ylsulphonyl)phenyl]-2-hydroxy-2-methyl-3,3,3-trifluoropropanamide | 1.6 (s, 3H), 3.3 (s, 3H), 7.4 (d, 1H), 7.9 (m, 3H), 8.1 (s, 1H), 8.2 (d, 1H), 9.9 (s, 1H) | 477 | Ex 265 |
| 42 | (R)-N-[2-Chloro-4-(2-oxo-1,3-dimethylbenzimidazolidin-5-ylsulphonyl)phenyl]-2-hydroxy-2-methyl-3,3,3-trifluoropropanamide | 1.5 (s, 3H), 3.3 (d, 6H), 7.3 (d, 1H), 7.7 (t, 2H), 8.0 (t, 2H), 8.1 (s, 1H), 8.2 (d, 1H), 9.9 (s, 1H) | 490 | Ex 266 |
| 43 | (R)-N-{2-Chloro-4-[4-(2-oxo-pyrrolidin-1-yl)phenylsulphonyl]phenyl}-2-hydroxy-2-methyl-3,3,3-trifluoropropanamide | 1.6 (s, 3H), 2.1 (m, 2H), 2.5 (t, 2H), 3.9 (t, 2H), 7.9 (m, 6H), 8.1 (s, 1H), 8.3 (d, 1H), 9.9 (s, 1H) | 489 | Ex 267 |

-continued

| Ex | Compound | NMR | MS | SM |
|---|---|---|---|---|
| 44 | (R)-N-[2-Chloro-4-(1,2,3,4-H-1,3-dimethyl-2,4-dioxoquinazolin-6-ylsulphonyl)phenyl]-2-hydroxy-2-methyl-3,3,3-trifluoropropanamide | 1.6 (s, 3H), 3.2 (s, 3H), 3.5 (s, 3H), 7.6 (d, 1H), 8.0 (d, 2H), 8.2 (s, 1H), 8.3 (m, 2H), 8.5 (s, 1H), 9.9 (s, 1H) | 518 | Ex 268 |
| 45 | (R)-N-{2-Chloro-4-(4,5-diphenyl-2-oxazolylsulphonyl)phenyl}-2-hydroxy-2-methyl-3,3,3-trifluoropropanamide | (CDCl$_3$) 1.75 (s, 3H), 3.8 (brs, 1H), 7.3–7.45 (m, 6H), 7.5–7.65 (m, 4H), 8.1 (dd, 1H), 8.2 (d, 1H), 8.75 (d, 1H), 9.4 (brs, 1H) | 551 (M + H)$^+$ | Ex 272 |
| 46 | (R)-N-{2-Chloro-4-(1-ethyltetrazol-5-ylsulphonyl)phenyl}-2-hydroxy-2-methyl-3,3,3-trifluoropropanamide | (CDCl$_3$) 1.65 (t, 3H), 1.75 (s, 3H), 3.7 (brs, 1H), 4.85 (q, 2H), 8.05 (dd, 1H), 8.2 (d, 1H), 8.8 (d, 1H), 9.5 (brs, 1H) | 428 (M + H)$^+$ | Ex 273 |
| 47 | (R)-N-{2-Chloro-4-(4-iso-propyl-4,5-dihydro-1H-1,2,4-triazol-5-one-3-ylsulphonyl)phenyl}-2-hydroxy-2-methyl-3,3,3-trifluoropropanamide | (CDCl$_3$) 1.55 (d, 6H), 1.75 (s, 3H), 3.8 (brs, 1H), 4.8 (m, 1H), 7.9 (dd, 1H), 8.05 (d, 1H), 8.8 (d, 1H), 9.45 (brs, 1H), 10.2 (brs, 1H) | 457 (M + H)$^+$ | Ex 274 |
| 48 | (R)-N-{2-Chloro-4-[3-fluoro-4-(2-hydroxyethylsulphonyl)-phenylsulphonyl]phenyl}-2-hydroxy-2-methyl-3,3,3-trifluoropropanamide | 1.6 (s, 3H), 3.55–3.65 (m, 2H), 3.65–3.8 (m, 2H), 4.80 (m 1H), 8.00–8.15 (m, 4H), 8.15–8.3 (m, 2H), 8.35 (d, 1H), 9.95 (brs, 1H) | 532 | Ex 311 |
| 49 | (R)-N-[2-Chloro-4-(3-chloro-4-methylsulphonylphenylsulphonyl)phenyl]-2-hydroxy-2-methyl-3,3,3-trifluoropropanamide | (CDCl$_3$) 1.75 (s, 3H), 3.25 (s, 3H), 3.45 (brs, 1H), 7.9 (dd, 1H), 7.95–8.1 (m, 2H), 8.1 (d, 1H), 8.3 (d, 1H), 8.56 (d, 1H), 9.3 (brs, 1H) | 518 | Ex 8 |
| 50 | (R)-N-[2-Chloro-4-(3-fluoro-4-methylsulphonylphenylsulphonyl)phenyl]-2-hydroxy-2-methyl-3,3,3-trifluoropropanamide | (CDCl$_3$) 1.75 (s, 3H), 3.2 (s, 3H), 3.4 (s, 1H), 7.8 (dd, 1H), 7.9 (dd, 2H), 8.0 (d, 1H), 8.1–8.15 (m, 1H), 8.7 (d, 1H), 9.3 (brs, 1H) | 502 | Ex 9 |
| 51 | (R)-N-{2-Chloro-4-(3-t-butoxycarbonylaminopropylsulphonyl)phenyl}-2-hydroxy-2-methyl-3,3,3-trifluoropropanamide | (CDCl$_3$): 1.55 (s, 9H), 1.78 (s, 3H), 1.86–1.97 (m, 2H), 3.13 (t, 2H), 3.21–3.26 (m, 2H), 3.86 (s, 1H), 4.65 (t, 1H), 7.80–7.82 (m, 1H), 8.04 (s, 1H), 8.68 (d, 1H), 9.34 (s, 1H) | 487 | Ex 405 |
| 52 | (R)-N-{2-Chloro-4-(2H-benzimidazole-2-one-5-yl-sulphonyl)phenyl}-2-hydroxy-2-methyl-3,3,3-trifluoropropanamide | 1.6 (s, 3H), 7.1 (d, 1H), 7.4 (s, 1H), 7.6 (d, 1H), 7.9 (d, 1H), 8.0 (s, 1H), 8.2 (d, 1H), 11.0 (s, 1H), 11.2 (s, 1H) | 462 | Ex 269 |
| 53 | (R)-N-{2-Chloro-4-(4-acetyl-phenylsulphonyl)phenyl}-2-hydroxy-2-methyl-3,3,3-trifluoropropanamide | 1.6 (s, 3H), 2.6 (s, 3H), 8.0 (s, 2H), 8.1 (s, 3H), 8.2 (s, 1H), 8.3 (d, 1H), 9.9 (s, 1H) | 448 | Ex 270 |

EXAMPLE 54

(R)-N-{2-Chloro-4-[2-(2-hydroxyethylamino)phenylsulphonyl]phenyl}-2-hydroxy-2-methyl-3,3,3-trifluoropropanamide Ethanolamine (0.014 ml) was added to a solution of (R)-N-[2-chloro-4-(2-fluoro-phenylsulphonyl)phenyl]-2-hydroxy-2-methyl-3,3,3-trifluoropropanamide (Method 63) (0.10 g) in NMP (1.5 ml) and the solution was heated at 120° C. for 18 hours then cooled. Saturated aqueous ammonium chloride solution (10 ml) was added and the mixture was extracted with ethyl acetate (2×20 ml). The organic extracts were combined, washed with brine and dried. Volatile material was removed by evaporation and the residue was purified by chromatography on a silica gel Mega Bond Elut column eluting with 0–50% ethyl acetate/hexane to give the title compound (0.074 g) as a solid. Mp 68–70° C.; NMR (CDCl$_3$): 1.75 (s, 3H), 3.3 (q, 2H), 3.90 (m, 2H), 3.95 (brs, 1H), 6.50 (brt, 1H), 6.70 (d, 1H) 6.80 (m, 1H), 7.4 (m, 1H), 7.85 (m, 2H), 8.00 (d, 1H), 8.55 (d, 1H), 9.25 (brs, 1H); MS (ESP$^-$): 465; EA: found: C, 46.6; H, 4.0; N, 5.8%; C$_{18}$H$_{18}$ClF$_3$N$_2$O$_5$S requires: C, 46.31; H, 3.89; N, 6.00%.

EXAMPLES 55–85

Following the procedure of Example 54 and using the appropriate starting materials the following compounds were prepared.

| Ex | Compound | NMR | MS |
|---|---|---|---|
| 55 | (R)-N-{2-Chloro-4-[4-(3-hydroxypropylamino)phenyl-sulphonyl]phenyl}-2-hydroxy-2-methyl-3,3,3-trifluoropropanamide | 1.6 (s, 3H), 1.66 (m, 2H), 3.1 (m, 2H), 3.46 (m, 2H), 4.45 (t, 1H), 6.64 (d, 2H), 6.74 (t, 1H), 7.6 (d, 2H), 7.82 (dd, 1H), 7.98 (d, 1H), 8.2 (d, 1H), 9.8 (brs, 1H) | 479 |

-continued

| Ex | Compound | NMR | MS |
|---|---|---|---|
| 56 | (R)-N-{2-Chloro-4-[4-(2-hydroxypropylamino)phenyl-sulphonyl]phenyl}-2-hydroxy-2-methyl-3,3,3-trifluoropropanamide | 1.09 (d, 3H), 1.6 (s, 3H), 3.0 (m, 2H), 3.77 (m, 1H), 4.72 (d, 1H), 6.7 (d, 2H), 6.74 (t, 1H), 7.59 (d, 2H), 7.85 (dd, 1H), 7.96 (d, 1H), 8.22 (d, 1H), 9.8 (brs, 1H) | 479 |
| 57 | (R)-N-{2-Chloro-4-[4-(2-acetamido-ethylamino)phenylsulphonyl]phenyl}-2-hydroxy-2-methyl-3,3,3-trifluoropropanamide | 1.6 (s, 3H), 1.79 (s, 3H), 3.15 (m, 4H), 6.69 (d, 2H), 6.82 (m, 1H), 7.63 (d, 2H), 7.85 (dd, 1H), 7.93 (m, 1H), 8.0 (d, 1H), 8.2 (d, 1H), 9.8 (brs, 1H) | 506 |
| 58 | (R)-N-(2-Chloro-4-{4-[2-(2-hydroxyethoxy)ethylamino]phenyl-sulphonyl}phenyl)-2-hydroxy-2-methyl-3,3,3-trifluoropropanamide | 1.6 (s, 3H), 3.25 (m, 2H), 3.4–3.6 (m, 6H), 4.59 (m, 1H), 6.7 (d, 2H), 6.79 (t, 1H), 7.68 (d, 2H), 7.88 (dd, 1H), 7.99 (d, 1H), 8.22 (d, 1H), 9.8 (brs, 1H) | 511 (M + H)$^+$ |
| 59 | (R)-N-{2-Chloro-4-[4-(4-hydroxy-butylamino)phenylsulphonyl]phenyl}-2-hydroxy-2-methyl-3,3,3-trifluoropropanamide | 1.4–1.63 (m, 7H), 3.04 (m, 2H), 3.4 (m, 2H), 4.38 (t, 1H), 6.62 (d, 2H), 6.76 (t, 1H), 7.6 (d, 1H), 7.82 (dd, 1H), 7.46 (d, 1H), 8.22 (d, 1H), 9.78 (brs, 1H) | 495 (M + H)$^+$ |
| 60 | (R)-N-{2-Chloro-4-[4-(2,2-dimethyl-3-hydroxypropylamino)phenyl-sulphonyl]phenyl}-2-hydroxy-2-methyl-3,3,3-trifluoropropanamide | 0.84 (s, 6H), 1.59 (s, 3H), 2.97 (d, 2H), 3.19 (d, 2H), 4.59 (m, 1H), 6.52 (m, 1H), 6.72 (d, 2H), 7.59 (d, 2H), 7.83 (dd, 1H), 7.94 (d, 1H), 8.21 (d, 1H), 9.8 (brs, 1H) | 509 (M + H)$^+$ |
| 61 | (R)-N-[2-Chloro-4-[4-(2,3-dihydroxypropylamino)phenyl-sulphonyl]phenyl}-2-hydroxy-2-methyl-3,3,3-trifluoropropanamide | 1.59 (s, 3H), 2.99 (m, 1H), 3.2 (m, 1H), 3.3 (m, partially obscured by water peak), 3.59 (m, 1H), 4.63 (t, 1H), 4.83 (d, 1H), 6.7 (d, 2H), 6.78 (t, 1H), 7.6 (d, 2H), 7.84 (dd, 1H), 7.99 (d, 1H), 8.2 (d, 1H), 9.85 (brs, 1H) | 495 |
| 62 | (R)-N-{2-Chloro-4-[4-(1,3-dihydroxyprop-2-ylamino)phenyl-sulphonyl]phenyl}-2-hydroxy-2-methyl-3,3,3-trifluoropropanamide | 1.45 (s, 3H), 3.3 (brs, 5H), 4.5 (brs, 2H), 6.3 (d, 1H), 6.59 (d, 2H), 7.47 (d, 2H), 7.7 (dd, 1H), 7.83 (d, 1H), 8.08 (d, 1H), 9.7 (brs, 1H) | 495 |
| 63 | (R)-N-{2-Fluoro-4-[4-(2-hydroxy-ethylamino)phenylsulphonyl]phenyl}-2-hydroxy-2-methyl-3,3,3-trifluoropropanamide | (CDCl$_3$) 1.69 (s, 3H), 2.84 (t, 1H), 3.27–3.33 (m, 2H), 3.8–3.86 (m, 2H), 5.9 (t, 1H), 6.59 (d, 1H), 6.75 (s, 1H), 7.60–7.68 (m, 4H), 8.53 (t, 1H), 9.27 (s, 1H) | 449 |
| 64 | (R)-N-{2-Chloro-4-[2-(3-hydroxy-pyrrolidin-1-yl)phenylsulphonyl] phenyl}-2-hydroxy-2-methyl-3,3,3-trifluoropropanamide | (CDCl$_3$) 1.75 (s, 3H), 1.85–1.95 (m, 1H), 2.1–2.25 (m, 1H), 2.9 (q, 1H), 3.05–3.2 (m, 3H), 3.75 (d, 1H), 4.48 (brs, 1H), 7.27–7.32 (m, 2H), 7.55 (t, 1H), 7.8 (t, 1H), 8.07 (dd, 1H), 8.14 (d, 1H), 8.5 (d, 1H), 9.2 (brs, 1H) | 491 |
| 65 | (R)-N-{2-Chloro-4-[2-(N,N-dimethylaminoethylamino)phenyl-sulphonyl]phenyl}-2-hydroxy-2-methyl-3,3,3-trifluoropropanamide | (CDCl$_3$) 1.75 (s, 3H), 2.3 (s, 6H), 2.6 (t, 2H), 3.14 (q, 2H), 6.5 (brt, 1H), 6.6 (d, 1H), 6.72 (t, 1H), 7.35 (t, 1H), 7.86 (t, 2H), 8.0 (d, 1H), 8.55 (d, 1H), 9.3 (brs, 1H) | 492 |
| 66 | (R)-N-{2-Chloro-4-[2-morpholino phenylsulphonyl]phenyl}-2-hydroxy-2-methyl-3,3,3-trifluoropropanamide | (CDCl$_3$) 1.76 (s, 3H), 2.8 (brs, 4H), 3.6 (brs, 1H), 3.74 (brs, 4H), 7.3 (d, 1H), 7.4 (t, 1H), 7.62 (t, 1H), 7.75 (d, 1H), 8.1 (s, 1H), 8.27 (d, 1H), 8.52 (d, 1H), 9.2 (brs, 1H) | 491 |
| 67 | (R)-N-{2-Chloro-4-[2-(4-methyl-piperazin-1-yl)phenylsulphonyl] phenyl}-2-hydroxy-2-methyl-3,3,3-trifluoropropanamide | (CDCl$_3$) 1.75 (s, 3H), 2.32 (s, 3H), 2.5 (brs, 4H), 2.83 (t, 4H), 7.3 (t, 1H), 7.37 (t, 1H), 7.6 (t, 1H), 7.72 (dd, 1H), 8.1 (s, 1H), 8.25 (d, 1H), 8.53 (d, 1H), 9.4 (brs, 1H) | 504 |
| 68 | (R)-N-[2-Chloro-4-(4-benzyl-aminophenylsulphonyl)phenyl]-2-hydroxy-2-methyl-3,3,3-trifluoropropanamide | 1.74 (s, 3H), 4.35 (s, 2H), 6.58–6.63 (m, 2H), 7.26–7.39 (m, 5H), 7.62–7.70 (m, 2H), 7.72–7.80 (m, 1H), 7.94 (s, 1H), 8.50–8.57 (m, 1H), 9.18 (brs, 1H) | 511 |
| 69 | (R)-N-[2-Chloro-4-(3-chloro-4-(2-hydroxyethylamino)phenylsulphonyl) phenyl]-2-hydroxy-2-methyl-3,3,3-trifluoropropanamide | (CDCl$_3$) 1.75 (s, 3H), 3.4 (q, 2H), 3.5 (s, 1H), 3.85 (q, 2H), 5.25 (m, 1H), 6.65 (d, 1H), 7.65 (d, 1H), 7.75–7.85 (m, 2H), 7.95 (d, 1H), 8.55 (d, 1H), 9.15 (brs, 1H) | 501 (M + H)$^+$ |
| 70 | (R)-N-[2-Chloro-4-(3-fluoro-4-(2-hydroxyethylamino)phenylsulphonyl) phenyl]-2-hydroxy-2-methyl-3,3,3-trifluoropropanamide | (CDCl$_3$) 1.75 (s, 3H), 3.35 (q, 2H), 3.65 (s, 1H), 3.9 (t, 2H), 4.8 (m, 1H), 6.7 (t, 1H), 7.5 (dd, 1H), 7.60 | 485 (M + H)$^+$ |

| Ex | Compound | NMR | MS |
|---|---|---|---|
| | trifluoropropanamide | (dd, 1H), 7.8 (dd, 1H), 7.9 (d, 1H), 8.55 (d, 1H), 9.2 (brs, 1H) | |
| 71 | (R)-N-{2-Chloro-4-[4-(2-hydroxyethylamino)phenylsulphonyl]phenyl}-2-hydroxy-2-methyl-3,3,3-trifluoropropanamide | (CDCl$_3$ + DMSO-$\delta_6$) 1.6 (s, 3H), 3.2 (q, 2H), 3.7 (m, 3H), 5.15 (t, 1H), 6.51 (d, 2H), 7.14 (s, 1H), 7.58 (d, 2H), 7.68 (d, 1H), 7.83 (d, 1H), 8.49 (d, 1H), 9.64 (brs, 1H) | 465 |
| 72 | (R)-N-{2-Chloro-4-[4-(2-methoxyethylamino)phenylsulphonyl]phenyl}-2-hydroxy-2-methyl-3,3,3-trifluoropropanamide | (CDCl$_3$) 1.76 (s, 3H), 3.29–3.28 (m, 2H), 3.39 (s, 3H), 3.6 (t, 2H), 3.75 (s, 1H), 4.64 (t, 1H), 6.59 (d, 2H), 7.69 (d, 2H), 7.8 (dd, 1H), 7.94 (d, 1H), 8.54 (d, 1H), 9.2 (brs, 1H) | 481 (M + H)$^+$ |
| 73 | (R)-N-(2-Chloro-4-[4-morpholino phenylsulphonyl]phenyl)-2-hydroxy-2-methyl-3,3,3-trifluoropropanamide | (CDCl$_3$) 1.73 (s, 3H), 3.25–3.34 (m, 4H), 3.8–3.9 (m, 5H), 6.99 (d, 2H), 7.72–7.86 (m, 3H), 7.96 (d, 1H), 8.57 (d, 1H), 9.29 (brs, 1H) | 493 (M + H)$^+$ |
| 74 | (R)-N-{2-Chloro-4-[4-(2-methylsulphanylethylamino)phenylsulphonyl]phenyl}-2-hydroxy-2-methyl-3,3,3-trifluoropropanamide | (CDCl$_3$) 1.74 (s, 3H), 2.1 (s, 3H), 2.76 (t, 2H), 3.36 (q, 2H), 3.7 (s, 1H), 4.72 (t, 1H), 6.6 (d, 2H), 7.7 (d, 2H), 7.79 (dd, 1H), 7.94 (d, 1H), 8.54 (d, 1H), 9.21 (brs, 1H) | 497 (M + H)$^+$ |
| 75 | (R)-N-{2-Chloro-4-[4-(2-furylmethylamino)phenylsulphonyl]phenyl}-2-hydroxy-2-methyl-3,3,3-trifluoropropanamide | (CDCl$_3$) 1.78 (s, 3H), 3.66 (brs, 1H), 4.34 (d, 2H), 4.63 (t, 1H), 6.22 (m, 1H), 6.35 (m, 1H), 6.66 (d, 2H), 7.36 (d, 1H), 7.69 (d, 2H), 7.8 (dd, 1H), 7.93 (d, 1H), 8.55 (d, 1H), 9.2 (brs, 1H) | 501 |
| 76 | (R)-N-{2-Chloro-4-[4-({1-ethylpyrrolidin-2-yl}methylamino)phenylsulphonyl]phenyl}-2-hydroxy-2-methyl-3,3,3-trifluoropropanamide | (CDCl$_3$) 1.1 (t, 3H), 1.73 (s, 3H), 3.4 (t, 1H), 5.4 (brs, 1H), 6.59 (d, 2H), 7.68 (d, 2H), 7.7–7.8 (m, 1H), 7.93 (d, 1H), 8.54 (d, 1H), 9.36 (brs, 1H) | 532 |
| 77[1] | (R)-N-{2-Chloro-4-[4-(iso-propylamino)phenylsulphonyl]phenyl}-2-hydroxy-2-methyl-3,3,3-trifluoropropanamide | 1.12 (s, 3H), 1.14 (s, 3H), 1.6 (s, 3H), 3.61 (m, 1H), 6.62 (m, 3H), 7.6 (d, 2H), 7.83 (dd, 1H), 7.97 (d, 1H), 8.20 (d, 1H), 9.86 (brs, 1H) | 463 |
| 78[1] | (R)-N-{2-Chloro-4-[4-(cyclopropylmethylamino)phenylsulphonyl]phenyl}-2-hydroxy-2-methyl-3,3,3-trifluoropropanamide | 0.18 (m, 2H), 0.46 (m, 2H), 0.99 (m, 1H), 1.58 (s, 3H), 2.9 (m, 2H), 6.65 (d, 2H), 6.90 (t, 1H), 7.60 (d, 2H), 7.83 (dd, 1H), 7.95 (m, 2H), 8.19 (d, 1H), 9.87 (brs, 1H) | 475 |
| 79[1] | (R)-N-{2-Chloro-4-[4-(pyrrolidin-1-yl)phenylsulphonyl]phenyl}-2-hydroxy-2-methyl-3,3,3-trifluoropropanamide | 1.6 (s, 3H), 1.94 (m, 4H), 3.28 (m, 4H), 6.62 (d, 2H), 7.7 (d, 2H), 7.85 (dd, 1H), 7.9–8.02 (brs, 1H), 7.99 (d, 1H), 8.2 (d, 1H), 9.86 (brs, 1H) | 475 |
| 80 | (R)-N-{2-Chloro-4-[4-(3-hydroxypyrrolidin-1-yl)phenylsulphonyl]phenyl}-2-hydroxy-2-methyl-3,3,3-trifluoropropanamide | 1.68 (s, 3H), 1.99 (m, 1H), 2.08 (m, 1H), 3.2 (d, 1H), 3.37–3.42 (m, 2H), 4.47 (brs, 1H), 5.04 (d, 1H), 6.66 (d, 2H), 7.75 (d, 2H), 7.9 (dd, 1H), 8.04 (d, 1H), 8.26 (d, 1H), 9.9 (brs, 1H) | 491 |
| 81 | (R)-N-{2-Chloro-4-[4-(4-hydroxypiperidin-1-yl)phenylsulphonyl]phenyl}-2-hydroxy-2-methyl-3,3,3-trifluoropropanamide | 1.42 (m, 2H), 1.68 (s, 3H), 1.82 (m, 2H), 3.12 (m, 2H), 3.75 (m, 3H), 4.77 (d, 1H), 7.08 (d, 2H), 7.79 (d, 2H), 7.9–8.1 (brs), 7.94 (dd, 1H), 8.09 (d, 1H), 8.3 (d, 1H), 9.9 (brs, 1H) | 505 |
| 82 | (R)-N-{2-Chloro-4-[4-thiomorpholino phenylsulphonyl]phenyl}-2-hydroxy-2-methyl-3,3,3-trifluoropropanamide | 1.59 (s, 3H), 2.6 (m, 4H), 3.78 (m, 4H), 7.0 (d, 2H), 7.71 (d, 2H), 7.88 (dd, 1H), 8.0 (brs, 1H), 8.02 (d, 1H), 8.25 (d, 1H), 9.87 (brs, 1H) | 509 (M + H)$^+$ |
| 83 | (R)-N-{2-Chloro-4-[4-(4-hydroxymethylpiperidin-1-yl)phenylsulphonyl]phenyl}-2-hydroxy-2-methyl-3,3,3-trifluoropropanamide | 1.15 (m, 2H), 1.6 (s, 3H), 1.69 (m, 2H), 2.82 (m, 2H), 3.27 (m, 2H), 3.9 (m, 2H), 4.45 (t, 1H), 7.0 (d, 2H), 7.69 (d, 2H), 7.89 (dd, 1H), 8.0 (d, 1H), 8.22 (d, 1H), 9.85 (brs, 1H) | 519 |
| 84 | (R)-N-{2-Chloro-4-[4-(3-hydroxymethylpiperidin-1-yl)phenylsulphonyl]phenyl}-2-hydroxy-2-methyl-3,3,3-trifluoropropanamide | 1.27 (m, 1H), 1.5 (m, 1H), 1.69 (s, 3H), 1.7 (m, 3H), 2.76 (m, 2H), 2.94 (m, 1H), 3.89 (m, 2H), 4.6 (t, 1H), 7.03 (d, 2H), 7.77 (d, 2H), 7.94 (dd, 1H), 8.09 (d, 1H), 8.3 (d, 1H), 9.92 (brs, 1H) | 519 |
| 85 | (R)-N-{2-Chloro-4-[4-(4-{2-hydroxyethyl}piperazin-1-yl)phenylsulphonyl]phenyl}-2- | 1.15 (m, 2H), 1.6 (s, 3H), 1.69 (m, 2H), 2.82 (m, 2H), 3.27 (m, 2H), 3.9 (m, 2H), 4.45 (t, 1H), 7.0 (d, | 534 |

| Ex | Compound | NMR | MS |
|---|---|---|---|
| | hydroxy-2-methyl-3,3,3-trifluoropropanamide | 2H), 7.69 (d, 2H), 7.89 (dd, 1H), 8.0 (d, 1H), 8.22 (d, 1H), 9.85 (brs, 1H) | |

[1]Reaction was carried out in a sealed tube

EXAMPLE 86
(R)-N-{2-Chloro-4-[4-(methylsulphinyl)phenylsulphonyl]phenyl}-2-hydroxy-2-methyl-3,3,3-trifluoropropanamide t-Butylhydroperoxide (0.36 ml of a 3M solution in toluene) was added to a solution of (R)-N-{2-chloro-4-[4-(methylsulphanyl)phenylsulphonyl]phenyl}-2-hydroxy-2-methyl-3,3,3-trifluoropropanamide (Example 2) (0.247 g) and d-10-camphorsulphonic acid (0.012 g) in chloroform (5 ml) and the mixture was stirred at ambient temperature for 64 hours. The reaction mixture was transferred directly to a silica gel Mega Bond Elut column and eluted with 0–80% ethyl acetate/hexane to give the title compound (0.237 g) as a foam. NMR (CDCl$_3$): 1.74 (s, 3H), 2.74 (s, 3H), 4.2 (brs, 1H), 7.79 (d, 2H), 7.89 (dd, 1H), 8.0 (m, 1H), 8.1 (d, 2H) 8.65 (d, 1H), 9.38 (brs, 1H); MS (ESP$^-$): 468; EA: found: C, 43.3; H, 3.1; N, 2.98%; C$_{17}$H$_{15}$ClF$_3$NO$_5$S$_2$ requires: C, 43.3; H, 3.1; N, 2.8%.

EXAMPLES 87–103

Following the procedure of Example 86 and using the appropriate starting materials the following compounds were prepared.

| Ex | Compound | NMR (CDCl$_3$) | MS | SM |
|---|---|---|---|---|
| 87[1] | (R)-N-{2-Chloro-4-[4-(methylsulphinyl)phenylsulphinyl]phenyl}-2-hydroxy-2-methyl-3,3,3-trifluoropropanamide | 1.72 (s, 3H), 2.76 (s, 3H), 5.0 (brm, 1H), 7.53 (m, 1H), 7.7–7.82 (m, 5H), 8.56 (m, 1H), 9.35 (brs, 1H) | 452 | Ex 189 |
| 88 | (R)-N-{2-Chloro-4-[3-(methylsulphinyl)phenylsulphonyl]phenyl}-2-hydroxy-2-methyl-3,3,3-trifluoropropanamide | 1.70 (s, 3H), 2.80 (s, 3H), 5.60 (brs, 1H), 7.70–7.75 (m, 1H), 7.85 (d, 2H), 8.00 (s, 1H), 8.05 (d, 1H), 8.20 (s, 1H), 8.65 (d, 1H), 9.55 (s, 1H) | 468 | Ex 4 |
| 89 | (R)-N-[2-Chloro-4-(4-hydroxyphenylsulphinyl)phenyl]-2-hydroxy-2-methyl-3,3,3-trifluoropropanamide | (DMSO-$d_6$) 1.6 (s, 3H), 6.9–7.0 (m, 3H), 7.5 (d, 2H), 7.6 (dd, 1H), 7.8 (s, 1H), 7.9 (s, 1H), 8.1 (d, 1H), 9.8 (s, 1H) | 406 | Ex 252 |
| 90 | (R)-N-{2-Chloro-4-[4-(methylsulphinyl)phenylsulphanyl]phenyl}-2-hydroxy-2-methyl-3,3,3-trifluoropropanamide | 1.72 (s, 3H), 2.73 (m, 3H), 4.72 (m, 1H), 7.34 (d, 2H), 7.41 (d, 1H), 7.5–7.6 (m, 3H), 8.45 (d, 2H), 9.2 (brd, 1H) | 436 | Ex 189 |
| 91 | (R)-N-{2-Chloro-4-[4-(2-hydroxyethylsulphinyl)phenylsulphonyl]phenyl}-2-hydroxy-2-methyl-3,3,3-trifluoropropanamide | (CDCl$_3$ + DMSO-$d_6$) 1.58 (s, 3H), 2.84 (m, 1H), 2.98 (m, 1H), 3.75 (m, 1H), 3.94 (m, 1H), 4.66 (t, 1H), 7.45 (s, 1H), 7.73 (d, 2H), 7.76 (dd, 1H), 7.91 (d, 1H), 7.99 (d, 2H), 8.6 (d, 1H), 9.72 (brs, 1H) | 498 | Ex 284 |
| 92 | (R)-N-(2-Chloro-4-methylsulphinylphenyl)-2-hydroxy-2-methyl-3,3,3-trifluoropropanamide | 1.77 (s, 3H), 2.74 (s, 3H), 4.7 and 4.75 (2xbrs, 1H), 7.49 (t, 1H), 7.74 (d, 1H), 8.59 (m, 1H), 9.3 (brd, 1H) | 328 | Ex 191 |
| 93 | (R)-N-(2-Fluoro-4-ethylsulphinylphenyl)-2-hydroxy-2-methyl-3,3,3-trifluoropropanamide | (DMSO-$d_6$) 1.09–1.18 (m, 3H), 1.68 (s, 3H), 2.65–2.76 (m, 1H), 2.78–2.86 (m, 1H), 4.54 (s, 1H), 7.21–7.28 (m, 1H), 7.34–7.43 (m, 1H), 8.42–8.50 (m, 1H), 8.85 (brs, 1H) | 326 | Ex 424 |
| 94 | (R)-N-(2-Fluoro-4-methylsulphinylphenyl)-2-hydroxy-2-methyl-3,3,3-trifluoropropanamide | (DMSO-$d_6$) 1.68 (s, 3H), 2.65 (s, 3H), 4.50 (s, 1H), 7.26–7.32 (m, 1H), 7.42–7.50 (m, 1H), 8.47 (t, 1H), 8.85 (s, 1H) | 312 | Ex 196 |
| 95 | (R)-N-[2-Chloro-4-(3-hydroxypropylsulphinyl)phenyl]-2-hydroxy-2-methyl-3,3,3-trifluoropropanamide | (DMSO-$d_6$) 1.44–1.56 (m, 1H), 1.6 (s, 3H), 1.69–1.78 (m, 1H), 2.77–2.87 (m, 1H), 2.98–3.08 (m, 1H), 3.43 (t, 2H), 7.65 (d, 1H), 7.81 (s, 1H), 7.92 (s, 1H), 8.18 (d, 1H), 9.85 (s, 1H) | 372 | Ex 328 |
| 96 | (R)-N-[2-Chloro-4-(cyclohexylsulphinyl)phenyl]-2-hydroxy-2-methyl-3,3,3-trifluoropropanamide | 1.20–1.26 (m, 6H), 1.76 (s, 3H), 1.80–1.86 (m, 4H), 2.52–2.60 (m, 1H), 4.60 and 4.89 (2xs, 1H), 7.36–7.44 (m, 1H), 7.57 and 7.68 (2xs, 1H), 8.50–8.55 (m, 1H), 9.21 and 9.23 (2xs, 1H) | 396 | Ex 417 |

-continued

| Ex | Compound | NMR (CDCl$_3$) | MS | SM |
|----|----------|----------------|----|----|
| 97 | (R)-N-[2-Fluoro-4-(4-ethyl-sulphinylphenylsulphonyl)phenyl]-2-hydroxy-2-methyl-3,3,3-trifluoropropanamide | (DMSO-$\delta_6$) 0.98 (t, 3H), 1.56 (s, 3H), 2.73–2.81 (m, 1H), 3.02–3.13 (m, 1H), 7.84–7.86 (m, 2H), 7.94–8.05 (m, 2H), 8.14 (d, 2H) | 466 | Ex 10 |
| 98 | (R)-N-{2-Chloro-4-[3-chloro-4-(2-hydroxyethylsulphinyl)-phenylsulphonyl]phenyl}-2-hydroxy-2-methyl-3,3,3-trifluoropropanamide | 1.75 (s, 3H), 2.55 (t, 1H), 2.85–2.95 (m, 1H), 3.40–3.55 (m, 1H), 4.05–4.15 (m, 1H), 7.95 (dd, 1H), 7.95 (d, 1H), 8.00–8.15 (m, 3H), 8.65 (d, 1H), 9.3 (brs, 1H) | 532 | Ex 310 |
| 99 | (R)-N-{2-Chloro-4-[3-fluoro-4-(2-hydroxyethylsulphinyl)-phenylsulphonyl]phenyl}-2-hydroxy-2-methyl-3,3,3-trifluoropropanamide | (DMSO-$\delta_6$) 1.6 (s, 3H), 2.9–3.0 (m, 1H), 3.1–3.23 (m, 1H), 3.65–3.85 (m, 2H), 5.1 (t, 1H), 7.95 (t, 1H), 8.0–8.15 (m, 3H), 8.2 (m, 1H), 8.3 (d, 1H), 9.9 (brs, 1H) | 518 (M + H)$^+$ | Ex 311 |
| 100 | (R)-N-[2-Chloro-4-(3-chloro-4-methylsulphinylphenyl-sulphonyl)phenyl]-2-hydroxy-2-methyl-3,3,3-trifluoropropanamide | 1.75 (s, 3H), 2.85 (s, 3H), 3.65 (brs, 1H), 7.9 (m, 1H), 7.95 (s, 1H), 8.0–8.1 (m, 2H), 8.15 (d, 1H), 8.65 (d, 1H), 9.3 (brs, 1H) | 504 (M + H)$^+$ | Ex 8 |
| 101 | (R)-N-[2-Chloro-4-(3-fluoro-4-methylsulphinylphenyl-sulphonyl)phenyl]-2-hydroxy-2-methyl-3,3,3-trifluoropropanamide | 1.74 (s, 3H), 2.85 (s, 3H), 3.95 (d, 1H), 7.70 (d, 1H), 7.8–8.1 (m, 4H), 8.65 (d, 1H), 9.35 (brs, 1H) | 488 (M + H)$^+$ | Ex 9 |
| 102 | (R)-N-[2-Chloro-4-(4-N,N-diethylcarbamoylphenyl-sulphinyl)phenyl]-2-hydroxy-2-methyl-3,3,3-trifluoropropanamide | (DMSO-$\delta_6$) 1.0–1.1 (m, 3H), 1.1–1.20 (m, 3H), 1.6 (s, 3H), 3.1–3.2 (m, 2H), 3.3–3.4 (m, 2H), 7.5 (d, 2H), 7.7–7.80 (m, 3H), 7.85–7.95 (m, 2H), 8.2 (d, 1H), 9.85 (s, 1H) | 491 (M + H)$^+$ | Ex 234 |
| 103 | (R)-N-[2-Chloro-4-(4-{3-hydroxypiperidin-1-yl-carbonyl}phenylsulphinyl)phenyl]-2-hydroxy-2-methyl-3,3,3-trifluoropropanamide | (DMSO-$\delta_6$) 1.1–1.15 (m, 4H), 1.6 (s, 3H), 2.9 (s, 1H), 3.5 (s, 1H), 3.7–3.9 (m, 4H), 7.5 (d, 2H), 7.85 (s, 1H), 7.7–7.9 (m, 3H), 7.95 (s, 1H), 8.2 (d, 1H), 9.8 (s, 1H) | 519 (M + H)$^+$ | Ex 238 |

[1]A further molar equivalent of t-butylhydroperoxide solution was added after 18 hours, and the eluent used in the purification was 0–100% ethyl acetate/hexane

EXAMPLE 104
(R)-N-[4-(4-Acetamidophenylsulphonyl)-2-chlorophenyl]-2-hydroxy-2-methyl-3,3,3-trifluoropropanamide Oxalyl chloride (0.047 ml) was added to a stirred suspension of (R)-(+)-2-hydroxy-2-methyl-3,3,3-trifluoropropanoic acid (Method 9) (0.077 g) in DCM (2.5 ml) containing DMF (1 drop). The mixture was stirred at ambient temperature for 2 hours and was then added to a solution of 4-(4-acetamidophenylsulphonyl)-2-chloroaniline (Method 10) (0.160 g) in DCM (2.5 ml) and stirred a further 2 hours. Ether (50 ml) was added and the mixture was washed with water (2×50 ml) and brine then dried. Volatile material was removed by evaporation and the residue was purified by chromatography on a silica gel Mega Bond Elut column eluting with 0–70% ethyl acetate/toluene to give the title compound (0.025 g) as a solid. NMR: 1.6 (s, 3H), 2.05 (s, 3H), 7.1–7.3 (brm, 1H), 7.8 (d, 2H), 7.9 (m, 3H), 7.97–8.05 (brs, 2H), 8.25 (d, 1H), 10.36 (brs, 1H); MS (ESP$^-$): 463; EA: found: C, 47.8; H, 3.6; N, 5.4%; $C_{18}H_{16}ClF_3N_2O_5S.0.2\ C_7H_8$ requires: C, 48.2; H, 3.7; N, 5.8%.

EXAMPLES 105–112

Following the procedure of Example 104 and using the appropriate starting materials the following compounds were prepared.

| Ex | Compound | NMR | MS |
|----|----------|-----|-----|
| 105 | (R)-N-{2-Chloro-4-[2-(methoxy-carbonyl)phenylsulphanyl]phenyl}-2-hydroxy-2-methyl-3,3,3-trifluoropropanamide | | 432 |
| 106 | (R)-N-{2-Chloro-4-[2-(ethoxy-carbonyl)phenylsulphanyl]phenyl}-2-hydroxy-2-methyl-3,3,3-trifluoropropanamide | 1.3 (t, 3H), 1.6 (s, 3H), 4.3 (q, 2H), 6.85 (d, 1H), 7.25 (t, 1H), 7.35–7.55 (m, 2H), 7.7 (d, 1H), 7.9 (dd, 2H), 8.15 (d, 1H), 9.8 (brs, 1H) | 446 |
| 107 | (R)-N-(2-Fluoro-4-phenylsulphanyl-phenyl)-2-hydroxy-2-methyl-3,3,3-trifluoropropanamide | 1.55 (s, 3H), 7.1 (d, 1H), 7.2 (m, 1H), 7.3–7.5 (m, 5H), 7.6 (s, 1H), 7.7 (t, 1H), 9.65 (s, 1H) | 358 |
| 108[1] | N-(2,4-Dimethoxyphenyl)-2-hydroxy-2-methyl-3,3,3-trifluoropropanamide | 1.6 (s, 3H), 3.8 (s, 3H), 3.9 (s, 3H), 6.55 (dd, 1H), 6.7 (d, 1H), 7.7 (s, 1H), 8.05 (d, 1H), 9.3 (brs, 1H) | 292 |

-continued

| Ex | Compound | NMR | MS |
|---|---|---|---|
| 109[1] | N-[4-Chloro-2-(2-chlorobenzoyl) phenyl]-2-hydroxy-2-methyl-3,3,3-trifluoropropanamide | 1.6 (s, 3H), 7.26 (s, 1H), 7.5–7.57 (m, 1H), 7.6–7.7 (m, 4H), 7.8 (d, 1H), 7.9 (brs, 1H), 8.7 (d, 1H), 12.2 (brs, 1H) | 404 |
| 110[1] | N-(2-Methoxy-4-methoxycarbonyl-phenyl)-2-hydroxy-2-methyl-3,3,3-trifluoropropanamide | 1.6 (s, 3H), 3.85 (s, 3H), 4.0 (s, 3H), 7.6 (s, 1H), 7.65 (d, 1H), 7.93 (s, 1H), 8.37 (d, 1H), 9.7 (brs, 1H) | 320 |
| 111[1] | N-[2-Bromo-4-(iso-propyl)phenyl]-2-hydroxy-2-methyl-3,3,3-trifluoropropanamide | 1.2 (d, 6H), 1.6 (s, 3H), 2.9 (m, 1H), 7.28 (dd, 1H), 7.5 (d, 1H), 7.75 (brs, 1H), 7.9 (d, 1H), 9.6 (brs, 1H) | 352 and 354 |
| 112[1] | N-[2-Chloro-4-(t-butyl)phenyl]-2-hydroxy-2-methyl-3,3,3-trifluoropropanamide | 1.25 (s, 9H), 1.6 (s, 3H), 7.4 (dd, 1H), 7.5 (d, 1H), 7.7 (brs, 1H), 7.9 (d, 1H), 9.6 (brs, 1H) | 322 |
| 113[1] | N-(2-Bromo-4-ethylphenyl)-2-hydroxy-2-methyl-3,3,3-trifluoropropanamide | 1.2 (t, 3H), 1.6 (s, 3H), 2.6 (q, 2H), 7.2 (dd, 1H), 7.5 (d, 1H), 7.7 (brs, 1H), 7.9 (d, 1H), 9.6 (brs, 1H) | 338 and 340 |

[1]Racemic 2-hydroxy-2-methyl-3,3,3-trifluoropropanoic acid was used

EXAMPLE 114
N-(2-Fluoro-4-phenylsulphonylphenyl)-2-hydroxy-2-methylpropanamide Hydrogen peroxide (0.45 ml of a 30 wt. % solution in water) was added to a solution of N-(2-fluoro-4-phenylsulphanylphenyl)-2-hydroxy-2-methylpropanamide (Example 205) (0.34 g) in glacial acetic acid (1.1 ml) and the mixture was stirred and heated at 100° C. for 2 hours then cooled Water (2 ml) was added to the resultant precipitate and the solid was collected, washed further with water (2×5 ml) and dried in vacuo at 60° C. to give the title compound (0.347 g) as a solid. Mp 155.5–156.5° C.; NMR: 1.34 (s, 6H), 6.08 (brs, 1H), 7.56–7.7 (m, 3H), 7.8 (d, 1H), 7.9 (d, 1H), 7.96 (d, 2H), 8.31 (t, 1H), 9.5 (s, 1H); MS (ESP$^-$): 336; EA: found: C, 57.1; H, 4.7; N, 4.1; S, 9.7%; $C_{16}H_{16}FNO_4S$ requires: C, 57.0; H, 4.8; N, 4.2; S, 9.5%

EXAMPLES 115–170

Following the procedure of Example 114, using the appropriate starting materials, and using extraction followed by chromatography to isolate and purify the product when necessary, the following compounds were prepared.

| Ex | Compound | NMR | MS | SM |
|---|---|---|---|---|
| 115 | (R)-N-{2-Chloro-4-[4-(dimethyl-aminosulphonyl)phenylsulphonyl]phenyl}-2-hydroxy-2-methyl-3,3,3-trifluoropropanamide | 1.6 (s, 3H), 2.65 (s, 6H), 7.9–7.95 (d, 3H), 8.0 (dd, 1H), 8.2–8.25 (m, 3H), 8.35 (d, 1H), 9.3 (s, 1H) | 513 | Ex 251 |
| 116 | (R)-N-[2-Chloro-4-(4-sulphamoylphenylsulphonyl)phenyl]-2-hydroxy-2-methyl-3,3,3-trifluoropropanamide | 1.70 (s, 3H), 6.40 (brs, 2H), 7.20 (s, 1H), 7.80 (d, 1H), 7.95 (s, 1H), 8.00–8.10 (m, 4H), 8.7 (d, 1H), 9.80 (s, 1H) | 485 | Ex 254 |
| 117 | (R)-N-{2-Chloro-4-[4-(guanidinosulphonyl)phenyl-sulphonyl]phenyl}-2-hydroxy-2-methyl-3,3,3-trifluoropropanamide | 1.60 (s, 3H), 6.7 (s, 4H), 7.15 (d, 2H), 7.25 (d, 1H), 7.65–7.70 (m, 3H), 7.90 (s, 1H), 8.1 (d, 1H), 9.75 (s, 1H) | 527 | Ex 255 |
| 118 | (R)-N-{2-Chloro-4-[4-(pyrrolidin-1-ylsulphonyl) phenylsulphonyl]phenyl}-2-hydroxy-2-methyl-3,3,3-trifluoropropanamide | (CDCl$_3$) 1.75 (s, 3H), 1.8–1.85 (m, 4H), 3.2–3.3 (m, 4H), 3.55 (s, 1H), 7.85 (dd, 1H), 7.95 (d, 2H), 8.05 (d, 1H), 8.1 (d, 2H), 8.65 (d, 1H), 9.3 (s, 1H) | 539 | Ex 250 |
| 119 | (R)-N-[2-Chloro-4-(4-hydroxy-phenylsulphonyl)phenyl]-2-hydroxy-2-methyl-3,3,3-trifluoropropanamide | 1.6 (s, 3H), 6.95 (d, 2H), 7.8 (d, 2H), 7.9 (dd, 1H), 8.05 (dd, 2H), 9.9 (s, 1H), 10.7 (s, 1H) | 422 | Ex 252 |
| 120 | (R)-N-{2-Chloro-4-[4-(ethoxy-carbonyl)phenylsulphonyl]phenyl}-2-hydroxy-2-methyl-3,3,3-trifluoropropanamide | 1.4 (t, 3H), 1.76 (s, 3H), 3.6 (s, 1H), 4.4 (q, 2H), 7.88 (dd, 1H), 7.99 (m, 3H), 8.18 (d, 2H), 8.64 (d, 1H), 9.3 (brs, 1H) | 478 | Ex 190 |
| 121 | (R)-N-[2-Chloro-4-(4-carboxy-phenylsulphonyl)phenyl]-2-hydroxy-2-methyl-3,3,3-trifluoropropanamide | 1.79 (s, 3H), 8.19 (dd, 2H), 8.32 (s, 4H), 8.36 (d, 1H), 8.52 (d, 1H), 10.1 (brs, 1H), 13.7 (brs, 1H) | 450 | Ex 291 |
| 122 | (R)-N-{2-Chloro-4-[4-(1,1-dioxothiomorpholinocarbonyl)phenylsulphonyl]phenyl}-2-hydroxy-2-methyl-3,3,3-trifluoropropanamide | 1.61 (s, 3H), 3.1–3.4 (brs, 4H), 3.6 (brs, 2H), 4.0 (brs, 2H), 7.73 (d, 2H), 8.02 (dd, 1H), 8.09 (d, 2H), 8.2 (d, 1H), 8.32 (d, 1H), 9.9 (brs, 1H) | 567 | Ex 300 |

-continued

| Ex | Compound | NMR | MS | SM |
|---|---|---|---|---|
| 123 | (R)-N-[2-Chloro-4-(1-methyl-imidazol-2-ylsulphonyl)phenyl]-2-hydroxy-2-methyl-3,3,3-trifluoropropanamide | 1.7 (s, 3H), 4.01 (s, 3H), 7.18 (d, 1H), 7.56 (d, 1H), 8.05 (dd, 1H), 8.13 (d, 1H), 8.42 (d, 1H), 10.0 (brs, 1H) | 410 | Ex 257 |
| 124 | (R)-N-{2-Chloro-4-[4-(1,1-dioxo-thiazolidin-3-ylcarbonyl)phenyl-sulphonyl]phenyl}-2-hydroxy-2-methyl-3,3,3-trifluoropropanamide | 1.6 (s, 3H), 3.45 (m, 2H), 4.02 (brs, 2H), 4.64 (s, 2H), 7.74 (d, 2H), 8.02 (dd, 1H), 8.1 (d, 2H), 8.19 (d, 1H), 8.33 (d, 1H), 9.9 (brs, 1H) | 553 | Ex 301 |
| 125 | (R)-N-[2-Chloro-4-(2-carboxy-phenylsulphonyl)phenyl]-2-hydroxy-2-methyl-3,3,3-trifluoropropanamide | 1.60 (s, 3H), 7.47–7.57 (m, 2H), 7.63–7.68 (m, 1H), 7.98 (d, 1H), 8.06 (d, 1H), 8.22 (d, 1H), 8.27 (s, 1H), 9.92 (s, 1H) | 450 | Ex 292 |
| 126 | (R)-N-(2-Fluoro-4-ethyl-sulphonylphenyl)-2-hydroxy-2-methyl-3,3,3-trifluoropropanamide | (DMSO-$\delta_6$ + AcOH-$\delta_4$) 1.07 (t, 3H), 1.81 (s, 3H), 3.17–3.23 (q, 2H), 7.67–7.75 (m, 2H), 8.15–8.21 (t, 2H) | 342 | Ex 93 |
| 127 | (R)-N-(2-Fluoro-4-mesyl-phenyl)-2-hydroxy-2-methyl-3,3,3-trifluoropropanamide | 1.57 (s, 3H), 3.23 (s, 3H), 7.73–7.76 (m, 2H), 7.85 (d, 1H), 8.03 (d, 1H), 9.92 (s, 1H) | 328 | Ex 196 |
| 128 | (R)-N-[2-Chloro-4-(2-hydroxy-ethylsulfonyl)phenyl]-2-hydroxy-2-methyl-3,3,3-trifluoropropanamide | 1.60 (s, 3H), 3.5 (t, 2H), 3.65–3.71 (m, 2H), 4.84 (t, 1H), 7.86–7.89 (m, 1H), 8.05 (s, 1H), 8.31 (d, 1H), 9.89 (brs, 1H) | 374 | Ex 415 |
| 129 | (R)-N-[2-Chloro-4-(cyclopropyl-methylsulphonyl)phenyl]-2-hydroxy-2-methyl-3,3,3-trifluoropropanamide | 0.11–0.14 (m, 1H), 0.43–0.45 (m, 1H), 0.81–0.87 (m, 1H), 1.61 (s, 3H), 3.32 (d, 2H), 7.85–7.90 (m, 1H), 8.01 (m, 1H), 8.34 (d, 1H) | 384 | Ex 416 |
| 130 | (R)-N-[2-Chloro-4-(3-hydroxypropylsulphonyl)phenyl]-2-hydroxy-2-methyl-3,3,3-trifluoropropanamide | 1.61 (s, 3H), 1.64–1.71 (m, 2H), 3.32–3.43 (m, 4H), 7.87–7.90 (m, 1H), 8.03 (s, 1H), 8.34 (d, 1H) | 388 | Ex 328 |
| 131 | (R)-N-[2-Chloro-4-(N-methyl-carbamoylmethylsulphonyl)phenyl]-2-hydroxy-2-methyl-3,3,3-trifluoropropanamide | 1.63 (s, 3H), 2.52 (d, 3H), 4.28 (s, 2H), 7.83 (d, 1H), 8.10–8.13 (m, 1H), 8.29 (d, 1H) | 401 | Ex 420 |
| 132 | (R)-N-[2-Chloro-4-(iso-propyl-sulphonyl)phenyl]-2-hydroxy-2-methyl-3,3,3-trifluoropropanamide | 1.10–1.13 (d, 6H), 1.60 (s, 3H), 3.34–3.42 (m, 1H), 7.8–7.82 (d, 1H), 8.92 (s, 1H), 8.41 (d, 1H). | 372 | Ex 421 |
| 133 | (R)-N-[2-Chloro-4-(cyclopentyl-sulphonyl)phenyl]-2-hydroxy-2-methyl-3,3,3-trifluoropropanamide | 1.55–1.60 (m, 7H), 1.76–1.86 (m, 4H), 3.81–3.89 (m, 1H), 7.86–7.89 (m, 1H), 8.02 (s, 1H), 8.34 (d, 1H). | 398 | Ex 422 |
| 134 | (R)-N-[2-Chloro-4-(iso-butyl-sulphonyl)phenyl]-2-hydroxy-2-methyl-3,3,3-trifluoropropanamide | 0.97 (s, 6H), 1.61 (s, 3H), 1.97–2.05 (m, 1H), 3.26–3.34 (m, 2H), 7.68–7.92 (m, 1H), 8.05 (s, 1H), 8.31 (d, 1H), 9.92 (s, 1H) | 386 | Ex 423 |
| 135 | (R)-N-[2-Chloro-4-(cyclohexyl-sulphonyl)phenyl]-2-hydroxy-2-methyl-3,3,3-trifluoropropanamide | 1.13–1.26 (m, 6H), 1.61 (s, 3H), 1.71–1.76 (m, 2H), 1.84–1.88 (m, 2H), 3.31–3.35 (m, 1H), 7.80–7.84 (m, 1H), 7.92 (s, 1H), 8.34 (d, 1H) | 412 | Ex 96 |
| 136 | N-[2-Fluoro-4-(4-mesylphenyl-sulphonyl)phenyl]-2-hydroxy-2-difluoromethyl-3,3-difluoropropanamide | 3.26 (s, 3H), 6.42 (t, 2H), 7.85–7.94 (m, 2H), 8.01 (d, 1H), 8.14 (d, 1H), 8.25 (d, 1H) | 486 | Ex 200 |
| 137 | (R)-N-{2-Fluoro-4-[2-hydroxyethylsulphonyl)phenyl-sulphonyl]phenyl}-2-hydroxy-2-methyl-3,3,3-trifluoropropanamide | 1.57 (s, 3H), 3.54 (t, 2H), 3.65–3.71 (m, 2H), 4.66 (t, 1H), 7.86 (d, 1H), 7.97–8.05 (m, 2H), 8.07 (d, 1H), 8.21 (d, 1H) | 498 | Ex 309 |
| 138 | (R)-N-[2-Fluoro-4-(4-ethyl-sulphonylphenylsulphonyl)phenyl]-2-hydroxy-2-methyl-3,3,3-trifluoropropanamide | 1.05–1.10 (t, 3H), 1.55 (s, 3H), 3.31–3.39 (q, 2H), 7.87 (d, 1H), 7.98–8.05 (m, 1H), 8.11 (d, 2H), 8.24 (d, 2H) | 482 | Ex 97 |
| 139 | (R)-N-{2-Fluoro-4-[4-(N-methylcarbamoylmethyl sulphonyl)phenylsulphonyl]phenyl}-2-hydroxy-2-methyl-3,3,3-trifluoropropanamide | 1.57 (s, 3H), 2.5 (d, 3H), 4.34 (s, 2H), 7.86 (d, 1H), 8.0–8.02 (m, 1H), 8.07–8.13 (m, 3H), 8.23 (d, 2H) | 525 | Ex 308 |
| 140 | (R)-N-[2-Bromo-4-(4-mesyl-phenylsulphonyl)phenyl]-2-hydroxy-2- | 1.6 (s, 3H), 3.27 (s, 3H), 8.02–8.08 (m, 2H), 8.15 (d, | 528 | Ex 201 |

-continued

| Ex | Compound | NMR | MS | SM |
|---|---|---|---|---|
| | methyl-3,3,3-trifluoropropanamide | 2H), 8.26 (d, 2H), 8.33 (s, 1H), 8.36 (d, 1H), 9.91 (s, 1H) | | |
| 141 | (R)-N-[2-Chloro-4-(N,N-dimethylcarbamoylmethyl-sulphonyl)phenyl]-2-hydroxy-2-methyl-3,3,3-trifluoropropanamide | 1.68 (s, 3H), 2.85 (s, 3H), 3.05 (s, 3H), 4.72 (s, 2H), 7.93 (d, 2H), 8.08 (s, 1H), 8.44 (d, 1H) | 415 | Ex 402 |
| 142 | (R)-N-[2-Chloro-4-(methoxy-carbonylmethylsulphonyl)phenyl]-2-hydroxy-2-methyl-3,3,3-trifluoropropanamide | 1.62 (s, 3H), 3.6 (s, 3H), 4.74 (s, 2H), 7.9 (d, 2H), 8.07 (s, 1H), 8.33 (d, 1H) | 402 | Ex 403 |
| 143 | (R)-N-[2-Mesyl-4-(2-mesyl-phenylsulphonyl)phenyl]-2-hydroxy-2-methyl-3,3,3-trifluoropropanamide | 1.6 (s, 3H), 3.28 (s, 3H), 3.5 (s, 3H), 8.02–8.05 (m, 2H), 8.18–8.21 (m, 2H), 8.39 (s, 1H), 8.5–8.53 (d, 1H), 8.62 (d, 1H), 11.1 (brs, 1H) | 528 | Ex 11 |
| 144 | (R)-N-(2-Chloro-4-ethyl-sulphonylphenyl)-2-hydroxy-2-methyl-3,3,3-trifluoropropanamide | 1.07 (t, 3H), 1.6 (s, 3H), 3.32 (q, 2H), 7.85 (d, 1H), 8.01 (s, 1H), 8.32 (d, 1H) | 358 | Ex 327 |
| 145 | (R)-N-{2-Chloro-4-[4-(N-methylcarbamoylmethyl-sulphonyl)phenylsulphonyl]phenyl}-2-hydroxy-2-methyl-3,3,3-trifluoropropanamide | 1.60 (s, 3H), 3.3 (3H, s), 4.35 (s, 2H), 8.0–8.40 (m, 7H), 9.95 (bs, 1H) | 541 | Ex 288 |
| 146 | (R)-N-[2-Chloro-4-(4-cyclopropylmethylsulphonyl-phenylsulphonyl)-phenyl]-2-hydroxy-2-methyl-3,3,3-trifluoropropanamide | 0.15 (q, 2H), 0.55 (q, 2H), 0.9–1.00 (m, 1H), 1.75 (s, 3H), 3.05 (d, 2H), 3.65 (s, 1H), 7.9 (dd, 1H), 8. (dd, 1H), 8.05–8.15 (m, 4H), 8.65 (d, 1H), 9.35 (brs, 1H) | 524 | Ex 287 |
| 147 | (R)-N-[2-Chloro-4-(4-ethylsulphonylphenylsulphonyl)phenyl]-2-hydroxy-2-methyl-3,3,3-trifluoropropanamide | 1.25 (t, 3H), 1.75 (s, 3H), 3.1 (q, 2H), 3.5 (s, 1H), 7.9 (dd, 1H), 8.0–8.15 (m, 5H), 8.65 (d, 1H), 9.3 (brs, 1H) | 498 | Ex 7 |
| 148 | (R)-N-{2-Chloro-4-[4-(iso-propylsulphonyl)phenyl-sulphonyl]phenyl}-2-hydroxy-2-methyl-3,3,3-trifluoropropanamide | 1.3 (d, 6H), 1.75 (s, 3H), 3.2 (m, 1H), 3.95 (s, 1H), 7.9 (dd, 1H), 8.05 (m, 3H), 8.1 (dd, 2H), 8.7 (dd, 1H), 9.4 (brs 1H). | 512 | Ex 6 |
| 149[1] | N-(2-Chloro-4-phenylsulphonyl-phenyl)dichloroacetamide | 6.86 (s, 1H), 7.5–7.75 (m, 3H), 7.9–8.03 (m, 4H), 10.47 (brs, 1H) | 376 and 378 | See[1] |
| 150[1] | N-(2-Chloro-4-phenylsulphonyl-phenyl)-2,2-dimethyl-propanamide | 1.2 (s, 9H), 7.6 (t, 2H), 7.7 (t, 1H), 7.84–7.92 (m, 2H), 8.0 (d, 2H), 8.05 (d, 1H), 9.1 (brs, 1H) | 350 | See[1] |
| 151[1] | N-(2-Chloro-4-phenylsulphonyl-phenyl)cyclopropylcarboxamide | 0.8 (m, 4H), 2.1 (m, 1H), 7.6–7.72 (m, 3H), 7.85 (dd, 1H), 7.95 (d, 2H), 8.03 (s, 1H), 8.1 (d, 1H), 9.9 (brs, 1H) | 334 | See[1] |
| 152[1] | N-(2-Chloro-4-phenylsulphonyl-phenyl)-2-chloropropanamide | 1.6 (d, 3H), 4.95 (q, 1H), 7.6 (t, 2H), 7.7 (t, 1H), 7.9 (dd, 1H), 8.0 (d, 2H), 8.05–8.1 (m, 2H), 10.09 (brs, 1H) | 356 and 358 | See[1] |
| 153[1] | N-(2-Chloro-4-phenylsulphonyl-phenyl)-2-methylpropanamide | 1.1 (d, 6H), 2.8 (m, 1H), 7.6 (t, 2H), 7.7 (t, 1H), 7.85 (dd, 1H), 7.95 (d, 2H), 8.0–8.1 (m, 2H), 9.6 (s, 1H) | 336 | See[1] |
| 154 | (R)-N-[2-Fluoro-4-(2-mesyl-phenylsulphonyl)phenyl]-2-hydroxy-2-methyl-3,3,3-trifluoropropanamide | 1.55 (s, 3H), 3.5 (s, 3H), 7.73–7.78 (m, 2H), 7.85 (dd, 1H), 7.98 (d, 1H), 8.0–8.06 (m, 2H), 8.2 (m, 1H), 8.5 (m, 1H), 9.9 (brs, 1H) | 468 | Ex 12 |
| 155 | (R)-N-[2-Fluoro-4-(4-mesyl-phenylsulphonyl)phenyl]-2-hydroxy-2-methyl-3,3,3-trifluoropropanamide | 1.6 (s, 3H), 3.3 (s, 3H), 7.78 (s, 1H), 7.9 (d, 1H), 7.95–8.1 (m, 2H), 8.15 (d, 2H), 8.25 (d, 2H), 9.85 (s, 1H) | 468 | Ex 194 |
| 156 | (R)-N-{2-Chloro-4-[2-(N,N-diethylcarbamoyl)phenyl sulphonyl]phenyl}-2-hydroxy-2-methyl-3,3,3-trifluoropropanamide | 1.06 (m, 3H), 1.25 (m, 3H), 1.59 (s, 3H), 3.08 (m, 2H), 3.39 (m, 1H), 3.67 (m, 1H), 7.41 (d, 1H), 7.66 (t, 1H), 7.78 (t, 1H), 7.98 (d, 1H), 8.16 (m, 2H), 8.27 (d, 1H), 9.90 (brs, 1H) | 505 | Ex 232 |

-continued

| Ex | Compound | NMR | MS | SM |
|---|---|---|---|---|
| 157 | (R)-N-[2-Chloro-4-(2,3-dihydroxypropyl)sulphonyl-phenyl]-2-hydroxy-2-methyl-3,3,3-trifluoropropanamide | 1.60 (s, 3H), 3.15–3.23 (m, 2H), 3.36–3.44 (m, 2H), 3.36–3.44 (m, 2H), 3.81–3.89 (m, 1H), 4.86 (t, 1H), 4.94 (d, 1H), 7.86–7.89 (m, 1H), 8.02 (s, 1H), 8.31 (d, 1H), 9.89 (s, 1H) | 404 | Ex 425 |
| 158 | (R)-N-[2-Chloro-4-(2-hydroxy-propyl)sulphonylphenyl]-2-hydroxy-2-methyl-3,3,3-trifluoropropanamide | 1.11 (d, 3H), 1.60 (s, 3H), 3.39–3.44 (m, 2H), 4.00–4.05 (m, 1H), 4.84 (d, 1H), 7.86–7.89 (m, 1H), 8.02 (s, 1H). 8.31 (d, 1H), 9.89 (s, 1H) | 388 | Ex 426 |
| 159 | (R)-N-[2-Chloro-4-t-butyl-sulphonylphenyl]-2-hydroxy-2-methyl-3,3,3-trifluoropropanamide | 1.26 (s, 9H), 1.63 (s, 3H), 7.81–7.84 (m, 1H), 7.89 (s, 1H), 8.39 (d, 1H) | 386 | Ex 427 |
| 160 | (R)-N-[2-Chloro-4-(4-{3-hydroxy-propoxy}phenylsulphonyl)phenyl]-2-hydroxy-2-methyl-3,3,3-trifluoropropanamide | ($CDCl_3$) 1.75 (s, 3H), 2.1–2.2 (m, 2H), 3.8–3.9 (m, 1H), 4.05–4.2 (m, 2H), 4.2–4.25 (m, 1H), 4.65 (s, 1H), 7.0 (d, 2H), 7.7–7.85 (m, 3H), 7.9 (s, 1H), 8.6 (d, 2H), 9.4 (s, 1H) | 480 | Ex 397 |
| 161 | (R)-N-[2-Chloro-4-(4-{carbamoylmethoxy}phenyl-sulphonyl)phenyl]-2-hydroxy-2-methyl-3,3,3-trifluoropropanamide | 1.6 (s, 3H), 4.55 (s, 2H), 7.1–7.2 (m, 2H), 7.35 (s, 1H), 7.5 (s, 1H), 7.85–7.95 (m, 3H), 8.0 (s, 1H), 8.1 (s, 1H), 8.2–8.3 (m, 1H), 9.85 (s, 1H) | 481 $(M + H)^+$ | Ex 399 |
| 162 | (R)-N-[2-Chloro-4-(4-{N,N-dimethylcarbamoylmethoxy}phenylsulphonyl)phenyl]-2-hydroxy-2-methyl-3,3,3-trifluoropropanamide | ($CDCl_3$) 1.75 (s, 3H), 3.0 (s, 3H), 3.1 (s, 3H), 4.75 (s, 2H), 6.9 (d, 1H), 7.0 (d, 1H), 7.8–7.9 (m, 3H), 8.0 (s, 1H), 8.6 (d, 2H), 9.3 (s, 1H) | 507 | Ex 400 |
| 163 | (R)-N-(2-Chloro-4-{4-[2-(N-oxy-morpholino)ethylaminocarbonyl]phenylsulphonyl}phenyl)-2-hydroxy-2-methyl-3,3,3-trifluoropropanamide | 1.6 (s, 3H), 3.1 (d, 2H), 3.2–3.3 (m, 2H), 3.3–3.4 (m, 2H), 3.7 (d, 2H), 3.8 (d, 2H), 4.1–4.2 (m, 2H), 7.9–8.0 (m, 5H), 8.1–8.2 (m, 3H), 8.3 (d, 1H), 10.6 (s, 1H) | 580 $(M + H)^+$ | Ex 237 |
| 164 | (R)-N-[2-Chloro-4-(4-{3-hydroxypiperidin-1-ylcarbonyl}phenyl-sulphonyl)phenyl]-2-hydroxy-2-methyl-3,3,3-trifluoropropanamide | 1.3–1.5 (2H, m), 1.6 (s, 3H), 1.7–1.9 (m, 2H), 2.8–3.0 (m, 2H), 3.4–3.6 (m, 2H), 3.6–3.7 (m, 1H), 4.1 (d, 1H), 7.6 (d, 2H), 8.0–8.1 (m, 4H), 8.2 (s, 1H), 8.3 (d, 1H), 9.9 (s, 1H) | 535 $(M + H)^+$ | Ex 238 |
| 165 | (R)-N-[2-Fluoro-4-(4-mesylphenylsulphonyl)phenyl]-2-hydroxy-2-trifluoromethyl-3,3,3-trifluoropropanamide | 3.33 (s, 3H), 7.72-7.77 (m, 1H), 7.86–7.91 (m, 1H), 8.02 (d, 1H), 8.16 (d, 2H), 8.27 (d, 2H), 9.91 (s, 1H), 10.6 (s, 1H) | 522 | Ex 413 |
| 166 | (R)-N-[2-Chloro-4-(2-hydroxybutylsulphonyl)phenyl}-2-hydroxy-2-methyl-3,3,3-trifluoropropanamide | 0.80 (t, 3H), 1.28–1.33 (m, 1H), 1.41–1.50 (m, 1H), 1.61 (s, 3H), 3.40 (d, 2H), 3.78–3.80 (m, 1H), 4.80 (d, 1H), 7.86–7.89 (m, 1H), 8.02 (s, 1H), 8.29 (d, 1H) | 402 | Ex 408 |
| 167 | (R)-N-{2-Chloro-4-(2-hydroxy-2-methylpropylsulphonyl) phenyl}-2-hydroxy-2-methyl-3,3,3-trifluoropropanamide | 1.25 (s, 6H), 1.61 (s, 3H), 3.47 (s, 2H), 7.86–7.89 (m, 1H), 8.01 (s, 1H), 8.29 (d, 1H) | 402 | Ex 409 |
| 168 | (R)-N-{2-Chloro-4-propyl-sulphonylphenyl}-2-hydroxy-2-methyl-3,3,3-trifluoropropanamide | 0.90 (t, 3H), 1.26–1.35 (m, 2H), 1.61 (s, 3H), 3.32–3.38 (m, 2H), 7.86–7.89 (m, 1H), 8.02 (s, 1H), 8.32 (d, 1H), 9.88 (s, 1H) | 372 | Ex 410 |
| 169 | (R)-N-{2-Chloro-4-(butyl-sulphonyl)phenyl}-2-hydroxy-2-methyl-3,3,3-trifluoropropanamide | 0.82 (t, 3H), 1.26–1.35 (m, 2H), 1.45–1.55 (m, 2H), 1.61 (s, 3H), 3.31–3.41 (m, 2H), 7.86–7.90 (m, 1H), 8.02 (s, 1H), 8.32 (d, 1H) | 386 | Ex 411 |
| 170 | (R)-N-{2-Chloro-4-(3-carboxy-phenylsulphonyl)phenyl}-2-hydroxy-2-methyl-3,3,3-trifluoropropanamide | 1.58 (s, 3H), 7.76 (t, 1H), 8.03 (d, 2H), 8.22 (m, 3H), 8.3 (d, 1H), 8.4 (s, 1H), 9.88 (s, 1H) | 450 | Ex 293 |

[1]The starting material was prepared by acylation of 2-chloro-4-phenylsulphanylaniline (Method 5) with the appropriate acid chloride using procedure of Method 23. Solvent was removed under a stream of argon and the intermediate was used without purification.

EXAMPLE 171

N-[2-Chloro-4-(4-acetamidophenylsulthonyl)phenyl]-2-hydroxy-2-methylpropanamide A solution of lithium hydroxide monohydrate (0.106 g) in water (1 ml) was added to a stirred solution of N-[2-chloro-4-(4-acetamidophenylsulphonyl)phenyl]-2-acetoxy-2-methylpropanamide (Method 16) (0.230 g) in methanol (2 ml) and the mixture was stirred at ambient temperature for 2 hours. Water (5 ml) was added and the solution was acidified to pH 2–3 with 1M hydrochloric acid. Ethyl acetate (20 ml) was added and the organic layer was washed with water (20 ml) and brine, then dried. Volatile material was removed by evaporation and the off-white solid was washed with ether to give the title compound (0.150 g) as a solid. NMR (CDCl$_3$):1.3 (s, 6H), 2.2 (s, 3H), 7.4 (s, 1H), 7.7 (d, 2H), 7.8 (m, 3H), 7.9 (s, 1H), 8.7 (d, 1H), 9.6 (s, 1H); MS (ESP$^-$): 409.

EXAMPLES 172–181

Following the procedure of Example 171 and using the appropriate starting material the following compounds were prepared.

| Ex | Compound | NMR | MS | SM |
|---|---|---|---|---|
| 172 | N-{2-Chloro-4-[4-N-(2,2-dimethylpropanamido)phenyl-sulphonyl]phenyl}-2-hydroxy-2-methylpropanamide | (CDCl$_3$) 1.3 (s, 9H), 1.6 (s, 6H), 7.5–7.9 (m, 7H), 8.6 (d, 1H), 9.6 (s, 1H) | 451 | Meth 25 |
| 173 | N-(2-Chloro-4-phenyl-sulphonylphenyl)-2-hydroxy-2-methylpropanamide | 1.37 (s, 6H), 6.26 (s, 1H), 7.6–7.7 (m, 3H), 7.9–8.0 (m, 3H), 8.1 (d, 1H), 8.51 (d, 1H), 9.8 (brs, 1H) | 352 | Meth 33 |
| 174 | (R)-N-[2-Chloro-4-(4-ureido-phenylsulphanyl)phenyl]-2-hydroxy-2-methyl-3,3,3-trifluoropropanamide | 1.6 (s, 3H), 5.9 (s, 2H), 7.1 (d, 1H), 7.2 (s, 1H), 7.3 (d, 2H), 7.5 (d, 2H), 7.7 (s, 1H), 7.8 (d, 1H), 8.7 (s, 1H), 9.6 (s, 1H) | 432 | Meth 34 |
| 175 | (R)-N-[2-Chloro-4-(2-ureido-phenylsulphanyl)phenyl]-2-hydroxy-2-methyl-3,3,3-trifluoropropanamide | | 432 | Meth 35 |
| 176 | (R)-N-[2-Fluoro-4-(4-nitro-phenylsulphanyl)phenyl]-2-hydroxy-2-methyl-3,3,3-trifluoropropanamide | 1.6 (s, 3H), 7.3 (d, 2H), 7.4 (d, 1H), 7.6 (d, 1H), 7.9 (t, 1H), 8.2 (d, 2H) | 403 | Meth 39 |
| 177 | (R)-N-{2-Chloro-4-[4-(2-chloro-acetylamino)phenylsulphanyl]phenyl}-2-hydroxy-2-methyl-3,3,3-trifluoropropanamide | | 465 | Meth 19 |
| 178 | (R)-N-{2-Chloro-4-[4-(2-morpholinoacetylamino)phenyl-sulphanyl]phenyl}-2-hydroxy-2-methyl-3,3,3-trifluoropropanamide | 1.6 (s, 3H), 3.2 (s, 6H), 3.8 (s, 4H), 7.2 (d, 1H), 7.3 (s, 1H), 7.4 (d, 2H), 7.7 (d, 2H), 7.8 (s, 1H), 7.9 (d, 1H), 9.7 (s, 1H) | 516 | Meth 41 |
| 179 | (R)-N-{2-Chloro-4-[4-(3-t-butylureido)phenylsulphanyl]phenyl}-2-hydroxy-2-methyl-3,3,3-trifluoropropanamide | 1.2 (s, 9H), 1.6 (s, 3H), 6.1 (s, 1H), 7.1 (d, 1H), 7.2 (s, 1H), 7.3 (d, 2H), 7.4 (d, 2H), 7.7 (s, 1H), 7.8 (d, 1H), 8.6 (s, 1H), 9.6 (s, 1H) | 488 | Meth 43 |
| 180 | (R)-N-{2-Chloro-4-[4-(3-phenylureido)phenylsulphanyl]phenyl}-2-hydroxy-2-methyl-3,3,3-trifluoropropanamide | 1.6 (s, 3H), 7.0 (t, 1H), 7.1 (d, 1H), 7.3 (m, 3H), 7.4 (t, 4H), 7.6 (d, 2H), 7.8 (s, 1H), 7.9 (d, 1H) 8.8 (s, 1H), 9.0 (s, 1H) 9.6 (s, 1H) | 508 | Meth 44 |
| 181 | (R)-N-(2-Chloro-4-{3-t-butoxy-2-hydroxypropylamino}phenyl)-2-hydroxy-2-methyl-3,3,3-trifluoropropanamide | (CDCl$_3$) 1.23 (s, 9H), 1.73 (s, 3H), 2.55 (d, 1H), 3.12 (m, 1H), 3.27 (m, 1H), 3.4 (m, 1H), 3.5 (m, 1H), 3.95 (s, 2H), 4.24 (s, 1H), 6.53 (dd, 1H), 6.67 (s, 1H), 7.95 (d, 1H), 8.34 (s, 1H) | 411 | Meth 50 |

EXAMPLE 182

N-[2-Chloro-4-(4-mesylaminophenylsulphonyl)phenyl]-2-hydroxy-2-methylpropanamide m-Chloroperoxybenzoic acid (50%, 0.55 g) was added to a solution of N-[2-chloro-4-(4-mesylaminophenylsulphanyl)phenyl]-2-hydroxy-2-methylpropanamide (Example 207) (0.22 g) in DCM (5 ml) and the mixture was stirred at ambient temperature for 15 hours. DCM (10 ml) was added, followed by saturated aqueous sodium carbonate solution (20 ml) and the mixture was poured onto a Varian Chem Elut column. After 3 minutes the column was washed through with DCM (20 ml) and the organic fractions concentrated. The residue was purified by flash chromatography eluting with 40–70% ethyl acetate/hexane to give the title compound (0.15 g) as a foam. NMR (CDCl$_3$): 1.8 (s, 6H), 3.1 (s, 3H), 7.3 (m, 3H), 7.9 (m, 4H), 9.6 (m, 2H); MS (ESP$^-$): 445; EA: found: C, 45.1; H, 4.4; N, 6.2%, $C_{17}H_{19}ClN_2O_6S_2 \cdot 0.3H_2O$ requires C, 45.1; H, 4.4; N, 6.2%.

EXAMPLE 183

Following the procedure of Example 182 and using the appropriate starting materials the following compound was prepared.

| Ex | Compound | NMR | MS | SM |
|---|---|---|---|---|
| 183 | (R)-N-(1-Oxy-6-methyl-5-phenylsulphonylpyridin-2-yl)-2-hydroxy-2-methyl-3,3,3-trifluoropropanamide | 1.6 (s, 3H), 2.5 (s, 3H), 7.7 (m, 3H), 7.9 (s, 2H), 8.1 (m, 2H), 8.4 (d, 1H) | 403 | Ex 211 |

EXAMPLE 184

N-[2-Amino-4-(phenylsulphonyl)phenyl]-2-hydroxy-2-methyl-3,3,3-trifluoropropanamide A suspension of N-[2-nitro-4-(phenylsulphonyl)phenyl]2-hydroxy-2-methyl-3,3,3-trifluoropropanamide (*J. Med. Chem.*, 1996, 39, 4592) (0.293 g) in methanol (5 ml) was added to a stirred suspension of 10% palladium on carbon (0.03 g) in methanol (2 ml) under an atmosphere of argon. A solution of ammonium formate (0.176 g) in water (2 ml) was added and the mixture was heated under reflux for 2 hours then cooled. Ethyl acetate (20 ml) was added and the mixture was filtered through diatomaceous earth. The filter was washed with ethyl acetate (2×10 ml) and the filtrates were combined, washed with water and brine then dried. Volatile material was removed by evaporation to give the title compound (0.261 g) as a solid. NMR: 1.55 (s, 3H), 5.3 (s, 2H), 7.1 (dd, 1H), 7.3 (d, 1H), 7.4 (m, 2H), 7.5–7.7 (m, 3H), 7.85 (d, 2H), 9.6 (s, 1H); MS (ESP$^-$): 387.

EXAMPLE 185

N-[2-Acetamido-4-(phenylsulphonyl)phenyl]-2-hydroxy-2-methyl-3,3,3-trifluoropropanamide Acetyl chloride (0.018 ml) was added to an ice-cooled solution of N-[2-amino-4-(phenylsulphonyl)phenyl]-2-hydroxy-2-methyl-3,3,3-trifluoropropanamide (Example 184) (0.097 g) in pyridine (1 ml) and the solution was allowed to warm up to ambient temperature over 2 hours. Water was added and the mixture was extracted with ethyl acetate. The organic extracts were combined, washed with brine and dried. Volatile material was removed by evaporation and the residue was purified by chromatography on a silica gel Mega Bond Elut column eluting with 10–40% ethyl acetate/hexane to give the title compound (0.89 g) as a solid. Mp 205–207° C., NMR: 1.5 (s, 3H), 2.1 (s, 3H), 7.57–7.75 (m, 4H), 7.8–7.9 (m, 2H) 7.9–8.05 (m, 3H), 9.8 (brs, 1H), 10.1 (brs, 1H); MS (ESP$^-$): 429.

EXAMPLE 186

Following the procedure of Example 185 and using methanesulphonyl chloride to replace acetyl chloride the following compound was prepared.

| Ex | Compound | NMR | MS |
|---|---|---|---|
| 186 | 2-Hydroxy-2-methyl-N-[2-mesylamino-4-(phenylsulphonyl)phenyl]-3,3,3-trifluoropropanamide | 1.55 (s, 3H), 3.0 (s, 3H), 7.5–7.75 (m, 3H), 7.8–8.0 (m, 5H), 8.3 (d, 1H), 9.6 (brs, 1H), 10.1 (brs, 1H) | 465 |

EXAMPLE 187

(R)-N-[2-Chloro-4-(2-fluorophenylsulphanyl)phenyl]-2-hydroxy-2-methyl-3,3,3-trifluoropropanamide Tetrakis(triphenylphosphine)palladium(0) (0.147 g) was added to a deoxygenated mixture of (R)-N-(2-chloro-4-iodophenyl)-2-hydroxy-2-methyl-3,3,3-trifluoropropanamide (Example 197) (1.0 g), 2-fluorothiophenol (0.263 ml) and sodium methoxide (0.288 g) in ethanol (50 ml). The mixture was then further deoxygenated by evacuation and refilling with argon (3 cycles), and then heated under reflux with stirring under argon for 18 hours. The mixture was treated with a further portion of tetrakis(triphenylphosphine)palladium(0) (0.147 g), heated for a further 24 hours then cooled and filtered. Volatile material was removed by evaporation and the residue was purified by flash chromatography eluting with 20% ethyl acetate/hexane to give the title compound (0.906 g) as an oil. NMR (CDCl$_3$): 1.75 (s, 3H), 3.58 (s, 1H), 7.1 (t, 2H), 7.2–7.35 (m, 3H), 7.37 (d, 1H), 8.3 (d, 1H), 8.82 (brs, 1H); MS (ESP−): 392.

EXAMPLES 188–196

Following the procedure of Example 187 and using the appropriate starting materials the following compounds were prepared.

| Ex | Compound | NMR and MS |
|---|---|---|
| 188 | (R)-N-[2-Chloro-4-(4-fluorophenylsulphanyl)phenyl]-2-hydroxy-2-methyl-3,3,3-trifluoropropanamide | (CDCl$_3$): 1.74 (s, 3H), 3.79 (s, 1H), 7.04 (t, 2H), 7.2 (dd, 1H), 7.27 (d, 1H), 7.38 (dd, 2H), 8.27 (d, 1H), 8.87 (brs, 1H); MS (ESP+): 394 (M + H)+. |
| 189 | (R)-N-[2-Chloro-4-{4-(methylsulphanyl)phenylsulphanyl}phenyl]-2-hydroxy-2-methyl-3,3,3-trifluoropropanamide | 1.57 (s, 3H), 3.29 (s, 3H), 7.2–7.4 (m, 6H), 7.8 (brs, 1H), 7.9 (d, 1H), 9.7 (brs, 1H) |
| 190[1] | (R)-N-[2-Chloro-4-{4-(ethoxycarbonyl)phenylsulphanyl}phenyl]-2-hydroxy-2-methyl-3,3,3-trifluoropropanamide | (CDCl$_3$): 1.4 (t, 3H), 1.79 (s, 3H), 3.68 (s, 1H), 4.35 (q, 2H), 7.24 (d, 2H), 7.41 (dd, 1H), 7.51 (d, 1H), 7.92 (d, 2H), 8.42 (d, 1H), 9.0 (brs, 1H) |
| 191[2] | (R)-N-[2-Chloro-4-methylsulphanylphenyl]-2-hydroxy-2-methyl-3,3,3-trifluoropropanamide | (CDCl$_3$): 1.76 (s, 3H), 2.5 (s, 3H), 3.82 (brs, 1H), 7.19 (dd, 1H). 7.3 (d, 1H), 8.28 (d, 1H), 8.8 (brs, 1H) |
| 192 | (R)-N-[2-Chloro-4-(pyrid-4-ylsulphanyl)phenyl]-2-hydroxy-2-methyl-3,3,3-trifluoropropanamide | (CDCl$_3$): 1.68 (s, 3H), 6.98 (m, 2H), 7.26 (s, 1H), 7.5 (dd, 1H), 7.6 (d, 1H), 8.32 (m, 2H), 8.56 (d, 1H), 9.38 (brs, 1H) |
| 193 | (R)-N-[2-Fluoro-4-(4-fluorophenylsulphanyl)phenyl]-2-hydroxy-2-methyl-3,3,3-trifluoropropanamide | (CDCl$_3$): 1.73 (s, 3H), 3.63 (s, 1H), 7.02–7.07 (m, 4H), 7.36–7.42 (m, 2H), 8.19–8.23 (m, 1H), 8.50 (s, 1H); MS (ESP−): 376. |
| 194 | (R)-N-[2-Fluoro-4-(4-methylsulphanylphenylsulphanyl)phenyl]-2-hydroxy-2-methyl-3,3,3-trifluoropropanamide | 1.6 (s, 3H), 7.05 (d, 1H), 7.1 (d, 1H), 7.3 (d, 2H), 7.35 (d, 2H), 7.5–7.7 (m, 2H), 9.6 (s, 1H); MS (ESP−): 404. |
| 195 | (R)-N-[2-Fluoro-4-(2-fluorophenylsulphanyl)phenyl]-2-hydroxy-2-methyl-3,3,3-trifluoropropanamide | 1.6 (s, 3H), 7.1 (d, 1H), 7.15–7.5 (brm, 5H), 7.6 (brs, 1H), 7.7 (t, 1H), 9.6 (brs, 1H); MS (ESP−): 376. |
| 196[2] | (R)-N-[2-Fluoro-4-(methylsulphanyl)phenyl]-2-hydroxy-2-methyl-3,3,3-trifluoropropanamide | (CDCl$_3$) 1.73 (s, 3H), 2.47 (s, 3H), 3.63 (s, 1H), 7.0–7.05 (m, 2H), 8.17 (t, 1H), 8.83 (s, 1H) |

[1]The thiol used as starting material was methyl 4-mercaptobenzoate
[2]Sodium methanethiolate was used instead of a thiol as starting material EXAMPLE 197
(R)-N-(2-Chloro-4-iodonhenyl)-2-hydroxy-2-methyl-3,3,3-trifluoropropanamide Oxalyl chloride (1.07 ml) was added dropwise to a stirred suspension of (R)-(+)-2-hydroxy-2-methyl-3,3,3-trifluoropropanoic acid (Method 9) (1.95 g) in DCM (42 ml) and DMF (0.8 ml). The mixture was stirred at ambient temperature for 2 hours and was then added over 35 minutes to a solution of 2-chloro-4-iodoaniline (2.5 g) and 2,6-di-t-butylpyridine (2.94 ml) in DCM (40 ml) and stirred a further 18 hours. Volatile material was removed by evaporation and the residue was purified by flash chromatography on silica gel eluting with DCM to give the title compound (2.85 g) as a solid. NMR: 1.6 (s, 3H), 7.7 (m, 2H), 7.8 (d, 1H), 7.9 (brs, 1H); MS (ESP−): 392.

EXAMPLES 198–201

Following the procedure of Example 197 and using the appropriate starting material the following compounds were prepared.

| Ex | Compound | NMR | MS | SM |
|---|---|---|---|---|
| 198 | (R)-N-(2-Chloro-4-benzyl-phenyl)-2-hydroxy-2-methyl-3,3,3-trifluoropropanamide | 1.7 (s, 3H), 3.75 (brs, 1H), 3.95 (s, 2H), 7.1–7.25 (m, 7H), 8.15 (d, 1H), 8.75 (brs, 1H) | 358 | Meth 30 |
| 199 | (R)-N-[2-Fluoro-4-iodophenyl]-2-hydroxy-2-methyl-3,3,3-trifluoropropanamide | (CDCl$_3$) 1.56 (s, 3H), 3.57 (s, 1H), 7.44–7.50 (m, 2H), 8.08 (t, 2H), 8.56 (brs, 1H) | 376 | 2-Fluoro-4-iodoaniline |
| 200[1] | N-[2-Fluoro-4-(4-methylsulphanylphenylsulphanyl)phenyl]-2-hydroxy-2- | (CDCl$_3$) 2.47 (s, 3H), 3.94 (brs, 2H), 6.15 (t, 1H), 6.94–7.00 (d, 1H), 7.02– | 422 | Meth 6 |

| Ex | Compound | NMR | MS | SM |
|---|---|---|---|---|
| | difluoromethyl-3,3-difluoropropanamide | 7.05 (d, 1H), 7.18–7.21 (d, 2H), 7.28–7.31 (d, 2H), 8.15 (t, 1H), 8.52 (s, 1H) | | |
| 201[2] | (R)-N-[2-Bromo-4-{4-methyl-sulphanylphenylsulphanyl}phenyl]-2-hydroxy-2-methyl-3,3,3-trifluoromethyl-propanamide | (CDCl$_3$) 1.76 (s, 3H), 2.5 (s, 3H), 3.66 (s, 1H), 7.2 (d, 2H), 7.3–7.33 (m, 3H), 7.47 (d, 1H), 8.25 (d, 1H), 9.8 (s, 1H) | 466 | Meth 11 |

[1] 2-Difluoromethyl-2-hydroxy-3,3-difluoropropanoic acid (prepared as described by W.J. Middleton and R.V. Lindsey Jnr. J. Am. Chem. Soc., 1964, 86, 4948) was used instead of (R)-(+)-2-hydroxy-2-methyl-3,3,3-trifluoropropanoic acid.
[2] 2,6-diphenylpyridine was used in place of 2,6-di-t-butylpyridine

EXAMPLE 202

(R)-N-{2-Chloro-4-([5-ethoxycarbonyl-3-pyridyl]sulphanyl)phenyl}-2-hydroxy-2-methyl-3,3,3-trifluoropropanamide Caesium fluoride (0.26 g) was added to a solution of (R)-N-(2-chloro-4-(triisopropylsilylsulphanyl)phenyl]-2-hydroxy-2-methyl-3,3,3-trifluoropropanamide (0.74 g) (Method 28) in anhydrous DMA (5 ml) under argon and the mixture was stirred for 17 hours. Copper(I) chloride (0.17 g) followed by 3-bromo-5-carboethoxypyridine (0.37 g) were added and the mixture was heated to 155° C. for 4 hours and allowed to cool to ambient temperature. Ethyl acetate (20 ml) and brine (20 ml) were added and the mixture was filtered through a pad of diatomaceous earth which was washed with ethyl acetate (3×50 ml). The filtrates were combined, washed with brine (3×50 ml) and then dried. Volatile material was removed by evaporation and the residue was purified on a silica gel Mega Bond Elut column eluting with 10–40% ethyl acetate/iso-hexane to give the title compound (in 53% yield) as a foam. NMR (CDCl$_3$): 1.39 (t, 3H), 1.57 (s, 3H), 4.00 (s, 1H), 4.40 (q, 2H), 7.34–7.37 (m, 1H), 7.46 (d, 1H), 8.18 (s, 1H), 8.42 (d, 1H), 8.62 (s, 1H), 9.03 (s, 1H), 9.04 (s, 1H); MS (ESP$^-$): 447.

EXAMPLE 203

By the method of Example 202 and using the appropriate starting materials the following compound was prepared.

| Ex | Compound | NMR | MS | SM |
|---|---|---|---|---|
| 203 | (R)-N-{2-Chloro-4-(4-{pyrimidin-2-yl}phenylsulphanyl)phenyl}-2-hydroxy-2-methyl-3,3,3-trifluoropropanamide | 1.6 (s, 3H), 7.38–7.52 (m, 4H), 7.65 (d, 1H), 7.9 (brs, 1H), 8.06 (d, 1H), 8.38 (d, 2H), 8.9 (d, 2H), 9.79 (brs, 1H) | 452 | Ex 197 and Meth 52 |

EXAMPLE 204

Following the procedure of Method 22 (see below) and using Example 197 as the starting material the following compound was prepared.

| Ex | Compound | NMR |
|---|---|---|
| 204 | (R)-N-[2-Chloro-4-{4-nitrophenyl-sulphanyl}phenyl]-2-hydroxy-2-methyl-3,3,3-trifluoropropanamide | (CDCl$_3$) 1.8 (s, 3H), 5.0 (s, 1H), 7.2 (d, 2H), 7.5 (d, 1H), 7.6 (s, 1H), 8.1 (d, 2H), 8.6 (d, 1H), 9.3 (s, 1H). |

EXAMPLE 205
N-(2-Fluoro-4-phenylsulphanylphenyl)-2-hydroxy-2-methylpropanamide 2-Acetoxy-2-methylpropanoyl chloride (0.47 ml) was added to a solution of 2-fluoro-4-phenylsulphanylaniline (Method 7) (0.64 g) and pyridine (0.28 ml) in DCM (10 ml). The solution was stirred at ambient temperature for 90 minutes then volatile material was removed by evaporation. The residue was dissolved in methanol (20 ml) and a solution of lithium hydroxide monohydrate (0.378 g) in water (2.5 ml) was added. Stirring was continued for another 1 hour then the mixture was acidified to pH 1 with 2M hydrochloric acid and concentrated by evaporation to about 5 ml. Water (10 ml) was added and the product was extracted with ethyl acetate. Organic layers were washed with brine then combined and dried. Volatile material was removed by evaporation and the residue was purified by chromatography on a silica gel Mega Bond Elut column eluting with 10–20% ethyl acetate/hexane to yield the title compound (0.784 g) as a solid. Mp 91–92.5° C.; NMR: 1.34 (s, 6H), 5.96 (s, 1H), 7.15 (d, 1H), 7.23 (dd, 1H), 7.27–7.4 (m, 5H), 8.02 (t, 1H), 9.3 (s, 1H); MS (ESP$^-$): 304; EA: found: C, 62.8; H, 5.3; N. 4.5; S. 10.5%; $C_{16}H_{16}FNO_2S$ requires: C, 62.9; H, 5.3; N, 4.6; S, 10.5%. pared.

EXAMPLE 206

Following the procedure of Example 205 using the appropriate starting materials the following compound was pre 7.1–7.4 (m, 7H), 8.4 (d, 1H), 9.3 (s, 1H); MS (ESP$^-$):413; EA: found: C, 48.9; H, 4.4; N, 6.5%; $C_{17}H_{19}ClN_2O_4S_2$ requires C, 49.2; H, 4.6; N, 6.8%.

EXAMPLES 208–209

Following the procedure of Method 30 (see below) and using the appropriate starting materials the following compounds were prepared.

| Ex | Compound | NMR | MS | SM |
|---|---|---|---|---|
| 208 | (R)-N-(2-Chloro-4-aminophenyl)-2-hydroxy-2-methyl-3,3,3-trifluoropropanamide | 1.53 (s, 3H), 5.32 (s, 2H), 6.50 (d, 1H), 6.66 (s, 1H), 7.39 (d, 1H), 7.45 (s, 1H), 9.30 (s, 1H) | 281 | Meth 60 |
| 209 | (R)-N-(2-Methyl-4-aminophenyl)-2-hydroxy-2-methyl-3,3,3-trifluoropropanamide | (CDCl$_3$) 1.69 (s, 3H), 2.15 (s, 3H), 3.60 (brs, 2H), 4.02 (brs, 1H), 6.48–6.57 (m, 2H), 7.28–7.35 (m, 1H), 7.62 (brs, 1H). | 261 | Meth 62 |

EXAMPLE 210
(R)-N-(2-Chloro-4-mercaptophenyl)-2-hydroxy-2-methyl-3,3,3-trifluoropropanamide Trifluoroacetic anhydride (5 ml) was added to (R)-N-(2-chloro-4-methylsulphinyl-phenyl)-2-hydroxy-2-methyl-3,3,3-trifluoropropanamide (Example 92) (0.188 g). The mixture was stirred and heated under reflux for 45 minutes then cooled and evaporated to dryness. A mixture of triethylamine (5 ml) and methanol (5 ml) was added to the residue. This mixture was stirred for a further 45 minutes then evaporated to dryness. The residue was dissolved in chloroform (50 ml), washed with saturated aqueous ammonium chloride solution (50 ml), dried and concentrated by evaporation to give the title compound (0.177 g) as a gum which was used without purification. MS (ESP$^-$): 298.

| Ex | Compound | HPLC | MS | SM |
|---|---|---|---|---|
| 206 | (R)-N-[2-Chloro-4-(2-nitroanilino)phenyl]-2-hydroxy-2-methyl-3,3,3-trifluoropropanamide | 8.08 minutes (HPLC Method d) | 402 | Meth 47 |

EXAMPLE 207
N-[2-Chloro-4-(4-mesylaminophenylsulphanyl)phenyl]-2-hydroxy-2-methylpropanamide A solution of lithium hydroxide monohydrate (0.177 g) in water (1.8 ml) was added to a stirred solution of N-{2-chloro-4-[4-(N,N-dimesylamino)phenylsulphanyl]phenyl}-2-acetoxy-2-methylpropanamide (Method 26) (0.45 g) in methanol (3.5 ml) and the mixture was stirred at ambient temperature for 4 hours. Water (3 ml) was added and the solution was acidified to pH 2–3 with 1M hydrochloric acid. DCM (20 ml) was added and the organic layer was washed with water (20 ml) and brine, then dried. Volatile material was removed by evaporation and the residue was purified by flash chromatography eluting with 30–70% ethyl acetate/hexane to give the title compound (0.30 g) as a solid. Mp 138–140° C.; NMR (CDCl$_3$): 1.5 (s, 6H), 3.0 (s, 3H),

EXAMPLE 211

The indicated starting material was coupled with an appropriate thiol or halide using the method of Example 250 and acylated using the procedure of Example 197.

| Ex | Compound | MS | SM |
|---|---|---|---|
| 211 | (R)-N-[6-Methyl-5-phenylsulphanylpyridin-2-yl]-2-hydroxy-2-methyl-3,3,3-trifluoropropanamide | 357 (M + H)$^+$ | 2-methyl-3-bromo-6-aminopyridine |

EXAMPLE 212

Following the procedure of Method 63 (see below) and using the appropriate starting material the following compound was prepared.

| Ex | Compound | NMR | SM |
|---|---|---|---|
| 212[1] | (R)-N-[2-Chloro-4-(4-mesyl phenylsulphonyl)phenyl]-2-hydroxy-2-methyl-3,3,3-trifluoropropanamide | (CDCl$_3$) 1.73 (s, 3H), 3.08 (s, 3H), 3.7 (brs, 1H), 7.89 (dd, 1H), 8.02 (d, 1H), 8.08–8.15 (m, 4H), 8.67 (d, 1H), 9.33 (brs, 1H) | Ex 189 |

[1] 5 equivalents of m-Chloroperoxybenzoic acid

EXAMPLES 213–214

Following the procedure of Method 13 (see below) and using the appropriate starting material the following compounds were prepared.

| Ex | Compound | NMR | MS | SM |
|---|---|---|---|---|
| 213 | (R)-N-{2-Chloro-4-[2-(methoxycarbonyl)phenylsulphonyl]phenyl}-2-hydroxy-2-methyl-3,3,3-trifluoropropanamide | 1.6 (s, 3H), 3.85 (s, 3H), 7.6 (m, 1H), 7.8–7.9 (m, 2H), 7.95 (dd, 1H), 7.9–8.05 (brs, 1H), 8.1 (d, 1H), 8.2–8.35 (m, 2H), 9.9 (brs, 1H) | 464 | Ex 105 |
| 214 | (R)-N-{2-Chloro-4-[2-(ethoxycarbonyl)phenylsulphonyl]phenyl}-2-hydroxy-2-methyl-3,3,3-trifluoropropanamide | 1.3 (t, 3H), 1.58 (s, 3H), 4.3 (q, 2H), 7.65 (dd, 1H), 7.8 (m, 2H), 7.95 (dd, 1H), 9.0 (brs, 1H), 8.1 (d, 1H), 8.2 (dd, 1H), 8.3 (d, 1H), 9.95 (brs, 1H) | 478 | Ex 106 |

EXAMPLE 215
(R)-N-{2-Chloro-4-[4-(N,N-dimethylcarbamoyl)phenylsulphonyl]phenyl}-2-hydroxy-2-methyl-3,3,3-trifluoropropanamide Oxalyl chloride (0.45 ml) was added to a stirred suspension of (R)-N-[2-chloro-4-(4-carboxyphenylsulphonyl)phenyl]-2-hydroxy-2-methyl-3,3,3-trifluoropropanamide (Example 121) (1.81 g) in DCM (100 ml) containing DMF (10 drops). The mixture was stirred for 5 hours and then a solution of dimethylamine (4.2 ml, 2M solution in methanol) was added, and the solution was stirred overnight. The reaction mixture was washed with dilute hydrochloric acid solution (2×25 ml) then dried. Volatile material was removed by evaporation and the residue was purified by chromatography on a silica gel Mega Bond Elut column eluting with 0–10% methanol/DCM to yield the title compound (0.68 g) as a solid. M.p. 120.5° C. (Mettler FP62 apparatus); NMR: (CDCl$_3$): 1.70 (s, 3H), 2.90 (s, 3H), 3.10 (s, 3H), 5.20 (s, 1H), 7.55 (d, 2H), 7.85 (d, 1H), 7.90–8.00 (m, 3H), 8.60 (d, 1H), 9.40 (s, 1H); MS (ESP$^-$): 477.

EXAMPLES 216–249

Following the procedure of Example 215 using the appropriate starting materials the following compounds were prepared.

| Ex | Compound | NMR | MS | SM |
|---|---|---|---|---|
| 216 | (R)-N-{2-Chloro-4-[4-(N,N-diethylcarbamoyl)phenylsulphonyl]phenyl}-2-hydroxy-2-methyl-3,3,3-trifluoropropanamide | (CDCl$_3$) 1.05–1.15 (brm, 3H), 1.2–1.3 (brm, 3H), 1.7 (s, 3H), 3.1–3.3 (m, 2H), 3.5–3.65 (m, 2H), 5.1 (s, 1H), 7.5 (d, 2H), 7.85 (d, 1H), 7.95–8.0 (m, 3H), 8.6 (d, 1H), 9.4 (brs, 1H) | 505 | Ex 121 |
| 217 | (R)-N-(2-Chloro-4-{4-[N-(3-hydroxypropyl)carbamoyl]phenylsulphonyl}phenyl)-2-hydroxy-2-methyl-3,3,3-trifluoropropanamide | 1.65 (s, 3H), 1.7–1.75 (m, 2H), 3.25–3.35 (m, 2H), 3.4–3.5 (m, 2H), 4.45 (dd, 1H), 7.95–8.05 (m, 4H), 8.1 (d, 2H), 8.2 (s, 1H), 8.35 (d, 1H), 8.6–8.7 (m, 1H), 9.9 (brs, 1H) | 507 | Ex 121 |
| 218 | (R)-N-(2-Chloro-4-{4-[N-(2,3-dihydroxypropyl)carbamoyl]phenylsulphonyl}phenyl)-2-hydroxy-2-methyl-3,3,3-trifluoropropanamide | 1.6 (s, 3H), 3.1–3.2 (m, 1H), 3.3–3.5 (m, 2H), 3.6–3.7 (m, 2H), 7.85 (brs, 1H), 7.95–8.0 (m, 1H), 8.05–8.10 (m, 3H), 8.10–8.15 (m, 1H), 8.2 (d, 1H), 8.3 (d, 1H), 8.7 (dd, 1H), 9.9 (s, 1H) | 523 | Ex 121 |
| 219 | R)-N-[2-Chloro-4-(4-carbamoylphenylsulphonyl)phenyl]-2-hydroxy-2-methyl-3,3,3-trifluoropropanamide | (CDCl$_3$) 1.65 (s, 3H), 7.60 (s, 1H), 7.95 (dd, 1H), 8.0–8.05 (m, 4H), 8.05–8.1 (m, 1H), 8.1–8.2 (m, 2H), 8.3 (d, 1H), 9.9 (s, 1H) | 449 | Ex 121 |
| 220 | (R)-N-{2-Chloro-4-[4-(4-t-butoxycarbonylpiperazin-1-ylcarbonyl)phenylsulphonyl] | (CDCl$_3$) 1.45 (s, 9H), 1.7 (s, 3H), 3.25–3.55 (brm, 7H), 3.7–3.8 (m, 2H), 7.5 (d, 2H), 7.85 (dd, 1H), | 618 | Ex 121 |

| Ex | Compound | NMR | MS | SM |
|---|---|---|---|---|
| | phenyl}-2-hydroxy-2-methyl-3,3,3-trifluoropropanamide | 7.95–8.0 (m, 3H), 8.6 (d, 1H), 9.35 (s, 1H) | | |
| 221 | (R)-N-(2-Chloro-4-{4-[N-(2-hydroxy-1.1-dimethylethyl) carbamoyl]phenylsulphonyl} phenyl)-2-hydroxy-2-methyl-3,3,3-trifluoropropanamide | 1.25 (s, 6H), 1.6 (s, 3H), 3.5 (d, 2H), 4.8 (dd, 1H), 7.75 (s, 1H), 7.9 (d, 2H), 7.95 (dd, 2H), 8.05 (d, 2H), 8.15 (d, 2H), 8.3 (d, 1H), 9.90 (s, 1H) | 521 | Ex 121 |
| 222 | (R)-N-{2-Chloro-4-[4-(N-pyrimidin-2-ylcarbamoyl) phenylsulphonyl]phenyl}-2-hydroxy-2-methyl-3,3,3-trifluoropropanamide | (CDCl$_3$) 1.75 (s, 3H), 5.2 (brs, 1H), 6.6 (dd, 1H), 7.1 (dd, 1H), 7.8–7.9 (m, 1H), 8.0 (d, 1H), 8.05 (s, 1H), 8.25 (d, 2H), 8.60–8.7 (m, 3H), 9.05 (s, 1H), 9.6 (s, 1H) | 527 | Ex 121 |
| 223 | (R)-N-{2-Chloro-4-[4-(N-methylcarbamoyl)phenyl-sulphonyl]phenyl}-2-hydroxy-2-methyl-3,3,3-trifluoropropanamide | (CDCl$_3$) 1.7 (s, 3H), 3.0 (d, 3H), 4.2 (s, 1H), 6.2 (brs, 1H), 7.8–7.9 (m, 3H), 7.9–8.0 (m, 3H), 8.6 (d, 1H), 9.35 (brs, 1H) | 463 | Ex 121 |
| 224 | (R)-N-{2-Chloro-4-[2-(4-methylpiperazin-1-ylcarbonyl) phenylsulphonyl]phenyl}-2-hydroxy-2-methyl-3,3,3-trifluoropropanamide | (DMSO-$\delta_6$ + AcOH-$\delta_4$) 1.55 (s, 3H), 2.68 (brs, 3H), 2.97–3.02 (brm, 2H), 3.10–3.13 (brm, 2H), 3.30–3.32 (brm, 2H), 3.84–3.86 (brm, 2H), 7.40 (d, 1H), 7.6 (t, 1H), 7.7 (t, 1H), 7.89–7.94 (m, 1H), 8.05–8.07 (m, 2H), 8.32 (d, 1H) | 532 | Ex 125 |
| 225 | (R)-N-{2-Chloro-4-[2-(morpholinocarbonyl)phenyl-sulphonyl]phenyl}-2-hydroxy-2-methyl-3,3,3-trifluoropropanamide | (DMSO-$\delta_6$ + AcOH-$\delta_4$) 1.55 (s, 3H), 3.02–3.07 (m, 2H), 3.52–3.94 (m, 6H), 7.35 (d, 1H), 7.58 (t, 1H), 7.89–7.92 (m, 1H), 8.03 (d, 1H), 8.10 (s, 1H), 8.32 (d, 1H); | 519 | Ex 125 |
| 226 | (R)-N-{2-Chloro-4-[2-(thiazolidin-3-ylcarbonyl) phenylsulphonyl]phenyl}-2-hydroxy-2-methyl-3,3,3-trifluoropropanamide | (At 373K): 1.64 (s, 3H), 3.0–3.06 (brm, 2H), 3.40–3.45 (brm, 1H), 3.87–3.9 (brm, 1H), 4.12–4.2 (brm, 1H), 4.61–4.67 (brm, 1H), 7.47 (d, 1H), 7.68 (t, 1H), 7.78 (t, 1H), 7.95 (d, 1H), 8.09–8.12 (m, 1H), 8.31 (d, 1H), 9.71 (brs, 1H) | 521 | Ex 125 |
| 227 | (R)-N-[2-Chloro-4-(N,N-diethylcarbamoylmethyl-sulphonyl)phenyl]-2-hydroxy-2-methyl-3,3,3-trifluoropropanamide | 0.92–0.97 (t, 3H), 1.06–1.1 (t, 3H), 1.62 (s, 3H), 3.15–3.2 (q, 2H), 3.33–3.38 (q, 2H), 4.68 (s, 2H), 7.86–7.9 (m, 1H), 8.02 (s, 1H), 8.29 (d, 1H), 9.94 (s, 1H) | 445 | Ex 314 |
| 228 | (R)-N-[2-Chloro-4-(carbamoyl-methylsulphonyl)phenyl]-2-hydroxy-2-methyl-3,3,3-trifluoropropanamide | 1.62 (s, 3H), 4.29 (s, 2H), 7.86 (d, 1H), 8.0 (s, 1H), 8.3 (d, 1H), 9.92 (s, 1H) | 387 | Ex 314 |
| 229 | (R)-N-{2-Chloro-4-[N-(2-hydroxyethyl)carbamoylmethyl sulphonyl]phenyl}-2-hydroxy-2-methyl-3,3,3-trifluoropropanamide | 1.63 (s, 3H), 3.02–3.07 (m, 2H), 3.28–3.34 (m, 2H), 4.44 (s, 2H), 4.65 (t, 1H), 7.84–7.86 (m, 2H), 8.0 (s, 1H), 8.31 (d, 1H). | 431 | Ex 314 |
| 230 | (R)-N-[2-Chloro-4-(N-iso-propylcarbamoylmethyl-sulphonyl)phenyl]-2-hydroxy-2-methyl-3,3,3-trifluoropropanamide | 0.97 (d, 6H), 1.63 (s, 3H), 3.65–3.73 (m, 1H), 4.26 (s, 2H), 7.81–7.84 (m, 1H), 7.92 (s, 1H), 8.31 (d, 1H). | 429 | Ex 314 |
| 231 | (R)-N-[2-Chloro-4-(N-pyrimidin-2-ylcarbamoyl-methylsulphonyl)phenyl]-2-hydroxy-2-methyl-3,3,3-trifluoropropanamide | 1.62 (s, 3H), 4.81 (s, 2H), 6.51–6.55 (m, 2H), 7.2–7.23 (m, 1H), 7.88–7.91 (m, 1H), 7.97 (s, 1H), 8.33 (d, 1H), 9.95 (s, 1H), 10.9 (s, 1H) | 467 (M + H)$^+$ | Ex 314 |
| 232 | (R)-N-{2-Chloro-4-[2-(N,N-diethylcarbamoyl)phenyl-sulphanyl]phenyl}-2-hydroxy-2-methyl-3,3,3-trifluoropropanamide | 1.0 (t, 3H), 1.14 (t, 3H), 1.60 (s, 3H), 3.05 (q, 2H), 3.44 (m, 2H), 7.30 (m, 3H), 7.41 (m, 2H), 7.49 (s, 1H), 7.86 (brs, 1H), 7.95 (d, 1H), 9.73 (brs, 1H) | 473 | Ex 292 |
| 233 | (R)-N-[2-Chloro-4-(4-carbamoylphenylsulphinyl) phenyl]-2-hydroxy-2-methyl-3,3,3-trifluoropropanamide | 1.60 (s, 3H), 7.3 (d, 2H), 7.4 (d, 2H), 7.50 (dd, 1H), 7.65 (d, 1H), 7.8–8.0 (m, 3H), 8.1 (d, 1H), 9.80 (s, 1H) | 435 (M + H)$^+$ | Ex 280 |
| 234 | (R)-N-[2-Chloro-4-(4-N,N-diethylcarbamoylphenyl-sulphanyl)phenyl]-2-hydroxy-2-methyl-3,3,3-trifluoropropanamide | (CDCl$_3$) 1.05–1.25 (m, 6H), 1.7 (s, 3H), 3.2–3.3 (m, 2H), 3.4–3.5 (m, 2H), 5.25 (s, 1H), 7.2–7.3 (m, 3H), 7.35 (m, 3H), 7.45–7.5 (m, 1H), 7.95 (dd, 1H), 8.4 (d, 1H), 9.2 (s, 1H) | 475 (M + H)$^+$ | Ex 291 |
| 235 | (R)-N-[2-Chloro-4-(4-N,N-dimethylcarbamoylphenyl-sulphinyl)phenyl]-2-hydroxy- | 1.60 (s, 3H), 2.95 (d, 6H), 7.3 (d, 2H), 7.35–7.4 (m, 3H), 7.6 (s, 1H), 7.8–8.0 (m, 1H), 8.05 (d, 1H), 9.8 | 464 (M + H)$^+$ | Ex 280 |

| Ex | Compound | NMR | MS | SM |
|---|---|---|---|---|
| | 2-methyl-3,3,3-trifluoropropanamide | (s, 1H) | | |
| 236 | (R)-N-[2-Chloro-4-(4-(2-hydroxyethoxycarbonyl)phenylsulphinyl)phenyl]-2-hydroxy-2-methyl-3,3,3-trifluoropropanamide | 1.6 (s, 3H), 1.75 (s, 1H), 3.9–4.0 (m, 2H), 4.4–4.5 (m, 2H), 7.35 (d, 2H), 7.5 (d, 1H), 7.7 (s, 1H), 7.8–8.0 (m, 3H), 8.1 (d, 1H), 9.8 (s, 1H) | 480 (M + H)+ | Ex 280 |
| 237 | (R)-N-[2-Chloro-4-(4-{2-morpholinoethylamino carbonyl}phenylsulphanyl)phenyl]-2-hydroxy-2-methyl-3,3,3-trifluoropropanamide | (CDCl$_3$) 1.75 (s, 3H), 2.4–2.6 (m, 4H), 2.6–2.7 (m, 2H), 3.5–3.6 (m, 2H), 3.7–3.8 (m, 4H), 6.8–6.9 (s, 1H), 7.2–7.3 (m, 3H), 7.35 (dd, 1H), 7.5 (s, 1H), 7.65 (d, 2H), 8.4 (d, 1H), 9.25 (s, 1H) | 532 (M + H)+ | Ex 291 |
| 238 | (R)-N-[2-Chloro-4-(4-{3-hydroxypiperidin-1-ylcarbonyl}phenylsulphanyl)phenyl]-2-hydroxy-2-methyl-3,3,3-trifluoropropanamide | 1.0–1.05 (m, 1H), 1.05–1.10 (m, 4H), 1.3–1.4 (m, 2H), 1.6 (s, 3H), 4.0–4.1 (m, 3H), 7.25–7.4 (m, 4H), 7.4–7.45 (m, 1H), 7.6 (s, 1H), 7.85 (s, 1H), 8.05 (d, 1H), 9.80 (s, 1H) | 503 (M + H)+ | Ex 291 |
| 239 | (R)-N-[2-Chloro-4-(4-{N-[5-methylpyrazol-3-yl]carbamoyl}phenylsulphanyl)phenyl]-2-hydroxy-2-methyl-3,3,3-trifluoropropanamide | (CDCl$_3$) 1.75 (s, 3H), 2.2 (s, 3H), 5.35 (s, 1H), 5.6 (brs, 2H), 7.2–7.25 (m, 3H), 7.45 (dd, 1H), 7.55 (d, 1H), 8.0 (d, 2H), 8.4 (d, 1H), 9.0 (s, 1H) | 497 (M + H)+ | Ex 291 |
| 240 | (R)-N-[2-Chloro-4-(4-{N-[isoxazol-3-yl]carbamoyl}phenylsulphanyl)phenyl]-2-hydroxy-2-methyl-3,3,3-trifluoropropanamide | 1.6 (s, 3H), 5.5 (s, 2H), 5.85 (d, 1H), 7.35 (d, 2H), 7.5 (d, 1H), 7.95 (d, 1H), 8.1 (d, 1H), 8.3 (d, 2H), 8.8 (s, 1H), 9.8 (s, 1H) | 484 | Ex 291 |
| 241 | (R)-N-{2-Chloro-4-[3-(4-methylpiperazin-1-ylcarbonyl)phenylsulphonyl]phenyl}-2-hydroxy-2-methyl-3,3,3-trifluoropropanamide | 1.6 (s, 3H), 2.23 (m, 5H), 2.36 (brs, 1H), 3.2 (brs, 2H), 3.6 (brs, 2H), 7.7 (d, 2H), 7.9–8.13 (m, 4H), 8.23 (s, 1H), 8.31 (d, 1H), 9.9 (brs, 1H) | 532 | Ex 170 |
| 242 | (R)-N-{2-Chloro-4-[3-(N-methylcarbamoyl)phenylsulphonyl]phenyl}-2-hydroxy-2-methyl-3,3,3-trifluoropropanamide | 1.58 (s, 3H), 2.8 (d, 3H), 7.71 (t, 1H), 8.0 (d, 1H), 8.12 (m, 3H), 8.3 (d, 1H), 8.38 (s, 1H), 8.7 (d, 1H) | 463 | Ex 170 |
| 243 | (R)-N-{2-Chloro-4-[3-(pyrrolidin-1-ylcarbonyl)phenylsulphonyl]phenyl}-2-hydroxy-2-methyl-3,3,3-trifluoropropanamide | 1.59 (s, 3H), 1.84 (m, 4H), 3.32 (m, 2H), 3.48 (t, 2H), 7.68 (t, 1H), 7.83 (d, 1H), 7.98–8.1 (m, 3H), 8.19 (s, 1H), 8.3 (d, 1H) | 505 (M + H)+ | Ex 170 |
| 244 | (R)-N-{2-Chloro-4-[3-carbamoylphenylsulphonyl]phenyl}-2-hydroxy-2-methyl-3,3,3-trifluoropropanamide | 1.58 (s, 3H), 7.6 (s, 1H), 7.7 (t, 1H), 8.0 (d, 1H), 8.13 (m, 3H), 8.25 (brs, 1H), 8.3 (d, 1H), 8.41 (s, 1H) | 449 | Ex 170 |
| 245 | (R)-N-{2-Chloro-4-{3-[N'-(2-N,N-dimethylaminoethyl)carbamoyl]phenylsulphonyl}phenyl}-2-hydroxy-2-methyl-3,3,3-trifluoropropanamide | 1.58 (s, 3H), 2.20 (s, 6H), 2.44 (m, 2H), 3.37 (m, 2H), 7.71 (t, 1H), 7.99 (dd, 1H), 8.14 (m, 3H), 8.32 (d, 1H), 8.4 (s, 1H), 8.7 (t, 1H) | 522 | Ex 170 |
| 246 | (R)-N-{2-Chloro-4-[3-N,N-dimethylcarbamoylphenylsulphonyl]phenyl}-2-hydroxy-2-methyl-3,3,3-trifluoropropanamide | (CDCl$_3$) 1.71 (s, 3H), 2.98 (s, 3H), 3.12 (s, 3H), 4.35 (s, 1H), 7.6 (m, 2H), 7.84 (dd, 1H), 7.98 (m, 3H), 8.6 (d, 1H), 9.23 (s, 1H) | 477 | Ex 170 |
| 247 | (R)-N-{2-Chloro-4-[3-(pyrrolidin-1-ylcarbonyl)phenylsulphonyl]phenyl}-2-hydroxy-2-methyl-3,3,3-trifluoropropanamide | Retention time 25.39 minutes (HPLC Method c) | 533 | Ex 170 |
| 248 | (R)-N-{2-Chloro-4-[3-(morpholinocarbonyl)phenylsulphonyl]phenyl}-2-hydroxy-2-methyl-3,3,3-trifluoropropanamide | Retention time 27.28 minutes (HPLC Method c) | 519 | Ex 170 |
| 249 | (R)-N-{2-Chloro-4-[3-(thiomorpholinocarbonyl)phenylsulphonyl]phenyl}-2-hydroxy-2-methyl-3,3,3-trifluoropropanamide | Retention time 29.70 minutes (HPLC Method c) | 535 | Ex 170 |

EXAMPLE 250

(R)-N-{2-Chloro-4-[4-(pyrrolidin-1-ylsulphonyl)phenylsulphanyl]phenyl}-2-hydroxy-2-methyl-3,3,3-trifluoropropanamide Copper (1) chloride (0.038 g) was added to a mixture of (R)-N-(2-chloro-4-mercaptophenyl)-2-hydroxy-2-methyl-3,3,3-trifluoropropanamide (Example 210) (0.21 g), N-(4-iodobenzenesulphonyl)pyrrolidine (0.258 g) and sodium methoxide (0.042 g) in DMA (5 ml). The mixture was heated at 150° C. with stirring for 4 hours then cooled and the DMA removed by evaporation. Ethyl acetate (20 ml) and water (20 ml) was added and the mixture was filtered. The aqueous layer was extracted with ethyl acetate (3×20 ml) and the organic layers were combined and dried. Volatile material was removed by evaporation and the residue was purified on a silica gel Mega Bond Elut column, eluting with methanol/DCM 0–10% to give the title compound (0.16 g) as a solid. NMR (CDCl$_3$): 1.75 (s, 3H), 1.75–1.85 (m, 4H), 3.2–3.3 (m, 4H), 4.0 (s, 1H), 7.2–7.3 (m, 2H), 7.4–7.45 (m, 1H), 7.6 (s, 1), 7.7 (d, 2H), 8.45 (d, 1H), 9.15 (s, 1H); MS (ESP$^-$): 507.

EXAMPLES 251–279

Following the procedure of Example 250 using the appropriate starting materials the following compounds were prepared.

| Ex | Compound | NMR | MS | SM |
|---|---|---|---|---|
| 251 | (R)-N-{2-Chloro-4-[4-(dimethylaminosulphonyl)phenylsulphanyl]phenyl}-2-hydroxy-2-methyl-3,3,3-trifluoropropanamide | (CDCl$_3$) 1.75 (s, 3H), 2.7 (s, 6H), 3.6 (s, 1H), 7.25 (d, 2H), 7.45 (dd, 1H), 7.6 (d, 1H), 7.7 (d, 2H), 8.45 (d, 1H), 9.1 (s, 1H) | 481 | Ex 210 |
| 252 | (R)-N-[2-Chloro-4-(4-hydroxyphenylsulphanyl)phenyl]-2-hydroxy-2-methyl-3,3,3-trifluoropropanamide | (CDCl$_3$) 1.75 (s, 3H), 4.1 (s, 1H), 6.75 (d, 2H), 6.85 (d, 2H), 7.3–7.4 (m, 3H), 8.2 (d, 1H), 8.9 (s, 1H) | 390 | Ex 197 |
| 253 | (R)-N-[2-Chloro-4-(3-fluorophenylsulphanyl)phenyl]-2-hydroxy-2-methyl-3,3,3-trifluoropropanamide | (CDCl$_3$) 1.75 (s, 3H), 3.75 (s, 1H), 6.9–7.0 (m, 2H), 7.05 (d, 1H), 7.2–7.3 (m, 1H), 7.35 (dd, 1H), 7.45 (d, 1H), 8.4 (d, 1H), 9.0 (s, 1H) | 392 | Ex 197 |
| 254 | (R)-N-[2-Chloro-4-(4-sulphamoylphenylsulphanyl)phenyl]-2-hydroxy-2-methyl-3,3,3-trifluoropropanamide | (CDCl$_3$) 1.7 (s, 3H), 5.2 (s, 2H), 6.7 (s, 1H), 7.2–7.25 (m, 2H), 7.4 (dd, 1H), 7.5 (d, 1H), 7.8 (d, 2H), 8.5 (d, 1H), 9.55 (s, 1H) | 453 | Ex 210 |
| 255 | (R)-N-{2-Chloro-4-[4-(guanidinosulphonyl)phenylsulphanyl]phenyl}-2-hydroxy-2-methyl-3,3,3-trifluoropropanamide | 1.6 (s, 3H), 6.75 (s, 4H), 7.35 (d, 2H), 7.5 (d, 1H), 7.6–7.7 (m, 3H), 7.9 (s, 1H), 8.1 (d, 1H), 9.8 (s, 1H) | 495 | Ex 210 |
| 256 | (R)-N-[2-Chloro-4-(thiazol-2-ylsulphanyl)phenyl]-2-hydroxy-2-methyl-3,3,3-trifluoropropanamide | 1.62 (s, 3H), 7.64 (dd, 1H), 7.75 (d, 1H), 7.82 (d, 1H), 7.87 (d, 1H), 8.12 (d, 1H), 9.8 (brs, 1H) | 383 (M + H)$^+$ | Ex 197 |
| 257 | (R)-N-[2-Chloro-4-(1-methylimidazol-2-ylsulphanyl)phenyl]-2-hydroxy-2-methyl-3,3,3-trifluoropropanamide | 1.6 (s, 3H), 3.64 (s, 3H), 7.1 (dd, 1H), 7.12 (d, 1H), 7.23 (d, 1H), 7.49 (d, 1H), 7.86 (d, 1H), 9.7 (brs, 1H) | 380 (M + H)$^+$ | Ex 197 |
| 258 | (R)-N-[2-Chloro-4-(5-methyl-1,3,4-thiadiazol-2-ylsulphanyl)phenyl]-2-hydroxy-2-methyl-3,3,3-trifluoropropanamide | 1.63 (s, 3H), 2.66 (s, 3H), 7.7 (dd, 1H), 7.94 (d, 1H), 8.15 (d, 1H), 9.7 (brs, 1H) | 396 | Ex 197 |
| 259 | (R)-N-[2-Chloro-4-(pyrimidin-2-ylsulphanyl)phenyl]-2-hydroxy-2-methyl-3,3,3-trifluoropropanamide | 1.64 (s, 3H), 7.29 (t, 1H), 7.62 (dd, 1H), 7.83 (d, 1H), 7.9 (brs, 1H), 8.1 (d, 1H), 8.63 (d, 2H), 9.8 (brs, 1H) | 378 (M + H)$^+$ | Ex 197 |
| 260 | (R)-N-[2-Chloro-4-(imidazol-2-ylsulphanyl)phenyl]-2-hydroxy-2-methyl-3,3,3-trifluoropropanamide | 1.6 (s, 3H), 7.2 (d, 1H), 7.3 (s, 2H), 7.75 (d, 1H), 7.87 (dd, 1H), 9.7 (brs, 1H), 12.9 (brs, 1H) | 364 | Ex 197 |
| 261 | (R)-N-[2-Chloro-4-(benzothiazol-2-ylsulphanyl)phenyl]-2-hydroxy-2-methyl-3,3,3-trifluoropropanamide | (CDCl$_3$) 1.8 (s, 3H), 3.9 (s, 1H), 7.25–7.3 (m, 1H), 7.4 (t, 1H), 7.7 (dd, 2H), 7.8 (dd, 1H), 7.9 (d, 1H), 8.5 (d, 1H), 9.2 (brs, 1H) | 433 (M + H)$^+$ | Ex 197 |
| 262 | (R)-N-[2-Chloro-4-(5-chlorobenzothiazol-2-ylsulphanyl)phenyl]-2-hydroxy-2-methyl-3,3,3-trifluoropropanamide | (CDCl$_3$) 1.75 (s, 3H), 2.7 (s, 6H), 3.6 (s, 1H), 7.25 (d, 2H), 7.45 (dd, 1H), 7.6 (d, 1H), 7.7 (d, 2H), 8.45 (d, 1H), 9.1 (s, 1H) | 467 (M + H)$^+$ | Ex 210 |
| 263 | (R)-N-[2-Chloro-4-(N-methyl-4-mesylaminophenylsulphanyl) | 1.6 (s, 3H), 2.9 (s, 3H), 3.2 (s, 3H), 7.4 (m, 5H), | 481 | Ex 210 |

-continued

| Ex | Compound | NMR | MS | SM |
|---|---|---|---|---|
| | phenyl]-2-hydroxy-2-methyl-3,3,3-trifluoropropanamide | 7.5 (s, 1H), 7.8 (s, 1H), 8.0 (d, 1H) | | |
| 264 | (R)-N-[2-Chloro-4-(2-nitrophenylsulphanyl)phenyl]-2-hydroxy-2-methyl-3,3,3-trifluoropropanamide | | 419 | Ex 210 |
| 265[1,2] | (R)-N-[2-Chloro-4-(2,3-H-2-oxo-3-methylbenzoxazol-6-ylsulphanyl)phenyl]-2-hydroxy-2-methyl-3,3,3-trifluoropropanamide | 1.6 (s, 3H), 3.4 (s, 3H), 7.2 (d, 1H), 7.4 (m, 3H), 7.5 (s, 1H), 7.8 (s, 1H), 7.9 (d, 1H), 9.7 (s, 1H) | 445 | Ex 210 |
| 266[1,3] | (R)-N-[2-Chloro-4-(2-oxo-1,3-dimethylbenzimidazolidin-5-ylsulphanyl)phenyl]-2-hydroxy-2-methyl-3,3,3-trifluoropropanamide | | 458 | Ex 210 |
| 267[1,4] | (R)-N-{2-Chloro-4-[4-(2-oxo-pyrrolidin-1-yl)phenylsulphanyl]phenyl}-2-hydroxy-2-methyl-3,3,3-trifluoropropanamide | 1.6 (s, 3H), 2.0 (m, 2H), 2.7 (s, 1H), 2.9 (s, 1H), 3.8 (t, 2H), 7.2 (d, 1H), 7.3 (s, 1H), 7.4 (d, 2H), 7.7 (d, 2H), 7.9 (d, 1H) | 457 | Ex 210 |
| 268 | (R)-N-[2-Chloro-4-(1,2,3,4-H-1,3-dimethyl-2,4-dioxoquinazolin-6-ylsulphanyl)phenyl]-2-hydroxy-2-methyl-3,3,3-trifluoropropanamide | 1.6 (s, 3H), 3.2 (s, 3H), 3.5 (s, 3H), 7.3 (d, 1H), 7.5 (m, 2H), 7.8 (d, 2H), 7.9 (s, 1H), 8.0 (d, 2H) | 486 | Ex 210 and Meth 54 |
| 269 | (R)-N-{2-Chloro-4-(2H-benzimidazol-2-one-5-ylsulphanyl)phenyl}-2-hydroxy-2-methyl-3,3,3-trifluoropropanamide | 1.6 (s, 3H), 7.0 (m, 2H), 7.1 (m, 3H), 7.7 (s, 1H), 7.8 (d, 1H), 9.6 (s, 1H) 10.7 (s, 1H), 10.8 (s, 1H) | 430 | Ex 210 and Meth 58 |
| 270 | (R)-N-{2-Chloro-4-(4-acetylphenylsulphanyl)phenyl}-2-hydroxy-2-methyl-3,3,3-trifluoropropanamide | 1.6 (s, 3H), 2.6 (s, 3H), 7.3 (d, 2H), 7.5 (d, 1H), 7.7 (s, 1H), 7.9 (d, 2H), 8.1 (d, 1H) | 416 | Ex 210 |
| 271 | (R)-N-{2-Chloro-4-(4-amino-3-carboxyphenylsulphanyl)phenyl}-2-hydroxy-2-methyl-3,3,3-trifluoropropanamide | 1.6 (s, 3H), 6.8 (d, 1H), 7.0 (d, 1H), 7.1 (s, 1H), 7.4 (d, 1H), 7.7 (s, 1H), 7.8 (d, 1H), 7.9 (s, 1H), 9.6 (s, 1H) | 433 | Ex 210 |
| 272 | (R)-N-{2-Chloro-4-(4,5-diphenyl-2-oxazolylsulphanyl)phenyl}-2-hydroxy-2-methyl-3,3,3-trifluoropropanamide | (CDCl$_3$) 1.75 (s, 3H), 4.0 (s, 1H), 7.25–7.4 (m, 6H), 7.45–7.55 (m, 2H), 7.65 (dd, 3H), 7.75 (d, 1H), 8.45 (d, 1H), 9.1 (brs, 1H) | 519 (M + H)$^+$ | Ex 197 |
| 273 | (R)-N-{2-Chloro-4-(1-ethyltetrazol-5-ylsulphanyl)phenyl}-2-hydroxy-2-methyl-3,3,3-trifluoropropanamide | (CDCl$_3$) 1.55 (t, 3H), 1.75 (s, 3H), 4.40 (q, 2H), 4.55 (s, 1H), 7.5 (dd, 1H), 7.65 (d, 1H), 8.45 (d, 1H), 9.20 (brs, 1H) | 396 (M + H)$^+$ | Ex 197 |
| 274 | (R)-N-{2-Chloro-4-(4-iso-propyl-4,5-dihydro-1H-1,2,4-triazol-5-one-3-ylsulphanyl)phenyl}-2-hydroxy-2-methyl-3,3,3-trifluoropropanamide | (CDCl$_3$) 1.55 (d, 6H), 1.8 (s, 3H), 3.7 (brs, 1H), 4.8 (m, 1H), 7.9 (m, 1H), 8.05 (d, 1H), 8.8 (d, 1H), 9.45 (brs, 1H), 10.15 (brs, 1H) | 457 (M + H)$^+$ | Ex 197 |
| 275 | (R)-N-{2-Chloro-4-(3-chloro-4-fluorophenylsulphanyl)phenyl}-2-hydroxy-2-methyl-3,3,3-trifluoropropanamide | 1.75 (s, 3H), 3.55 (s, 1H), 7.1 (t, 1H), 7.2–7.3 (m, 2H), 7.33–7.45 (m, 2H), 8.35 (d, 1H), 8.9 (brs, 1H) | 428 (M + H)$^+$ | Ex 197 |
| 276 | (R)-N-{2-Chloro-4-(3,4-difluorophenylsulphanyl)phenyl}-2-hydroxy-2-methyl-3,3,3-trifluoropropanamide | (CDCl$_3$) 1.75 (s, 3H), 3.7 (s, 1H), 7.0–7.1 (m, 3H), 7.3 (dd, 1H), 7.4 (d, 1H), 8.35 (d, 1H), 8.95 (brs, 1H) | 410 | Ex 197 and Meth 51 |
| 277 | (R)-N-{2-Chloro-4-(4-ethoxycarbonylimidazol-2-ylsulphanyl)phenyl}-2-hydroxy-2-methyl-3,3,3-trifluoropropanamide | 1.25 (t, 3H), 1.4 (s, 3H), 4.2 (q, 2H), 7.25 (d, 1H), 7.45 (s, 1H), 7.8 (s, 1H), 7.90 (d, 1H), 8.0 (s, 1H), 9.7 (s, 1H), 13.35 (s, 1H) | 438 (M + H)$^+$ | Ex 197 |
| 278[5] | (R)-N-{2-Chloro-4-(4-{3-methyl-1,2,4-oxadiazol-5-yl}phenylsulphanyl)phenyl}-2-hydroxy-2-methyl-3,3,3-trifluoropropanamide | 1.62 (s, 3H), 2.41 (s, 3H), 7.38 (d, 2H), 7.56 (dd, 1H), 7.77 (d, 1H), 7.97 (brs, 1H), 8.02 (d, 2H), 8.15 (d, 1H), 9.82 (brs, 1H) | 456 | Ex 210 |

-continued

| Ex | Compound | NMR | MS | SM |
|---|---|---|---|---|
| 279[5] | (R)-N-{2-Chloro-4-(4-{5-methyl-1,2,4-oxadiazol-3-yl}phenylsulphanyl)phenyl}-2-hydroxy-2-methyl-3,3,3-trifluoropropanamide | 1.6 (s, 3H), 2.68 (s, 3H), 7.4 (d, 2H), 7.5 (dd, 1H), 7.70 (d, 1H), 7.95 (m, 3H), 8.09 (d, 1H), 9.8 (brs, 1H) | 456 | Ex 210 |

[1]Potassium carbonate and DMF were used in place of sodium methoxide and DMA
[2]The 6-iodo-3-methyl-2(3H)-benzoxazolone used as starting material was prepared as described in European Patent Application EP 90-401759, CA 116:128665, RN 139487-06-2.
[3]The 1,3-dihydro-5-iodo-1,3-dimethyl-2H-benzimidazol-2-one used as starting material was prepared as described in European Patent Application EP 90-401759, CA 116:128665, RN 139487-04-0.
[4]The 1-(4-iodophenyl)-2-pyrrolidinone used as starting material was prepared as described in European Patent Application EP 89-402046, CA 115:183096, RN 7661-34-9.
[5]The oxadiazolylphenyliodide used as starting material was prepared as described in British patent application GB 92-18334.

EXAMPLE 280
(R)-N-[2-Chloro-4-(4-carboxyphenylsulphinyl)phenyl]2-hydroxy-2-methyl-3,3,3-trifluoropropanamide Oxone (1.47 g) as a solution in 1M sodium acetate solution (12 ml) was added to a mixture of (R)-N-[2-chloro-4-(4-carboxyphenylsulphanyl)phenyl]-2-hydroxy-2-methyl-3,3,3-trifluoropropanamide (Example 291) (1 g) in methanol (25 ml) and stirred for 2 hours. The reaction mixture was filtered and the solid washed with water and dried under vacuum to give the title compound as a solid (1.02 g) containing 9% of the corresponding sulphone. NMR: 1.6 (s, 3H), 7.75 (d, 1H), 7.8–7.9 (m, 3H), 7.95 (d, 1H), 8.0–8.05 (m, 3H), 8.15 (d, 1H), 9.8 (s, 1H); MS (ESP$^-$); 434.

EXAMPLES 281–283

Following the procedure of Example 280 (except that products were purified by chromatography with ethyl acetate/hexane as eluent) and using the appropriate starting materials the following compounds were prepared.

| Ex | Compound | NMR | MS | SM |
|---|---|---|---|---|
| 281 | (R)-N-[2-Chloro-4-(5-methyl-1,3,4-thiadiazol-2-ylsulphinyl)phenyl]-2-hydroxy-2-methyl-3,3,3-trifluoropropanamide | (CDCl$_3$) 1.76 (s, 3H), 2.81 (s, 3H), 3.9 and 3.91 (2xs, 1H), 7.7–7.78 (m, 1H), 7.87–7.9 (m, 1H), 8.69 (d, 1H), 9.23 (brs, 1H) | 412 | Ex 258 |
| 282 | (R)-N-[2-Chloro-4-(5-methyl-1,3,4-thiadiazol-2-ylsulphonyl)phenyl]-2-hydroxy-2-methyl-3,3,3-trifluoropropanamide | 1.62 (s, 3H), 2.84 (s, 3H), 8.12 (dd, 1H), 8.22 (d, 1H), 8.44 (d, 1H), 9.9 (brs, 1H) | 428 | Ex 281 |
| 283 | (R)-N-[2-Chloro-4-(4-ethenylsulphonyl)phenyl]-2-hydroxy-2-methyl-3,3,3-trifluoropropanamide | (CDCl$_3$) 1.76 (s, 3H), 3.05 (s, 1H), 6.07 (d, 1H), 6.46 (d, 1H), 6.57–6.68 (dd, 1H), 7.76–7.81 (m, 1H), 7.92 (s, 1H), 8.65 (d, 1H), 9.52 (s, 1H) | 356 | Ex 419 |

EXAMPLE 284
(R)-N-{2-Chloro-4-[4-(2-hydroxyethylsulphanyl)phenylsulphonyl]phenyl}-2-hydroxy-2-methyl-3,3,3-trifluoropropanamide 2-Mercaptoethanol (0.358 ml) was added dropwise to an ice/water-cooled suspension of sodium hydride (0.205 g) in NMP (6 ml). After effervescence had ceased, the cooling was removed and stirring continued a further 15 minutes. (R)-N-[2-Chloro-4-(4-fluorophenyl-sulphonyl)phenyl]-2-hydroxy-2-methyl-3,3,3-trifluoropropanamide (Method 69) (1.556 g) was added and the mixture was heated at 118° C. for 2 hours then cooled and poured onto saturated aqueous ammonium chloride solution (60 ml). The mixture was extracted with ethyl acetate (2×200 ml) and the organic extracts were washed with brine (300 ml) then dried. Volatile material was removed by evaporation and the residue was purified by chromatography eluting with 60% ethyl acetate/hexanes to give the title compound as a solid. NMR (CDCl$_3$): 1.74 (s, 31H), 1.91 (t, 1H), 3.19 (t, 2H), 3.62 (s, 1H), 3.82 (q, 21H), 7.4 (d, 2H), 7.8 (d, 2H), 7.83 (dd, 1H), 7.97 (d, 1H), 8.59 (d, 2H), 9.25 (brs, 1H); MS (ESP$^-$); 482; EA: found: C, 44.6; H, 3.6; N, 2.7%; C$_{18}$H$_{17}$ClF$_3$NO$_5$S$_2$ requires: C, 44.7; H, 3.5; N, 2.9%.

EXAMPLES 285–290

Following the procedure of Example 284 using the appropriate starting materials the following compounds were prepared.

| Ex | Compound | NMR | MS | SM |
|---|---|---|---|---|
| 285[1] | (R)-N-[2-Chloro-4-(pyrid-4-ylsulphanylphenylsulphonyl)phenyl]-2-hydroxy-2-methyl-3,3,3-trifluoropropanamide | ($CDCl_3$ + DMSO-$d_6$) 1.58 (s, 3H), 7.06 (d, 2H), 7.49 (brm, 3H), 7.75 (dd, 1H), 7.83 (d, 2H), 7.9 (d, 1H), 8.35 (d, 2H), 8.57 (d, 1H), 9.73 (brs, 1H) | 515 | Meth 69 |
| 286 | (R)-N-{2-Chloro-4-[4-(N,N-dimethylaminoethylsulphanyl)phenylsulphonyl]phenyl}-2-hydroxy-2-methyl-3,3,3-trifluoropropanamide | ($CDCl_3$) 1.7 (s, 3H), 2.3 (s, 6H), 2.6 (t, 2H), 3.1 (t, 2H), 7.35 (d, 2H), 7.75–7.7 (m, 3H), 7.95 (dd, 1H), 8.6 (d, 1H), 9.4 (brs, 1H) | 511 $(M + H)^+$ | Meth 69 |
| 287 | (R)-N-{2-Chloro-4-[4-(cyclopropylmethylsulphanyl)phenylsulphonyl]phenyl}-2-hydroxy-2-methyl-3,3,3-trifluoropropanamide | 0.3 (q, 2H), 0.6 (q, 2H), 1.05 (m, 1H), 1.7 (s, 3H), 3.5 (d, 2H), 4.9 (s, 1H), 7.35 (d, 2H), 7.8 (d, 2H), 7.9 (m, 2H), 8.6 (d, 1H), 9.4 (brs, 1H) | 492 | Meth 69 |
| 288 | (R)-N-{2-Chloro-4-[4-(N-methylcarbamoylmethylsulphanyl)phenylsulphonyl]phenyl}-2-hydroxy-2-methyl-3,3,3-trifluoropropanamide | 1.75 (s, 3H), 2.8 (d, 3H), 3.70 (s, 2H), 4.7 (s, 1H), 6.65 (m, 1H), 7.3 (d, 2H), 7.7 (m, 3H), 7.95 (dd, 1H), 8.6 (d, 1H), 9.45 (brs, 1H) | 509 | Meth 69 |
| 289 | (R)-N-{2-Chloro-4-[4-(N,N-diethylaminoethylsulphanyl)phenylsulphonyl]phenyl}-2-hydroxy-2-methyl-3,3,3-trifluoropropanamide | 1.05 (t, 6H), 1.8 (s, 3H), 2.6 (q, 4H), 2.85 (t, 2H), 3.1 (t, 2H), 7.3 (d, 2H), 7.7–7.85 (m, 3H), 7.95 (dd, 1H), 8.6 (d, 1H), 9.5 (brs, 1H) | 537 | Meth 69 |
| 290 | (R)-N-{2-Chloro-4-[2-(2-hydroxyethylsulphanyl)phenylsulphonyl]phenyl}-2-hydroxy-2-methyl-3,3,3-trifluoropropanamide | ($CDCl_3$) 1.75 (s, 3H), 2.67 (brt, 1H), 3.12 (t, 2H), 3.65 (q, 2H), 3.75 (brs, 1H), 7.4–7.47 (m, 1H), 7.5–7.6 (m, 2H), 7.86 (dd, 1H), 8.07 (d, 1H), 8.26 (d, 1H), 8.6 (d, 1H), 9.3 (brs, 1H) | 482 | Meth 63 |

[1] Two equivalents of sodium hydride and 4-mercaptopyridine were used.

EXAMPLE 291

(R)-N-[2-Chloro-4-(4-carboxyphenylsulphanyl)phenyl]-2-hydroxy-2-methyl-3,3,3-trifluoropropanamide A mixture of 4-mercaptobenzoic acid (0.308 g), (R)-N-(2-chloro-4-iodophenyl)-2-hydroxy-2-methyl-3,3,3-trifluoropropanamide (Example 197) (0.786 g) and copper (I) oxide (0.143 g) in DMF (5 ml) was stirred and heated under reflux for 1 hour. More 4-mercaptobenzoic acid (0.308 g) was added and heating was continued for a further 2 hours. The mixture was cooled, filtered, and the filter washed with DMF (5 ml). The filtrates were concentrated by evaporation and the residual solid was extracted with boiling ethyl acetate (2×60 ml). The extracts were absorbed onto deactivated silica (silica deactivated by treatment with 10% water) and purified by chromatography eluting with 5% methanol/ethyl acetate to give the title compound (0.803 g) as a solid. NMR: 1.63 (s, 3H), 7.31 (d, 2H), 7.5 (dd, 1H), 7.68 (d, 1H), 7.89 (d, 2H), 8.22 (d, 1H), 9.8 (brs, 1H); MS ($ESP^-$): 418; EA: found: C, 48.2; H, 3.1; N. 3.2%; $CH_{17}H_{13}NClF_3O_4S$ requires C, 48.6; H, 3.1; N, 3.3%.

EXAMPLES 292–293

Following the procedure of Example 291 and using the appropriate starting materials the following compounds were prepared.

| Ex | Compound | NMR | MS |
|---|---|---|---|
| 292 | (R)-N-[2-Chloro-4-{2-carboxyphenylsulphanyl}phenyl]-2-hydroxy-2-methyl-3,3,3-trifluoropropanamide | 1.6 (s, 3H), 6.52 (d, 1H), 7.24 (t, 1H), 7.40 (t, 1H), 7.50–7.55 (m, 1H), 7.71 (s, 1H), 7.89–7.92 (m, 1H), 8.15 (d, 1H), 9.8 (s, 1H) | 418 |
| 293 | (R)-N-{2-Chloro-4-(3-carboxyphenylsulphanyl)phenyl}-2-hydroxy-2-methyl-3,3,3-trifluoropropanamide | 1.58 (s, 3H), 7.39 (d, 1H), 7.48–7.59 (m, 3H), 7.83 (m, 3H), 8.01 (d, 1H), 9.72 (s, 1H) | 418 |

EXAMPLE 294

(R)-N-{2-Chloro-4-[4-(N-2-hydroxyethylcarbamoyl)phenylsulphonyl]phenyl}-2-hydroxy-2-methyl-3,3,3-trifluoropropanamide A solution of 1,1'-carbonyldiimidazole (0.169 g) and (R)-N-[2-chloro-4-(4-carboxyphenylsulphonyl)phenyl]-2-hydroxy-2-methyl-3,3,3-trifluoropropanamide (Example 121) (0.30 g) in DMF (1 ml)/ethyl acetate (9 ml) was heated at 50° C. for 30 minutes. Ethanolamine (0.055 ml) was added and the mixture was heated and stirred a further 17 hours. The mixture was cooled, diluted with ethyl acetate (50 ml), washed with dilute aqueous hydrochloric acid (25 ml), water (25 ml), saturated aqueous sodium hydrogen carbonate solution (25 ml) and brine, then dried. Volatile material was removed by evaporation and the residue was purified by chromatography, eluting with 2.5% methanol/ethyl acetate to give the title compound (0.25 g) as a solid. NMR (CDCl$_3$+DMSO-$\delta_6$): 1.58 (s, 3H), 3.44 (m, 2H), 3.62 (m, 2H), 4.26 (t, 1H), 7.05 (s, 1H), 7.76 (dd, 1H), 7.83–8.01 (m, 6H), 8.56 (d, 1H); 9.73 (brs, 1H); MS (ESP$^-$): 495.

EXAMPLES 295–303

Following the procedure of Example 294 using the appropriate starting materials the following compounds were prepared.

| Ex | Compound | NMR | MS | SM |
|---|---|---|---|---|
| 295 | (R)-N-(2-Chloro-4-{4-[N'-(2-N,N-dimethylaminoethyl)carbamoyl]phenylsulphonyl}phenyl)-2-hydroxy-2-methyl-3,3,3-trifluoropropanamide | (CDCl$_3$ + DMSO-$\delta_6$) 1.6 (s, 3H), 2.26 (s, 6H), 2.47 (m, 2H), 3.43 (m, 2H), 7.48 (s, 1H), 7.75 (m, 1H), 7.82–7.98 (m, 5H), 8.54 (d, 1H), 9.73 (brs, 1H) | 520 | Ex 121 |
| 296 | (R)-N-{2-Chloro-4-[4-(morpholinocarbonyl)phenylsulphonyl]phenyl}-2-hydroxy-2-methyl-3,3,3-trifluoropropanamide | (DMSO-$\delta_6$ + AcOH-$\delta_4$) 1.62 (s, 3H), 3.4 (s, 4H), 3.58 (m, 4H), 7.6 (d, 2H), 7.9–8.1 (m, 4H), 8.35 (d, 1H) | 519 | Ex 121 |
| 297 | (R)-N-{2-Chloro-4-[4-(4-methyl-piperazin-1-ylcarbonyl)phenylsulphonyl]phenyl}-2-hydroxy-2-methyl-3,3,3-trifluoropropanamide | (DMSO-$\delta_6$ + AcOH-$\delta_4$) 1.6 (s, 3H), 2.35 (s, 1H), 2.68 (m, 4H), 3.5 (brs, 4H), 7.58 (d, 2H), 7.85–8.05 (m, 4H), 8.38 (d, 1H) | 532 | Ex 121 |
| 298 | (R)-N-{2-Chloro-4-[4-(pyrrolidin-1-ylcarbonyl)phenylsulphonyl]phenyl}-2-hydroxy-2-methyl-3,3,3-trifluoropropanamide | 1.58 (s, 3H), 1.7–1.89 (m, 4H), 3.23 (m, 2H), 3.41 (m, 2H), 7.7 (d, 2H), 8.0 (m, 4H), 8.18 (s, 1H), 8.3 (d, 1H), 9.88 (brs, 1H) | 503 | Ex 121 |
| 299 | (R)-N-(2-Chloro-4-{4-[N-(2-methoxyethyl)carbamoyl]phenylsulphonyl}phenyl)-2-hydroxy-2-methyl-3,3,3-trifluoropropanamide | 1.57 (s, 3H), 3.22 (m, 2H), 3.4 (m, 2H), 7.9–8.02 (m, 4H), 8.08 (d, 2H), 8.14 (s, 1H), 8.3 (d, 1H), 8.72 (m, 1H), 9.9 (brs, 1H) | 507 | Ex 121 |
| 300 | (R)-N-{2-Chloro-4-[4-(thiomorpholinocarbonyl)phenylsulphonyl]phenyl}-2-hydroxy-2-methyl-3,3,3-trifluoropropanamide | 1.59 (s, 3H), 2.52 (brs, 2H), 2.64 (brs, 2H), 3.42 (brs, 2H), 3.81 (brs, 2H), 7.72 d, 2H), 7.96–8.1 (m, 4H), 8.17 (s, 1H), 8.31 (d, 1H), 9.89 (brs, 1H) | 535 | Ex 121 |
| 301 | (R)-N-{2-Chloro-4-[4-(thiazolidin-3-ylcarbonyl)phenylsulphonyl]phenyl}-2-hydroxy-2-methyl-3,3,3-trifluoropropanamide | 1.59 (s, 3H), 2.96 (brs, 1H), 3.03 (brs, 1H), 3.6 (brs, 1H), 3.8 (brs, 1H), 4.42 (brs, 1H), 4.62 (brs, 1H), 7.76 (d, 2H), 8.02 (m, 2H), 8.06 (d, 2H), 8.18 (s, 1H), 8.32 (d, 1H), 9.9 (brs, 1H) | 521 | Ex 121 |
| 302 | (R)-N-(2-Chloro-4-{2-[N-(2-hydroxyethyl)carbamoyl]phenylsulphonyl}phenyl)-2-hydroxy-2-methyl-3,3,3-trifluoropropanamide | 1.65 (s, 3H), 3.3–3.5 (m, 4H), 4.7 (t, 1H), 7.55 (d, 1H), 7.7–7.82 (m, 2H), 8.05–8.1 (m, 2H), 8.1 (dd, 1H), 8.28 (d, 1H), 8.34 (d, 1H), 8.55 (brt, 1H), 9.97 (brs, 1H) | 493 | Ex 125 |
| 303 | (R)-N-(2-Chloro-4-{4-[N-(2-hydroxy-1-methylethyl)carbamoyl]phenyl-sulphinyl}phenyl)-2-hydroxy-2-methyl-3,3,3-trifluoropropanamide | 1.0–1.1 (m, 3H), 1.6 (s, 3H), 3.3–3.4 (m, 1H), 4.6–4.7 (m, 2H), 6.8 (d, 1H), 7.3 (d, 1H), 7.7 (d, 1H), 7.7–7.8 (m, 1H), 7.9–7.95 (m, 3H), 8.0–8.2 (m, 3H), 9.8 (s, 1H) | 493 (M + H)$^+$ | Ex 280 |

EXAMPLE 304
(R)-N-[2-Chloro-4-(4-anilinocarbonylphenylsulphonyl)phenyl]-2-hydroxy-2-methyl-3,3,3-trifluoropropanamide 1-(3-Dimethylaminopropyl)-3-ethylcarbodiimide hydrochloride (0.195 g) was added to a solution of 4-(dimethylamino)pyridine (0.25 g), (R)-N-[2-chloro-4-(4-carboxyphenyl-sulphonyl)phenyl]-2-hydroxy-2-methyl-3,3,3-trifluoropropanamide (Example 121) (0.317 g) and aniline (0.075 ml) in DCM (30 ml) and the mixture was stirred for 6 days. Solvent was then removed by evaporation and the residue was partitioned between ethyl acetate (50 ml) and dilute aqueous hydrochloric acid (25 ml). The aqueous layer was further extracted with ethyl acetate (50 ml). The organic extracts were combined, washed with brine and dried. Volatile material was removed by evaporation and the residue was purified by chromatography eluting with 40% ethyl acetate/hexane to give the title compound (0.179 g) as a solid. NMR (CDCl$_3$+DMSO-$\delta_6$): 1.59 (s, 3H), 7.03 (t, 1H), 7.25 (t, 2H), 7.48 (brs, 1H), 7.64 (d, 2H), 7.78 (dd, 1H), 7.92 (m, 3H), 8.06 (d, 2H), 8.56 (d, 1H), 9.72 (s, 1H), 9.9 (s, 1H); MS (ESP$^-$): 525.

EXAMPLES 305–306

Following the procedure of Example 304 and using Example 125 as the starting material the following compounds were prepared.

EXAMPLE 308

(R)-N-{2-Fluoro-4-[4-(N-methylcarbamoylmethylsulphanyl)phenylsulphonyl]phenyl}-2-hydroxy-2-methyl-3,3,3-trifluoropropanamide (R)-N-[2-Fluoro-4-(4-fluorophenylsulphonyl)phenyl]-2-hydroxy-2-methyl-3,3,3-trifluoropropanamide (0.65 g) (Method 71) was added to a deoxygenated mixture of mercaptoacetamide (0.14 ml) and sodium methoxide (0.08 g) in anhydrous NMP (2 ml). The reaction mixture was heated to 140° C. for 6 hours then cooled, diluted with ether (80 ml), washed with saturated aqueous ammonium chloride (100 ml) and dried. Volatile material was removed by

| Ex | Compound | NMR | MS |
|---|---|---|---|
| 305 | (R)-N-{2-Chloro-4-[2-(pyrrolidin-1-ylcarbonyl)phenylsulphonyl]phenyl}-2-hydroxy-2-methyl-3,3,3-trifluoropropananiide | 1.59 (s, 3H), 1.76–1.89 (m, 4H), 3.02 (t, 2H), 3.47 (t, 2H), 7.44–7.47 (m, 1H), 7.63–7.68 (m, 1H), 7.97–8.0 (m, 1H), 8.12 (d, 1H), 8.18 (s, 1H), 8.24 (d, 1H) | 503 |
| 306[1] | (R)-N-(2-Chloro-4-{2-[N'-(2-N,N-dimethylaminoethyl)carbamoyl]phenylsulphonyl}phenyl)-2-hydroxy-2-methyl-3,3,3-trifluoropropanamide hydrochloride | (DMSO-$\delta_6$ + AcOH-$\delta_4$): 1.56 (s, 3H), 2.85 (s, 6H), 3.30 (t, 2H), 3.62 (t, 2H), 7.52 (d, 1H), 7.64–7.73 (m, 2H), 7.96–8.00 (m, 1H), 8.07–8.1 (m, 1H), 8.15 (s, 1H), 8.15 (d, 1H) | 520 |

[1]The initially formed product was treated with hydrogen chloride (1M solution in ethyl acetate).

EXAMPLE 307

(R)-N-[2-Chloro-4-(thien-2-ylmethylsulphonyl)phenyl]-2-hydroxy-2-methyl-3,3,3-trifluoropropanamide N-Methylmorpholine-N-oxide (0.75 g) and 4 Å molecular sieves (0.215 g) were added to a solution of (R)-N-[2-chloro-4-(thien-2-ylmethylsulphanyl)phenyl]-2-hydroxy-2-methyl-3,3,3-trifluoropropanamide (Example 418) (0.085 g) in deoxygenated acetonitrile (10 ml) and the mixture was stirred for 5 minutes. Tetrapropylammonium perruthenate (0.037 g) was then added and the mixture was heated at 45° C. for 2.5 hours then cooled. Ethyl acetate (50 ml) was added, the mixture filtered and volatile material was removed by evaporation. The residue was purified by chromatography on a silica gel Mega Bond Elut column eluting with 20–50% ethyl acetate/iso-hexane to give the title compound (0.034 g) as a yellow solid. NMR (CDCl$_3$): 1.61 s, 3H), 5.05 (s, 2H), 6.94 (s, 1H), 6.98–7.0 (m, 1H), 7.53 (d, 1H), 7.91 (s, 1H), 8.28 (d, 1H), 9.94 (s, 1H); MS (ESP$^-$): 426.

evaporation and the residue was purified by chromatography on a silica gel Mega Bond Elut column eluting with 10–60% ethyl acetate/hexane to give the title compound (0.46 g) as a gum. NMR (CDCl$_3$) 1.75 (s, 3H), 2.8 (d, 3H), 3.69 (s, 2H), 7.3 (d, 2H), 7.69–7.75 (m, 2H), 7.83 (d, 1H), 8.8–8.85 (m, 1H), 9.0 (s 1H); MS (ESP$^-$): 493.

EXAMPLES 309–311

Following the procedure of Example 308 using the appropriate starting materials the following compounds were prepared.

| Ex | Compound | NMR | MS | SM |
|---|---|---|---|---|
| 309 | (R)-N-{2-Fluoro-4-[4-(2-hydroxyethylsulphanyl)phenylsulphonyl]phenyl}-2-hydroxy-2-methyl-3,3,3-trifluoropropanamide | (CDCl$_3$) 1.73 (s, 3H), 3.18 (t, 2H), 3.52 (s, 1H), 3.8–3.84 (m, 2H), 7.39 (d, 2H), 7.65–7.73 (m, 1H), 7.78 (d, 1H), 8.5–8.55 (m, 1H), 8.84 (s, 1H) | 466 | Meth 71 |
| 310 | (R)-N-{2-Chloro-4-[3-chloro-4-(2-hydroxyethylsulphanyl)-phenylsulphonyl]phenyl}-2-hydroxy-2-methyl-3,3,3-trifluoropropanamide | (CDCl$_3$) 1.75 (s, 3H), 1.95 (t, 1H), 3.2 (t, 2H), 3.75 (s, 1H), 3.9 (q, 2H), 7.35 (d, 1H), 7.7 (dd, 1H), 7.8–7.9 (m, 2H), 7.95 (d, 1H), 8.60 (d, 1H), 9.3 (s, 1H) | 516 | Meth 72 |
| 311 | (R)-N-{2-Chloro-4-[3-fluoro-4-(2-hydroxyethylsulphanyl)-phenylsulphonyl]phenyl}-2-hydroxy-2-methyl-3,3,3-trifluoropropanamide | 1.6 (s, 3H), 3.15 (t, 2H), 3.6 (q, 2H), 5.0 (t, 1H), 7.65 (t, 1H), 7.75 (dd, 1H), 7.85 (dd, 1H), 7.90–8.1 (m, 2H), 8.2 (d, 1H), 8.3 (d, 1H), 9.9 (brs, 1H) | 500 | Meth 66 |

EXAMPLE 312

(R)-N-[2-Chloro-4-(N,N-dimethylaminoethylsulphonyl)phenyl]-2-hydroxy-2-methyl-3,3,3-trifluoropropanamide A 2M solution of dimethylamine (0.06 ml) in anhydrous methanol was added to a deoxygenated solution of (R)-N-[2-chloro-4-(ethenylsulphonyl)phenyl]-2-hydroxy-2-methyl-3,3,3-trifluoropropanamide (Example 283) (0.044 g)

in anhydrous THF (1 ml). The mixture was allowed to stir at ambient temperature under argon for 2 hours then volatile material was removed by evaporation to give the title compound (in 89% yield) as a solid. NMR: 1.69 (s, 3H), 2.65 (s, 6H), 2.55 (t, 2H), 3.55 (t, 2H), 7.9 (d, 1H), 8.08 (s, 1H), 8.34 (d, 1H); MS (ESP−): 403.

EXAMPLE 313
(R)-N-[2-Ethenyl-4-(4-mesylphenylsulphonyl)phenyl]-2-hydroxy-2-methyl-3,3,3-trifluoropropanamide Tributylvinyltin (0.28 ml) was added to a deoxygenated suspension of (R)-N-[2-bromo-4-(4-mesylphenylsulphonyl)phenyl]-2-hydroxy-2-methyl-3,3,3-trifluoropropanamide (Example 140) (0.50 g) and tris(dibenzylideneacetone)dipalladium(O) (0.05 g) in anhydrous toluene (10 ml). The mixture was heated under reflux with stirring. After 14 hours a further portion of tris(dibenzylideneacetone)dipalladium (0) (0.05 g) and tributylvinyltin (0.28 ml) was added and heating was continued for a further 7 hours. The reaction mixture was allowed to cool and volatile materials were removed by evaporation. The residue was purified on a silica gel Mega Bond Elut column eluting with 5–50% ethyl acetate/hexane to give the title compound (0.146 g) as a solid. NMR (CDCl$_3$) 1.74 (s, 3H), 3.06 (s, 3H), 5.65–5.82 (dd, 2H), 6.67–6.77 (dd, 1H), 7.86–7.89 (dd, 1H), 7.95 (s, 1H), 8.06–8.16 (m, 4H), 8.35 (d, 1H), 8.79 (s, 1H); MS (ESP−): 477.

EXAMPLE 314
(R)-N-[2-Chloro-4-(carboxymethylsulphonyl)phenyl]-2-hydroxy-2-methyl-3,3,3-trifluoropropanamide Sodium hydroxide (2.5 ml of a 2M aqueous solution) was added to a stirred solution of (R)-N-[2-chloro-4-(methoxycarbonylmethylsulphonyl)phenyl]-2-hydroxy-2-methyl-3,3,3-trifluoropropanamide (Example 142) (0.36 g) in methanol (6 ml) and the mixture was stirred for 1 hour. Hydrochloric acid (3 ml of a 2M aqueous solution) was added and volatile material was removed by evaporation. Ethyl acetate (80 ml) was added and the mixture washed with brine (50 ml), dried and volatile material removed by evaporation. The residue was dissolved in DCM (50 ml), washed with saturated sodium hydrogen, carbonate solution (100 ml). The aqueous layer was treated with hydrochloric acid (25 ml, 10% v/v) and extracted into ethyl acetate (2×100 ml) and dried. Volatile material was removed by evaporation to give the title compound (0.28 g) as a foam. NMR: 1.62 (s, 3H), 4.57 (s, 2H), 7.9 (d, 2H), 8.02 (s, 1H), 8.06 (s, 1H), 8.32 (d, 1H). 9.92 (s, 1H); MS (ESP−): 388.

EXAMPLE 315
(R)-N-[2-Chloro-4-(N,N-dimethylaminopropylsulphonyl)phenyl]-2-hydroxy-2-methyl-3,3,3-trifluoropropanamide A solution of potassium permanganate (0.12 g) in water (8 ml) was added to a stirred solution of (R)-N-[2-chloro-4-(3-N,N-dimethylaminopropylsulphanyl)phenyl]-2-hydroxy-2-methyl-3,3,3-trifluoropropanamide (Example 404) (0.198 g) in glacial acetic acid (10 ml). The reaction mixture was stirred for 30 minutes then sodium sulphite was added until the reaction mixture became clear and colourless. Ethyl acetate (100 ml) was added and the mixture was washed with brine (2×50 ml), saturated aqueous sodium hydrogencarbonate solution (150 ml) and dried. Volatile material was removed by evaporation and the residue purified by chromatography on a silica gel Mega Bond Elut column eluting with 0–15% methanol/ethyl acetate to give the title compound (in 33% yield) as a solid. NMR: 1.61 (s, 3H), 1.61–1.68 (m, 2H), 2.05 (s, 6H), 2.23 (t, 2H), 3.28–3.36 (m, 2H), 7.89 (d, 1H), 8.04 (s, 1H), 8.33 (d, 1H); MS (ESP−): 415.

EXAMPLES 316–326

Following the procedure of Example 315 and using the appropriate starting materials following compounds were prepared.

| Ex | Compound | NMR | MS | SM |
|---|---|---|---|---|
| 316 | (R)-N-[2-Chloro-4-(benzothiazol-2-ylsulphonyl)phenyl]-2-hydroxy-2-methyl-3,3,3-trifluoropropanamide | (CDCl$_3$) 1.75 (s, 3H), 3.4 (brs, 1H), 7.5–7.6 (m, 2H), 7.95 (dd, 1H), 8.1 (dd, 1H), 8.15 (dd, 1H), 8.2 (d, 1H), 8.7 (d, 1H), 9.3 (bis, 1H) | 465 (M + H)+ | Ex 261 |
| 317 | (R)-N-[2-Chloro-4-(5-chlorobenzothiazol-2-ylsulphonyl)phenyl]-2-hydroxy-2-methyl-3,3,3-trifluoropropanamide | (CDCl$_3$) 1.75 (s, 3H), 3.4 (s, 1H), 7.5–7.55 (m, 2H), 8.0–8.15 (m, 2H), 8.2 (d, 1H), 8.7 (d, 1H), 9.35 (brs, 1H) | 498 (M + H)+ | Ex 262 |
| 318 | (R)-N-[2-Chloro-4-(4-{N-[5-methylpyrazol-3-yl]carbamoyl}phenylsulphonyl)phenyl]-2-hydroxy-2-methyl-3,3,3-trifluoropropanamide | 1.65 (s, 3H), 2.25 (s, 3H), 5.4 (brs, 2H), 5.6 (s, 1H), 7.95–8.05 (m, 2H), 8.1–8.2 (m, 5H), 8.3 (d, 1H), 9.90 (s, 1H) | 530 (M + H)+ | Ex 239 |
| 319 | (R)-N-[2-Chloro-4-(4-{N-[isoxazol-3-yl]carbamoyl}phenylsulphonyl)phenyl]-2-hydroxy-2-methyl-3,3,3-trifluoropropanamide | 1.6 (s, 3H), 7.0 (s, 1H), 8.0 (d, 2H), 8.05 (d, 1H), 8.1–8.15 (m, 3H), 8.2 (d, 1H), 8.3 (d, 1H), 8.85 (d, 1H), 9.90 (s, 1H), 11.65 (s, 1H) | 516 | Ex 240 |
| 320 | (R)-N-[2-Chloro-4-(4-ethoxycarbonylimidazol-2-ylsulphonyl)phenyl]-2-hydroxy-2-methyl-3,3,3-trifluoropropanamide | 1.25 (t, 3H), 1.6 (s, 3H), 4.25 (q, 2H), 8.0 (dd, 1H), 8.1 (s, 1H), 8.15 (d, 2H), 8.4 (d, 1H), 9.95 (s, 1H), 11.95 and 14.55 (2xbrs, 1H) | 470 (M + H)+ | Ex 277 |
| 321 | (R)-N-{2-Chloro-4-[4-(1',1'-dioxothiomorpholino)phenyl sulphonyl]phenyl}-2-hydroxy-2-methyl-3,3,3-trifluoropropanamide | 1.6 (s, 3H), 3.12 (brs, 4H), 3.9 (brs, 4H), 7.14 (d, 2H), 7.78 (d, 2H), 7.92 (dd, 1H), 8.06 (d, 1H), 8.22 (d, 1H), 9.9 (brs, 1H) | 539 | Ex 82 |
| 322 | (R)-N-{2-Chloro-4-(4-{3-methyl-1,2,4-oxadiazol-5- | 1.6 (s, 3H), 2.43 (s, 3H), 8.04 (dd, 2H), 8.20–8.25 (m, 3H), 8.27–8.37 | 488 | Ex 278 |

-continued

| Ex | Compound | NMR | MS | SM |
|---|---|---|---|---|
|  | yl}phenylsulphonyl)phenyl}-2-hydroxy-2-methyl-3,3,3-trifluoropropanamide | (m, 3H), 9.94 (brs, 1H) |  |  |
| 323 | (R)-N-{2-Chloro-4-(4-{5-methyl-1,2,4-oxadiazol-3-yl}phenylsulphonyl)phenyl}-2-hydroxy-2-methyl-3,3,3-trifluoropropanamide | 1.61 (s, 3H), 2.69 (s, 3H), 8.02 (dd, 1H) : 8.15–8.25 (m, 5H), 8.34 (d, 1H), 9.9 (brs, 1H) | 488 | Ex 279 |
| 324 | (R)-N-{2-Chloro-4-(4-pyrimidin-2-ylphenyl-sulphonyl)phenyl}-2-hydroxy-2-methyl-3,3,3-trifluoropropanamide | (CDCl$_3$) 1.76 (s, 3H), 3.82 (s, 1H), 7.28 (m, 1H), 7.9 (dd, 1H), 8.0–8.08 (m, 3H), 8.58–8.67 (m, 3H), 8.85 (d, 2H), 9.3 (brs, 1H) | 484 | Ex 203 |
| 325 | (R)-N-{2-Chloro-4-(3-acetamidopropylsulphonyl)phenyl}-2-hydroxy-2-methyl-3,3,3-trifluoropropanamide | (DMSO-$d_6$ + AcOD-$d_4$): 1.59 (s, 3H), 1.61–1.69 (m, 2H), 1.73 (s, 3H), 3.05 (t, 2H), 3.25–3.31 (m, 2H), 7.82–7.86 (m, 1H), 7.97 (s, 1H), 8.39 (s, 1H) | 429 | Ex 406 |
| 326 | (R)-N-{2-Chloro-4-([5-ethoxycarbonyl-3-pyridyl]sulphonyl)phenyl}-2-hydroxy-2-methyl-3,3,3-trifluoropropanamide | 1.34 (t, 3H), 1.59 (s, 3H), 4.37 (q, 2H), 8.07 (s, 1H), 8.12 (d, 1H), 8.33–8.36 (m, 2H), 8.69 (s, 1H), 9.30 (s, 1H), 9.43 (s, 1H), 9.93 (s, 1H) | 479 | Ex 202 |

EXAMPLE 327

(R)-N-[2-Chloro-4-(ethylsulphanyl)phenyl]-2-hydroxy-2-methyl-3,3,3-trifluoropropanamide Copper (I) chloride (0.5 g) and sodium ethanethiolate (0.54 g) were added sequentially to a deoxygenated solution of (R)-N-(2-chloro-4-iodophenyl)-2-hydroxy-2-methyl-3,3,3-trifluoropropanamide (Example 197) (2.0 g) in quinoline (6 ml) and pyridine (1.5 ml). The mixture was heated to 200° C. under argon for 18 hours, cooled dissolved in ethyl acetate (200 ml), washed with dilute aqueous hydrochloric acid (2×100 ml) and brine (2×50 ml) and then dried. Volatile material was removed by evaporation and the residue was purified by chromatography on silica gel eluting with 10–40% ethyl acetate/iso-hexane to give the title compound as a gum (1.4 g). NMR (CDCl$_3$): 1.29 (t, 3H), 1.57 (s, 3H), 2.91 (q, 2H), 3.69 (s, 1H), 7.24 (d, 1H), 7.35 (s, 1H), 8.24 (d, 1H), 8.77 (s, 1H); MS (ESP$^-$): 326.

EXAMPLE 328

Following the procedure of Example 327 and using the appropriate starting materials the following compound was prepared.

| Ex | Compound | NMR (CDCl$_3$) | MS |
|---|---|---|---|
| 328[1] | (R)-N-[2-Chloro-4-(3-hydroxypropylsulphanyl)phenyl]-2-hydroxy-2-methyl-3,3,3-trifluoropropanamide | 1.74 (s, 3H), 1.86–1.92 (m, 2H), 3.00–3.05 (t, 2H), 3.75–3.83 (t, 2H), 7.27 (d, 1H), 7.39 (s, 1H), 8.28 (d, 1H), 8.83 (brs, 1H). | 356 |

[1]Sodium ethanethiolate was replaced with the appropriate thiol and sodium methoxide was added to the reaction mixture.

EXAMPLE 329

(R)-N-{2-Chloro-4-[4-(N-methylcarbamoylmethylsulphinyl)phenylsulphonyl]phenyl}-2-hydroxy-2-methyl-3,3,3-trifluoropronanamide A sample of (R)-N-{2-chloro-4-[4-(N-methylcarbamoylmethylsulphanyl)phenyl-sulphonyl]phenyl}-2-hydroxy-2-methyl-3,3,3-trifluoropropanamide (Example 288) was left standing open to air for approximately one week then purified by chromatography on silica gel eluting with 0–5% methanol/DCM to give (in 10% yield) the title compound as a solid. NMR (CDCl$_3$): 1.7 (s, 3H), 2.8 (d, 3H), 3.4 (d, 1H), 3.75 (d, 1H), 3.9 (s, 1H), 6.6 (m, 1H), 7.75 (d, 2H), 7.85 (m, 1H), 8.0 (dd, 1H), 8.1 (d, 2H), 8.65 (d, 1H), 9.35 (brs, 1H); MS (ESP$^-$): 525.

EXAMPLE 330

By the method of Example 329 using the appropriate starting material the following compound was prepared.

| Ex | Compound | NMR | MS | SM |
|---|---|---|---|---|
| 330[1] | (R)-N-[2-Chloro-4-(4-cyclopropylmethylsulphinyl-phenylsulphonyl)phenyl]-2-hydroxy-2-methyl-3,3,3-trifluoropropanamide | (CDCl$_3$) 0.3 (m, 2H), 0.65 (m, 2H), 0.9–1.0 (m, 1H), 1.7 (s, 3H), 2.65–2.8 (m, 1H), 2.8–2.95 (m, 1H), 5.64 (d, 1H), 7.7–7.9 (m, 3H), 7.95 (m, 1H), 8.05–8.1 (d, 2H), 8.65 (d, 1H), 9.6 (brs, 1H) | 508 | Ex 287 |

[1]The eluent for chromatography was 25–100% DCM/hexane

EXAMPLE 331

(R)-N-[2-Chloro-4-(3-nitrophenylsulphanyl)phenyl]-2-hydroxy-2-methyl-3,3,3-trifluoropropanamide A mixture of 3-nitrophenyldisulphide (0.176 g) and (R)-N-(2-chloro-4-iodophenyl)-2-hydroxy-2-methyl-3,3,3-trifluoropropanamide (Example 197) (0.15 g) in diphenyl ether (5 ml) was heated and stirred at 250° C. for 2 days. The reaction mixture was cooled, diluted with iso-hexane (5 ml) and purified by chromatography eluting with 10–100% DCM/hexane to give the title compound (0.05 g) as an oil. NMR (CDCl$_3$): 1.8 (s, 3H), 3.6 (s, 1H), 7.4–7.55 (m, 4H), 8.1 (brs, 2H), 8.45 (d, 1H), 9.05 (brs, 1H); MS (ESP$^+$): 421 (M+H)$^+$.

EXAMPLE 332

(R)-N-[2-Chloro-4-(N-phenylcarbamoyl)phenyl]-2-hydroxy-2-methyl-3,3,3-trifluoropropanamide A mixture of (R)-N-(2-chloro-4-iodophenyl)-2-hydroxy-2-methyl-3,3,3-trifluoropropanamide (Example 197) (0.35 g), aniline (0.117 ml), tributylamine (0.232 ml) and dichlorobis-(triphenylphosphine)palladium(II) (0.009 g) was heated at 100° C. under an atmosphere of carbon monoxide for 4 hours. Ethyl acetate (10 ml) was added and the mixture was washed with water and brine then was dried. Volatile material was removed by evaporation and the residue was purified by chromatography on a silica gel Mega Bond Elut column eluting with 5–50% ethyl acetate/hexane followed by passing through a Varian Isolute SCX column to give the title compound (0.17 g) as a solid. NMR: 1.6 (s, 3H), 7.1 (t, 1H), 7.35 (t, 2H), 7.75 (d, 2H), 7.92 (s, 1H), 7.98 (dd, 1H), 8.12 (s, 1H), 8.2 (d, 1H), 9.8 (s, 1H), 10,26 (brs, 1H); MS (ESP-): 386.

EXAMPLES 333–334

By the method of Example 332 using Example 197 as the starting materials the following compounds were prepared.

poured into water (50 ml) and extracted with ethyl acetate (2×50 ml). The extracts were washed with brine then dried. Volatile material was removed by evaporation and the residue was purified by chromatography on a silica gel Mega Bond Elut column eluting with 40–100% ethyl acetate/hexane then triturated with hexane to give the title compound (0.112 g) as a solid. NMR (CDCl$_3$): 1.6 (s, 6H), 7.5–7.7 (m, 6H), 7.9 (d, 2H); MS (EI): 318 (M$^+$).

EXAMPLE 336

(R)-N-{2-Chloro-4-[2-(iso-pronylaminocarbonyl)phenylsulphonyl]phenyl}-2-hydroxy-2-methyl-3,3,3-trifluoropropanamide N-Methylmorpholine (1.22 ml) and o-benzotriazol-1-yl-N,N,N',N'-tetramethyluronium hexafluorophosphate (0.092 g) were added to a solution of (R)-N-[2-chloro-4-(2-carboxyphenylsulphonyl)phenyl]-2-hydroxy-2-methyl-3,3,3-trifluoropropanamide (Example 125) (0.10 g) and 2-propylamine (0.024 ml) in DCM (20 ml) at 0° C. The reaction mixture was stirred at this temperature for 30 minutes then allowed to warm to room temperature. stirred for a further 3 hours then evaporated to dryness. The residue was purified by chromatography on a silica gel Mega Bond Elut column eluting with 50% ethyl acetate/hexane then triturated with ether/hexane to give the title compound (0.05 g) as a solid. NMR (CDCl$_3$): 1.3 (d, 6H), 1.6 (s, 3H), 4.2–4.32 (m, 1H), 5.8 (brd, 1H), 7.4 (d, 1H), 7.5–7.7 (m, 3H), 7.9 (dd, 1H), 8.05–8.13 (m, 2H), 8.6 (d, 1H), 9.3 (brs, 1H); MS (ESP$^-$): 491.

| Ex | Compound | NMR | MS |
|---|---|---|---|
| 333 | (R)-N-[2-Chloro-4-(N-n-butylcarbamoyl)phenyl]-2-hydroxy-2-methyl-3,3,3-trifluoropropanamide | 0.88 (t, 3H), 1.3 (m, 2H), 1.48 (m, 2H), 1.6 (s, 3H), 3.2 (t, 2H), 7.83 (dd, 1H), 7.9 (s, 1H), 8.0 (d, 1H), 8.12 (d, 1H), 8.5 (brt, 1H), 9.8 (s, 1H) | 365 |
| 334 | (R)-N-[2-Chloro-4-(piperidin-1-ylcarbonyl)phenyl]-2-hydroxy-2-methyl-3,3,3-trifluoropropanamide | (DMSO-$\delta_6$ + AcOH-$\delta_4$, at 373K): 1.5 (m, 4H), 1.6 (m, 4H), 3.44 (m, 4H), 7.35 (d, 1H), 7.46 (s, 1H), 8.15 (d, 1H) | 377 |

EXAMPLE 335

3-Hydroxy-3-methyl-1-(2-fluoro-4-phenylsulphonylphenyl)but-1-yne

Bis(triphenylphosphine)palladium(II) chloride (0.034 g) was added to a solution of 2-methyl-3-butyn-2-ol (0.11 ml) and 2-fluoro-4-phenylsulphonylbromobenzene (Method 1) (0.548 g) in triethylamine (3 ml) and DMF (1 ml) and the mixture was heated at 70° C. for 18 hours. The mixture was

EXAMPLES 337–349

The aniline starting material was acylated with an appropriate acid chloride by the procedure of Method 17 or sulphonylated with an appropriate sulphonyl chloride by the procedure of Method 26 then hydrolysed by the procedure of Example 171. There were thus obtained the following compounds.

| Ex | Compound | NMR | MS | SM |
|---|---|---|---|---|
| 337 | (R)-N-[2-Chloro-4-(4-benzoyl-aminophenylsulphanyl)phenyl]-2-hydroxy-2-methyl-3,3,3-trifluoropropanamide | 1.6 (s, 3H), 7.2 (d, 1H), 7.3 (s, 1H), 7.5 (m, 5H), 7.9 (m, 6H), 10.4 (s,1H) | 493 | Meth 12 |
| 338 | (R)-N-[2-Chloro-4-(4-t-butyl-carbonylaminophenylsulphanyl)phenyl]-2-hydroxy-2-methyl-3,3,3-trifluoropropanamide | 1.2 (s, 9H), 1.6 (s, 3H), 7.2 (d, 1H), 7.3 (s, 1H), 7.4 (d, 2H), 7.7 (d, 2H), 7.9 (d, 1H), 9.3 (s, 1H), 9.7 (s, 1H) | 473 | Meth 12 |
| 339 | (R)-N-{2-Chloro-4-[4-(4-chloro-benzoylamino)phenylsulphanyl]phenyl}-2-hydroxy-2-methyl-3,3,3-trifluoropropanamide | 1.6 (s, 3H), 7.2 (d, 1H), 7.3 (s, 1H), 7.4 (d, 2H), 7.6 (d, 2H), 7.9 (m, 6H), 9.7 (s, 1H), 10.4 (s, 1H) | 527 | Meth 12 |
| 340 | (R)-N-{2-Chloro-4-[4-(2-methoxy-acetylamino)phenylsulphanyl]phenyl}-2-hydroxy-2-methyl-3,3,3-trifluoropropanamide | 1.5 (s, 3H), 3.3 (s, 3H), 4.0 (s, 2H), 7.2 (d, 1H), 7.3 (s, 1H), 7.4 (d, 2H), 7.7 (d, 3H), 7.9 (d, 1H), 9.6 (s, 1H), 9.9 (s, 1H) | 461 | Meth 12 |
| 341 | (R)-N-{2-Chloro-4-[4-(pyrid-3-ylcarbonylamino)phenylsulphanyl]phenyl}-2-hydroxy-2-methyl-3,3,3-trifluoropropanamide | 1.6 (s, 3H), 7.2 (d, 1H), 7.3 (s, 1H), 7.5 (d, 2H), 7.7 (s, 1H), 7.8 (m, 4H), 7.9 (d, 1H), 8.8 (d, 2H), 9.7 (s, 1H), 10.6 (s, 1H) | 494 | Meth 12 |
| 342 | (R)-N-[2-Chloro-4-(2-mesylamino-phenylsulphanyl)phenyl]-2-hydroxy-2-methyl-3,3,3-trifluoropropanamide | 1.6 (s, 3H), 3.0 (s, 3H), 7.4 (m, 7H), 7.8 (s, 1H), 8.0 (d, 1H), 9.7 (s, 1H) | 467 | Meth 36 |
| 343 | (R)-N-[2-Chloro-4-(2-acetylamino-phenylsulphanyl)phenyl]-2-hydroxy-2-methyl-3,3,3-trifluoropropanamide | 1.6 (s, 3H), 2.0 (s, 3H), 7.2 (m, 2H), 7.3 (m, 3H), 7.6 (d, 1H), 7.8 (s, 1H), 7.9 (d, 1H), 9.5 (s, 1H), 9.7 (s, 1H) | 431 | Meth 36 |
| 344 | (R)-N-[2-Chloro-4-(4-mesylamino-phenylsulphanyl)phenyl]-2-hydroxy-2-methyl-3,3,3-trifluoropropanamide | 1.6 (s, 3H), 3.0 (s, 3H), 7.2 (m, 3H), 7.3 (s, 1H), 7.2 (d, 2H), 7.8 (s, 1H), 7.9 (d, 1H), 9.7 (s, 1H), 9.9 (s, 1H) | 467 | Meth 12 |
| 345 | (R)-N-{2-Chloro-4-[4-(phenyl-sulphonylamino)phenyl-sulphanyl]phenyl}-2-hydroxy-2-methyl-3,3,3-trifluoropropanamide | 1.6 (s, 3H), 7.1 (t, 3H), 7.2 (s, 1H), 7.3 (d, 2H), 7.6 (m, 3H), 7.8 (m, 3H), 7.9 (d, 1H), 9.7 (s, 1H), 10.5 (s, 1H) | 529 | Meth 12 |
| 346[1] | (R)-N-{2-Chloro-4-[4-(ethenyl-sulphonylamino)phenylsulphanyl]phenyl}-2-hydroxy-2-methyl-3,3,3-trifluoropropanamide | 1.6 (s, 3H), 6.1 (m, 2H), 7.8 (q, 1H), 7.2 (m, 3H), 7.4 (m, 3H), 7.8 (s, 1H), 7.9 (d, 1H), 9.7 (s, 1H), 10.25 (s, 1H) | 479 | Meth 12 |
| 347 | (R)-N-[2-Chloro-4-(3-mesylamino-phenylsulphanyl)phenyl]-2-hydroxy-2-methyl-3,3,3-trifluoropropanamide | 1.6 (s, 3H), 3.0 (s, 3H), 7.0 (d, 1H), 7.1 (d, 2H), 7.3 (m, 2H), 7.5 (s, 1H), 7.8 (s, 1H), 8.0 (s, 1H), 9.7 (s, 1H), 9.8 (s, 1H). | 467 | Meth 37 |
| 348 | (R)-N-[2-Fluoro-4-(4-mesylamino-phenylsulphanyl)phenyl]-2-hydroxy-2-methyl-3,3,3-trifluoropropanamide | 1.6 (s, 3H), 3.0 (s, 3H), 7.1 (m, 2H), 7.2 (d, 2H), 7.4 (d, 2H), 7.6 (m, 2H), 9.6 (s, 1H), 10.0 (s, 1H) | 451 | Meth 38 |
| 349 | (R)-N-[2-Fluoro-4-(4-acetylamino-phenylsulphanyl)phenyl]-2-hydroxy-2-methyl-3,3,3-trifluoropropanamide | 1.6 (s, 3H), 2.1 (s, 3H), 7.0 (m, 2H), 7.4 (d, 2H), 7.6 (m, 4H), 10.1 (s, 1H) | 415 | Meth 38 |

[1] 2-Chloroethylsulphonyl chloride was used for the sulphonylation; HCl was eliminated in hydrolysis step.

EXAMPLES 350–352

Following the procedure of Method 10 and using the appropriate starting material the following compounds were prepared.

| Ex | Compound | NMR | MS | SM |
|---|---|---|---|---|
| 350 | (R)-N-[2-Fluoro-4-(4-aminophenylsulphonyl)phenyl]-2-hydroxy-2-methyl-3,3,3-trifluoropropanamide | 1.6 (s, 3H), 6.2 (s, 2H), 6.6 (d, 2H), 7.5 (d, 2H), 7.7 (q, 3H), 7.9 (9t, 1H), 9.8 (s, 1H) | 405 | Meth 65 |
| 351 | (R)-N-[2-Chloro-4-(2-aminophenylsulphonyl)phenyl]-2-hydroxy-2-methyl-3,3,3-trifluoropropanamide | 1.6 (s, 3H), 6.2 (s, 2H), 6.6 (t, 1H), 6.8 (d, 1H), 7.3 (t, 1H), 7.7 (d, 1H), 7.9 (m, 2H), 8.1 (s, 1H), 8.2 (d, 1H), 9.9 (s, 1H) | 421 | Meth 67 |
| 352 | (R)-N-[2-Chloro-4-(3-aminophenylsulphonyl)phenyl]-2-hydroxy-2-methyl-3,3,3-trifluoropropanamide | 1.59 (s, 3H), 5.65 (s, 2H), 6.78 (d, 1H), 7.01 (d, 1H), 7.07 (s, 1H), 7.2 (t, 1H), 7.88 (d, 1H), 7.98 (s, 1H), 8.27 (d, 1H) | 421 | Meth 68 |

EXAMPLE 353

(R)-N-[2-Chloro-4-(4-dimethylaminoacetylaminophenylsulphanyl)phenyl]-2-hydroxy-2methyl-3,3,3-trifluoropropanamide Dimethylamine (0.17 ml of a 40% solution in water) was added to a solution of (R)-N-{2-chloro-4-[4-(2-chloroacetylamino)phenylsulphanyl]phenyl}-2-acetoxy-2-methyl-3,3,3-trifluoropropanamide (Method 19) (0.25 g) in acetone (1.5 ml). After 24 hours volatile material was removed by evaporation and the residue was dissolved in ethyl acetate, washed with water, and the organic layer was poured onto a Varian Chem Elut column. Elution with ethyl acetate gave the title compound (0.25 g) as a foam. NMR: 1.6 (s, 3H), 3.1 (s, 2H), 3.3 (s, 6H), 7.2 (d, 1H), 7.3 (s, 1H), 7.4 (d, 2H), 7.7 (m, 3H), 7.9 (d, 1H), 9.7 (s, 1H) 9.9 (s, 1H); MS (ESP⁻): 474.

EXAMPLE 354

(R)-N-{2-Chloro-4-[4-(3-ethylureido)phenylsulphonyl[phenyl}-2-hydroxy-2-methyl-3,3,3-trifluoropropanamide (R)-2,3,4,5-H₄-3-{2-Chloro-4-[4-(3-ethylureido)phenylsulphanyl]phenyl}-2,4-dioxo-5-methyl-5-trifluoromethyloxazole (Method 42) was oxidised by the procedure of Method 63 then hydrolysed by the method of Example 171 to give the title compound. NMR: 1.0 (s, 3H), 1.6 (s, 3H), 3.1 (s, 2H), 6.2 (s, 1H), 7.6 (d, 2H), 7.9 (m, 5H), 8.2 (d, 1H), 9.0 (s, 1H), 9.8 (s, 1H); MS (ESP⁻): 492.

EXAMPLE 355

By the procedure of Example 354 using the appropriate starting materials the following compound was prepared.

| Ex | Compound | NMR | MS | SM |
|---|---|---|---|---|
| 355 | (R)-N-[2-Chloro-4-(4-aminophenylsulphonyl)phenyl]-2-hydroxy-2-methyl-3,3,3-trifluoropropanamide | (CDCl₃) 1.8 (s, 3H), 3.8 (s, 1H), 4.2 (s, 2H), 6.6 (d, 3H), 7.7 (d, 2H), 7.8 (d, 1H), 7.9 (s, 1H), 8.6 (d, 1H), 9.3 (s, 1H) | 421 | Meth 40 |

EXAMPLES 356–380

The aniline starting material was acylated with an appropriate acid chloride by the procedure of Method 17 or sulphonylated with an appropriate sulphonyl chloride by the procedure of Method 26. There were thus obtained the following compounds.

| Ex | Compound | NMR or HPLC | MS | SM |
|---|---|---|---|---|
| 356 | (R)-N-[2-Chloro-4-(4-methylphenylsulphonamido)phenyl]-2-hydroxy-2-methyl-3,3,3-trifluoropropanamide | 1.55 (s, 3H), 2.33 (s, 3H), 7.08 (d, 1H), 7.18 (s, 1H), 7.38 (m, 2H), 7.68 (m, 4H), 9.54 (s, 1H), 10.43 (brs, 1H) | 435 | Ex 208 |
| 357 | (R)-N-[2-Chloro-4-(phenylsulphonamido)phenyl]-2-hydroxy-2-methyl-3,3,3- | (CDCl₃) 1.72 (s, 3H), 3.55 (s, 1H), 6.52 (s, 1H), 6.92 (d, 1H), 7.30 (s, 1H), 7.50 (t, 2H), 7.59 (m, 1H), | 423 (M + H)⁺ | Ex 208 |

-continued

| Ex | Compound | NMR or HPLC | MS | SM |
|---|---|---|---|---|
| | trifluoropropanamide | 7.78 (d, 2H), 8.24 (d, 1H), 8.80 (s, 1H) | | |
| 358 | (R)-N-[2-Chloro-4-(4-methoxyphenylsulphonamido)phenyl]-2-hydroxy-2-methyl-3,3,3-trifluoropropanamide | 1.55 (s, 3H), 3.80 (s, 3H), 7.09 (m, 3H), 7.19 (s, 1H), 7.65 (s, 1H), 7.73 (m, 3H), 9.56 (s, 1H) | 451 | Ex 208 |
| 359 | (R)-N-[2-Chloro-4-(4-acetyl-aminophenylsulphonamido)phenyl]-2-hydroxy-2-methyl-3,3,3-trifluoropropanamide | 1.55 (s, 3H), 2.06 (s, 3H), 7.08 (d, 1H), 7.19 (s, 1H), 7.70 (m, 6H), 9.53 (s, 1H), 10.27 (s, 1H), 10.36 (brs, 1H) | 478 | Ex 208 |
| 360 | (R)-N-[2-Chloro-4-(4-t-butyl-phenylsulphonamido)phenyl]-2-hydroxy-2-methyl-3,3,3-trifluoropropanamide | 11.46 minutes (HPLC Method b) | 479 $(M + H)^+$ | Ex 208 |
| 361 | (R)-N-[2-Chloro-4-(3,4-di-methoxyphenylsulphonamido)phenyl]-2-hydroxy-2-methyl-3,3,3-trifluoropropanamide | 8.02 minutes (HPLC Method a) | 483 $(M + H)^+$ | Ex 208 |
| 362 | (R)-N-[2-Chloro-4-(4-fluoro-phenylsulphonamido)phenyl]-2-hydroxy-2-methyl-3,3,3-trifluoropropanamide | 8.28 minutes (HPLC Method a) | 439 | Ex 208 |
| 363 | (R)-N-[2-Chloro-4-(2-chloro-phenylsulphonamido)phenyl]-2-hydroxy-2-methyl-3,3,3-trifluoropropanamide | 8.34 minutes (HPLC Method a) | 455 | Ex 208 |
| 364 | (R)-N-[2-Chloro-4-(2-methyl-phenylsulphonamido)phenyl]-2-hydroxy-2-methyl-3,3,3-trifluoropropanamide | 8.35 minutes (HPLC Method a) | 435 | Ex 208 |
| 365 | (R)-N-[2-Chloro-4-(4-methoxybenzoylamino)phenyl]-2-hydroxy-2-methyl-3,3,3-trifluoropropanamide | 8.27 minutes (HPLC Method a) | 415 | Ex 208 |
| 366 | (R)-N-[2-Chloro-4-(t-butyl-carboxamido)phenyl]-2-hydroxy-2-methyl-3,3,3-trifluoropropanamide | 8.3 minutes (HPLC Method a) | 365 | Ex 208 |
| 367 | (R)-N-(2-Chloro-4-acetamido-phenyl)-2-hydroxy-2-methyl-3,3,3-trifluoropropanamide | 7.21 minutes (HPLC Method a) | 323 | Ex 208 |
| 368 | (R)-N-[2-Chloro-4-(benzyl-carboxamido)phenyl]-2-hydroxy-2-methyl-3,3,3-trifluoropropanamide | 8.28 minutes (HPLC Method a) | 399 | Ex 208 |
| 369 | (R)-N-[2-Chloro-4-(2-chloro-pyrid-3-ylcarboxamido)phenyl]-2-hydroxy-2-methyl-3,3,3-trifluoropropanamide | 7.76 minutes (HPLC Method a) | 421 | Ex 208 |
| 370[1] | (R)-N-[2-Chloro-4-(isoxazol-5-ylcarboxamido)phenyl]-2-hydroxy-2-methyl-3,3,3-trifluoropropanamide | 9.41 minutes (HPLC Method b) | 376 | Ex 208 |
| 371 | (R)-N-[2-Chloro-4-(N'-(3-methylsulphanylpropyl)-2-mesylphenylsulphonamido)phenyl]-2-hydroxy-2-methyl-3,3,3-trifluoropropanamide | 1.62 (m, 1H), 1.96 (s, 3H), 2.50 (m, 2H), 3.41 (s, 3H), 3.88 (t, 2H), 7.29 (dd, 1H), 7.47 (s, 1H), 7.80–8.03 (m, 5H), 8.27 (d, 1H), 9.73 (s, 1H) | 587 | Ex 390 |
| 372 | (R)-N-[2-Chloro-4-(N'-(3-methylsulphanylpropyl)phenyl-sulphonamido)phenyl]-2-hydroxy-2-methyl-3,3,3-trifluoropropanamide | 1.58 (m, 5H), 1.95 (s, 3H), 2.45 (m, 2H), 3.61 (t, 2H), 7.10 (dd, 1H), 7.28 (s, 1H), 7.63 (m, 4H), 7.75 (m, 1H), 7.90 (brs, 1H), 8.00 (d, 1H), 9.73 (brs, 1H). | 509 | Ex 390 |
| 373 | (R)-N-{2-Chloro-4-[N'-(3-methylsulphanylpropyl)-4-methylphenylsulphonamido]phenyl}-2-hydroxy-2-methyl-3,3,3-trifluoropropanamide | 1.60 (m, 5H), 1.95 (s, 3H), 2.46 (m, 5H), 3.60 (t, 2H), 7.08 (dd, 1H), 7.30 (s, 1H), 7.43 (q, 4H), 7.80 (brs, 1H), 7.97 (d, 1H), 9.71 (brs, 1H) | 523 | Ex 390 |
| 374 | (R)-N-[2-Methyl-4-(phenyl-sulphonamido)phenyl]-2-hydroxy-2-methyl-3,3,3-trifluoropropanamide | (CDCl$_3$) 1.71 (s, 3H), 2.21 (s, 3H), 3.62 (s, 1H), 6.41 (brs, 1H), 6.83 (dd, 1H), 6.98 (m, 1H), 7.40–7.48 (m, 2H), 7.50–7.60 (m, 1H), 7.65–7.70 (s, 1H), 7.71–7.7 9m, 1H), 8.00 (brs, 1H). | 402 | Ex 209 |
| 375 | (R)-N-[2-Methyl-4-(2-phenyl-E-ethenylsulphonamido)phenyl]-2-hydroxy-2-methyl- | (CDCl$_3$) 1.6 (s, 3H), 2.22 (s, 3H), 3.75 (brs, 1H), 6.48 (brs, 1H), 6.75 (d, 1H), 6.99–7.06 (m, 1H), | 427 | Ex 209 |

-continued

| Ex | Compound | NMR or HPLC | MS | SM |
|---|---|---|---|---|
|  | 3,3,3-trifluoropropanamide | 7.07–7.10 (m, 1H), 7.30–7.42 (m, 5H), 7.55 (d, 1H), 7.69–7.73 (m, 1H), 8.06 (brs, 1H). |  |  |
| 376 | (R)-N-[2-Methyl-4-(4-methyl-phenylsulphonamido)phenyl]-2-hydroxy-2-methyl-3,3,3-trifluoropropanamide | (CDCl$_3$) 1.66 (s, 3H), 2.17 (s, 3H), 2.38 (s, 3H), 3.70 (brs, 1H), 6.53 (brs, 1H), 6.80–6.85 (m, 1H), 6.95–6.98 (m, 1H), 7.20–7.28 (m, 1H), 7.61–7.69 (m, 3H), 8.05 (brs, 1H). | 415 | Ex 209 |
| 377 | (R)-N-[2-Methyl-4-(2-mesyl-phenylsulphonamido)phenyl]-2-hydroxy-2-methyl-3,3,3-trifluoropropanamide | (CDCl$_3$) 1.68 (s, 3H), 2.15 (s, 3H), 3.48 (s, 3H), 3.65 (s, 1H), 6.97–7.04 (m, 2H), 7.59–7.88 (m, 3H), 7.94–8.11 (m, 2H), 8.11 (brs, 1H), 8.30–8.33 (m, 1H). | 479 | Ex 209 |
| 378 | (R)-N-[2-Methyl-4-(2-trifluoromethylphenyl-sulphonamido)phenyl]-2-hydroxy-2-methyl-3,3,3-trifluoropropanamide | (CDCl$_3$) 1.50 (s, 3H), 2.18 (s, 3H), 3.60 (s, 1H), 6.61 (brs, 1H), 6.87–6.92 (m, 1H), 6.98–7.02 (m, 1H), 7.50–7.75 (m, 3H), 7.84–7.92 (m, 1H), 7.97–8.10 (m, 2H). | 469 | Ex 209 |
| 379 | (R)-N-(2-Methyl-4-mesyl-aminophenyl)-2-hydroxy-2-methyl-3,3,3-trifluoropropanamide | (CDCl$_3$) 1.75 (s, 3H), 2.27 (s, 3H), 3.00 (s, 3H), 3.62 (brs, 1H), 6.28 (brs, 1H), 7.08–7.14 (m, 1H), 7.11–7.14 (m, 1H), 7.77–7.82 (m, 1H), 8.06 (brs, 1H). | 339 | Ex 209 |
| 380 | (R)-N-[2-Methyl-4-(2-chloro-phenylsulphonamido)phenyl]-2-hydroxy-2-methyl-3,3,3-trifluoropropanamide | (CDCl$_3$) 1.72 (s, 3H), 2.22 (s, 3H), 3.67 (s, 1H), 5.91–5.98 (m, 1H), 6.21–6.29 (m, 1H), 6.38 (brs, 1H), 6.48–6.58 (m, 1H), 6.93–7.00 (m, 1H), 7.01–7.05 (m, 1H), 7.70–7.78 (m, 1H), 8.05 (brs, 1H). | 351 | Ex 209 |

[1]The product formed as a precipitate which was collected and washed with DCM.

EXAMPLE 381
(R)-N-[2-Chloro-4-(3-phenylureido)phenyl]-2-hydroxy-2-methyl-3,3,3-trifluoropropanamide A mixture of (R)-N-[2-chloro-4-aminophenyl]-2-hydroxy-2-methyl-3,3,3-trifluoropropanamide (Example 208) (0.198 g) and phenyl isocyanate (0.09 ml) in diethyl ether (10 ml) was stirred for 22 hours then evaporated to dryness. The residue was partitioned between water (25 ml) and ethyl acetate (50 ml). The organic phase was washed with brine (25 ml), dried and concentrated by evaporation to give the title compound (170 mg) as a foam. NMR: 1.66 (s, 3H), 7.04 (t, 1H), 7.35 (m, 3H), 7.52 (d, 1H), 7.71 (s, 1H), 7.86 (m, 2H), 8.77 (s, 1H), 8.92 (s, 1H), 9.63 (s, 1H); MS (ESP$^-$): 400.

EXAMPLE 382
(R)-N-{2-Chloro-4-[N-(4-methylphenylsulphonyl)(N-methyl)amino]phenyl}-2-hydroxy-2-methyl-3,3,3-trifluoropropanamide A mixture of (R)-N-[2-chloro-4-(4-methylphenylsulphonamido)phenyl]-2-hydroxy-2-methyl-3,3,3-trifluoropropanamide (Example 356) (0.137 g), anhydrous potassium carbonate (0.043 g) and iodomethane (0.038 ml) in acetone (8 ml) was stirred for 64 hours. Volatile material was removed by evaporation and the residue was dissolved in ethyl acetate, washed with water and brine then dried. Volatile material was removed by evaporation and the residue was purified by elution through a Varian Isolute silica 10 g column with 30% ethyl acetate/hexane as eluent to give the title compound (0.079 g). NMR: 1.60 (s, 3H), 2.38 (s, 3H), 3.11 (s, 3H), 7.11 (d, 3H), 7.32 (s, 1H), 7.43 (m, 4H), 7.94 (d, 1H), 9.67 (brs, 1H); MS (ESP$^-$): 449.

EXAMPLES 383–387

By the method of Example 382 and using the appropriate starting materials the following compounds were prepared.

| Ex | Compound | HPLC | MS | SM |
|---|---|---|---|---|
| 383 | (R)-N-{2-Chloro-4-[N-(4-t-butylphenylsulphonyl)(N-methyl)amino]phenyl}-2-hydroxy-2-methyl-3,3,3-trifluoropropanamide | 12.36 minutes (HPLC Method b) | 493 (M + H)$^+$ | Ex 360 |
| 384 | (R)-N-{2-Chloro-4-[N-(3,4-dimethoxypheny l-sulphonyl)(N-methyl)amino]phenyl}-2-hydroxy-2-methyl-3,3,3-trifluoropropanamide | 10.7 minutes (HPLC Method b) | 497 (M + H)$^+$ | Ex 361 |
| 385 | (R)-N-{2-Chloro-4-[N-(4-fluorophenylsulphonyl)(N-methyl)amino]phenyl}-2-hydroxy-2-methyl-3,3,3-trifluoropropanamide | 11.14 minutes (HPLC Method b) | 455 (M + H)$^+$ | Ex 362 |
| 386 | (R)-N-{2-Chloro-4-[N-(2-chlorophenylsulphonyl)(N-methyl)amino]phenyl}-2-hydroxy-2-methyl-3,3,3-trifluoropropanamide | 11.24 minutes (HPLC Method b) | 471 (M + H)$^+$ | Ex 363 |

| Ex | Compound | HPLC | MS | SM |
|---|---|---|---|---|
| 387 | (R)-N-{2-Chloro-4-[N-(2-methylphenylsulphonyl)(N-methyl)amino]phenyl}-2-hydroxy-2-methyl-3,3,3-trifluoropropanamide | 11.3 minutes (HPLC Method b) | 449 | Ex 364 |

EXAMPLES 388–389

Following the procedure of Method 30 (see below) and using the appropriate starting materials the following compounds were prepared.

| Ex | Compound | NMR | MS | SM |
|---|---|---|---|---|
| 388 | (R)-N-[2-Chloro-4-(2-aminoanilino)phenyl]-2-hydroxy-2-methyl-3,3,3-trifluoropropanamide | 1.56 (s, 3H), 4.76 (s, 2H), 6.56 (t, 1H), 6.66 (m, 2H), 6.75 (d, 1H), 6.89 (t, 1H), 6.97 (d, 1H), 7.40 (s, 1H), 7.52 (m, 2H), 9.39 (s, 1H) | 372 | Ex 206 |
| 389 | (R)-N-(2-Methoxy-4-amino-phenyl)-2-hydroxy-2-methyl-3,3,3-trifluoropropanamide | (CDCl$_3$) 1.51 (s, 3H), 3.74 (s, 3H), 5.00 (brs, 2H), 6.05–6.15 (m, 1H), 6.28–6.37 (m, 1H), 7.53 (brs, 1H), 7.72–7.78 (m, 1H), 9.08 (brs, 1H) | 277 | Meth 61 |

EXAMPLE 390

(R)-N-[2-Chloro-4-(3-methylsulphanylpropylamino)phenyl]-2-hydroxy-2-methyl-3,3,3-trifluoropropanamide Sodium triacetoxyborohydride (0.297 g) was added to a solution of 3-methylsulphanylpropionaldehyde (0.1 ml) and (R)-N-(2-chloro-4-aminophenyl)-2-hydroxy-2-methyl-3,3,3-trifluoropropanamide (Example 208) (0.282 g) in 1,2-dichloroethane (6 ml). The mixture was stirred for 16 hours. Saturated aqueous sodium hydrogen carbonate (25 ml) was added and the mixture was extracted with ethyl acetate (40 ml). The extracts were washed with brine (15 ml) then dried. Volatile material was removed by evaporation and the residue was purified by chromatography on a Varian Isolute silica column eluting with 25% ethyl acetate/hexane. The resulting solid was triturated with ether to give the title compound (0.089 g) as a solid. NMR: 1.54 (s, 3H), 1.78 (m, 2H), 2.05 (s, 3H), 2.55 (q, 2H), 3.09 (q, 2H), 5.93 (t, 1H), 6.54 (dd, 1H), 6.65 (s, 1H), 7.46 (m, 2H), 9.33 (s, 1H); MS (ESP$^-$): 369.

EXAMPLES 391–393

By the method of Example 390 and using the appropriate starting materials and Example 208 the following compounds were prepared.

| Ex | Compound | NMR | MS |
|---|---|---|---|
| 391 | (R)-N-[2-Chloro-4-(benzyl-amino)phenyl]-2-hydroxy-2-methyl-3,3,3-trifluoropropanamide | 1.54(s, 3H), 4.26(d, 2H), 6.53(m, 2H), 6.65(s, 1H), 7.20(m, 1H), 7.30(m, 4H), 7.40(d, 1H), 7.45(s, 1H), 9.30(s, 1H) | 371 |
| 392 | (R)-N-[2-Chloro-4-(1-methylpyrrol-2-ylmethyl amino)phenyl]-2-hydroxy-2-methyl-3,3,3-trifluoropropanamide | 1.56(s, 3H), 3.55(s, 3H), 4.15(d, 2H), 5.88(m, 1H), 5.97(m, 1H), 6.13(t, 1H), 6.65(m, 2H), 6.77(s, 1H), 7.46(d, 2H), 9.37(brs, 1H) | 374 |
| 393[1] | (R)-N-[2-Chloro-4-(pyridin-4-ylmethylamino)phenyl]-2-hydroxy-2-methyl-3,3,3-trifluoropropanamide | 1.54(s, 3H), 4.34(d, 2H), 6.53(dd, 1H), 6.65(s, 1H), 6.69(t, 1H), 7.33(d, 2H), 7.41(d, 1H), 7.53(brs, 1H), 8.48(d, 2H), 9.37(s, 1H) | 372 |

[1] The first-formed product was the Schiff base which was then reduced by the procedure of Method 30 to give the indicated compound.

EXAMPLE 394

(R)-N-[2-Chloro-4-(phenylsulphonyl)phenyl]-2-aminopropanamide

TFA (0.5 ml) was added drop wise to a solution of (R)-N-[2-chloro-4-(phenylsulphonyl)phenyl]-2-(t-butoxycarbonylamino)propanamide (Method 2) (0.090 g) in dry DCM (5 ml). The resulting mixture was stirred at room temperature for 3 hours. Volatile material was removed by evaporation. The resulting residue was re-dissolved in DCM (10 ml), and volatile material was removed by evaporation. This was repeated, the resulting residue was dried for 30 minutes on a high vacuum line. The residue was then dissolved in DCM and passed through a Varian Isolute SPE column containing basic residues, with DCM as the eluent to give the title compound (0.067 g) as a gum. NMR (CDCl$_3$): 1.32–1.40 (d, 3H), 1.52 (brs, 2H), 3.51–3.64 (q, 1H), 7.40–7.55 (m, 3H), 7.71–7.80 (m, 1H), 7.81–7.95 (m, 3H) 8.58–8.65 (m, 1H), 10.46 (brs, 1H). MS: (ESP$^+$) 339.3 (M+H)$^+$.

EXAMPLES 395–396

By the method of Example 394 and using the appropriate starting materials the following compounds were prepared.

| Ex | Compound | NMR | MS | SM |
|---|---|---|---|---|
| 395 | (R)-N-{2-Chloro-4-[4-(piperazin-1-ylcarbonyl)phenylsulphonyl]phenyl}-2-hydroxy-2-methyl-3,3,3-trifluoropropanamide | 1.65(s, 3H), 2.65(brs, 2H), 2.8 (brs, 2H), 3.2(brs, 2H), 3.6(brs, 2H), 7.65(d, 2H), 8.0–8.15(m, 4H), 8.2(s, 1H), 8.4(d, 2H), 9.6(s, 1H) | 518 | Ex 220 |
| 396 | (R)-N-{2-Chloro-4-(3-aminopropylsulphonyl)phenyl}-2-hydroxy-2-methyl-3,3,3-trifluoropropanamide | 1.56(s, 3H), 1.61–1.66(m, 2H), 2.62(t, 2H), 3.34–3.39(t, 2H), 7.78–7.82(m, 1H), 7.94(s, 1H), 8.35(d, 1H) | 387 | Ex 51 |

EXAMPLE 397

(R)-N-[2-Chloro-4-(4-{3-hydroxypropoxy}phenylsulphinyl)phenyl]-2-hydroxy-2-methyl-3,3,3-trifluoropropanamide Sodium hydride (0.06 g of a 60% dispersion in oil) was added to a solution of (R)-N-[2-chloro-4-(4-hydroxyphenylsulphinyl)phenyl]-2-hydroxy-2-methyl-3,3,3-trifluoropropanamide (Example 89) (0.5 g) in DMF (5 ml) at 0° C. The mixture was stirred for 15 minutes then 3-bromopropanol (0.12 ml) was added as a solution in DMF (3 ml). The mixture was stirred at ambient temperature for 16 hours. Volatile material was removed by evaporation and the residue was purified by chromatography on a silica gel Mega Bond Elut column eluting with 0–10% methanol/DCM to give the title compound (0.34 g) as a gum. NMR (CDCl$_3$): 1.25 (dd, 2H), 1.7 (s, 3H), 1.8 (s, 1H), 3.8–3.9 (m, 2H), 4.1–4.2 (m, 2H), 5.1 (s, 1H), 6.95 (d, 2H), 7.4 (d, 1H), 7.5 (d, 2H), 7.6–7.65 (m, 1H), 8.45–8.55 (m, 1H), 9.3 (s, 1H); MS (ESP$^-$): 464.

EXAMPLES 398–400

By the procedure of Example 397 and using Example 89 as the starting materials the following compounds were prepared.

EXAMPLE 401

By the procedure of Method 26 (see below) and using Example 396 as the starting materials the following compound was prepared.

| Ex | Compound | NMR | MS |
|---|---|---|---|
| 401 | (R)-N-{2-Chloro-4-(3-mesylaminopropylsulphonyl)phenyl}-2-hydroxy-2-methyl-3,3,3-trifluoropropanamide | 1.61(s, 3H), 1.67–1.77(m, 2H), 2.84(s, 3H), 2.96–3.02(m, 2H), 3.36–3.42(m, 2H), 7.02(t, 1H), 7.86–7.9(m, 1H), 8.02(s, 1H), 8.34(d, 1H), 9.92(s, 1H) | 465 |

EXAMPLE 402

(R)-N-[2-Chloro-4-(N,N-dimethylcarbamoylmethylsulphanyl)phenyl]-2-hydroxy-2-methyl-3,3,3-trifluoropropanamide Tetrabutylammonium fluoride (1.1 ml of a 1M solution in THF) was added to (R)-N-(2-chloro-4-(triisopropylsilylsulphanyl)phenyl]-2-hydroxy-2-methyl-3,3,3-trifluoropropanamide (Method 28) (0.50 g) in anhydrous THF (5 ml) at −70° C. After 15 minutes 2-chlorodimethylacetamide (0.17 ml) was added and the mixture was allowed to warm up then was stirred at ambient temperature for 45 minutes. Ethyl acetate (80 ml) was added and the mixture was washed with brine (100 ml) then dried

| Ex | Compound | NMR | MS |
|---|---|---|---|
| 398[1] | (R)-N-[2-Chloro-4-(4-{3-aminopropoxy}phenylsulphinyl)phenyl]-2-hydroxy-2-methyl-3,3,3-trifluoropropanamide | 1.6(s, 3H), 1.95–2.0(m, 2H), 2.90–3.0 (m, 2H), 4.0–4.1(m, 2H), 7.1(m, 2H), 7.6–7.7(m, 3H), 7.7–7.9(m, 4H), 8.1 (d, 1H), 9.85(s, 1H) | 465 (M + H)$^+$ |
| 399 | (R)-N-[2-Chloro-4-(4-{carbamoylmethoxy}phenylsulphinyl)phenyl]-2-hydroxy-2-methyl-3,3,3-trifluoropropanamide | 1.6(s, 3H), 4.45(d, 2H), 6.9–7.0(m, 1H), 7.0–7.2(m, 2H), 7.3–7.5(m, 2H), 7.5–7.6(m, 1H), 7.6–7.7(m, 2H), 7.8 (s, 1H), 8.1(d, 1H), 9.8(s, 1H) | 463 |
| 400 | (R)-N-[2-Chloro-4-(4-{N,N-dimethylcarbamoylmethoxy}phenylsulphinyl)phenyl]-2-hydroxy-2-methyl-3,3,3-trifluoropropanamide | 1.6(s, 3H), 2.8(s, 3H), 3.0(s, 3H), 4.8–5.0(m, 2H), 6.8(d, 1H), 7.0–7.1 (m, 2H), 7.35(d, 1H), 7.5–7.6(d, 2H), 7.8(d, 1H), 8.15(d, 1H), 9.8(s, 1H) | 491 |

[1] An extra molar equivalent of sodium hydride was used. The halide was 3-aminopropyl bromide, hydrobromide salt.

and volatile material was removed by evaporation. The residue was purified on a silica gel Mega Bond Elut column eluting with 10–50% ethyl acetate/hexane to give the title compound (0.30 g) as a solid. NMR (CDCl$_3$) 1.72 (s, 3H), 2.97 (s, 3H), 3.08 (s, 3H), 3.71 (s, 2H), 4.76 (s, 1H), 7.32–7.36 (m, 1H), 7.53 (d, 1H), 8.32 (d, 1H), 9.05 (s, 1H); MS (ESP$^-$): 383.

EXAMPLES 403–412

Following the procedure of Example 402 and using the appropriate starting materials the following compounds were prepared.

EXAMPLE 413
N-[2-Fluoro-4-(4-methylsulphanylphenylsulphanyl) phenyl]-2-hydroxy-2-trifluoromethyl-3,3,3-trifluoropropanamide Tetra-n-butylammonium fluoride (0.48 ml of a 1M solution in THF) was added to a stirred solution of N-[2-fluoro-4-(4-methylsulphanylphenylsulphanyl)phenyl]-2-(t-butyldimethylsilyloxy)-2-trifluoromethyl-3,3,3-trifluoropropanamide (0.278 g) (Method 55) in anhydrous THF (5 ml) at −78° C. under argon. After 30 minutes ethyl acetate (50 ml) was added and the mixture was washed with

| Ex | Compound | NMR | MS | SM |
|---|---|---|---|---|
| 403 | (R)-N-[2-Chloro-4-(methoxycarbonylmethyl sulphanyl)phenyl]-2-hydroxy-2-methyl-3,3,3-trifluoropropanamide | (CDCl$_3$) 1.75(s, 3H), 3.55(s, 3H), 3.72(s, 2H), 7.33–7.37(m, 1H), 7.49(s, 1H), 8.32(d, 1H), 8.85(s, 1H) | 370 | Meth 28 |
| 404 | (R)-N-[2-Chloro-4-({3-N,N-dimethylamino-propyl}sulphanyl)phenyl]-2-hydroxy-2-methyl-3,3,3-trifluoropropanamide | (CDCl$_3$) 1.76(s, 3H), 1.78–1.83 (m, 2H), 2.24(s, 6H), 2.43(t, 2H), 2.93(t, 2H), 7.24(d, 1H), 7.36(s, 1H), 8.30(d, 1H), 9.25(s, 1H) | 383 | Meth 28 |
| 405[1] | (R)-N-[2-Chloro-4-(3-t-butoxycarbonylamino-propylsulphanyl)phenyl]-2-hydroxy-2-methyl-3,3,3-trifluoropropanamide | (CDCl$_3$): 1.44(s, 9H), 1.76(s, 3H), 1.81(t, 2H), 2.92(t, 2H), 3.20–3.26(m, 2H), 3.97(s, 1H), 4.60(s, 1H), 7.23–7.28(m, 1H), 7.36(s, 1H), 8.28(d, 1H), 8.86(s, 1H) | 455 | Meth 28 and Meth 20 |
| 406[1] | (R)-N-{2-Chloro-4-(3-acetamidopropyl-sulphanyl)phenyl}-2-hydroxy-2-methyl-3,3,3-trifluoropropanamide | (CDCl$_3$): 1.75(s, 3H), 1.83(t, 2H), 2.05(s, 3H), 2.91(t, 2H), 3.33–3.4 (m, 2H), 5.63(brs, 1H), 7.25–7.27 (m, 1H), 7.36(s, 1H), 8.3(d, 1H), 9.06(s, 1H) | 397 | Meth 28 and Meth 21 |
| 407[1] | (R)-N-{2-Chloro-4-(2-propenylsulphanyl)phenyl}-2-hydroxy-2-methyl-3,3,3-trifluoropropanamide | (CDCl$_3$) 1.76(s, 3H), 3.52–3.60 (m, 2H), 5.07–5.15(m, 2H), 5.78–6.10(m, 1H), 7.27–7.28(m, 1H), 7.40(s, 1H), 8.27(d, 1H), 8.78(s, 1H) | 338 | Meth 28 and allyl bromide |
| 408[2] | (R)-N-{2-Chloro-4-(2-hydroxybutylsulphanyl) phenyl}-2-hydroxy-2-methyl-3,3,3-trifluoropropanamide | (CDCl$_3$) 0.97(t, 3H), 1.47-(CDCl$_3$) 1.62(m, 3H), 1.74(s, 3H), 2.25(d, 1H), 2.28–2.29(m, 1H), 3.09–3.14 (m, 1H), 7.29–7.34(m, 1H), 7.44 (s, 1H), 7.44(s, 1H), 8.30(d, 1H), 8.86(s, 1H) | 370 | Meth 28 |
| 409[3] | (R)-N-{2-Chloro-4-(2-hydroxy-2-methylpropyl-sulphanyl)phenyl}-2-hydroxy-2-methyl-3,3,3-trifluoropropanamide | (CDCl$_3$) 1.31(s, 6H), 1.71(s, 3H), 3.09(s, 2H), 7.32–7.36(m, 1H), 7.46(s, 1H), 8.23(d, 1H), 8.81(s, 1H) | 370 | Meth 28 |
| 410[1,4] | (R)-N-{2-Chloro-4-propylsulphanylphenyl}-2-hydroxy-2-methyl-3,3,3-trifluoropropanamide | (CDCl$_3$) 1.02(t, 3H), 1.62–1.69 (m, 2H), 1.75(s, 3H), 2.87(t, 2H), 3.66(s, 1H), 7.24–7.27(m, 1H), 7.36(s, 1H), 8.25(d, 1H), 8.77(s, 1H) | 340 | Meth 28 |
| 411[1,4] | (R)-N-{2-Chloro-4-(n-butylsulphanyl)phenyl}-2-hydroxy-2-methyl-3,3,3-trifluoropropanamide | (CDCl$_3$) 0.92(t, 3H), 1.38–1.50 (m, 2H), 1.59–1.66(m, 2H), 1.74 (s, 3H), 2.89(t, 2H), 3.65(s, 1H), 7.23–7.26(m, 1H), 7.36(s, 1H), 8.25(d, 1H), 8.76(s, 1H) | 354 | Meth 28 |
| 412[5] | (R)-N-[2-Ethynyl-4-(4-mesylphenylsulphonyl) phenyl]-2-hydroxy-2-methyl-3,3,3-trifluoropropanamide | (CDCl$_3$ + 1 drop DMSO-$\delta_6$) 1.84(s, 3H), 3.05(s, 3H), 3.64(s, 1H), 6.60(s, 1H), 7.92(m, 1H), 8.05(d, 1H), 8.09–8.13(m, 4H), 8.68(d, 1H), 9.91(s, 1H) | 474 | Meth 57 |

[1]The alkylation reaction was carried out with heating under reflux and with addition of sodium iodide.
[2]For alkylation: heated under reflux and 1,2-epoxybutane replaced an alkyl halide.
[3]For alkylation: heated under reflux and 1,2-epoxy-2-methylpropane was used.
[4]The thiol intermediate was isolated and purified; sodium methoxide was used as base for the subsequent alkylation step.
[5]Only the desilylation step was carried out.

aqueous hydrochloric acid (2M, 30 ml) and brine (30 ml) then dried. Volatile material was removed by evaporation and the residue was purified on a silica gel Mega Bond Elut column eluting with 10–30% ethyl acetate/iso-hexane to give the title compound (0.199 g) as a pale yellow solid. NMR (CDCl$_3$): 2.50 (s, 3H), 5.12 (s, 1H), 6.98 (d, 1H), 7.05 (d, 1H), 7.23 (d, 2H), 7.35 (d, 2H), 8.05–8.08 (m, 1H); MS (ESP$^-$): 458,

EXAMPLE 414
(R)-N-{2-Chloro-4-(2-propenylsulphonyl)phenyl}-2-hydroxy-2-methyl-3,3,3-trifluoropropanamide A solution of Oxone (1.44 g) in water (15 ml) was added to a solution of (R)-N-{2-chloro-4-(2-propenylsulphanyl)phenyl}-2-hydroxy-2-methyl-3,3,3-trifluoropropanamide (Example 407) (0.389 g) in methanol (15 ml). The mixture was stirred for 1.5 hours. Water (50 ml) was added and the mixture extracted into ethyl acetate (100 ml) and dried. Volatile material was removed by evaporation and the residue purified on a silica gel Mega Bond Elut column eluting with 20–30% ethyl acetate/iso-hexane to give the title compound as a foam (0.180 g). NMR: 1.61 (s, 3H), 4.18 (d, 2H), 5.18–5.32 (m, 2H), 5.61–5.75 (m, 1H), 7.82–7.85 (m, 1H), 7.98 (s, 1H), 8.01 (s, 1H), 8.33 (d, 1H), 9.91 (s, 1H); MS (ESP$^-$): 370.

EXAMPLE 415
(R)-N-[2-Chloro-4-(2-hydroxyethylsulphanyl)phenyl]-2-hydroxy-2-methyl-3,3,3-trifluoropropanamide A solution of (R)-N-[2-chloro-4-iodophenyl]-2-hydroxy-2-methyl-3,3,3-trifluoropropanamide (Example 197) (0.8 g) in pyridine (1 ml) was added to a deoxygenated solution of 2-mercaptoethanol (0.18 ml), sodium methoxide (0.14 g) and copper (I) chloride (0.2 g) in quinoline (2 ml) and pyridine (2 ml). The mixture was heated to 190° C. under argon for 18 hours. The mixture was allowed to cool to room temperature then dissolved in ethyl acetate (100 ml), washed with dilute aqueous hydrochloric acid (2×50 ml) and brine (2×50 ml) then dried. Volatile material was removed by evaporation and the residue was purified by chromatography on a silica gel Mega Bond Elut column eluting with 10–60% ethyl acetate/iso-hexane to give the title compound as a gum. NMR (CDCl$_3$): 1.76 (s, 3H), 3.10 (t, 2H), 3.75–80 (m, 2H), 7.31–7.34 (m, 1H), 7.47 (s, 1H), 8.31 (d, 1H), 8.86 (s, 1H); MS (ESP$^-$): 342.

EXAMPLES 416–427

Following the procedure of Example 415 and using the appropriate starting materials the following compounds were prepared.

| Ex | Compound | NMR (CDCl$_3$) | MS |
|---|---|---|---|
| 416 | (R)-N-[2-Chloro-4-(cyclopropyl-methylsulphanyl)phenyl]-2-hydroxy-2-methyl-3,3,3-trifluoropropanamide | 0.10–0.13(m, 1H), 0.5–0.55(m, 1H), 0.81–0.89(m, 1H), 1.76(s, 3H), 2.84 (d, 2H), 7.26–7.30(m, 1H), 7.42(s, 1H), 8.26(d, 1H), 8.78(s, 1H) | 352 |
| 417 | (R)-N-[2-Chloro-4-(cyclohexyl-sulphanyl)phenyl]-2-hydroxy-2-methyl-3,3,3-trifluoropropanamide | 1.23–1.31(m, 6H), 1.57(s, 3H), 1.73–1.76(m, 4H), 3.02–3.10(m, 1H), 7.31–7.34(m, 1H), 7.44(s, 1H), 8.28 (d, 1H), 8.81(s, 1H) | 380 |
| 418 | (R)-N-[2-Chloro-4-(thien-2-ylmethylsulphanyl)phenyl]-2-hydroxy-2-methyl-3,3,3-trifluoropropanamide | 1.77(s, 3H), 3.66(s, 1H), 4.27(s, 2H), 6.83–6.90(m, 2H), 7.16–7.19(d, 1H), 7.17(d, 1H), 7.38(s, 1H), 8.28 (d, 1H), 8.86(brs, 1H) | 394 |
| 419 | (R)-N-[2-Chloro-4-(N,N-dimethyl-aminoethylsulphanyl)phenyl]-2-hydroxy-2-methyl-3,3,3-trifluoropropanamide. | 1.73(s, 3H), 2.26(s, 6H), 2.55(t, 2H), 3.02(t, 2H), 7.26–7.28(m, 1H) 7.40(s, 1H), 8.31(d, 1H), 8.07(s, 1H) | 369 |
| 420 | (R)-N-[2-Chloro-4-(N-methyl-carbamoylmethylsulphanyl)phenyl]-2-hydroxy-2-methyl-3,3,3-trifluoropropanamide | 1.73(s, 3H), 2.84(d, 3H), 3.6(s, 2H), 6.65(brs, 1H), 7.21–7.26(m, 1H), 7.34(s, 1H), 8.34(d, 1H), 8.92(s, 1H) | 369 |
| 421 | (R)-N-[2-Chloro-4-(iso-propyl-sulphanyl)phenyl]-2-hydroxy-2-methyl-3,3,3-trifluoropropanamide | 1.23–1.30(m, 6H), 1.73(s, 3H), 3.28–3.36(m, 1H), 7.31–7.34(m, 1H), 7.44 (s, 1H), 7.78(d, 1H), 8.84(brs, 1H) | 340 |
| 422 | (R)-N-[2-Chloro-4-(cyclopentyl-sulphanyl)phenyl]-2-hydroxy-2-methyl-3,3,3-trifluoropropanamide | 1.52–1.63(m, 7H), 1.71–1.78(m, 4H), 3.52–3.57(m, 1H), 7.26–7.28(m, 1H), 7.2(s, 1H), 8.26(d, 1H), 8.78(s, 1H) | 366 |
| 423 | (R)-N-[2-Chloro-4-(iso-butyl-sulphanyl)phenyl]-2-hydroxy-2-methyl-3,3,3-trifluoropropanamide | 1.02(s, 6H), 1.73(s, 3H), 1.81–1.89 (m, 1H), 2.8(d, 2H), 3.67(s, 1H), 7.26–7.31(m, 1H), 7.36(s, 1H), 8.26 (d, 1H), 8.76(s, 1H) | 354 |
| 424[1] | (R)-N-[2-Fluoro-4-ethylsulphanyl-phenyl]-2-hydroxy-2-methyl-3,3,3-trifluoropropanamide | 1.20(t, 3H), 1.65(s, 3H), 2.81–2.89 (q, 2H), 3.60(s, 1H), 7.00–7.05(m, 2H), 8.13(t, 1H), 8.40(brs, 1H) | 310 |
| 425 | (R)-N-[2-Chloro-4-(2,3-dihydroxypropyl)sulphanylphenyl]-2-hydroxy-2-methyl-3,3,3-trifluoropropanamide | 1.71(s, 3H), 3.00–3.05(m, 2H), 3.52–3.60(m, 1H), 3.68–3.78(m, 2H), 6.65 (s, 1H), 7.28–7.31(m, 1H), 7.44(s, 1H), 8.34(d, 1H), 9.42(s, 1H) | 372 |
| 426 | (R)-N-[2-Chloro-4-(2-hydroxypropyl)sulphanylphenyl]-2-hydroxy-2-methyl-3,3,3-trifluoropropanamide | 1.28(d, 3H), 1.76(s, 3H), 2.81–2.92 (m, 1H), 3.02–3.1(m, 1H), 3.65(s, 1H), 3.81–3.89(m, 1H), 7.34(d, 1H), 7.44(s, 1H), 8.31(d, 1H), 8.84(s, 1H) | 356 |

-continued

| Ex | Compound | NMR (CDCl₃) | MS |
|---|---|---|---|
| 427 | (R)-N-[2-Chloro-4-t-butylsulphanylphenyl]-2-hydroxy-2-methyl-3,3,3-trifluoropropanamide | 1.28(s, 9H), 1.76(s, 3H), 3.57(s, 1H), 7.44–7.47(m, 1H), 7.60(s, 1H), 8.63(d, 1H), 8.92(s, 1H) | 354 |

[1]Sodium ethanethiolate was used in place of thiol and sodium methoxide.

EXAMPLE 428

(R)-N-(2-Chloro-4-{(4-acetamidophenyloxy)sulphonyl}phenyl)-2-hydroxy-2-methyl-3,3,3-trifluoropropanamide A solution of (R)-N-{2-chloro-4-[4-chlorosulphonyl]phenyl}-2-hydroxy-2-methyl-3,3,3-trifluoropropanamide (Method 73) (366 mg, 1.00 mmol) in DCM (25 ml) was added to a stirred solution of 4-acetamidophenol (151 mg, 1.00 mmol), dimethylaminopyridine (10 mg, 0.08 mmol) and pyridine (0.45 ml, 2.0 mmol) in DCM (25 ml). The resultant mixture was stirred at ambient temperature overnight, evaporated to dryness and the residue treated with 1M aqueous hydrochloric acid (25 ml). The aqueous solution was extracted with ethyl acetate, the ethyl acetate extracts were washed with saturated sodium hydrogen carbonate solution, brine, dried and evaporated to give, as a foam, the title compound (450 mg, 0.94 mmol); NMR 1.6 (s, 3H), 2.0 (s, 3H), 7.00 (d, 2H), 7.55 (d, 2H), 7.8 (dd, 1H), 8.0 (d, 1H), 8.1 (s, 1H), 8.4 (d, 1H), 9.9 (s, 1H), 10.03 (s, 1H); MS: m/z 479.

Preparation of Starting Materials

The starting materials for the Examples above are either commercially available or are readily prepared by standard methods from known materials. For example the following reactions are illustrations but not limitations of the preparation of some of the starting materials used in the above reactions.

Methods 1–2

Following the procedure of Method 63 (see below) and using the appropriate starting material the following compounds were prepared.

| Meth | Compound | NMR | SM |
|---|---|---|---|
| 1 | 2-Fluoro-4-phenylsulphonyl-bromobenzene | (CDCl₃): 7.5–7.75(m, 6H), 7.91(d, 2H) | Meth 8 |
| 2[1] | (R)-N-[2-Chloro-4-(phenylsulphonyl)phenyl]-2-(t-butoxycarbonylamino)propanamide | (CDCl₃): 1.32–1.41(m, 12H), 4.20–4.32(m, 1H), 4.71–4.80(m, 1H), 7.40–7.54(m, 3H), 7.70–7.78(m, 3H), 7.82–7.92(m, 1H), 8.94(s, br, 1H) | Meth 48 |

[1]The crude compound was purified by passing through an ISOLUTE SPE column containing basic residues using DCM.

Methods 3–8

Following the procedure of Example 187 and using the appropriate starting materials (SM1 and SM2) the following compounds were prepared.

| Meth | Compound | SM 1 | SM 2 |
|---|---|---|---|
| 3[1] | 2-Chloro-4-(2-methoxycarbonyl)phenylsulphanylaniline | 2-chloro-4-iodoaniline | methyl thiosalicylate |
| 4 | 2-Chloro-4-(2-ethoxycarbonyl)phenylsulphanylaniline | 2-chloro-4-iodoaniline | methyl thiosalicylate |
| 5 | 2-Chloro-4-phenylsulphanyl-aniline | 2-chloro-4-iodoaniline | thiophenol |
| 6 | 2-Fluoro-4-(4-methylsulphanyl)phenylsulphanyl)aniline | 2-Fluoro-4-iodoaniline thiophenol | 4-(methylsulphanyl) |
| 7 | 2-Fluoro-4-phenylsulphanylaniline | 2-Fluoro-4-iodoaniline | thiophenol |
| 8[2] | 2-Fluoro-4-phenylsulphanyl-1-bromobenzene | 2-Fluoro-4-iodobromobenzene | thiophenol |

[1]Methanol was used as the reaction solvent in place of ethanol.
[2]Double the amount of palladium catalyst was used. Product used without purification.

Method 9

(R)-(+)-2-Hydroxy-2-methyl-3,3,3-trifluoropropanoic acid

The title compound was resolved according to the resolution method described in European Patent Application No. EP 524781 (described for the preparation of the (S)-(−) acid) except that (1S, 2R)-norephedrine was used in place of (1R, 2S)-norephedrine or (S)-(−)-1-phenylethylamine. NMR analysis of the acid in the presence of (R)-(+)-1-phenylethylamine gave an enantiomerical purity of >98%; NMR (CDCl₃): 1.27 (s, 3H) for the (R)-enantiomer, 1.21 (s, 3H) for the (S)-enantiomer.

Method 10

(4-Acetamidophenylsulphonyl)-2-chloroaniline

Iron powder (2.5 g) was added to a stirred mixture of 4-(4-acetamidophenyl-sulphonyl)-2-chloro-nitrobenzene (Method 13) (0.67 g), water (2 ml), concentrated hydrochloric acid (0.5 ml) and ethanol (10 ml). The mixture was heated under reflux for 1 hour then evaporated to near dryness and partitioned between ethyl acetate and water. The organic layer was separated, the aqueous layer was extracted with ethyl acetate (3×15 ml). The organic extracts were combined and dried. Volatile material was removed by evaporation and the residue was purified by chromatography on a silica gel Mega Bond Elut column eluting with 0–2% methanol/DCM to give the title compound (0.18 g) as a solid. NMR: 2.05 (s, 3H), 6.4 (s, 2H), 6.8 (d, 1H), 7.5 (d, 1H), 7.6 (d, 1H), 7.8 (q, 4H), 10.3 (brs, 1H); MS (ESP⁻): 323.

Methods 11–12

Following the procedure of Method 10 and using the appropriate starting material the following compounds were prepared.

| Meth | Compound | NMR | SM |
|---|---|---|---|
| 11 | 2-Bromo-4-(4-methylsulphanyl-phenylsulphanyl)aniline | (CDCl$_3$) 2.44(s, 3H), 4.2(s, 2H), 6.73(d, 1H), 7.05–7.22(m, 5H), 7.52(d, 1H) | Meth 27 |
| 12 | (R)-N-[2-Chloro-4-{4-aminophenylsulphanyl}phenyl]-2-acetoxy-2-methyl-3,3,3-trifluoropropanamide | 1.8(s, 3H), 2.2(s, 3H), 5.5(s, 2H), 6.6(d, 2H), 7.0(m, 3H), 7.2(d, 2H), 9.8(s, 1H) | Meth 18 |

Method 13
4-(4-Acetamidophenylsulphonyl)-2-chloronitrobenzene

Hydrogen peroxide (0.9 ml of a 30 wt. % solution in water) was added to a solution of 4-(4-acetamidophenylsulphanyl)-2-chloronitrobenzene (Method 14) (0.78 g) in glacial acetic acid (5 ml) and the mixture was stirred and heated at 95° C. for 75 minutes then poured into water (15 ml) and extracted with ethyl acetate (3×10 ml). The organic extracts were combined, washed with brine and then dried. Volatile material was removed by evaporation and the residue was purified by chromatography on a silica gel Mega Bond Elut column eluting with 0–50% ethyl acetate/hexane to give the title compound (0.68 g). NMR: 2.05 (s, 3H), 7.8 (d, 2H), 7.98 (d, 2H), 8.2–8.3 (m, 2H), 8.35–8.45 (m, 1H), 10.4 (brs, 1H); MS (ESP$^-$): 353.

Method 14
4-(4-Acetamidophenylsulphanyl)-2-chloronitrobenzene

A solution of 2-amino-4-(4-acetamidophenylsulphanyl)nitrobenzene (Method 15) (2.4 g) in warm glacial acetic acid (15 ml) was poured onto ice (24 ml). Concentrated hydrochloric acid (4.5 ml) was added and the mixture was stirred and cooled to <5° C. A solution of sodium nitrite (0.601 g) in water (5 ml) was added over 7 minutes and the mixture was stirred for 2 hours at 0–5° C. Aqueous sulphamic acid solution (10% w/v) was added until a negative starch iodide test was observed. In a separate flask toluene was added to a solution of cuprous chloride (0.852 g) in water (1.2 ml) and concentrated hydrochloric acid (1.3 ml) and the mixture was cooled to <0° C. The first preparation (diazonium salt) was then added to the cold cuprous chloride mixture over 5 minutes and the resultant mixture was stirred at ambient temperature for 18 hours. The organic layer was separated and the aqueous layer was extracted with toluene (3×10 ml). The organic extracts were combined, washed with water and brine then dried. Volatile material was removed by evaporation and the residue was purified by chromatography on a silica gel Mega Bond Elut column eluting with 0–15% ethyl acetate/hexane to give the title compound (0.789 g). NMR: 2.1 (s, 3H), 7.1 (dd, 1H), 7.3 (d, 1H), 7.5 (d, 2H), 7.7 (d, 2H), 7.95 (d, 1H), 10.2 (brs, 1H).

Method 15
2-Amino-4-(4-acetamidophenylsulphanyl)nitrobenzene

Sodium (0.269 g) was added to ethanol (20 ml) and the resultant solution was allowed to cool to ambient temperature and 4-acetamidothiophenol (1.94 g) was added. The mixture was stirred for 5 minutes and 5-chloro-2-nitroaniline (2 g) was added. The mixture was then heated under reflux under argon for 3 hours and allowed to cool. The resultant solid was collected by filtration, washed with ethanol then dried to give the title compound (2.46 g) as a solid. NMR: 2.05 (s, 3H), 6.3 (dd, 1H), 6.6 (s, 1H), 7.4 (brs, 2H), 7.5 (d, 2H), 7.7 (d, 2H), 7.9 (d, 1H); MS (ESP$^+$): 304 (M+H)$^+$.

Method 16
N-[2-Chloro-4-(4-acetamidophenylsulphonyl)phenyl]-2-acetoxy-2-methylpropanamide m-Chloroperoxybenzoic acid (50%, 0.735 g) was added to a solution of N-[2-chloro-4-(4-acetamidophenylsulphanyl)phenyl]-2-acetoxy-2-methylpropanamide (Method 17) (0.30 g) in DCM (10 ml) and the mixture was stirred at ambient temperature for 15 hours. Ethyl acetate (20ml) was added and the solution was washed with saturated aqueous sodium carbonate solution (10 ml) and brine then dried. Volatile material was removed by evaporation and the residue was purified by flash chromatography eluting with 50–80% ethyl acetate/hexane to give the title compound (0.29 g) as a solid. NMR (CDCl$_3$): 1.7 (s, 6H), 2.2 (2×s, 2×H), 7.5 (s, 1H), 7.7 (d, 2H), 7.8 (m, 3H), 8.0 (m, 1H), 8.6 (m, 2H); MS (ESP$^-$): 451; EA: found: C, 52.9; H, 4.4; N, 6.1%, C$_{20}$H$_{21}$ClN$_2$O$_6$S requires C, 53.0; H, 4.6; N, 6.2%.

Method 17
N-[2-Chloro-4-(4-acetamidophenylsulphanyl)phenyl]-2-acetoxy-2-methylpropanamide N-[2-Chloro-4-(4-aminophenylsulphanyl)phenyl]-2-acetoxy-2-methylpropanamide (Method 22) (0.50 g) was dissolved in DCM (10 ml) and cooled to 0–5° C. in an ice bath. Triethylamine (0.46 ml) was added followed by dropwise addition of acetyl chloride (0.1 ml) and the mixture was allowed to warm to ambient temperature over 2 hours. Ethyl acetate (20 ml) was added and the solution was washed with water (2×10 ml) and brine then dried. Volatile material was removed by evaporation and the residue was purified by flash chromatography eluting with 40–80% ethyl acetate/hexane to give the title compound (0.470 g) as a solid. NMR (CDCl$_3$): 1.8 (s, 6H), 2.2 (d, 6H), 7.2–7.3 (m, 5H), 7.5 (d, 2H), 8.3 (d, 1H), 8.4 (s, 1H); MS (ESP$^-$): 419; EA: found: C, 56.7; H, 5.0; N, 6.0%; C$_{20}$H$_{21}$ClN$_2$O$_4$S.0.4 EtOAc requires C, 56.9; H, 5.3; N, 6.1%.

Methods 18–21

Following the procedure of Method 17 and using the appropriate starting material the following compounds were prepared.

| Meth | Compound | NMR | SM |
|---|---|---|---|
| 18 | (R)-N-[2-Chloro-4-{4-nitrophenylsulphanyl}phenyl]-2-acetoxy-2-methyl-3,3,3-trifluoropropanamide | 1.8(s, 3H), 2.2(s, 3H), 7.4(t, 3H), 7.6(d, 2H), 7.8(s, 1H), 8.2(d, 2H), 9.8(s, 1H). | Ex 204 |
| 19 | (R)-N-[2-Chloro-4-{4-(2-chloroacetylamino)-phenyl sulphanyl}-phenyl]-2-acetoxy-2-methyl-3,3,3-trifluoropropanamide | 1.8(s, 3H), 2.2(s, 3H), 4.3(s, 2H), 7.1(s, 2H), 7.2(s, 1H), 7.4(d, 2H), 7.7(d, 2H), 9.9(s, 1H), 10.45(s, 1H) | Meth 12 |
| 20[1,2] | 3-(t-Butoxycarbonyl-amino)-1-bromopropane | (CDCl$_3$): 1.44(s, 9H), 2.00–2.09(m, 2H), 3.33–3.30(m, 2H), 3.42(t, 2H) | 3-amino-propyl-bromide.HBr |
| 21[2] | 3-Acetamido-1-bromopropane | (CDCl$_3$): 1.96(s, 3H), 2.01–2.1(m, 2H), 3.34–3.46(m, 4H), 5.65–5.75(brs, 1H) | 3-amino-propyl-bromide.HBr |

[1]The acylating agent was di-tert-butyl dicarbonate;
[2]An additional equivalent of triethylamine was used.

Method 22
N-[2-Chloro-4-(4-aminophenylsulphanyl)phenyl]-2-acetoxy-2-methylpropanamide Copper (I) chloride (0.90 g) was added to a mixture of N-[2-chloro-4-iodophenyl]-2-acetoxy-3- methylpropanamide (Method 23) (8.3 g), 4-aminothiophenol (1.07 ml) and potassium carbonate (9.1 g) in DMF (100 ml). The mixture was heated at 135° C. with stirring under argon for 3 hours, cooled and then filtered through diatomaceous earth. The filter was washed with ethyl acetate (3×20 ml) and the filtrates were combined and washed with water (50 ml), brine and dried. The volatile material was removed by evaporation. The crude product was purified by flash chromatography eluting with 20–40% ethyl acetate/hexane to give the title compound (4.99 g) as a solid. Mp 130–132° C.; NMR (CDCl$_3$): 1.7 (s, 6H), 2.1 (s, 3H), 3.8 (s, 2H), 6.6 (d, 2H), 7.1 (m, 2H), 7.2 (m, 2H), 8.2 (d, 1H), 8.4 (s, 1H); MS (ESP$^-$): 377.

Method 23

N-[2-Chloro-4-iodophenyl]-2-acetoxy-3-methylpropanamide

2-Chloro-4-iodoaniline (5 g) was dissolved in DCM (100 ml) and cooled to 0–5° C. in an ice bath. Pyridine (2.1 ml) was added followed by dropwise addition of 2-acetoxy-2-methylpropanoyl chloride (3.44 ml) and the mixture was allowed to warm to ambient temperature over 15 hours. The solvent was removed by evaporation and the residue was purified by flash chromatography eluting with 10–50% ethyl acetate/hexane to give the title compound (7.5 g) as a solid. Mp 156–158° C.; NMR (CDCl$_3$): 1.7 (s, 6H), 2.2 (s, 3H), 7.6 (d, 1H), 7.7 (d, 1H), 8.2 (d, 1H), 8.4 (s, 1H); MS (ESP$^-$): 380.

Method 24

Following the procedure of Method 23 and using the appropriate starting material the following compound was prepared.

| Meth | Compound | NMR | SM |
|---|---|---|---|
| 24 | (R)-N-[2-Chloro-4-nitrophenyl]-2-acetoxy-2-methyl-3,3,3-trifluoro-propanamide | 1.8(s, 3H), 2.2(s, 3H), 7.58(d, 1H), 8.26(d, 1H), 8.41(s, 1H), 10.23(s, 1H) | 2-Chloro-4-nitroaniline and Meth 49 |

Method 25

Following the procedure of Methods 23, 22, 17 and 16 and using the appropriate starting material the following compound was prepared.

| Meth | Compound |
|---|---|
| 25[1] | N-[2-Chloro-4-{4-N-(2,2-dimethylpropanamido)phenylsulphonyl}phenyl]-2-acetoxy-2-methylpropanamide |

[1]Starting material was 2-chloro-4-iodoaniline; Method 17: 2,2-dimethylpropanoyl chloride was used in place of acetyl chloride.

Method 26

N-[2-Chloro-4-{4-(N,N-dimesylamino)phenylsulphanyl}phenyl]-2-acetoxy-2-methylpropanamide N-[2-Chloro-4-(4-aminophenylsulphanyl)phenyl]-2-acetoxy-2-methylpropanamide (Method 22) (0.50 g) was dissolved in DCM (10 m) and cooled to 0–5° C. in an ice bath. Triethylamine (0.55 ml) was added followed by dropwise addition of methylsulphonyl chloride (0.11 ml) and the mixture was allowed to warm to ambient temperature over 2 hours. The solution was concentrated then the solid was dissolved in DCM (5 ml) and water (5 ml) was added. The solution was loaded onto a Varian Chem Elut column and after 3 minutes was washed through with DCM (20 ml). The DCM layer was then concentrated and the solid washed with ether and filtered to give the title compound (0.58 g) as a solid. NMR (CDCl$_3$): 1.7 (s, 6H), 2.2 (s, 3H), 3.4 (s, 6H), 7.2 (s, 4H), 7.4 (d, 1H), 7.5 (d, 1H), 8.4 (d, 1H), 8.5 (d, 1H); MS (ESP$^-$): 533; EA: found: C, 44.4; H, 4.5; N, 5.1%; C$_{20}$H$_{23}$ClN$_2$O$_7$S$_3$ requires C, 44.9; H, 4.3; N, 5.2%.

Method 27

2-Bromo-4-(4-methylsulphanylphenylsulphanyl)nitrobenzene t-Butyl nitrite (3.1 ml) was added to a slurry of copper (II) bromide (4.4 g) in acetonitrile (85 ml) at 0° C. 2-Amino-4-(4-methylsulphanylphenylsulphanyl)nitrobenzene (5.09 g), (prepared by the method described in J. Med. Chem., 1975, 18, 1164 for the preparation of 2-nitro-5-phenylsulphanylaniline but using 4-methylsulphanylthiophenol in place of thiophenol) was added portionwise over 5 minutes and the mixture was stirred a further 2 hours at 0° C., allowed to warm to ambient temperature, and stirred a further 16 hours. Volatile material was removed by evaporation and the residue was purified by flash chromatography on silica gel eluting with 10–30% ethyl acetate/hexane to give the title compound (4.5 g) as a solid. NMR (CDCl$_3$) 2.52 (s, 3H), 7.03–7.08 (m, 1H), 7.3 (d, 2H), 7.36–7.38 (m, 1H), 7.44 (d, 2H), 7.77 (d, 1H).

Method 28

(R)-N-(2-Chloro-4-(triisopropylsilylsulphanyl)phenyl]-2-hydroxy-2-methyl-3,3,3-trifluoropropanamide Triisopropylsilanethiol (2.8 ml) was added to a stirred suspension of sodium hydride (60% mineral oil dispersion, 0.53 g) in anhydrous THF (40 ml) cooled to 1° C. under argon. After 15 minutes at this temperature tetrakis(triphenylphosphine)palladium (0) (1.21 g) was added and this solution was added to (R)-N-(2-chloro-4-iodophenyl)-2-hydroxy-2-methyl-3,3,3-trifluoropropanamide (Example 197) (5.2 g) in anhydrous toluene (40 ml) and the mixture was heated to 85° C. for 2 hours. The mixture was allowed to cool to ambient temperature, ethyl acetate (200 ml) was added and the mixture was washed with brine (100 ml) and dried. Volatile material was removed by evaporation and the residue was purified on a silica gel flash column eluting with 1–20% ethyl acetate/hexane to give the title compound (6.51 g) as a gum. NMR (CDCl$_3$) 1.07–1.1 (d, 18H), 1.20–1.28 (m, 3H), 1.74 (s, 3H), 3.64 (s, 1H), 7.39–7.42 (m, 1H), 7.53 (s, 1H), 8.23 (d, 1H), 8.81 (s, 1H); MS (ESP$^-$): 454.

Method 29

2-Chloro-4-benzylnitrobenzene

Sodium borohydride (1.45 g) was added to a solution of 3-chloro-4-nitrobenzophenone (2.0 g) (prepared as described by R. B. Davis and J. D. Benigni, J. Org. Chem., 1962, 27, 1605) in ethanol and the mixture was stirred for 18 hours. Volatile material was removed by evaporation and the residue was suspended in water (100 ml) and cautiously acidified with dilute aqueous hydrochloric acid (50 ml) and stirred a further 2 hours. The reaction mixture was basified with 2M aqueous sodium hydroxide solution and extracted with DCM. The extracts were combined, dried and concentrated by evaporation to give an oil. This was dissolved in TFA (12.1 ml) with cooling with an ice bath then treated dropwise with triethylsilane (5.05 ml) and stirred overnight. The reaction mixture was poured onto aqueous sodium carbonate solution and extracted with DCM. The extracts were combined, dried and evaporated to give an oil which was purified by chromatography eluting with 20–50% ethyl acetate/hexane to give the title compound (0.60 g) as an oil. NMR (CDCl$_3$): 4.0 (s, 3H), 7.1–7.4 (m, 8H); MS (CI): 247 (M$^+$).

Method 30
2-Chloro-4-benzylaniline

A solution of 2-chloro-4-benzylnitrobenzene (Method 29) (0.60 g) in ethyl acetate was treated with 10% Pd/C (0.06 g) under argon. The mixture was then stirred under a hydrogen atmosphere for 10 hours. The mixture was filtered under argon and extracted with aqueous hydrochloric acid (50% v/v, 50 ml). The aqueous layer was separated, basified with 2M aqueous NaOH and extracted with ethyl acetate to give the title compound as an oil (0.237 g). NMR: 3.6 (s, 2H), 5.1 (brs, 2H), 6.7 (d, 1H), 6.9 (dd, 1H), 7.0 (d, 1H), 7.1–7.3 (m, 5H); MS (CI): 218 ($M^+$)

Methods 31–32

Following the procedure of Method 30 and using the appropriate starting materials the following compounds were prepared.

| Meth | Compound | NMR | MS | SM |
|---|---|---|---|---|
| 31 | 3-chloro-4-[di-(t-butyloxy-carbonyl)-amino]aniline | 1.33(s, 18H), 5.42(s, 2H), 6.48(dd, 1H), 6.62(s, 1H), 6.89(d, 1H) | 341 | Meth 45 |
| 32 | (R)-N-(2-Chloro-4-amino-phenyl)-2-acetoxy-2-methyl-3,3,3-trifluoro-propanamide | 1.78(s, 3H), 2.15(s, 3H), 5.46(brs, 2H), 6.50(d, 1H), 6.64(s, 1H), 6.80(d, 1H), 9.53(s, 1H) | 325 | Meth 24 |

Method 33
N-[2-Chloro-4-phenylsulphonylphenyl]-2-acetoxy-2-methylpropanamide

2-Chloro-4-phenylsulphanylaniline (Method 5) was acylated with 2-acetoxy-2-methylpropanoyl chloride by the procedure of Method 23 then the crude product was oxidised by the procedure of Example 114 to give the title compound (in 91% yield) as a gummy solid. NMR 1.57 (s, 6H), 2.05 (s, 3H), 7.6–7.75 (m, 4H), 7.8 (d, 1H), 7.92 (dd, 1H), 8.0 (apparent d, 2H), 8.08 (d, 1H), 9.4 (s, 1H).

Method 34
(R)-N-[2-Chloro-4-{4-ureidophenylsulphanyl}phenyl]-2-acetoxy-2-methyl-3,3,3-trifluoropropanamide Water (0.34 ml), acetic acid (0.54 ml) and sodium cyanate (0.104 g dissolved in 0.3 ml of water) were added to a solution of (R)-N-[2-chloro-4-{4-aminophenylsulphanyl}phenyl]-2-acetoxy-2-methyl-3,3,3-trifluoropropanamide (0.432 g) (Method 22) in THF (0.8 ml). The mixture was stirred for 2 hours then diluted with water (5 ml) and extracted with ethyl acetate (2×20 ml). The extracts were poured onto a Varian Chem Elut column and eluted with ethyl acetate. Volatile material was removed by evaporation and the residue was triturated with ether to give the title compound (0.31 g) as a solid. NMR: 1.8 (s, 3H), 2.2 (s, 3H), 5.9 (s, 2H), 7.1 (s, 3H), 7.4 (d, 2H), 7.5 (d, 2H). 8.8 (s, 1H), 9.9 (s, 1H); MS ($ESP^-$): 474.

Method 35

Following the procedure of Method 34 and using the appropriate starting materials the following compound was prepared.

| Meth | Compound | MS | SM |
|---|---|---|---|
| 35 | (R)-N-[2-Chloro-4-{2-ureidophenylsulphanyl}phenyl]-2-acetoxy-2-methyl-3,3,3-trifluoropropanamide | 476 $(M + H)^+$ | Meth 36 |

Methods 36–40

The indicated starting material was coupled with an appropriate thiol or halide using the method of Example 250, acylated using the procedure of Method 17 then reduced by the procedure of Method 10 to give the following compounds.

| Meth | Compound | NMR | MS | SM |
|---|---|---|---|---|
| 36 | (R)-N-[2-Chloro-4-{2-aminophenylsulphanyl}phenyl]-2-acetoxy-2-methyl-3,3,3-trifluoropropanamide | | 431 | Ex 210 |
| 37 | (R)-N-[2-Chloro-4-{3-aminophenylsulphanyl}phenyl]-2-acetoxy-2-methyl-3,3,3-trifluoropropanamide | 1.8(s, 13H), 2.2(s, 3H), 5.3(s, 2H), 6.5(t, 2H), 6.6(s, 1H), 7.0(t, 1H), 7.2(m, 3H), 9.9(s, 1H) | 431 | Ex 210 |
| 38[1] | (R)-N-[2-Fluoro-4-{4-aminophenylsulphanyl}phenyl]-2-acetoxy-2-methyl-3,3,3-trifluoropropanamide | 1.8(s, 3H), 2.2(s, 3H), 5.6(s, 2H), 6.6(d, 2H), 6.8(m, 2H), 7.1(t, 1H), 7.2(d, 2H), 9.9(s, 1H) | 415 | 2-fluoro-4-iodoaniline |
| 39[1,2] | (R)-N-[2-Fluoro-4-{4-nitrophenylsulphanyl}phenyl]-2-acetoxy-2-methyl-3,3,3-trifluoropropanamide | 1.8(s, 3H), 2.2(s, 3H), 7.4(m, 4H), 7.6(d, 1H), 8.2(d, 2H), 10.12 (s, 1H) | 445 | 2-fluoro-4-iodoaniline |
| 40[2,3] | (R)-2,3,4,5-$H_4$-3-[2-Chloro-4-(4-aminophenylsulphanyl)phenyl]-2,4-dioxo-5-methyl-5-trifluoromethyloxazole | ($CDCl_3$) 1.9(s, 3H), 3.9 (s, 2H), 6.7(d, 2H), 7.1 (m, 3H), 7.4(d, 2H) | 415 | Ex 197 |

[1] Acylation was by the method of Example 197 using (S)-2-acetoxy-2-methyl-3,3,3-trifluoromethylpropanoyl chloride (Method 49)
[2] The reduction step was omitted
[3] Thiol coupling was by procedure of Method 22 using 4-mercaptoaniline and acylation was with allylchloroformate

Method 41
(R)-N-[2-Chloro-4-{4-(2-morpholinoacetylamino)phenylsulphanyl}phenyl]-2-acetoxy-2-methyl-3,3,3-trifluoropropanamide Following the procedure of Example 353 except that morpholine was used in place of aqueous dimethylamine, the title compound was obtained (0.25 g) as a foam. NMR: 1.8 (s, 3H), 2.2 (s, 3H), 3.1 (s, 2H), 3.3 (s, 4H), 3.6 (m, 4H), 7.1 (s, 2H), 7.2 (s, 1H), 7.4 (d, 2H), 7.7 (d, 2H), 9.9 (s, 2H); MS (ESP$^-$): 558.

Method 42
(R)-2,3,4.5-H$_4$-3-{2-Chloro-4-[4-(3-ethylureido)phenylsulphanyl]phenyl}-2,4-dioxo-5-methyl-5-trifluoromethyloxazole Ethyl isocyanate (0.062 ml) was added to a solution of (R)-2,3,4,5-H$_4$-3-[2-chloro-4-(4-aminophenylsulphanyl)phenyl]-2,4-dioxo-5-methyl-5-trifluoromethyloxazole (Method 40) (0.3 g) in anhydrous ether (0.5 ml) and THF (2 ml) and the mixture was stirred for 24 hr. Volatile material was removed by evaporation and the residue was purified by chromatography on a silica gel Mega Bond Elut column eluting with eluting with 5–60% ethyl acetate/hexane to give the title compound (0.29 g) as a gummy solid. NMR: 1.8 (q, 2H), 2.0 (s, 3H), 3.1 (m, 3H), 6.1 (t, 1H), 7.2 (d, 2H), 7.5 (d, 2H), 7.6 (d, 2H), 7.6 (d, 1H), 8.7 (s, 1H); MS (ESP$^-$): 486.

Methods 43–44
Following the procedure of Method 42 and using the appropriate starting materials the following compounds were prepared.

| Meth | Compound | NMR | MS | SM |
|---|---|---|---|---|
| 43 | (R)-N-[2-Chloro-4-{4-(3-t-butyl-ureido)phenyl-sulphanyl}-phenyl]-2-acetoxy-2-methyl-3,3,3-trifluoro-propanamide | 1.3(s, 9H), 1.8(s, 3H), 2.2(s, 3H), 6.1(s, 1H), 7.1(s, 3H), 7.4(d, 2H), 7.5(d, 2H), 8.5(s, 1H), 9.9(s, 1H) | 530 | Meth 12 |
| 44 | (R)-N-[2-Chloro-4-{4-(3-phenyl-ureido)phenyl-sulphanyl}phenyl]-2-acetoxy-2-methyl-3,3,3-trifluoro-propanamide | 1.8(s, 3H), 2.2(s, 3H), 7.0(t, 1H), 7.1(d, 3H), 7.3(t, 2H), 7.4(m, 4H), 7.6(d, 2H), 8.7(s, 1H), 8.9(s, 1H), 9.9(s, 1H) | 550 | Meth 12 |

Method 45
N,N-di-(t-Butyloxycarbonyl)-2-chloro-4-nitroaniline

2-Chloro-4-nitroaniline (1.726 g) was added to an ice-cooled solution of di-t-butyl dicarbonate (2.401 g) in THF (50 ml). The mixture was allowed to warm to room temperature. 4-Dimethylaminopyridine (0.01 g) was added and the solution was stirred for a further 19 hours then heated at 60° C. for 26 hours. Volatile material was removed by evaporation and the residue was partitioned between water (100 ml) and DCM (200 ml). The organic phase was washed with brine then dried and reconcentrated. The residue was purified by chromatography on silica to give the title compound (1.261 g) as a solid. NMR: 1.35 (s, 18H), 7.78 (d, 1H), 8.22 (dd, 1H), 8.42 (s, 1H); MS: 372 (M$^+$).

Method 46
3-chloro-4-[di-(t-butyloxy-carbonyl)amino]-1-(2-nitroanilino)phenyl A mixture of 1,1'-bis(diphenylphosphino)ferrocene (0.1 g) and palladium (II) acetate (0.028 g) in toluene (4 ml) was stirred at 100° C. under Argon for one hour. This was added to a mixture of dried caesium carbonate (0.912 g), 3-chloro-4-[di-(t-butyloxy-carbonyl)amino]aniline (Method 31) (0.822 g) and 2-bromo-1-nitrobenzene (0.404 g) in toluene (7 ml). The mixture was stirred for 23 hours at 100° C. under argon then cooled, filtered and concentrated by evaporation. The residue was dissolved in ethyl acetate (75 ml), washed with 1M aqueous hydrochloric acid (2×5 ml), water (25 ml) and brine (25 ml) then dried. Volatile material was removed by evaporation and the residue was purified by chromatography on a silica gel Mega Bond Elut column eluting with 10% ethyl acetate/hexane to give the title compound (0.889 g) as a gum. NMR: 1.40 (s, 18H), 7.00 (t, 1H), 7.27 (m, 2H). 7.36 (d, 1H), 7.45 (s, 1H), 7.58 (t, 1H), 8.10 (d, 1H), 9.28 (s, 1H); MS (ESP$^-$): 462.

Method 47
2-chloro-4-(2-nitroanilino)aniline

TFA (3 ml) was added to a solution of 3-chloro-4-[di-(t-butyloxy-carbonyl)amino]-1-(2-nitroanilino)phenyl (Method 46) (0.88 g) in DCM (15 ml). After 2 hours the solution was evaporated to dryness. The residue was dissolved in ethyl acetate (100 ml), washed with 1M aqueous sodium hydroxide (50 ml), water (50 ml) and brine (50 ml) then dried and reconcentrated to give the title compound (0.45 g) as a solid; MS (ESP$^+$): 264 (M+H)$^+$.

Method 48
(R)-N-[2-Chloro-4-(phenylsulphanyl)phenyl]-2-(t-butoxycarbonylamino)propanamide
(Based on the procedure of Villeneuve, G. B. et al., Tetrahedron Letters (1997), 38 (37), 6489.)

Triphenylphosphine (0.0.612 g) was added to a cooled (−78° C.) solution of hexachloroacetone (0.18 ml) and N-t-butyloxycarbonyl-2-methylalanine (0.441 g) in dry DCM (15 ml) under argon. The resulting mixture was stirred at low temperature for 20 minutes. Then 2-chloro-4-(phenylsulphanyl)aniline (0.5 g) (Method 5) and dry triethylamine (0.33 ml) were added. The resulting mixture was slowly warmed to room temperature, under argon, before being stirred for 1 hour at room temperature. Saturated aqueous ammonium chloride solution (15 ml) was added and the mixture was extracted with DCM (2×50 ml). The organic extracts were combined, washed with brine and dried. Volatile material was removed by evaporation and the residue was purified by chromatography on a silica gel column eluting with 2% ethyl acetate/DCM to give the title compound. NMR (CDCl$_3$): 1.40–1.45 (m, 12H), 4.29–4.40 (m, 1H), 4.86–4.95 (m, 1H), 7.20–7.40 (m, 7H), 8.30–8.38 (m, 1H), 8.64 (brs, 1H); MS (ESP$^-$): 405.

Method 49
(S)-2-Acetoxy-2-methyl-3,3,3-trifluoropropanoyl chloride

Acetyl chloride (11.7 ml) was added dropwise to a stirred solution of (R)-2-hydroxy-2-methyl-3,3,3-trifluoropropanoic acid (10 g) (Method 9) in toluene (100 ml) cooled in an ice bath. The mixture was then heated to 80° C. and the suspension dissolved to give a clear solution. After 2 hours the reaction mixture was cooled and then concentrated to give an oil. This oil was then redissolved in DCM (140 ml) and DMF (4 drops) was added followed by oxalyl chloride (6 ml). The solution bubbled vigorously and the reaction mixture was left to stir for 15 hours. The resultant solution of the title compound was used directly without further purification.

Method 50
(R)-N-(2-Chloro-4-{3-t-butoxy-2-hydroxypropylamino}phenyl)-2-acetoxy-2-methyl-3,3,3-trifluoropropanamide t-Butyl glycidyl ether (0.19 ml) and copper(II) trifluoromethanesulphonate (0.018 g) were added to a solution of (R)-N-(2-chloro-4-aminophenyl)-2-acetoxy-2-methyl-3,3, 3-trifluoropropanamide (0.325 g) (Method 32) in diethyl ether (5 ml). The mixture was stirred for 40 hours then volatile material was removed by evaporation and the residue was purified by chromatography to give the title compound (0.141 g) as a foam; MS (ESP$^-$): 453.

Method 51

3,4-Difluorobenzenethiol

A solution of triphenylphosphine (37.0 g) and DMF (2 ml) in DCM (100 ml) was maintained at 20° C. with an ice bath during addition of 3,4-difluorobenzenesulphonyl chloride (10 g). The mixture was stirred at room temperature for 2 hours then aqueous hydrochloric acid (50 ml of a 1M solution) was added. The mixture was stirred for a further 1 hour. The organic layer was separated, dried and the solvent removed by evaporation to give the title compound as an oil which was used without purification.

Method 52

2-(4-Triisopropylsilylsulphanylphenyl)pyrimidine

Tetrakis(triphenylphosphine)palladium(0) (0.28 g) was added to a solution of 2-(4-bromophenyl)pyrimidine (1.751 g) (prepared as described in U.S. patent application Ser. No. 96-692,869 (CA 129:136175)) in toluene (40 ml) and the mixture was heated at 80° C. under argon for one hour. Trisopropylsilanethiol (2.14 ml) was added dropwise to a stirred suspension of sodium hydride (0.4 g of a 60% dispersion in oil) in dry THF (20 ml) cooled with ice/water. The cooling bath was removed and the mixture was stirred for 10 minutes to give a clear solution. This solution was added to the reagents in toluene and the mixture was stirred under reflux for 16 hours then cooled. Water (50 ml) was added and the mixture was extracted with ethyl acetate (3×50 ml). The extracts were combined, washed with brine (100 ml) and dried. Volatile material was removed by evaporation and the residue was purified by chromatography eluting with 20% ethyl acetate/hexane to give the title compound (1.49 g) as a solid; NMR (at 343K): 0.86–1.07 (m, 21H), 7.4 (t, 1H), 7.7 (m, 2H), 8.39 (m, 2H), 8.87 (m, 2H); MS (EI): 344 (M$^+$).

Method 53

6-Iodoquinazolinedione

A mixture of 2-amino-5-iodobenzoic acid (3.5 g) and urea (1.56 g) in NMP (15 ml) was heated at 160° C. for 6 hours then cooled. Water (200 ml) was added and the resultant precipitate was collected, washed with water and dried to give the title compound (3.35 g) as a solid. MS (CI$^+$): 289 (M+H)$^+$.

Method 54

1,3-Dimethyl-6-iodoquinazolinedione

Sodium hydride (0.24 g of a 60% dispersion in oil) was added portionwise to a stirred solution of 6-iodoquinazolinedione (0.58 g) (Method 53) and iodomethane (0.63 ml) in DMF (10 ml). The mixture was stirred for 1 hour then added cautiously to saturated aqueous ammonium chloride solution (200 ml). Extraction with ethyl acetate followed by recrystallization from ethanol plus a little chloroform gave the title compound (0.48 g) as a solid. MS (CI$^+$): 317 (M+H)$^+$.

Method 55

N-[2-Fluoro-4-(4-methylsulphanylphenylsulphanyl)phenyl]-2-t-butyldimethylsilyloxy-2-trifluoromethyl-3,3,3-trifluoropropanamide To a stirred solution of 2-t-butyldimethylsilyloxy-2-trifluoromethyl-3,3,3-trifluoropropanoic acid, t-butyldimethylsilyl ester (Method 56) (1.05 g) in DCM (10 ml) was added DMF (2 drops) and oxalyl chloride (0.23 ml). The reaction mixture was stirred for 17 hours and was then added to a solution of 2-fluoro-4-(4-methylsulphanylphenylsulphanyl) aniline (Method 6) (0.63 g) in DCM (5 ml) and pyridine (0.22 ml). The reaction mixture was stirred at ambient temperature for 48 hours, evaporated under reduced pressure and the residue purified by chromatography on a silica gel Mega Bond Elut column eluting with 5–20% ethyl acetate/iso-hexane to give the title compound (0.278 g) as a yellow gum. NMR (CDCl$_3$): 0.29 (s, 6H), 0.98 (s, 9H), 2.48 (s, 3H), 6.96–7.0 (m, 1H), 7.06 (d, 1H), 7.2 (d, 2H), 7.31 (d, 2H), 8.23 (t, 1H), 8.62 (brs, 1H).

Method 56

2-t-Butyldimethylsilyloxy-2-trifluoromethyl-3,3,3-trifluoropropanoic acid, t-butyldimethylsilyl ester A stirred solution of 2-hydroxy-2-trifluoromethyl-3,3,3-trifluoropropanoic acid (2.26 g) in anhydrous DMF (11 ml) under argon was treated with t-butyldimethylsilyl chloride (3.37 g) followed by imidazole (3.02 g). The reaction mixture was stirred for 17 hours then extracted with iso-hexane (3×100 ml) and the organic phase washed with aqueous sodium hydrogen carbonate (2×200 ml) and dried. Volatile material was removed by evaporation to give the title compound (3.09 g) as an oil. NMR (CDCl$_3$): 0.01 (s, 6H), 0.87 (s, 9H); MS (EI+) 383 (M–C$_4$H$_9$).

Method 57

(R)-N-[2-(2-Trimethylsilylethynyl)-4-(4-mesylphenylsulphonyl)phenyl]-2-hydroxy-2-methyl-3,3,3-trifluoropropanamide Bis(triphenylphosphine)palladium(II) chloride (0.01 g), triphenylphosphine (0.0038 g), trimethylsilylacetylene (0.17 ml), triethylamine (0.16 ml) and copper(I) iodide (0.0013 g) were added to a solution of (R)-N-[2-bromo-4-(4-mesylphenylsulphonyl)phenyl]-2-hydroxy-2-methyl-3,3,3-trifluoropropanamide (Example 140) (0.311 g) in anhydrous THF (10 ml) under argon. The mixture was heated at 50° C. for 3 hours then more bis(triphenylphosphine) palladium(II) chloride (0.01 g) and trimethylsilylacetylene (0.17 ml) were added and heating was continued for a further 3 hours. The reaction mixture was allowed to cool, ethyl acetate (50 ml) was added and the mixture was filtered through a pad of diatomaceous earth which was washed with ethyl acetate (3×20 ml). The filtrates were combined and volatile material was removed by evaporation. The residue was purified by chromatography eluting with 10–40% ethyl acetate/iso-hexane to give the title compound (in 89% yield) as a solid. NMR (CDCl$_3$): 0.29 (s, 9H), 1.74 (s, 3H), 3.05 (s, 3H), 3.69 (s, 1H), 7.88–7.92 (m, 1H), 8.02 (d, 1H), 8.05–8.13 (m, 4H), 8.61 (d, 1H), 9.46 (s, 1H); MS (ESP$^-$): 546.

Method 58

5-Iodo-2H-benzimidazol-2-one

A mixture of iodine monochloride and 2H-benzimidazole-2-one (0.67 g) (Method 59) in glacial acetic acid (8 ml) was heated to 80° C. for 1 hour then cooled. The mixture was partitioned between saturated aqueous sodium sulphite solution and DCM. The organic layer was evaporated to dryness then redissolved in ethyl acetate. The aqueous layer was extracted with ethyl acetate then all ethyl acetate extracts were combined and washed with saturated aqueous sodium hydrogen carbonate solution, water and brine. The organic extracts were passed through a Varian Chem Elut column and washed through with ethyl acetate. Volatile material was removed by evaporation to give the title compound (0.36 g) as a solid which was used without further purification. MS (ESP$^+$): 261 (M+H)$^+$.

Method 59
2H-Benzimidazol-2-one

A solution of phenylene diamine 6.48 g in dry THF (150 ml) was cooled to 5° C. A suspension of 1,1-carbonyldiimidazole (10.7 g) in THF (100 ml) was added to this solution over 15 minutes keeping the temperature below 10° C. The mixture was stirred for 16 hours and the resultant solid was collected and dried to give the title compound (4.5 g); NMR: 6.9 (s, 4H), 10.5 (s, 2H); MS (ESP$^+$): 135 (M+H)$^+$.

Methods 60–62

Following the procedure of Example 197 and using the appropriate starting material the following compounds were prepared.

| Meth | Compound | NMR | MS | SM |
|---|---|---|---|---|
| 60 | (R)-N-(2-Chloro-4-nitrophenyl)-2-hydroxy-2-methyl-3,3,3-trifluoropropanamide | 1.64(s, 3H), 8.13(s, 1H), 8.28(d, 1H), 8.39(d, 1H), 8.45(s, 1H), 10.0(s, 1H) | 311 | 2-Chloro-4-nitroaniline |
| 61 | (R)-N-(2-Methoxy-4-nitrophenyl)-2-hydroxy-2-methyl-3,3,3-trifluoropropanamide | (CDCl$_3$) 1.75(s, 3H), 4.07 (s, 3H), 7.72–7.75(m, 1H), 7.88–7.97(m, 1H), 8.50–8.58(m, 1H), 9.27(brs, 1H) | 307 | 2-Methoxy-4-nitroaniline |
| 62 | (R)-N-(2-Methyl-4-nitrophenyl)-2-hydroxy-2-methyl-3,3,3-trifluoropropanamide | (CDCl$_3$) 1.77(s, 3H), 2.39 (s, 3H), 3.5(s, 1H), 8.09–8.15(m, 2H), 8.30–8.38(m, 1H), 8.65(brs, 1H) | 291 | 2-Methyl-4-nitroaniline |

Method 63
(R)-N-[2-Chloro-4-(2-fluorophenylsulphonyl)phenyl]-2-hydroxy-2-methyl-3,3,3-trifluoropropanamide m-Chloroperoxybenzoic acid (55%, 2.39 g) was added to a solution of (R)-N-[2-chloro-4-(2-fluorophenylsulphanyl)phenyl]-2-hydroxy-2-methyl-3,3,3-trifluoropropanamide (Example 187) (0.906 g) in DCM (60 ml) and the mixture was stirred at ambient temperature for 6 hours. The mixture was then washed with saturated aqueous sodium hydrogen carbonate solution (3×100 ml), water (100 ml) and brine then dried. Volatile material was removed by evaporation and the residue was triturated with hexane to give the title compound (0.808 g) as a solid. Mp 90–92° C.; NMR (CDCl$_3$): 1.75 (s, 3H), 3.65 (brs, 1H), 7.15 (t, 1H), 7.35 (t, 1H), 7.60 (m, 1H), 7.95 (d, 1H), 8.10 (m, 2H), 8.60 (d, 1H), 9.30 (brs, 1H); MS (ESP$^-$): 424.

Methods 64–66

Following the procedure of Method 63 and using the appropriate starting material the following compounds were prepared.

| Meth | Compound | NMR | SM |
|---|---|---|---|
| 64 | (R)-N-[2-Fluoro-4-{2-fluoro-phenylsulphonyl}phenyl]-2-hydroxy-2-methyl-3,3,3-trifluoropropanamide | 1.59(s, 3H), 7.38–7.55(m, 2H), 7.7–7.9(m, 4H), 8.05(q, 2H), 9.85(brs, 1H) | Ex 195 |
| 65 | (R)-N-[2-Fluoro-4-(4-nitrophenyl-sulphonyl)phenyl]-2-hydroxy-2-methyl-3,3,3-trifluoropropanamide | 1.58(s, 3H), 7.75(s, 1H), 7.87 (dd, 1H), 8.0(dd, 1H), 8.08(d, 1H), 8.25(d, 2H), 8.4(d, 2H), 9.9(brs, 1H) | Ex 176 |
| 66 | (R)-N-[2-Chloro-4-(3,4-difluorophenylsulphonyl)phenyl]-2-hydroxy-2-methyl-3,3,3-trifluoropropanamide | (CDCl$_3$) 1.75(s, 3H), 7.25–7.35 (m, 1H), 7.4(t, 1H), 7.5–7.6(m, 1H), 7.65–7.9(m, 2H), 8.0(m, 1H), 8.1(m, 1H), 8.6(d, 1H), 9.3(brs, 1H) | Ex 276 |

Methods 67–68

Following the procedure of Method 16 and using the appropriate starting material the following compounds were prepared.

| Meth | Compound | NMR | SM |
|---|---|---|---|
| 67 | (R)-N-[2-Chloro-4-{2-nitrophenyl-sulphonyl}phenyl]-2-hydroxy-2-methyl-3,3,3-trifluoropropanamide | 1.6(s, 3H), 8.0(m, 5H), 8.1(s, 1H), 8.4(m, 2H), 9.9(s, 1H) | Ex 264 |
| 68 | (R)-N-[2-Chloro-4-{3-nitrophenyl-sulphonyl}phenyl]-2-hydroxy-2-methyl-3,3,3-trifluoropropanamide | (CDCl$_3$) 2.75(s, 3H), 3.55(s, 1H), 7.75(t, 1H), 7.9(dd, 1H), 8.1(s, 1H), 8.25(d, 1H), 8.45(d, 1H), 8.7 (d, 1H), 8.75(s, 1H), 9.3(brs, 1H) | Ex 331 |

Method 69
(R)-N-[2-Chloro-4-(4-fluorophenylsulphonyl)phenyl]-2-hydroxy-2-methyl-3,3,3-trifluoropropanamide Hydrogen peroxide (0.3 ml of a 30 wt. % solution in water) was added to a solution of (R)-N-[2-chloro-4-(4-fluorophenylsulphanyl)phenyl]-2-hydroxy-2-methyl-3,3,3-trifluoropropanamide (Example 188) (0.283 g) in glacial acetic acid (1.0 ml) and the mixture was stirred and heated at 100° C. for 80 minutes then allowed to cool. Ethyl acetate (40 ml) was added and the solution was washed with water (20 ml), saturated aqueous sodium hydrogen carbonate solution (20 ml) and brine and then dried. Volatile material was removed by evaporation and the residue was purified by chromatography on a silica gel Mega Bond Elut column eluting with 0–25% ethyl acetate/hexane to give the title compound (0.261 g; 72%) as a solid Mp 131–133 ° C.; NMR: 1.6 (s, 3H), 7.46 (t, 2H), 8.0 (dd, 1H), 8.08 (m, 2H), 8.15 (d, 1H), 8.3 (d, 1H), 9.85 (brs, 1H); MS (ESP$^+$): 426 (M+H)$^+$.

Method 70–72

Following the procedure of Method 69 and using the appropriate starting material the following compounds were prepared.

| Meth | Compound | NMR | SM |
|---|---|---|---|
| 70 | (R)-N-[2-Chloro-4-{3-fluoro-phenylsulphonyl}phenyl]-2-hydroxy-2-methyl-3,3,3-trifluoropropanamide | (CDCl$_3$) 1.75(s, 3H), 3.75(s, 1H), 7.10(dd, 1H), 7.30(dd, 1H), 7.50–7.70(m, 1H), 7.90(d, 1H), 8.05–8.10 (m, 2H), 8.65(d, 1H), 9.40(s, 1H) | Ex 253 |
| 71 | (R)-N-[2-Fluoro-4-{4-fluoro-phenylsulphonyl}phenyl]-2-hydroxy-2-methyl-3,3,3-trifluoropropanamide | 1.73(s, 3H), 4.26(s, 1H), 7.18(t, 2H), 7.8(t, 2H), 7.89–7.94(m, 2H), 8.56(t, 2H), 9.0(s, 1H) | Ex 193 |
| 72 | (R)-N-[2-Chloro-4-{3-chloro-4-fluorophenylsulphonyl} phenyl]-2-hydroxy-2-methyl-3,3,3-trifluoropropanamide | (CDCl$_3$) 1.75(s, 3H), 5.1(brs, 1H), 7.2–7.3(m, 1H), 7.6–7.9(m, 2H), 7.95–8.0(m, 2H), 8.65(d, 1H), 9.5 (brs, 1H) | Ex 275 |

Method 73
(R)-N-(2-Chloro-4-chlorosulphonylphenyl)-2-hydroxy-2-methyl-3,3,3-trifluoropropanamide (R)-N-(2-Chlorophenyl)-2-hydroxy-2-methyl-3,3,3-trifluoropropanamide (Method 74) (13.8 g, 52 mmol) was added in portions to a cooled (0° C.) solution of chlorosulphonic acid (25 ml) over 15 mins and then the mixture was heated to 85° C. After 4.5 h the reaction mixture was cooled in an ice bath and then poured very slowly onto a stirred ice-water mixture. After stirring for 15 mins, the mixture was extracted with ethyl acetate (2×100 ml) and the combined organic layer washed with brine, dried and concentrated to yield a brown oil. This oil was purified by flash column chromatography using 10:1, iso-hexane:ethyl acetate to yield the title compound as a pale yellow solid (11 g, 30 mmol). NMR: 1.6 (s, 3H), 7.55 (dd, 1H), 7.6 (d, 1H), 7.95 (d, 1H), 9.7 (brs, 1H); MS: 364.

Method 74
(R)-N-(2-Chlorophenyl)-2-hydroxy-2-methyl-3,3,3-trifluoropropanamide

Acetyl chloride (11.7 ml, 164 mmol) was added dropwise to a stirred solution of the (R)-2-hydroxy-2-methyl-3,3,3-trifluoropropanoic acid (Method 9) (10 g, 63 mmol) in toluene (100 ml) cooled in an ice bath. The mixture was then heated to 80° C. and the suspension dissolved to yield a clear solution. After 2 h the reaction mixture was cooled and then concentrated to yield a slight brown oil. This oil was then redissolved in DCM (140 ml) and DMF (4 drops) was added followed by oxalyl chloride (6 ml, 69 mmol). The solution bubbled vigorously and the reaction mixture was left to stir. After 15 h, this reaction mixture was added slowly to a stirred solution of 2-chloroaniline (8.7 g, 68 mmol) and pyridine (5.5 ml, 68 mmol) in DCM (150 ml). After 15 h stirring at room temperature, the resultant mixture was concentrated and the residue dissolved in methanol (500 ml). A solution of lithium hydroxide monohydrate (7.8 g, 0.19 mol) in water (120 ml) was then added and the mixture was stirred for 4 h. The mixture was then concentrated and the residue acidified to pH 2 (by addition of concentrated hydrochloric acid). Ethyl acetate(150 ml) was added and the mixture washed with water (2×100 ml) and brine, dried and evaporated to dryness. The residue was purified by flash column chromatography using 6:1, iso-hexane:ethyl acetate to yield the title compound as a white solid (13.8 g, 52 mmol). NMR: 1.6 (s, 3H), 7.1–7.25 (m, 1H), 7.3–7.4 (m, 1H), 7.55 (dd, 1H), 7.8 (s, 1H), 8.0 (dd, 1H), 9.7 (brs, 1H); MS: 266.

Method 75

Following the procedure of Method 63 and using the appropriate starting material the following compounds were prepared.

| Meth | Compound | NMR and MS | SM |
|---|---|---|---|
| 75 | (R)-N-[2-Chloro-4-(4-fluoro-phenylsulphinyl)phenyl]-2-hydroxy-2-methyl-3,3,3-trifluoropropanamide | (CDCl$_3$): 1.74(s, 3H), 4.16 and 4.24 (2 x br s, 1H), 7.19(t, 2H), 7.49(d, 1H), 7.63(dd, 2H), 7.7(d, 1H), 8.52(m, 1H), 9.2(br s, 1H); MS 408 | Ex 188 |

EXAMPLE 429

The following illustrate representative pharmaceutical dosage forms containing the compound of formula (I), or a pharmaceutically acceptable salt thereof (hereafter compound X), for therapeutic or prophylactic use in humans:

| (a) Tablet I | mg/tablet |
|---|---|
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph. Eur | 488.5 |
| Magnesium stearate | 1.5 |

| (e) Injection I | (50 mg/ml) |
|---|---|
| Compound X | 5.0% w/v |
| 1 N Sodium hydroxide solution | 15.0% v/v |
| 0.1 N Hydrochloric acid | (to adjust pH to 7.6) |
| Polyethylene glycol 400 | 4.5% w/v |
| Water for injection | to 100% |

| (f) Injection II | (10 mg/ml) |
|---|---|
| Compound X | 1.0% w/v |
| Sodium phosphate BP | 3.6% w/v |
| 0.1 N Sodium hydroxide solution | 15.0% v/v |
| Water for injection to | 100% |

(1 mg/ml. buffered

| (g) Injection III | to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note
The above formulations may be obtained by conventional procedures well known in the pharmaceutical art. The tablets (a)–(c) may be enteric coated by conventional means, for example to provide a coating of cellulose acetate phthalate.

What is claimed is:

1. A compound of formula (I'):

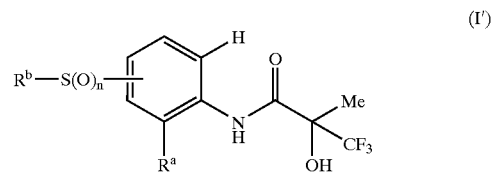

(I')

wherein:

n is 1 or 2;

R$^a$ is chloro, fluoro, bromo, nitro or methoxy;

R$^b$ is phenyl, wherein said phenyl is substituted by at least one group selected from ii), optionally one or more groups selected from i) and iii) and optionally further substituted with one group selected from iv):

i) —X$^a$—R$^c$ wherein X$^a$ is —O—, —S—, —SO—, —SO$_2$—NR$^d$— or —CONR$^e$— (wherein R$^d$ and R$^e$ each independently represents hydrogen or C$_{1-4}$alkyl which C$_{1-4}$alkyl is optionally substituted with one or more groups selected from hydroxy or C$_{1-4}$alkoxy) and R$^c$ is selected from hydrogen or C$_{1-6}$alkyl which C$_{1-6}$alkyl is optionally substituted with one or more hydroxy or C$_{1-4}$alkoxy, or X$^a$ is a direct bond and R$^c$ is C$_{1-6}$alkyl which C$_{1-6}$alkyl is optionally substituted with one or more hydroxy or C$_{1-4}$alkoxy, with the proviso that —X$^a$—R$^c$ is not C$_{1-4}$alkyl or C$_{1-4}$alkoxy;

ii) a 4–12 membered heterocyclic moiety containing 1–4 heteroatoms selected independently from O, N and S which heterocyclic moiety may be aromatic or non-aromatic and is optionally substituted with one or more groups selected from hydroxy, halo, C$_{1-4}$alkoxy, C$_{1-4}$alkyl or cyano;

iii) —X$^a$—C$_{1-6}$alkyl-X$^b$—R$^c$ wherein X$^a$ and R$^c$ are as defined hereinbefore and X$^b$ is —S—, —SO— or —SO$_2$—;

iv) cyano, hydroxy, halo, C$_{1-4}$alkoxy, C$_{1-4}$alkyl;

or a salt thereof;

or a pharmaceutically acceptable in vivo cleavable prodrug of said compound of formula (I); or a pharmaceutically acceptable salt of said compound or said prodrug.

2. A compound of formula (I'):

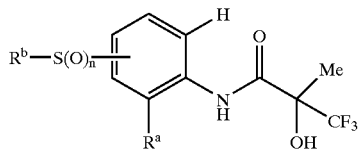

(I')

wherein:

n is 1 or 2;

$R^a$ is chloro, fluoro, bromo, nitro or methoxy;

$R^b$ is a carbon-linked 6-membered heteroaryl ring containing 1–2 nitrogen atoms or a carbon-linked 5-membered heteroaryl ring containing 1–3 heteroatoms selected independently from O, N and S, wherein said heteroaryl ring is substituted by one or more groups selected from i)–iii) and is optionally further substituted with a group selected from iv):

i) —$X^a$—$R^c$ wherein $X^a$ is —O—, —SO—, —$SO_2$—, —$NR^d$— or —$CONR^e$— (wherein $R^d$ and $R^e$ each independently represents hydrogen or $C_{1-4}$alkyl which $C_{1-4}$alkyl is optionally substituted with one or more groups selected from bydroxy or $C_{1-4}$alkoxy) and $R^c$ is selected from hydrogen or $C_{1-6}$alkyl which $C_{1-6}$alkyl is optionally substituted with one or more hydroxy or $C_{1-4}$alkoxy, or $X^a$ is a direct bond and $R^c$ is $C_{1-6}$alkyl which $C_{1-6}$alkyl is optionally substituted with one or more hydroxy or $C_{1-4}$alkoxy, with the proviso that —$X^a$—$R^c$ is not $C_{1-4}$alkyl or $C_{1-4}$alkoxy;

ii) a 4–12 membered heterocyclic moiety containing 1–4 heteroatoms selected independently from O, N and S which heterocyclic moiety may be aromatic or non-aromatic and is optionally substituted with one or more groups selected from hydroxy, halo, $C_{1-4}$alkoxy, $C_{1-4}$alkyl or cyano;

iii) —$X^a$—$C_{1-6}$alkyl-$X^b$—$R^c$ wherein $X^a$ and $R^c$ are as defined hereinbefore and $X^b$ is —S—, —SO— or —$SO_2$—;

iv) cyano, hydroxy, halo, $C_{1-4}$alkoxy, $C_{1-4}$alkyl;

and salts thereof;

and pharmaceutically acceptable in vivo cleavable prodrugs of said compound of formula (I);

or a pharmaceutically acceptable salt of said compound or said prodrug.

3. A compound of formula (I') as claimed in claim 1 or 2 wherein $R^a$ is chloro or fluoro.

4. A compound of formula (I') as claimed in claim 1 wherein $R^b$ is substituted by a 4–12 membered heterocyclic moiety containing 1–4 heteroatoms selected independently from O, N and S which heterocyclic moiety may be aromatic or non-aromatic.

5. A compound of formula (I') as claimed in claim 2 which is (R)-N-{2-Chloro-4-[4-(2-oxo-pyrrolidin-1-yl) phenysulphonyl]phenyl}-2-hydroxy-2-methyl-3,3,3-trifluoropropanaxnide;

or a salt thereof;

or a pharmaceutically acceptable in vivo cleavable prodrug of said compound of formula (I');

or a pharmaceutically acceptable salt of said compound or said prodrug.

6. A pharmaceutical composition which comprises a compound of the formula (I') as claimed in claim 1, 4, 5 or 2 or a pharmaceutically acceptable salt thereof, in association with a pharmaceutically acceptable excipient or carrier.

7. A process for preparing a compound of formula (I') as claimed in claim 1, 4, 5 or 2 or a pharmaceutically acceptable salt or an in vivo hydrolyzable ester thereof, which process (in which variable groups are as defined for formula (I') unless otherwise stated) comprises of:

(a) deprotecting a protected compound of formula (II'):

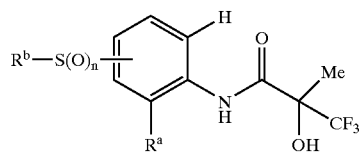

(II')

where Pg is an alcohol protecting group;

(b) oxidising a compound of formula (VI')

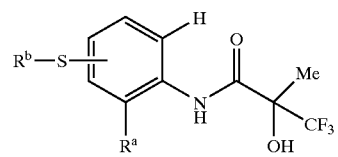

(VI')

(c) coupling a compound of formula (VII'):

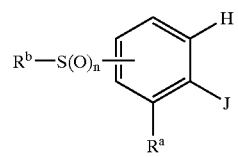

(VII')

wherein J is $NH_2$, with an acid of formula (VIII'):

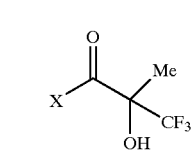

(VIII')

wherein X is OH;

(d) coupling an aniline of formula (VII') wherein J is —$NH_2$ with an activated acid derivative of formula (VIII');

(e) reacting a compound of formula (IX'):

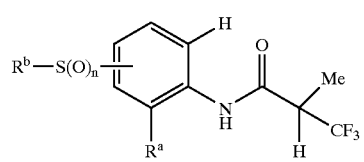

(IX')

with a base to yield the dianion, followed by treatment of the dianion with oxygen in the presence of a reducing agent; or by treatment with a peroxyacid; or (f) reacting a compound of formula (XII'):

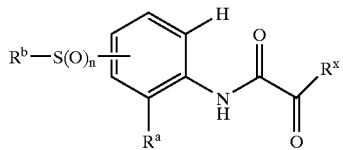

with a compound of formula R$^y$M wherein M is an alkali metal or a Grignard compound of formula R$^y$MgBr or R$^y$MgCl wherein one of R$^x$ and R$^y$ is CF$_3$ and the other is Me;

and thereafter optionally:
i) converting a compound of the formula (I') into another compound of the formula (I');
ii) removing any protecting groups; or
iii) forming a pharmaceutically acceptable salt or in vivo hydrolyzable ester.

8. A method for elevating PDH activity in a warm-blooded animal in need thereof, said method comprising administering to said animal a PDH activity-elevating amount of a compound of the formula (I') or prodrug or salt thereof, as claimed in claim 1, 4, 5 or 2.

9. A method of treating diabetes mellitus in a warm blooded animal in need thereof, said method comprising administering to said animal an effective amount of a compound of the formula (I') or prodrug or salt thereof, as claimed in claim 1, 4, 5 or 2.

10. A method of treating lactic academia in a warm blooded animal in need thereof, said method comprising administering to said animal an effective amount of a compound of the formula (I') or prodrug or salt thereof, as claimed in claim 1, 4, 5 or 2.

11. A method of treating obesity in a warm blooded animal in need thereof, said method comprising administering to said animal an effective amount of a compound of the formula (I') or prodrug or salt thereof, as claimed in claim 1, 4, 5 or 2.

* * * * *